US011110108B2

(12) United States Patent
Boucher et al.

(10) Patent No.: US 11,110,108 B2
(45) Date of Patent: Sep. 7, 2021

(54) METHOD FOR TREATING CANCER USING A COMBINATION OF DNA-DAMAGING AGENTS AND DNA-PK INHIBITORS

(71) Applicant: Vertex Pharmaceuticals Incorporated, Boston, MA (US)

(72) Inventors: Diane M. Boucher, Boston, MA (US); Shawn M. Hillier, Boston, MA (US); Wanjung Tsai, Boston, MA (US); Brian Hare, Boston, MA (US); William Markland, Boston, MA (US); David A. Newsome, Boston, MA (US); Marina S. Penney, Boston, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 16/336,195

(22) PCT Filed: Sep. 27, 2017

(86) PCT No.: PCT/US2017/053589
§ 371 (c)(1),
(2) Date: Mar. 25, 2019

(87) PCT Pub. No.: WO2018/064092
PCT Pub. Date: Apr. 5, 2018

(65) Prior Publication Data
US 2020/0016181 A1 Jan. 16, 2020

Related U.S. Application Data

(60) Provisional application No. 62/400,606, filed on Sep. 27, 2016, provisional application No. 62/497,943, filed on Dec. 8, 2016.

(51) Int. Cl.
| *A61K 31/704* | (2006.01) |
| *A61P 35/00* | (2006.01) |
| *A61K 9/127* | (2006.01) |
| *C07D 401/14* | (2006.01) |
| *C07D 403/14* | (2006.01) |
| *C07D 471/04* | (2006.01) |

(52) U.S. Cl.
CPC .......... *A61K 31/704* (2013.01); *A61K 9/1271* (2013.01); *A61P 35/00* (2018.01); *C07D 401/14* (2013.01); *C07D 403/14* (2013.01); *C07D 471/04* (2013.01)

(58) Field of Classification Search
CPC .. A61K 31/704; A61K 9/1271; A61K 31/506; A61K 45/06; A61K 31/7048; A61K 2300/00; A61P 35/00; A61P 43/00; C07D 401/14; C07D 403/14; C07D 471/04
See application file for complete search history.

(56) References Cited

U.S. PATENT DOCUMENTS

| 5,478,938 A | 12/1995 | Clemence et al. |
| 5,571,506 A | 11/1996 | Regan et al. |
| 5,571,815 A | 11/1996 | Schaper et al. |
| 5,595,756 A | 1/1997 | Bally et al. |
| 5,668,140 A | 9/1997 | Schaper et al. |
| 5,723,461 A | 3/1998 | Rosner et al. |
| 5,977,117 A | 11/1999 | Chan et al. |
| 6,004,979 A | 12/1999 | Clemence et al. |
| 6,057,371 A | 5/2000 | Glennon |
| 6,222,073 B1 | 4/2001 | Herwig et al. |
| 6,265,428 B1 | 7/2001 | Chan et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |

(Continued)

FOREIGN PATENT DOCUMENTS

| CA | 2716898 A1 | 9/2009 |
| CN | 102137854 A | 7/2011 |

(Continued)

OTHER PUBLICATIONS

Trosko (Mutation Research, 480-481 (2001), 219-229).*
Almarsson and M. J. Zaworotko, "Crystal engineering of the composition of pharmaceutical phases. Do pharmaceutical co-crystals represent a new path to improved medicines?" Chemical Communications, Aug. 5, 2004, (pp. 1889-1896).
Gavin P. Andrews et al., "Hot-melt extrusion: an emerging drug delivery technology", Pharmaceutical Technology Europe, vol. 21, Issue 1 (2009).

(Continued)

*Primary Examiner* — Snigdha Maewall
(74) *Attorney, Agent, or Firm* — Dechert LLP; Andrea L. C. Reid; Danielle M. Nihan

(57) ABSTRACT

Described herein are methods of treating a proliferative disease in a subject by administering a DNA-damaging agent and between about 8 and about 48 hours later administering to the subject a DNA-PK inhibitor. Exemplary DNA-PK inhibitors are represented by Formula (B-I): and by pharmaceutically acceptable salts thereof, wherein $R^1$, Q, Ring A, and Ring B are as defined herein.

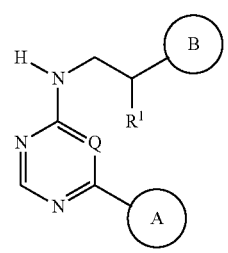

B-I

37 Claims, 32 Drawing Sheets

(56) References Cited

U.S. PATENT DOCUMENTS

| | | |
|---|---|---|
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,727,251 B2 | 4/2004 | Bebbington et al. |
| 6,743,791 B2 | 6/2004 | Cao et al. |
| 6,762,179 B2 | 7/2004 | Cochran et al. |
| 6,777,413 B2 | 8/2004 | Zhu et al. |
| 6,825,190 B2 | 11/2004 | Moon et al. |
| 6,844,347 B1 | 1/2005 | Schnidler et al. |
| 6,875,781 B2 | 4/2005 | Hong et al. |
| 6,884,804 B2 | 4/2005 | Choon-Moon |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,098,330 B2 | 8/2006 | Bebbington et al. |
| 7,115,739 B2 | 10/2006 | Bebbington et al. |
| 7,122,552 B2 | 10/2006 | Ledford |
| 7,144,911 B2 | 12/2006 | Flynn et al. |
| 7,179,912 B2 | 2/2007 | Halbrook et al. |
| 7,189,724 B2 | 3/2007 | An et al. |
| 7,208,507 B2 | 4/2007 | Hong et al. |
| 7,226,919 B2 | 6/2007 | Ledeboer et al. |
| 7,244,735 B2 | 7/2007 | Straub et al. |
| 7,253,187 B2 | 8/2007 | Cao et al. |
| 7,256,190 B2 | 8/2007 | Cochran et al. |
| 7,259,161 B2 | 8/2007 | Bethiel et al. |
| 7,271,179 B2 | 9/2007 | Bemis et al. |
| 7,300,929 B2 | 11/2007 | Baxter et al. |
| 7,304,061 B2 | 12/2007 | Hale et al. |
| 7,304,071 B2 | 12/2007 | Cochran et al. |
| 7,312,227 B2 | 12/2007 | Ledeboer et al. |
| 7,329,652 B2 | 2/2008 | Salituro et al. |
| 7,345,054 B2 | 3/2008 | Hale et al. |
| 7,358,258 B2 | 4/2008 | Hale et al. |
| 7,361,665 B2 | 4/2008 | Ledeboer et al. |
| 7,390,815 B2 | 6/2008 | Davies et al. |
| 7,407,962 B2 | 8/2008 | Aronov et al. |
| 7,419,984 B2 | 9/2008 | Bhatt et al. |
| 7,427,681 B2 | 9/2008 | Bebbington et al. |
| 7,452,555 B2 | 11/2008 | Childs |
| 7,456,190 B2 | 11/2008 | Maltais et al. |
| 7,473,691 B2 | 1/2009 | Davies et al. |
| 7,488,727 B2 | 2/2009 | Cochran et al. |
| 7,501,415 B2 | 3/2009 | Aronov et al. |
| 7,517,870 B2 | 4/2009 | Auricchio et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,592,340 B2 | 9/2009 | Bernis et al. |
| 7,625,913 B2 | 12/2009 | Bebbington et al. |
| 7,635,683 B2 | 12/2009 | Gai et al. |
| 7,666,895 B2 | 2/2010 | Flynn et al. |
| 7,691,853 B2 | 4/2010 | Bebbington et al. |
| 7,696,204 B2 | 4/2010 | McDonald et al. |
| 7,732,444 B2 | 6/2010 | Fleming et al. |
| 7,767,672 B2 | 8/2010 | Binch et al. |
| 7,820,685 B2 | 10/2010 | Binch et al. |
| 7,951,820 B2 | 5/2011 | Bebbington et al. |
| 7,968,565 B2 | 6/2011 | Arkin et al. |
| 7,982,037 B2 | 7/2011 | Bebbington et al. |
| 8,026,359 B2 | 9/2011 | Chen |
| 8,084,457 B2 | 12/2011 | Choidas et al. |
| 8,129,399 B2 | 3/2012 | Binch et al. |
| 8,268,811 B2 | 9/2012 | Mortimore et al. |
| 8,268,829 B2 | 9/2012 | Charrier et al. |
| 8,304,414 B2 | 11/2012 | Bebbington et al. |
| 8,372,850 B2 | 2/2013 | Jimenez et al. |
| 8,383,633 B2 | 2/2013 | Mortimore et al. |
| 8,410,133 B2 | 4/2013 | Jimenez et al. |
| 8,426,425 B2 | 4/2013 | Jimenez et al. |
| 8,455,500 B2 | 6/2013 | Okano et al. |
| 8,455,507 B2 | 6/2013 | Studley et al. |
| 8,476,287 B2 | 7/2013 | Okano et al. |
| 8,518,953 B2 | 8/2013 | Pierce et al. |
| 8,524,720 B2 | 9/2013 | Bebbington et al. |
| 8,541,428 B2 | 9/2013 | Gavish et al. |
| 8,546,392 B2 | 10/2013 | Hartmann et al. |
| 8,557,833 B2 | 10/2013 | Binch et al. |
| 8,563,549 B2 | 10/2013 | Burger et al. |
| 8,633,210 B2 | 1/2014 | Charrier et al. |
| 8,637,511 B2 | 1/2014 | Binch et al. |
| 8,664,219 B2 | 3/2014 | Jimenez et al. |
| 8,691,847 B2 | 4/2014 | Zhu et al. |
| 8,697,685 B2 | 4/2014 | Axten et al. |
| 8,697,698 B2 | 4/2014 | Bebbington et al. |
| 8,735,593 B2 | 5/2014 | Jimenez et al. |
| 8,779,127 B2 | 7/2014 | Charrier et al. |
| 8,784,782 B2 | 7/2014 | Tachdjian et al. |
| 8,785,444 B2 | 7/2014 | Mortimore et al. |
| 8,841,308 B2 | 9/2014 | Charrier et al. |
| 9,062,076 B2 | 6/2015 | Williams et al. |
| 9,296,701 B2 | 3/2016 | Charifson et al. |
| 9,340,557 B2 | 5/2016 | Maxwell et al. |
| 9,359,380 B2 | 6/2016 | Maxwell et al. |
| 9,376,448 B2 | 6/2016 | Charifson et al. |
| 9,592,232 B2 | 3/2017 | Charifson et al. |
| 9,878,993 B2 | 1/2018 | Charifson et al. |
| 9,925,188 B2 | 3/2018 | Charifson et al. |
| 10,039,761 B2 | 8/2018 | Nti-Addae et al. |
| 10,076,521 B2 | 9/2018 | Charifson et al. |
| 10,391,095 B2 | 8/2019 | Charifson et al. |
| 10,442,791 B2 | 10/2019 | Charifson et al. |
| 10,501,439 B2 | 12/2019 | Charifson et al. |
| 10,716,789 B2 | 7/2020 | Nti-Addae et al. |
| 2002/0111353 A1 | 8/2002 | Ledeboer et al. |
| 2003/0096813 A1 | 5/2003 | Cao et al. |
| 2003/0199525 A1 | 10/2003 | Hirst et al. |
| 2003/0199526 A1 | 10/2003 | Choquette et al. |
| 2003/0207873 A1 | 11/2003 | Harrington |
| 2003/0207886 A1 | 11/2003 | Plucker et al. |
| 2004/0097502 A1 | 5/2004 | Gellibert |
| 2004/0235834 A1 | 11/2004 | Farmer et al. |
| 2005/0054568 A1 | 3/2005 | Ling et al. |
| 2006/0142572 A1 | 6/2006 | Martinez-Botella et al. |
| 2006/0166936 A1 | 7/2006 | Binch et al. |
| 2006/0264427 A1 | 11/2006 | Smith et al. |
| 2007/0179125 A1 | 8/2007 | Fraysse et al. |
| 2007/0265263 A1 | 11/2007 | Cao et al. |
| 2007/0270420 A1 | 11/2007 | Harbeson et al. |
| 2008/0139585 A1 | 6/2008 | Rathinavelu et al. |
| 2008/0207616 A1 | 8/2008 | Aquila et al. |
| 2008/0267918 A1 | 10/2008 | Gai et al. |
| 2008/0280891 A1 | 11/2008 | Kelly et al. |
| 2009/0023729 A1 | 1/2009 | Nakamura et al. |
| 2009/0042865 A1 | 2/2009 | Frigerio et al. |
| 2009/0053192 A1 | 2/2009 | Millan et al. |
| 2009/0124612 A1 | 5/2009 | Albrecht et al. |
| 2009/0221581 A1 | 9/2009 | Wabnitz et al. |
| 2009/0298844 A1 | 12/2009 | Pollard |
| 2010/0137305 A1 | 6/2010 | Binch et al. |
| 2010/0137337 A1 | 6/2010 | George et al. |
| 2010/0197674 A1 | 8/2010 | Tamai et al. |
| 2011/0046104 A1 | 2/2011 | Mortimore et al. |
| 2011/0060013 A1 | 3/2011 | Mortimore et al. |
| 2011/0065739 A1 | 3/2011 | Ishikawa et al. |
| 2011/0144114 A1 | 6/2011 | Lochead et al. |
| 2011/0159111 A1* | 6/2011 | Curry ............... A61P 35/02 424/649 |
| 2011/0275643 A1 | 11/2011 | Liou et al. |
| 2011/0319618 A1 | 12/2011 | Nishio |
| 2012/0009151 A1 | 1/2012 | Han et al. |
| 2012/0202806 A1 | 8/2012 | Durrenberger et al. |
| 2013/0012489 A1 | 1/2013 | Mederski et al. |
| 2013/0150359 A1 | 6/2013 | Fuchss et al. |
| 2013/0172337 A1 | 7/2013 | Fuchss et al. |
| 2013/0209400 A1 | 8/2013 | Bach Tana et al. |
| 2013/0281431 A1 | 10/2013 | Charifson et al. |
| 2014/0045869 A1 | 2/2014 | Charifson et al. |
| 2014/0113012 A1 | 4/2014 | Schultz et al. |

(56) References Cited

U.S. PATENT DOCUMENTS

| | | | |
|---|---|---|---|
| 2014/0148434 | A1 | 5/2014 | Boyall et al. |
| 2014/0187772 | A1 | 7/2014 | Bebbington et al. |
| 2014/0194444 | A1 | 7/2014 | Jimenez et al. |
| 2014/0256703 | A1 | 9/2014 | Jimenez et al. |
| 2014/0275024 | A1 | 9/2014 | Maxwell et al. |
| 2014/0275059 | A1 | 9/2014 | Maxwell et al. |
| 2014/0275072 | A1 | 9/2014 | Mederski et al. |
| 2015/0111871 | A1 | 4/2015 | Charifson et al. |
| 2016/0045596 | A1 | 2/2016 | Geretti et al. |
| 2016/0250212 | A1 | 9/2016 | Charifson et al. |
| 2016/0339024 | A1 | 11/2016 | Nti-Addae et al. |
| 2016/0340341 | A1 | 11/2016 | Maxwell et al. |
| 2016/0354381 | A1 | 12/2016 | Maxwell et al. |
| 2016/0368899 | A1 | 12/2016 | Charifson et al. |
| 2017/0258789 | A1 | 9/2017 | Charifson et al. |
| 2020/0062732 | A1 | 2/2020 | Charifson et al. |
| 2020/0109130 | A1 | 4/2020 | Charifson et al. |

FOREIGN PATENT DOCUMENTS

| | | | |
|---|---|---|---|
| DE | 102006050512 | A1 | 4/2008 |
| DE | 102007044032 | A1 | 3/2009 |
| EA | 016028 | | 1/2012 |
| EP | 1678147 | A1 | 7/2006 |
| EP | 1701944 | A2 | 9/2006 |
| JP | H10251255 | | 9/1998 |
| JP | 2003511378 | A | 3/2003 |
| JP | 2005336138 | A | 12/2005 |
| JP | 2007008045 | A | 1/2007 |
| JP | 2007513172 | A | 5/2007 |
| JP | 2010505862 | A | 2/2010 |
| JP | 2011246389 | A | 12/2011 |
| WO | WO-1993022291 | A1 | 11/1993 |
| WO | WO-1998037079 | A1 | 8/1998 |
| WO | WO-1998054158 | A1 | 12/1998 |
| WO | WO-2000009496 | A1 | 2/2000 |
| WO | WO-2000042026 | A1 | 7/2000 |
| WO | WO-2001025220 | A1 | 4/2001 |
| WO | WO-2001027089 | A1 | 4/2001 |
| WO | WO-2001064646 | A2 | 9/2001 |
| WO | WO-2002020500 | A2 | 3/2002 |
| WO | WO-2004085418 | A2 | 10/2004 |
| WO | WO-2005026129 | A1 | 3/2005 |
| WO | WO-2005066139 | A2 | 7/2005 |
| WO | WO-2005089730 | A2 | 9/2005 |
| WO | WO-2005121121 | A2 | 12/2005 |
| WO | WO-2006044503 | A2 | 4/2006 |
| WO | WO-2006044732 | A2 | 4/2006 |
| WO | WO-2006108107 | A1 | 10/2006 |
| WO | 2006126010 | | 11/2006 |
| WO | WO-2006138418 | A2 | 12/2006 |
| WO | WO-2007056143 | A2 | 5/2007 |
| WO | WO-2007082899 | A1 | 7/2007 |
| WO | WO-2007109783 | A2 | 9/2007 |
| WO | WO-2008006583 | A1 | 1/2008 |
| WO | WO-2008008747 | A1 | 1/2008 |
| WO | WO-2008008852 | A2 | 1/2008 |
| WO | WO-2008028691 | A1 | 3/2008 |
| WO | WO-2008042639 | A1 | 4/2008 |
| WO | WO-2008070661 | A1 | 6/2008 |
| WO | WO-2008083346 | A1 | 7/2008 |
| WO | WO-2008092199 | A1 | 8/2008 |
| WO | WO-2008106202 | A1 | 9/2008 |
| WO | WO-2008115973 | A2 | 9/2008 |
| WO | WO-2008141065 | A1 | 11/2008 |
| WO | WO-2008144253 | A1 | 11/2008 |
| WO | WO-2008145616 | A1 | 12/2008 |
| WO | WO-2009004621 | A1 | 1/2009 |
| WO | WO-2009008991 | A2 | 1/2009 |
| WO | WO-2009016841 | A1 | 2/2009 |
| WO | WO-2009047359 | A1 | 4/2009 |
| WO | WO-2009105220 | A1 | 8/2009 |
| WO | WO-2009107391 | A1 | 9/2009 |
| WO | WO-2009109258 | A1 | 9/2009 |
| WO | WO-2009115517 | A2 | 9/2009 |
| WO | WO-2009152909 | A1 | 12/2009 |
| WO | WO-2010048149 | A2 | 4/2010 |
| WO | WO-2010064737 | A1 | 6/2010 |
| WO | WO-2010065899 | A2 | 6/2010 |
| WO | WO-2010093808 | A1 | 8/2010 |
| WO | WO-2011006074 | A1 | 1/2011 |
| WO | WO-2011022348 | A1 | 2/2011 |
| WO | WO-2011051535 | A1 | 5/2011 |
| WO | WO-2011113512 | A1 | 9/2011 |
| WO | 2012000632 | | 1/2012 |
| WO | WO-2012028233 | A1 | 3/2012 |
| WO | WO-2012138938 | A1 | 10/2012 |
| WO | WO-2013024282 | A2 | 2/2013 |
| WO | WO-2013032951 | A1 | 3/2013 |
| WO | WO-2013040515 | A1 | 3/2013 |
| WO | WO-2013043935 | A1 | 3/2013 |
| WO | WO-2013049701 | A1 | 4/2013 |
| WO | WO-2013072015 | A1 | 5/2013 |
| WO | WO-2013083991 | A1 | 6/2013 |
| WO | WO-2013112950 | A2 | 8/2013 |
| WO | 2013163190 | | 10/2013 |
| WO | WO-2014075077 | A1 | 5/2014 |
| WO | 2014159690 | | 10/2014 |
| WO | 2015058031 | | 4/2015 |
| WO | WO2015058067 | | 4/2015 |
| WO | WO-2015058067 | A1 * | 4/2015 .......... C07B 59/002 |
| WO | 2016014148 | | 1/2016 |
| WO | 2017059357 | | 4/2017 |

OTHER PUBLICATIONS

Berge, et al., "Pharmaceutical Salts" Journal of Pharmaceutical Sciences, Jan. 1977, vol. 66, (pp. 1-19).
Berenbaum, Morris C., "Criteria for analyzing interactions between biologically active agents", Advances in Cancer Research 1981; vol. 35, (pp. 269-335).
Bliss CI, "The toxicity of poisons applied jointly" Annals of Applied Biology Aug. 1939, vol. 26, (pp. 585-615).
Bolderson E, et al., "Recent advances in cancer therapy targeting proteins involved in DNA double-strand break repair" Clinical Cancer Research Oct. 15, 2009; vol. 15(20): (pp. 6314-6320).
Dobbs, TA, et al., "A structural model for regulation of NHEJ by DNA-PKcs autophosphorylation", DNA Repair Oct. 28, 2010; vol. 9, (pp. 307-1314).
Eisenhauer et. al., "New response evaluation criteria in solid tumours" European Journal of Cancer, vol. 45, Jan. 2009, (pp. 228-247).
Giuliani and Kaplan, "New doxorubicin analogs active against doxorubicin-resistant colon tumor xenografts in the nude mouse," Cancer Research, vol. 40, No. 12, Dec. 1980 (pp. 4682-4687).
Helleday T. et al., "DNA repair pathways as targets for cancer therapy" Nature Reviews Cancer 2008; vol. 8, (pp. 193-204).
Salles B. et al.,, "DNA-PK, a pharmacological target in cancer chemotherapy and radiotherapy?", Journal of Cancer Science and Therapy 2011; (pp. S8:1-11).
Stiff , T. et al., "ATM and DNA-PK function redundantly to phosphorylate H2AX after exposure to ionizing radiation", Cancer Research 2004; vol. 64, (pp. 2390-2396).
Trask et al., "Solvent-drop grinding: Green polymorph control of cocrystallisation", Chemical Communications, Issue 7, 2004, (pp. 890-891).
White DE et al., "KAP1, a novel substrate for PIKK family members, colocalizes with numerous damage response factors at DNA lesions" Cancer Research Dec. 15, 2006; vol. 66: (pp. 11594-11599).
Yu et al., "Synthesis and Biological Activites of a 3'-Azido Analogue of Doxorubicin Against Drug-Resistant Cancer Cells" International Journal of Molecular Sciesnces, Mar. 19, 2012, vol. 13: (pp. 3671-3684).
International Search Report and Written Opinion for PCT/US2017/053589 dated Dec. 15, 2017.
International Preliminary Report on Patentability for PCT/US2017/053589 dated Dec. 15, 2017.
Childs et al., "The Salt-Cocrystal Continuum: The Influence of Crystal Structure on Ionization State," Molecular Pharmaceutics. 2007;4(3):323-338.

(56) References Cited

OTHER PUBLICATIONS

Davis et al., Dynamics of the P13K-like protein kinase members ATM and DNA-PKcs at DNA double strand breaks. Cell Cycle. Jul. 2010; 9(13):2529-36.
Edelman et al., Targeted readiopharmaceutical therapy for advanced lung cancer: phase 1 trial of rhenium Re188 P2045, a somatostatin analog. J Thorac Oncol. 2009; 4(12):1550-4.
Goodwin et al., Beyond DNA repair: DNA-PK function in cancer. Cancer discovery. Oct. 1, 2014;4(10):1126-39. Published online Aug. 28, 2014. doi: 10.1158/2159-8290.CD-14-0358.
Gura, Systems for identifying new drugs are often faulty. Science. Nov. 7, 1997;278(5340):1041-2.
International Search Report and Written Opinion dated Aug. 29, 2013 in connection with Application No. PCT/US2013/037811.
International Search Report and Written Opinion dated Dec. 22, 2014 in connection with Application No. PCT/US2014/061033.
International Search Report and Written Opinion dated Dec. 22, 2014 in connection with Application No. PCT/US2014/061102.
International Search Report and Written Opinion dated May 27, 2014 in connection with Application No. PCT/US2014/024767.
Jordan, Tamoxifen: a most unlikely pioneering medicine. Nature Reviews Drug Discovery. Mar. 1, 2003;2(3):205-13.
Kashishian et al., DNA-dependent protein kinas inhibitors as drug candidates for the treatment of cancer. Mol Cancer Ther. 2003; 2(12):1257-64.
Kuntzinger et al., Protein phosphatase 1 regulators in DNA damage signaling. Cell Cycle. May 2011; 10(9): 1-7.
PCT International Search Report and Written Opinion from PCT/US2017/053589 dated Nov. 22, 2017.
Sporn et al., Chemoprevention of cancer. Carcinogenesis. Mar. 1, 2000;21(3):525-30.
Veuger et al., Radiosensitization and DNA repair inhibition by combined use of novel inhibitors of DNA-dependent protein kinase and poly(ADP-ribose) polymerase-1. Cancer Res. 2003; 63;6008-15.

\* cited by examiner

METHOD FOR TREATING CANCER USING A COMBINATION OF DNA-DAMAGING AGENTS AND DNA-PK INHIBITORS

CROSS-REFERENCE TO RELATED APPLICATIONS

This application claims benefit under 35 U.S.C. § 119(e) of U.S. provisional application Ser. No. 62/400,606, filed Sep. 27, 2016, and U.S. provisional application Ser. No. 62/497,943, filed Dec. 8, 2016, the entire contents of all which are incorporated herein by reference.

BACKGROUND OF THE INVENTION

Cancers as a group account for approximately 13% of all deaths each year with the most common being: lung cancer (1.4 million deaths), stomach cancer (740,000 deaths), liver cancer (700,000 deaths), colorectal cancer (610,000 deaths), and breast cancer (460,000 deaths). The three most common childhood cancers are leukemia (34%), brain tumors (23%), and lymphomas (12%). Rates of childhood cancer have increased by 0.6% per year between 1975 to 2002 in the United States and by 1.1% per year between 1978 and 1997 in Europe. This makes invasive cancer the leading cause of death in the developed world and the second leading cause of death in the developing world. Accordingly, there is a need to identify novel and efficacious therapeutic strategies that mitigate the limitations of current anti-cancer drugs.

SUMMARY OF THE INVENTION

The present invention is based, at least in part, on the unexpected discovery that DNA-dependent Protein Kinase (DNA-PK) inhibitors administered between about 8 and about 48 hours after DNA-damaging agents are particularly effective at treating proliferative diseases.

Accordingly, the invention relates to a method of treating a proliferative disorder in a subject, the method comprising administering to a subject in need thereof a DNA-damaging agent and administering to the subject a DNA-PK inhibitor between about 8 and about 48 hours after administration of the DNA-damaging agent. The invention further relates to a DNA-damaging agent for use in a method of treating a proliferative disorder in a subject, the method comprising administering to a subject in need thereof the DNA-damaging agent and administering to the subject a DNA-PK inhibitor between about 8 and about 48 hours after administration of the DNA-damaging agent. The present invention further relates to a DNA-PK inhibitor for use in a method of treating a proliferative disorder in a subject, the method comprising administering to a subject in need thereof a DNA-damaging agent and administering to the subject the DNA-PK inhibitor between about 8 and about 48 hours after administration of the DNA-damaging agent. The present invention further pertains to the use of a DNA-PK inhibitor in the manufacture of a medicament for treating a proliferative disorder in a subject, the treatment comprising administering to a subject in need thereof a DNA-damaging agent and administering to the subject the DNA-PK inhibitor between about 8 and about 48 hours after administration of the DNA-damaging agent.

In the most preferred embodiments, the DNA-damaging agent is a doxorubicin agent. As used herein, a doxorubicin agent includes doxorubicin in the free form, salts of doxorubicin, analogs of doxorubicin, or any doxorubicin agent in liposomes. Non-limiting examples of analogs of doxorubicin are 4'-epidoxorubicin, 4'-deoxydoxorubicin, and 4'-O-methyldoxorubicin, which are described in Giuliani et al., *Cancer Research*, 1980, 40: 4682-87, incorporated herein by reference, and 3'-azido doxorubicin, which is described in Yu et al., *Int. J. Mol. Sci.*, 2012, 13: 3671-3684, incorporated herein by reference. In some embodiments, such a doxorubicin agent is in liposomes (e.g., encapsulated in liposomes). The liposome can either be pegylated or non-pegylated. In some embodiments, a doxorubicin agent is a salt of doxorubicin. In some embodiments, a doxorubicin agent is a pharmaceutically acceptable salt of doxorubicin. In some embodiments, a doxorubicin agent is doxorubicin hydrochloride. In some embodiments, a doxorubicin agent is free form doxorubicin. In some embodiments, a doxorubicin agent is a salt of doxorubicin, such as a pharmaceutically acceptable salt of doxorubicin, in liposomes which can be pegylated or non-pegylated. In some embodiments, a doxorubicin agent is free form doxorubicin in liposomes which can be pegylated or non-pegylated. In some embodiments, a doxorubicin agent is doxorubicin hydrochloride in liposomes which can be pegylated or non-pegylated. In some embodiments, a doxorubicin agent is encapsulated in liposomes, which can either be pegylated or non-pegylated. In some embodiments, a doxorubicin agent is doxorubicin hydrochloride liposome. In some embodiments, a doxorubicin agent is doxorubicin hydrochloride. In some embodiments, a doxorubicin agent is encapsulated in liposomes, which can either be pegylated or non-pegylated. In some embodiments, the doxorubicin agent is pegylated liposomal doxorubicin, which is a pegylated liposome-encapsulated form of doxorubicin (e.g., DOXIL® and CAELYX®). In some embodiments, the doxorubicin agent is doxorubicin hydrochloride encapsulated in non-pegylated liposomes (e.g., MYOCET®). In certain embodiments, the pegylated liposomal doxorubicin is administered in a dosage range of about 14 mg/m$^2$ to about 80 mg/m$^2$, inclusive; a dosage range of about 18 mg/m$^2$ to about 72 mg/m$^2$, inclusive; a dosage range of about 25 mg/m$^2$ to about 55 mg/m$^2$, inclusive; a dosage range of about 30 mg/m$^2$ to about 50 mg/m$^2$, inclusive; or a dosage of about 40 mg/m$^2$ or 50 mg/m$^2$, inclusive.

In some embodiments, the DNA-damaging agent is in liposomes. In certain embodiments, the liposomes comprising the DNA-damaging agent are pegylated. In certain embodiments, the liposomes comprising the DNA-damaging agent are non-pegylated. Non-limiting examples of pegylated liposome carriers can be composed of cholesterol, fully hydrogenated soy phosphatidylcholine (HSPC), and N-(carbonyl-methoxypolyethylene glycol 2000)-1,2-distearoyl-sn-glycero-3-phosphoethanolamine sodium salt (MPEG-DSPE). Non-limiting examples of non-pegylated liposome carriers can be composed of phosphatidylcholine and cholesterol.

In alternative embodiments, the DNA-damaging agent comprises or is selected from chemotherapy. In some embodiments, the DNA-damaging agent comprises or is independently selected from radiomimetic neocarzinostatin, a platinating agent, a Topoisomerase I inhibitor, a Topoisomerase II inhibitor, an antimetabolite, an alkylating agent, an alkyl sulphonate, or an antibiotic, in particular a DNA damaging antibiotic.

In some further alternative embodiments, the DNA-damaging agent is a platinating agent comprising or selected from Cisplatin, Oxaliplatin, Carboplatin, Nedaplatin, Lobaplatin, Triplatin Tetranitrate, Picoplatin, Satraplatin, ProLindac, or Aroplatin.

In some further alternative embodiments, the DNA-damaging agent is a Topo I inhibitor comprising or selected from Camptothecin, Topotecan, Irinotecan/SN38, Rubitecan, or Belotecan. In some embodiments, the DNA-damaging agent is topoisomerase II inhibitor. In some embodiments, the DNA-damaging agent is a Topoisomerase II inhibitor comprising Etoposide, Daunorubicin, Aclarubicin, Epirubicin, Idarubicin, Amrubicin, Pirarubicin, Valrubicin, Zorubicin, or Teniposide. In some embodiments, the DNA-damaging agent is an anthracycline topoisomerase II inhibitor. In some embodiments, the DNA-damaging agent is daunorubicin, epirubicin, or idarubicin.

In some further alternative embodiments, the DNA-damaging agent is an antimetabolite comprising or selected from Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, 6-Mercaptopurine, 5-Fluorouracil, Azacitidine, or Hydroxyurea.

In some further alternative embodiments, the DNA-damaging agent is an alkylating agent comprising or selected from Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin, nitrogen mustards, nitrosoureas, triazenes, alkyl sulfonates, Procarbazine, aziridines, or Plicamycin.

In some further alternative embodiments, the DNA-damaging agent is a DNA-damaging antibiotic comprising or selected from Anthracyclines, Anthracenediones, or *Streptomyces* family.

In some embodiments, the cancer is a solid tumor. In some embodiments, the solid cancer is: oral cancer, lung cancer, gastrointestinal cancer, genitourinary tract cancer, liver cancer, bone cancer, cancer of the nervous system, gynecological cancer, skin cancer, thyroid gland cancer, or adrenal gland cancer. Expressed differently, the cancer is a solid tumor selected from the mentioned cancers.

In some embodiments, the cancer for treatment is oral cancer, where the oral cancer is buccal cavity cancer, lip cancer, tongue cancer, mouth cancer, pharynx cancer; cardiac cancer, where the cardiac cancer is sarcoma (angiosarcoma, fibrosarcoma, rhabdomyosarcoma, liposarcoma), myxoma, rhabdomyoma, fibroma, lipoma or teratoma; lung cancer, where the lung cancer is bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, or mesothelioma; gastrointestinal cancer, where the gastrointestinal cancer is esophageal cancer (squamous cell carcinoma, larynx, adenocarcinoma, leiomyosarcoma, lymphoma), stomach cancer (carcinoma, lymphoma, leiomyosarcoma), pancreatic cancer (ductal adenocarcinoma, insulinoma, glucagonoma, gastrinoma, carcinoid tumors, vipoma), small bowel or small intestinal cancer (adenocarcinoma, lymphoma, carcinoid tumors, Karposi's sarcoma, leiomyoma, hemangioma, lipoma, neurofibroma, fibroma), large bowel or large intestinal cancer (adenocarcinoma, tubular adenoma, villous adenoma, hamartoma, leiomyoma), colon cancer, colon-rectum cancer, colorectal cancer, or rectal cancer; genitourinary tract cancer, where the genitourinary tract cancer is kidney cancer (adenocarcinoma, Wilm's tumor [nephroblastoma], lymphoma), bladder cancer and urethral cancer (squamous cell carcinoma, transitional cell carcinoma, adenocarcinoma), prostate (adenocarcinoma, sarcoma), testicular cancer (seminoma, teratoma, embryonal carcinoma, teratocarcinoma, choriocarcinoma, sarcoma, interstitial cell carcinoma, fibroma, fibroadenoma, adenomatoid tumors, lipoma); liver cancer, where the linter cancer is hepatoma (hepatocellular carcinoma), cholangiocarcinoma, hepatoblastoma, angiosarcoma, hepatocellular adenoma, hemangioma, or biliary passages cancer; bone cancer, where the bone cancer is osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors; nervous system cancer, where the nervous system cancer is skull cancer (osteoma, hemangioma, granuloma, xanthoma, osteitis deformans), meninges cancer (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, or meningioma, glioma, sarcoma); gynecological cancer, where the gynecological cancer is uterine cancer (endometrial carcinoma), cervical cancer (cervical carcinoma, pre-tumor cervical dysplasia), ovarian cancer (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulval cancer (squamous cell carcinoma, intraepithelial carcinoma, adenocarcinoma, fibrosarcoma, melanoma), vaginal cancer (clear cell carcinoma, squamous cell carcinoma, botryoid sarcoma (embryonal rhabdomyosarcoma), fallopian tube cancer (carcinoma), or breast cancer; skin cancer, where the skin cancer is malignant melanoma, basal cell carcinoma, squamous cell carcinoma, Karposi's sarcoma, keratoacanthoma, moles dysplastic nevi, lipoma, angioma, dermatofibroma or keloids; thyroid gland cancer, where the thyroid cancer is papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, or paraganglioma; or adrenal glands cancer, where the adrenal glands cancer is neuroblastoma. Expressed differently, the cancer is a solid tumor selected from the listed cancers.

In some embodiments, the cancer is non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, endometrial cancer, or ovarian cancer.

In some embodiments, the cancer is non-small cell lung cancer, small cell lung cancer, or triple negative breast cancer. In some embodiments, the cancer is ovarian cancer or endometrial cancer.

In some embodiments, a method of treating a proliferative disorder in a subject comprises administering to the subject in need thereof a first dose of a DNA-damaging agent and between about 8 and about 48 hours later administering to the subject a compound that inhibits DNA-PK. In other words, a method of treating a proliferative disorder in a subject comprises administering to the subject in need thereof a first dose of a therapeutically effective amount of a DNA-damaging agent and between about 8 and about 48 hours later administering to the subject a therapeutically effective amount of a compound that inhibits DNA-PK, i.e. a DNA-PK inhibitor.

In some embodiments, the DNA-PK inhibitor is administered between about 8 and about 30 hours after administration of the DNA-damaging agent. In some embodiments, the DNA-PK inhibitor is administered between about 8 and about 20 hours after administration of the DNA-damaging agent. In some embodiments, the DNA-PK inhibitor is administered between about 12 and about 30 hours after administration of the DNA-damaging agent. In some embodiments, the DNA-PK inhibitor is administered between about 20 and about 28 hours after administration of the DNA-damaging agent. In some embodiments, the DNA-PK inhibitor is administered between about 10 and about 20 hours after administration of the DNA-damaging agent. In some embodiments, the DNA-PK inhibitor is administered between about 12 and about 18 hours after administration of the DNA-damaging agent. In some embodiments, the DNA-PK inhibitor is administered between about 14 and about 18 hours after administration of the DNA-damaging agent. In some embodiments, the DNA-PK inhibitor is administered about 14 and about 16 hours after administration of the DNA-damaging agent. In some embodiments, the DNA-PK inhibitor is administered about 8, 9, 10, 11, 12, 13, 14, 15, 16, 17, 18, 19, 20, or 24 hours after administration of the DNA-damaging agent. In some embodiments, the DNA-PK inhibitor is administered about 24 hours after administration of the DNA-damaging agent. In some embodiments, the DNA-PK inhibitor is administered about 18 hours after administration of the DNA-damaging agent. In some embodiments, the DNA-PK inhibitor is administered about 16 hours after administration of the DNA-damaging agent. In some embodiments, the DNA-PK inhibitor is administered about 14 hours after administration of the DNA-damaging agent. According to the most preferred embodiment, the DNA-damaging agent is a doxorubicin agent.

In certain embodiments, the DNA-PK inhibitor is Compound B-1. In certain embodiments, the DNA-PK inhibitor is a pharmaceutically acceptable salt of Compound B-1. In certain embodiments, the DNA-PK inhibitor is Compound B-2. In certain embodiments, the DNA-PK inhibitor is a pharmaceutically acceptable salt of Compound B-2. In certain embodiments, the DNA-PK inhibitor is a co-crystal of Compound B-1 and a co-crystal former (e.g., adipic acid, citric acid, fumaric acid, maleic acid, succinic acid, or benzoic acid). In certain embodiments, the DNA-PK inhibitor is a co-crystal of a pharmaceutically acceptable salt of Compound B-1 and a co-crystal former (e.g., adipic acid, citric acid, fumaric acid, maleic acid, succinic acid, or benzoic acid). In certain embodiments, the DNA-PK inhibitor is a co-crystal of Compound B-2 and a co-crystal former (e.g., adipic acid, citric acid, fumaric acid, maleic acid, succinic acid, or benzoic acid). In certain embodiments, the DNA-PK inhibitor is a co-crystal of a pharmaceutically acceptable salt of Compound B-2 and a co-crystal former (e.g., adipic acid, citric acid, fumaric acid, maleic acid, succinic acid, or benzoic acid). In certain embodiments, the DNA-PK inhibitor is a co-crystal of a Compound B-1 and adipic acid. In certain embodiments, the DNA-PK inhibitor is a co-crystal of Compound B-2 and adipic acid. In certain embodiments, the DNA-PK inhibitor is a co-crystal of a pharmaceutically acceptable salt of Compound B-1 and adipic acid. In certain embodiments, the DNA-PK inhibitor is a co-crystal of a pharmaceutically acceptable salt of Compound B-2 and adipic acid. In some embodiments, the DNA-PK inhibitor is Compound B-2 and is administered about 16 hours after administration of the DNA-damaging agent. In some embodiments, the DNA-PK inhibitor is Compound B-2 and is administered about 16 hours after administration of a doxorubicin agent. In certain embodiments, the doxorubicin agent is doxorubicin hydrochloride. In certain embodiments, the doxorubicin agent is pegylated liposomal doxorubicin. In some embodiments, the DNA-PK inhibitor is a co-crystal of Compound B-2 and adipic acid and is administered about 16 hours after administration of the DNA-damaging agent. In some embodiments, the DNA-PK inhibitor is a co-crystal of Compound B-2 and adipic acid and is administered about 16 hours after administration of a doxorubicin agent. In certain embodiments, the doxorubicin agent is doxorubicin hydrochloride. In certain embodiments, the doxorubicin agent is doxorubicin hydrochloride liposome.

In some embodiments, the method comprises administration of the DNA-PK inhibitor and the DNA-damaging agent for more than one cycle, wherein each cycle is independently about 7-days to about 28-days apart, and wherein a cycle comprises administering the DNA-damaging agent once on Day 1, and administering the DNA-PK inhibitor once to up to 5 consecutive times, each consecutive time independently being about 8 hours to about 32 hours apart. In some embodiments, up to ten cycles are used. In some embodiments, 1, 2, 3, 4, 5, 6, 7, 8, 9, or 10 cycles are used. In some embodiments, 1 to 8 cycles are used. In some embodiments, 2 to 8 cycles are used. In some embodiments, 1 to 6 cycles are used. In some embodiments, 2 to 6 cycles are used. In some embodiments, each cycle is about 7, 14, 21, 28, or 35 days apart. In some embodiments, each cycle is about 1 to about 6 months apart. In some embodiments, each cycle is about 21 days apart. In some embodiments, each cycle is about 28 days apart. As understood by one of ordinary skill in the art, it is possible that there is a delay between the start of subsequent in cases of hematogical or other qualifying parameters. In such cases, the next cycle may not start until, for example, the $5^{th}$ or $6^{th}$ week from the start of the prior cycle. In some embodiments, the DNA-PK inhibitor and the DNA-damaging agent are administered for at least 2 cycles, and wherein each cycle is about 28-days apart. In some embodiments, each consecutive time is about 20 to about 28 hours apart. In some embodiments, each consecutive time is about 20, 21, 22, 23, 24, 25, 26, 27, or 28 hours apart. In some embodiments, each consecutive time is about 24 hours apart. In certain embodiments, the DNA-PK inhibitor is administered for 3, 4, or 5 consecutive times per cycle, each of the consecutive time being about 24 hours apart. In certain embodiments, the time between each consecutive time is different from the time between other consecutive times. For example, the first consecutive time can be 22 hours from the first administration, the second consecutive can be 24 hours from the first, and the third consecutive time can be about 23 hours from the second. In some embodiments, up to six 28-day cycles are used in which DNA-damaging agent is administered on day one and DNA-PK inhibitor is administered on days 2-4 for each 28-day cycle. For example, the first administration of the DNA-PK inhibitor is about 14 to about 18 hours after administration of the DNA-damaging agent, the second administration of the DNA-PK inhibitor is 24 hours from the first administration, the third administration of the DNA-PK inhibitor is 24 hours from the second administration (i.e., 3 consecutive times used for administration of the DNA-PK inhibitor). In certain embodiments, the DNA-PK inhibitor and the DNA-damaging agent are administered for at least 2 cycles, and wherein each cycle is 28-days apart, and wherein the DNA-damaging agent is dosed on Day 1 and the DNA-PK inhibitor is dosed on Days 2, 3, and 4 per cycle. In certain embodiments, method comprises dosing DNA-PK inhibitor and the DNA-damaging agent for 2, 3, 4, 5, 6, 7, 8, 9, or 10 cycles.

In certain embodiments, the DNA-PK inhibitor is administered once, twice, or three times per day.

In some embodiments, the DNA-PK inhibitor is represented by Formula (B-I):

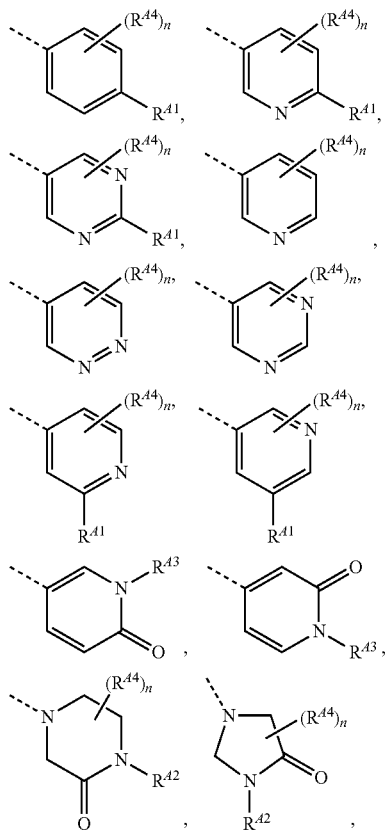

B-I or a pharmaceutically acceptable salt thereof,
wherein:
Q is N or CH;
$R^1$ is hydrogen, $CH_3$, or $CH_2CH_3$, or $R^1$ and the carbon to which it is bound form a $C=CH_2$ group;
Ring A is a ring system selected from the group consisting of:

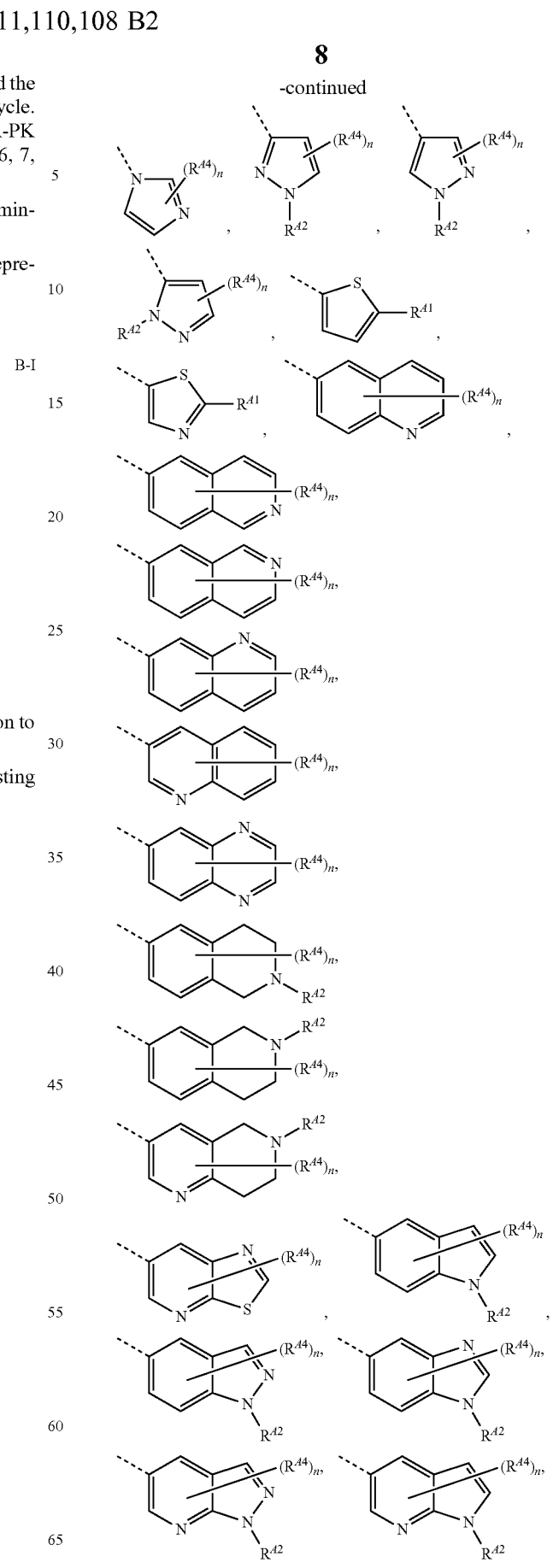

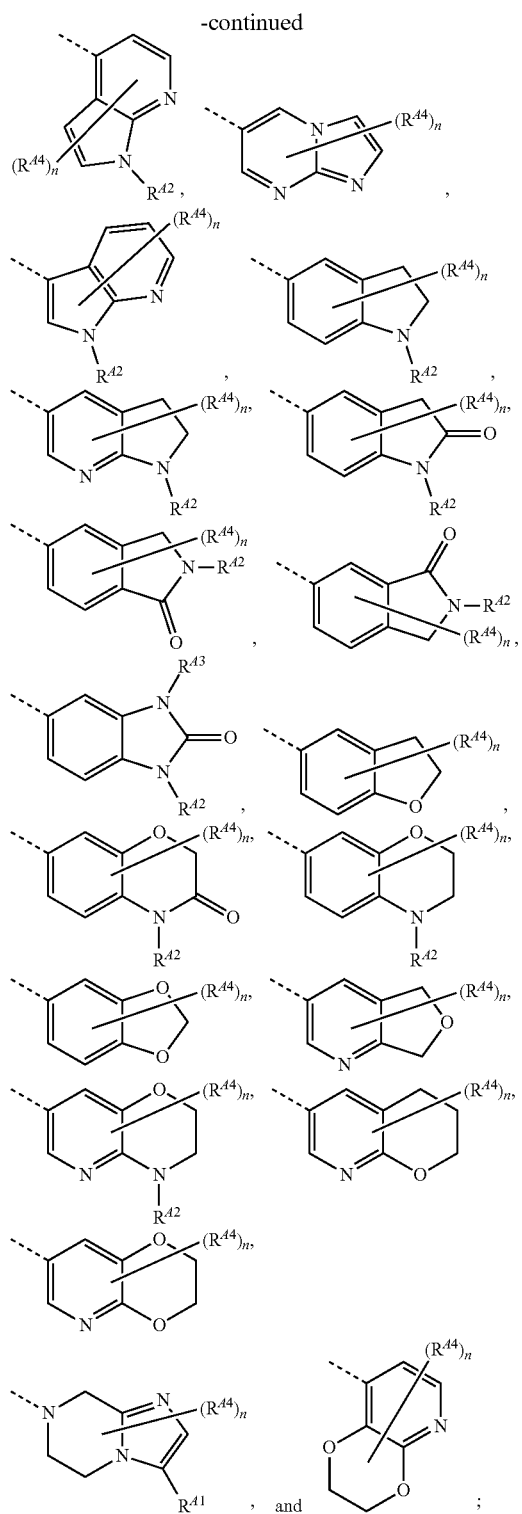

$R^{A1}$ is hydrogen, halogen, $C_{1-4}$alkyl, $C_{0-4}$alkyl-$C_{3-6}$cycloalkyl, $C_{0-4}$alkyl-$OR^{A1a}$, $C_{0-4}$alkyl-$SR^{A1a}$, $C_{0-4}$alkyl-$C(O)N(R^{A1a})_2$, $C_{0-4}$alkyl-CN, $C_{0-4}$alkyl-$S(O)$—$C_{1-4}$alkyl, $C_{0-4}$alkyl-$S(O)_2$—$C_{1-4}$alkyl, $C_{0-4}$alkyl-$C(O)OR^{A1b}$, $C_{0-4}$alkyl-$C(O)C_{1-4}$alkyl, $C_{0-4}$alkyl-$N(R^{A1b})C(O)R^{A1a}$, $C_{0-4}$alkyl-$N(R^{A1b})S(O)_2R^{A1a}$, $C_{0-4}$alkyl-$N(R^{A1a})_2$, $C_{0-4}$alkyl-$N(R^{A1b})$(3-6 membered-cycloalkyl), $C_{0-4}$alkyl-$N(R^{A1b})$(4-6 membered-heterocyclyl), $N(R^{A1b})C_{2-4}$alkyl-$N(R^{A1a})_2$, $N(R^{A1b})C_{2-4}$alkyl-$OR^{A1a}$, $N(R^{A1b})C_{1-4}$alkyl-(5-10 membered heteroaryl), $N(R^{A1b})C_{1-4}$alkyl-(4-6 membered heterocyclyl), $N(R^{A1b})C_{2-4}$alkyl-$N(R^{A1b})C(O)R^{A1a}$, $C_{0-4}$alkyl-$N(R^{A1b})C(O)C_{1-4}$alkyl, $C_{0-4}$alkyl-$N(R^{A1b})C(O)OC_{1-4}$alkyl, $C_{0-4}$alkyl-(3-10 membered-heterocyclyl), $C_{0-4}$alkyl-$C(O)$-(4-6 membered-heterocyclyl), $C_{0-4}$alkyl-O—$C_{0-4}$alkyl-(4-6 membered-heterocyclyl), $C_{0-4}$alkyl-(5-6 membered-heteroaryl), $C_{0-4}$alkyl-$C(O)$-(5-6 membered-heteroaryl), $C_{0-4}$alkyl-O—$C_{0-4}$alkyl-(5-6 membered-heteroaryl), $C_{0-4}$alkyl-$N(R^{A1a})$(4-6 membered-heterocyclyl), or $C_{0-4}$alkyl-$N(R^{A1b})$(5-6 membered-heteroaryl), wherein each of said $R^{A1}$ heterocyclyl is a ring system selected from aziridinyl, oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, tetrahydrothiophenedioxidyl, 1,1-dioxothietanyl, 2-oxa-6-azaspiro[3.4]octanyl, and isoindolinonyl wherein each of said $R^{A1}$ heteroaryl is a ring system selected from furanyl, thiophenyl, imidazolyl, benzoimidazolyl, oxazolyl, oxadiazolyl, thiazolyl, pyrazolyl, thiadiazolyl, pyridinyl, pyrimidinyl, pyrazinyl, triazolyl, and tetrazolyl, and wherein each of said $R^{A1}$ alkyl, cycloalkyl, phenyl, heterocyclyl, and heteroaryl groups is optionally substituted with up to three F atoms, up to two $C_{1-2}$alkyl groups, a $C_{3-6}$cycloalkyl group, a phenyl group, a benzyl group, an alkenyl-$C_{0-2}$alkyl group, an alkynyl-$C_{0-2}$alkyl group, up to two $C_{0-2}$alkyl-$OR^{A1b}$ groups, a $C_{0-2}$alkyl-$N(R^{A1b})_2$ group, a $SC_{1-4}$alkyl group, a $S(O)_2C_{1-4}$alkyl group, a $C(O)R^{A1b}$ group, a $C(O)OR^{A1b}$ group, a $C(O)N(R^{A1b})_2$ group, a —CN group, or a $C_{4-6}$heterocyclic ring system selected from oxetanyl, tetrahydrofuranyl, tetrahydropyran, piperidinyl, and morpholinyl;

each $R^{A1a}$ is, independently, hydrogen, $C_{1-4}$alkyl, $C_{3-6}$cycloalkyl, $C_{4-6}$heterocyclyl selected from oxetanyl, tetrahydrofuranyl, tetrahydropyran, pyrrolidinyl, and piperidinyl, $C_{5-6}$heteroaryl selected from imidazolyl, triazolyl, tetrazolyl, pyrazolyl, thiophenyl, thiazolyl, pyridinyl, pyrimidinyl, and pyrazinyl, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl, wherein each of said $R^{A1a}$ alkyl, cycloalkyl, heterocyclyl, and heteroaryl groups is optionally substituted with up to three F atoms, up to three 2H atoms, up to two $C_{1-2}$alkyl groups, a $C_{3-6}$cycloalkyl group, up to two $C_{0-2}$alkyl-$OR^{A1b}$ groups, a $C_{0-2}$alkyl-$N(R^{A1b})_2$ group, a $SC_{1-4}$alkyl group, a $C(O)R^{A1b}$ group, a $C(O)OR^{A1b}$ group, a $C(O)N(R^{A1b})_2$ group, or a —CN group;

each $R^{A1b}$ is, independently, hydrogen, $C_{1-2}$alkyl, or $C_{3-4}$cycloalkyl;

$R^{A2}$ is hydrogen, $C_{1-4}$alkyl, $C_{0-4}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)N(R^{A2a})_2$, $C_{0-2}$alkyl-$S(O)_2$—$C_{1-4}$alkyl, $C_{0-2}$alkyl-$C(O)OC_{1-4}$alkyl, $C_{0-2}$alkyl-$C(O)$-(4-6 membered)heterocyclyl, wherein each of said heterocyclyl is selected from oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, and 1,1-dioxothietanyl, and each of said $R^{A2}$ groups except hydrogen is optionally substituted with up to three F atoms, up to two $C_{1-2}$alkyl groups, a $C_{3-6}$cycloalkyl group, an alkenyl-$C_{0-2}$alkyl group, an alkynyl-$C_{0-2}$alkyl group, up to two $OR^{A2b}$ groups, a $C_{0-2}$alkyl- N($R^{A2b}$)$_2$ group, a S$C_{1-4}$alkyl group, a S(O)$_2C_{1-4}$alkyl group, a C(O)$R^{A2b}$ group, a C(O)O$R^{A2b}$ group, a C(O)N($R^{A2b}$)$_2$ group, or a —CN group;

each $R^{A2a}$ is, independently, hydrogen, $C_{1-4}$alkyl, a $C_{5-6}$heteroaryl selected from imidazolyl, triazolyl, tetrazolyl, pyrazolyl, thiophenyl, thiazolyl, pyridinyl, pyrimidinyl, and pyrazinyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl;

each $R^{A2b}$ is, independently, hydrogen, $C_{1-4}$alkyl, or $C_{3-4}$cycloalkyl;

$R^{A3}$ is hydrogen or $C_{1-2}$alkyl;

each $R^{A4}$ is, independently, deuterium, halogen, CN, $C_{1-4}$alkyl, or O$C_{1-4}$alkyl, wherein each $R^{A4}$ alkyl is optionally substituted with up to 3 F atoms, two non-geminal OH groups, or one O$C_{1-2}$alkyl, or two $R^{A4}$ together with an intervening saturated carbon atom form a spiro-linked cyclopropyl or cyclobutyl ring;

n is 0-3;

Ring B is a ring system selected from the group consisting of:

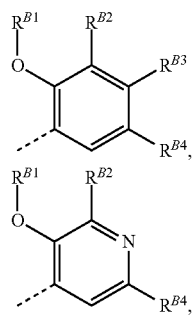
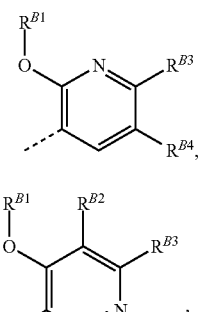
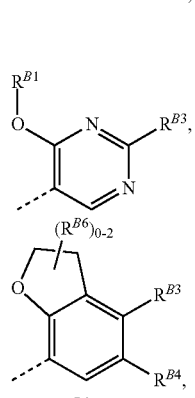
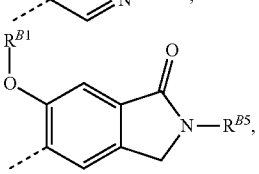
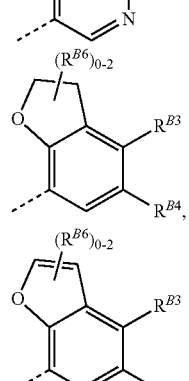
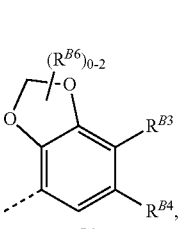
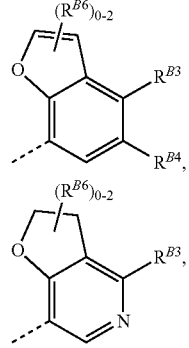
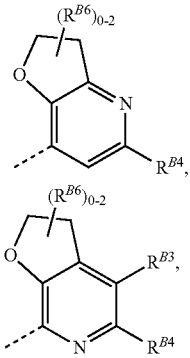

-continued

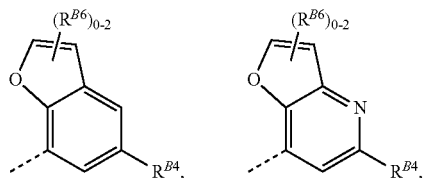
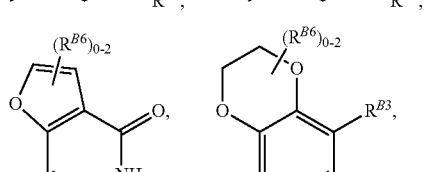
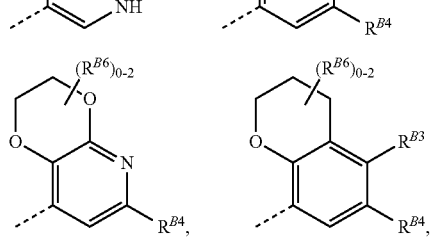
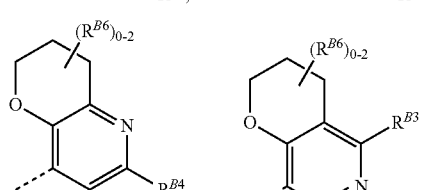
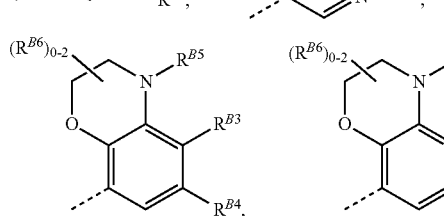
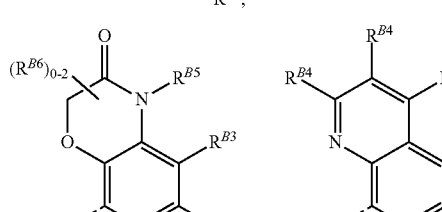
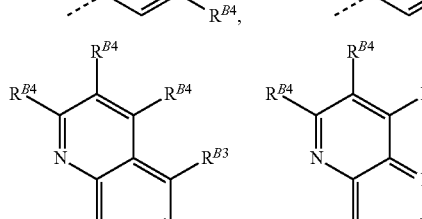
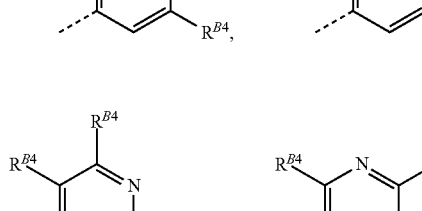
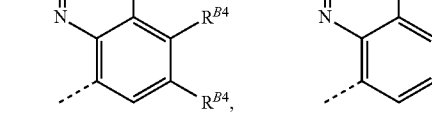

-continued

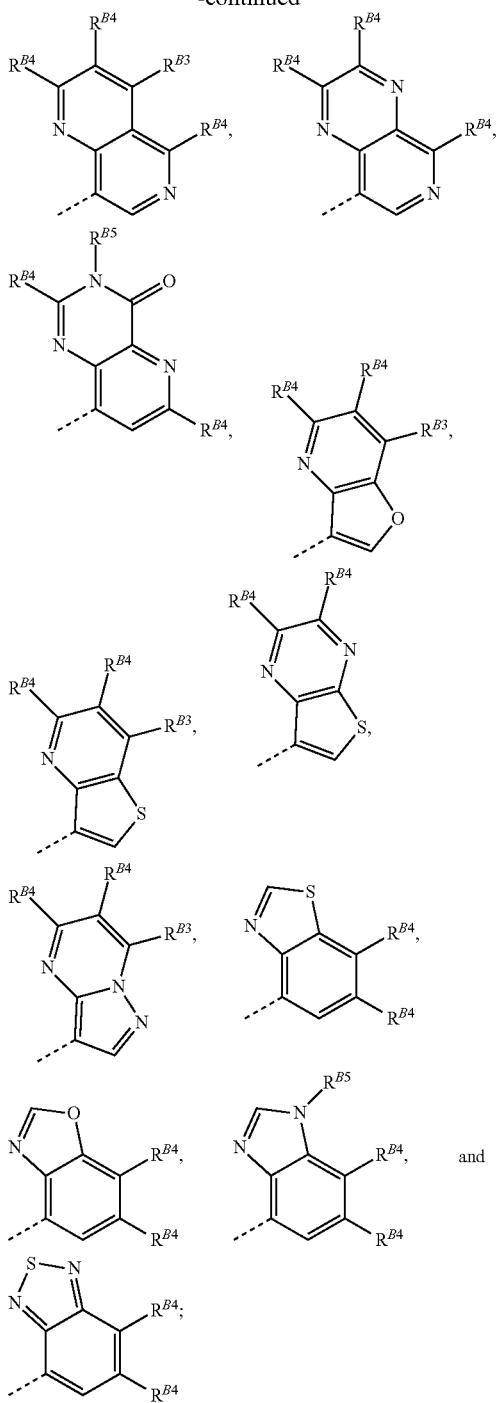

$R^{B1}$ is hydrogen, $C_{1-4}$alkyl, $(CH_2)_{0-1}C_{3-6}$cycloalkyl, $C(O)$$C_{1-2}$alkyl, $(CH_2)_{0-1}$-(4-6 membered)heterocyclyl ring wherein said heterocyclic ring is selected from oxetanyl, tetrahydrofuranyl, tetrahydropyran, dioxanyl, dioxolanyl, and pyrrolidinonyl, or $(CH_2)_{1-2}$(5-6 membered)heteroaryl ring wherein said heteroaryl ring is selected from pyridinyl, imidazolyl, and pyrazolyl, and wherein each of said $R^{B1}$ alkyl, cycloalkyl, phenyl, benzyl, heterocyclyl and heteroaryl groups is optionally substituted with up to 3 F atoms, up to two $C_{1-2}$alkyl groups, two non-geminal OH groups, or one $OC_{1-2}$alkyl;

$R^{B2}$ is hydrogen, $C_{1-4}$alkyl, or $OC_{1-4}$alkyl;

each $R^{B3}$ is, independently, hydrogen, halogen, $C_{1-4}$alkyl, $C_{2-4}$alkenyl, $C_{2-4}$alkynyl, CN, C(O)H, C(O)$C_{1-4}$alkyl, C(O)O$C_{1-4}$alkyl, C(O)$C_{1-4}$alkyl, C(O)$NH_2$, C(O)NH$C_{1-4}$alkyl, C(O)NH$(CH_2)_{0-1}C_{3-6}$cycloalkyl, C(O)NHCH$_2$oxetanyl, C(O)NHCH$_2$tetrahydrofuranyl, C(O)NHCH$_2$tetrahydropyranyl, C(O)NHphenyl, C(O)NHbenzyl, C(O)NHOH, C(O)NHO$C_{1-4}$alkyl, C(O)NHO$(CH_2)_{0-1}C_{3-6}$cycloalkyl, C(O)NHO$(CH_2)_{0-1}$oxetanyl, C(O)NHO$(CH_2)_{0-1}$tetrahydrofuranyl, C(O)NHO$(CH_2)_{0-1}$tetrahydropyranyl, C(O)NHOphenyl, C(O)NHObenzyl, $NH_2$, NHC(O)$C_{1-4}$alkyl, $OC_{1-4}$alkyl, $SC_{1-4}$alkyl, S(O)$C_{1-4}$alkyl, or a 5-membered-heteroaryl ring system selected from furanyl, thiophenyl, imidazolyl, pyrrole, pyrazolyl, and oxadiazolyl, wherein each $R^{B3}$ group except hydrogen or halogen is optionally substituted with Cl, up to three F atoms, up to two non-geminal OH groups, up to two $OC_{1-2}$alkyl, one $NH_2$, one NH$C_{1-2}$alkyl, one NHC(O)$C_{1-2}$alkyl, or one N($C_{1-2}$alkyl)$_2$;

each $R^{B4}$ is, independently, hydrogen, deuterium, halogen, $C_{1-4}$alkyl, $OC_{1-4}$alkyl, $SC_{1-4}$alkyl, $NH_2$, NH($C_{1-4}$alkyl), N($C_{1-4}$alkyl)$_2$, NHC(O)$C_{1-4}$alkyl, C(O)OH, C(O)O$C_{1-4}$alkyl, C(O)$NH_2$, C(O)NH$C_{1-4}$alkyl, C(O)N($C_{1-4}$alkyl)$_2$, CN, a morpholinyl ring, or an imidazolyl ring, wherein each $R^{B4}$ alkyl is optionally substituted with up to 3 F atoms, two non-geminal OH groups, or one $OC_{1-2}$alkyl;

$R^{B5}$ is hydrogen, $C_{1-4}$alkyl, C(O)$C_{1-4}$alkyl, C(O)O$C_{1-4}$alkyl, C(O)$NH_2$, C(O)NH$C_{1-4}$alkyl, or C(O)N($C_{1-4}$alkyl)$_2$, wherein said $R^{B5}$ alkyl is optionally substituted with up to 3 F atoms, two non-geminal OH groups, or one $OC_{1-2}$alkyl and $R^{B6}$ is F or $C_{1-2}$alkyl, or two $R^{B6}$ and an intervening carbon atom form a spirocyclopropyl or spirocyclobutyl ring.

In certain embodiments, the DNA-PK inhibitor is a compound of the formula:

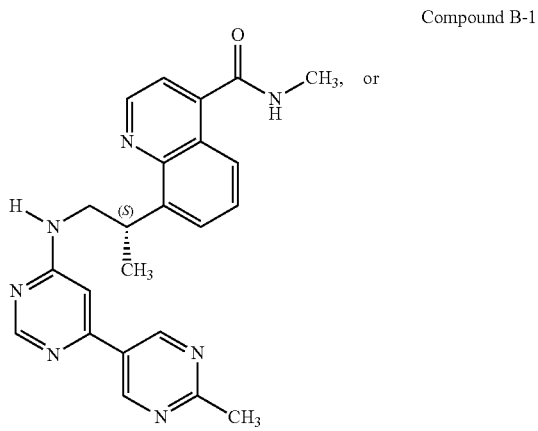

Compound B-1

-continued

Compound B-2

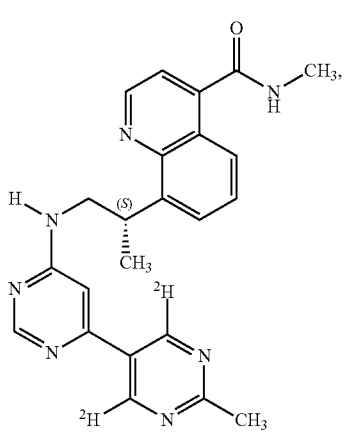

or a pharmaceutically acceptable salt thereof.

In certain embodiments, the DNA-PK inhibitor is a co-crystal comprising a Compound B-1, or a pharmaceutically acceptable salt thereof, and a co-crystal former (CCF) selected from adipic acid, citric acid, fumaric acid, maleic acid, succinic acid, and benzoic acid. In certain embodiments, the CCF is adipic acid. In certain embodiments, the DNA-PK inhibitor is a co-crystal comprising a Compound B-2, or a pharmaceutically acceptable salt thereof, and a co-crystal former (CCF) selected from adipic acid, citric acid, fumaric acid, maleic acid, succinic acid, and benzoic acid. In certain embodiments, the CCF is adipic acid. In certain embodiments, the molar ratio of adipic acid to Compound B-1 or adipic acid to Compound B-2 is about 1 to about 2. In certain embodiments, the co-crystal is administered in a range of about 50 mg to about 200 mg per day, inclusive; a range of about 50 mg to about 2000 mg per day, inclusive; or a range of about 100 mg to about 1500 mg per day, inclusive.

BRIEF DESCRIPTION OF THE DRAWINGS

FIG. 18A (the upper graph) shows the effect of Compound B-2 CoX in Combination with PLD on Tumor Volume in the CTG-1280 xenograft tumor model in nude mice. Mice were dosed with PLD or the combination of PLD and Compound B-2 to assess efficacy as described in the dosing regimen of FIG. 17 (n=5/group).

FIG. 18B (the lower graph) shows the effect of Compound B-2 CoX in Combination with PLD on body weight in the endometrial CTG-1280 xenograft nude mouse model (n=5/group).

FIG. 0.24 depicts an X-ray powder diffraction (XRPD) pattern of the co-crystal formed between Compound B-2 with adipic acid.

DETAILED DESCRIPTION OF THE INVENTION

Figure 1:
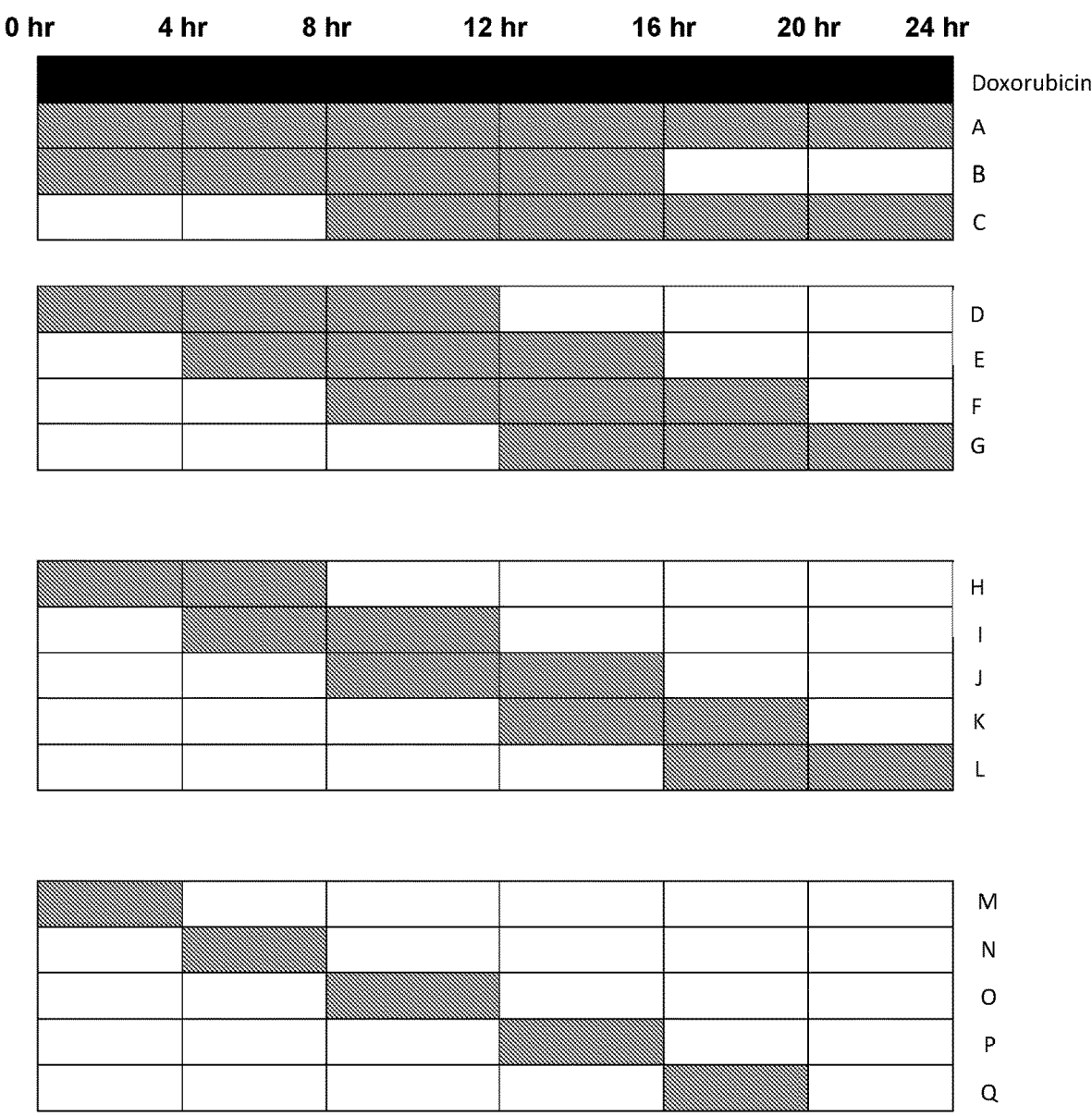
FIG. 1 shows the design of experiments to investigate effect of time of Compound B-2 addition and duration of exposure on potentiation of doxorubicin hydrochloride activity. Compound B-2 used in these experiments was not prepared as a co-crystal. A549 lung cancer cells were treated with doxorubicin for 24 hours (top row) and Compound B-2 was added at the same time as doxorubicin or 4, 8, 12 or 16 hours after addition of doxorubicin (rows A-Q). Total duration of Compound B-2 exposure varied between 4 and 16 hours. Each row (A-Q) represents one experiment with concentrations of doxorubicin and Compound B-2 titrated as described herein. In all experiments, cells were exposed to doxorubicin for the full 24 hours (black bar at top row). The duration and timing of exposure to Compound B-2 in each experiment is shown by the filled-in gray bar(s). White boxes indicates no exposure to Compound B-2 during that time period. Letters to the right for each experiment are referred to in the experimentals.

The present invention is based, at least in part, on the unexpected discovery that a DNA-PK inhibitor administered between about 8 and about 48 hours after administration of a DNA-damaging agent is particularly effective at treating proliferative diseases.

Accordingly, aspects of the invention provide a method of treating a proliferative disorder in a subject, the method comprising administering to a subject in need thereof a DNA-damaging agent and, between about 8 and about 48 hours later, administering to the subject a compound that inhibits DNA-PK (the "first dose"). In other words, aspects of the invention provide a method of treating a proliferative disorder in a subject, the method comprising administering to a subject in need thereof a therapeutically effective amount of a DNA-damaging agent and, between about 8 and about 48 hours later, administering to the subject a therapeutically effective amount of a compound that inhibits DNA-PK (the "first dose"). Expressed differently, aspects of the invention provide a method of treating a proliferative disorder in a subject, the method comprising administering to a subject in need thereof a (therapeutically effective amount of a) DNA-damaging agent and, during a phase of DNA repair induced by the DNA-damaging agent, administering to the subject a (therapeutically effective amount of a) compound that inhibits DNA-PK (the "first dose").

In some embodiments, the DNA-PK inhibitor is administered between about 8 and about 30 hours after administration of the DNA-damaging agent. In some embodiments, the DNA-PK inhibitor is administered between about 8 and about 20 hours after administration of the DNA-damaging agent. In some embodiments, the DNA-PK inhibitor is administered between about 10 and about 20 hours after administration of the DNA-damaging agent. In some embodiments, the DNA-PK inhibitor is administered between about 12 and about 18 hours after administration of the DNA-damaging agent. In some embodiments, the DNA-PK inhibitor is administered between about 14 and about 18 hours after administration of the DNA-damaging agent. In some embodiments, the DNA-PK inhibitor is administered about 14 and about 16 hours after administration of the DNA-damaging agent. In some embodiments, the DNA-PK inhibitor is administered about 14, 15, 16, 17, or 18 hours after administration of the DNA-damaging agent. In some embodiments, the DNA-PK inhibitor is administered about 16 hours after administration of the DNA-damaging agent. In some embodiments, the DNA-damaging agent is chemotherapy, most preferably a doxorubicin agent.

It is understood that, as used herein, ranges of numbers (e.g., for example, between about 8 and about 48 hours) are inclusive which means that the range includes both of the end points specified (e.g., in this instance, the end points of about 8 hours and about 48 hours are included within the range).

In some embodiments in which the DNA-damaging agent is given once per treatment cycle (e.g., 1 week treatment cycle, 2 week treatment cycle, 3 week treatment cycle, 4 week treatment cycle), the DNA-PK inhibitor may be administered between about 8 hours and about 48 hours (e.g., between about 8 hours and about 30 hours, between about 10 hours and about 20 hours, between about 14 hours and about 18 hours) after the DNA-damaging agent.

In certain embodiments, a second, third, and/or fourth dose of the DNA-PK inhibitor is administered on consecutive days after administering the first dose of the DNA-PK inhibitor during a given treatment cycle. See, e.g., FIG. 2 and FIG. 17. For example, in certain embodiments, the treatment cycle comprises administering a first dose and a second dose of the DNA-PK inhibitor. In certain embodiments, the treatment cycle comprises administering a first dose, a second dose, and a third dose of the DNA-PK inhibitor. In certain embodiments, the treatment cycle comprises administering a first dose, a second dose, a third dose, and a fourth dose of the DNA-PK inhibitor. In certain embodiments, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK) of a given treatment cycle. In certain embodiments, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK), and then the DNA-PK inhibitor is administered on day 4 (e.g., about 23-26 hours after the immediately prior administration of DNA-PK) of a given treatment cycle. In certain embodiments, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK), and then the DNA-PK inhibitor is administered on day 4 (e.g., about 23-26 hours after the immediately prior administration of DNA-PK), and then the DNA-PK inhibitor is administered on day 5 (e.g., about 23-26 hours after the immediately prior administration of DNA-PK), of a given treatment cycle.

In some embodiments, the method is part of a 1 week, 2 week, 3 week, 4 week, 5 week, 6, week, 7 week, or 8 week treatment cycle. In some embodiments, the method is part of a 1 week treatment cycle. In some embodiments, the method is part of a 2 week treatment cycle. In some embodiments, the method is part of a 3 week treatment cycle. In some embodiments, the method is part of a 4 week treatment cycle. In some embodiments, the method is part of a 5 week treatment cycle. In some embodiments, the method is part of a 6 week treatment cycle. In some embodiments, the method is part of a 7 week treatment cycle. In some embodiments, the method is part of a 8 week treatment cycle. In some embodiments, the DNA-damaging agent is administered once per treatment cycle. In some such embodiments, a DNA-damaging agent or DNA-PK inhibitor is not administered after the second dose of the DNA-PK inhibitor for the remaining portion of the treatment cycle. For instance, a method of treating a proliferative disorder using a 4 week treatment cycle may comprise administering the DNA-damaging agent on day 1, a first dose of a DNA-PK inhibitor on day 2 (e.g., about 14 to 18 hours after administration of the DNA-damaging agent) and further doses of the DNA-PK inhibitor on day 3 (the second dose), and/or day 4 (the third dose), and/or day 5 (the fourth dose) of the cycle.

In some such embodiments, for one cycle, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK). In other such embodiments, for one cycle, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK), and then the DNA-PK inhibitor is administered on day 4 (e.g., about 23-26 hours after the immediately prior administration of DNA-PK). In other such embodiments, for one cycle, a DNA-damaging agent is administered on day 1, the DNA-PK inhibitor is administered on day 2 (e.g., about 14 to 18 hours after administration of the DNA-damaging agent), and then the DNA-PK inhibitor is administered on day 3 (e.g., about 23-26 hours after the immediately prior administration of DNA-PK), and then the DNA-PK inhibitor is administered on day 4 (e.g., about 23-26 hours after the immediately prior administration of DNA-PK), and then the DNA-PK inhibitor is administered on day 5 (e.g., about 23-26 hours after the immediately prior administration of DNA-PK).

In some embodiments in which the DNA-damaging agent is given twice per treatment cycle (e.g., 2 week treatment cycle, 3 week treatment cycle, 4 week treatment cycle), the DNA-PK inhibitor may be administered between about 8 hours and about 48 hours (e.g., between about 8 hours and about 30 hours, between about 10 hours and about 20 hours, between about 14 hours and about 18 hours) after one administration of the DNA-damaging agent or after each administration. In certain embodiments, a first dose of a DNA-damaging agent may be administered on day 1 and a DNA-PK inhibitor may be administered between about 8 hours and about 48 hours (e.g., between about 8 hours and about 30 hours, between about 10 hours and about 20 hours, between about 14 hours and about 18 hours) later. In some such embodiments, a second dose of the DNA-damaging agent may be administered between about 5 days to about 9 days after a prior (e.g., immediately prior) administration of the DNA-damaging agent. For example, the second dose of the DNA-damaging agent may be administered about between about 5 days and about 9 days, between about 5 days and about 8 days, between about 5 days and about 7 days, between about 6 days and about 9 days, between about 6 days and about 8 days, or between about 6 days and about 7 days after the first dose of the DNA-damaging agent. In some instances, the second dose of the DNA-damaging agent may be administered after between about 6 days and about 8 days or after about 7 days. In some embodiments, a second dose of a DNA-PK inhibitor may be administered between about 8 hours and about 48 hours (e.g., between about 8 hours and about 30 hours, between about 10 hours and about 20 hours, between about 14 hours and about 18 hours) after the second dose of the DNA-damaging agent.

In some embodiments in which the DNA-damaging agent is administered three or more times per treatment cycle (e.g., 3-5 administrations), the DNA-PK inhibitor may be administered between about 8 hours and about 48 hours (e.g., between about 8 hours and about 30 hours, between about 10 hours and about 20 hours, between about 14 hours and about 18 hours) after at least one administration of the DNA-damaging agent (e.g., after one administration, after each of two administrations, after each of three administrations) or after each administration.

In some embodiments, two or more different DNA-damaging agents may be administered within a treatment cycle (e.g., 3 week treatment cycle, 4 week treatment cycle). The DNA-damaging agents may differ in mechanism of action and/or administration frequency. For instance, a first DNA-damaging agent administered twice per treatment cycle and a second DNA-damaging agent administered once per treatment cycle may be used. In some such embodiments, the first DNA-damaging agent and a second DNA-damaging agent may be administered as described above with respect to the administration of a single DNA-damaging agent. The DNA-PK inhibitor may be administered between about 8 hours and about 48 hours (e.g., between about 8 hours and about 30 hours, between about 10 hours and about 20 hours, between about 14 hours and about 18 hours) after at least one DNA-damaging agent (e.g., two DNA-damaging agents, after each of two administrations).

As used herein, the term "treatment cycle" has its ordinary meaning in the art and may refer to a course of treatment that is repeated on a regular schedule, including periods of rest. For example, a treatment cycle of four weeks may include administration of agents during week one followed by three weeks of rest (e.g., no treatment). In general, a DNA-PK inhibitor may be administered at least once per treatment cycle and between about 8 hours and about 48 hours (e.g., between about 8 hours and about 30 hours, between about 10 hours and about 20 hours, between about 14 hours and about 18 hours) after a DNA-damaging agent. In some embodiments, the methods, described herein, may be part of a 3 week or 4 week treatment cycle.

In some embodiments, treatment of a proliferative disorder using the methods described herein may result in a RECIST stable disease, a RECIST partial response, or a RECIST complete response. For instance, treatment may result in a RECIST partial or a RECIST complete response. As used herein, the term "RECIST partial response" has its ordinary meaning in the art and may refer to a 30% decrease in the sum of the longest diameter of target lesions as determined according to the RECIST (i.e., Response Evaluation Criteria in Solid Tumors) guidelines version 1.1 (see Eisenhauer et. al., Eur. J. Cancer. 45 (2009) 228-247). As used herein, the term "RECIST complete response" has its ordinary meaning in the art and may refer to the disappearance of all target lesions as determined according to the RECIST guidelines version 1.1. As used herein, the term "RECIST progressive disease" has its ordinary meaning in the art and may refer to a 20% increase in the sum of the longest diameter of target lesions as determined according to the RECIST guidelines version 1.1. As used herein, the term "RECIST stable disease" has its ordinary meaning in the art and may refer to small changes that do not meet above criteria as determined according to the RECIST guidelines version 1.1.

In general, treatment of a proliferative disorder with the methods described herein may reverse, alleviate, delaying the onset of, or inhibit the progress of the proliferative disorder. In some embodiments, the methods described herein may decrease the sum of the longest diameter of target lesions, decrease the sum of the longest diameter of non-target lesions, and/or decrease tumor burden by at least about 10%, at least about 20%, at least about 30%, at least about 40%, at least about 50%, or at least about 60%. In certain embodiments, the methods described herein may decrease the sum of the longest diameter of target lesions, decrease the sum of the longest diameter of non-target lesions, and/or decrease tumor burden by between about 20% and about 60% or between about 40% and about 60%.

In some embodiments, the methods described herein may be particularly advantageous for the treatment of proliferative disorders in subjects that are refractory, resistant, or sensitive to one or more DNA-damaging agents.

As used herein, the terms "refractory" has its ordinary meaning in the art and may refer to a proliferative disorder that progresses during treatment with an agent (e.g., DNA-damaging agent) (first line treatment). As used herein, the terms "resistant" has its ordinary meaning in the art and may refer to a proliferative disorder that recurs within a certain period of time after completing treatment with an agent (e.g., DNA-damaging agent). As used herein, the terms "sensitive" has its ordinary meaning in the art and may refer to a proliferative disorder that recurs after a certain period of time from completing treatment with an agent (e.g., DNA-damaging agent). In general, recurrence occurs after a longer period of time for a sensitive cancer than for a resistant cancer. The periods of time to classify a proliferative disorder as resistance or sensitive would be known to those of ordinary skill in the art and may depend on certain factors, such as the type of cancer, the treatment used, and the stage of cancer, amongst others. For instance, resistant ovarian cancer may refer to ovarian cancer that recurs within 6 months from completing treatment. Sensitive ovarian cancer may refer to ovarian cancer that recurs after greater than 6 months from completing treatment. For instance, resistant small cell lung cancer (SCLC) may refer to SCLC that recurs within 3 months from completing treatment. Sensitive SCLC may refer to SCLC that recurs after greater than 3 months from completing treatment.

Compounds

In some aspects of the present disclosure, the DNA-PK inhibitor is represented by Formula (B-I):

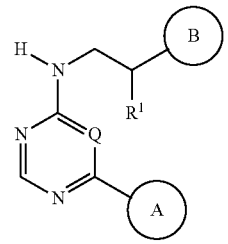

B-I or a pharmaceutically acceptable salt thereof, wherein:
Q is N or CH;
R¹ is hydrogen, $CH_3$, or $CH_2CH_3$, or R¹ and the carbon to which it is bound form a $C=CH_2$ group;
Ring A is a ring system selected from the group consisting of:
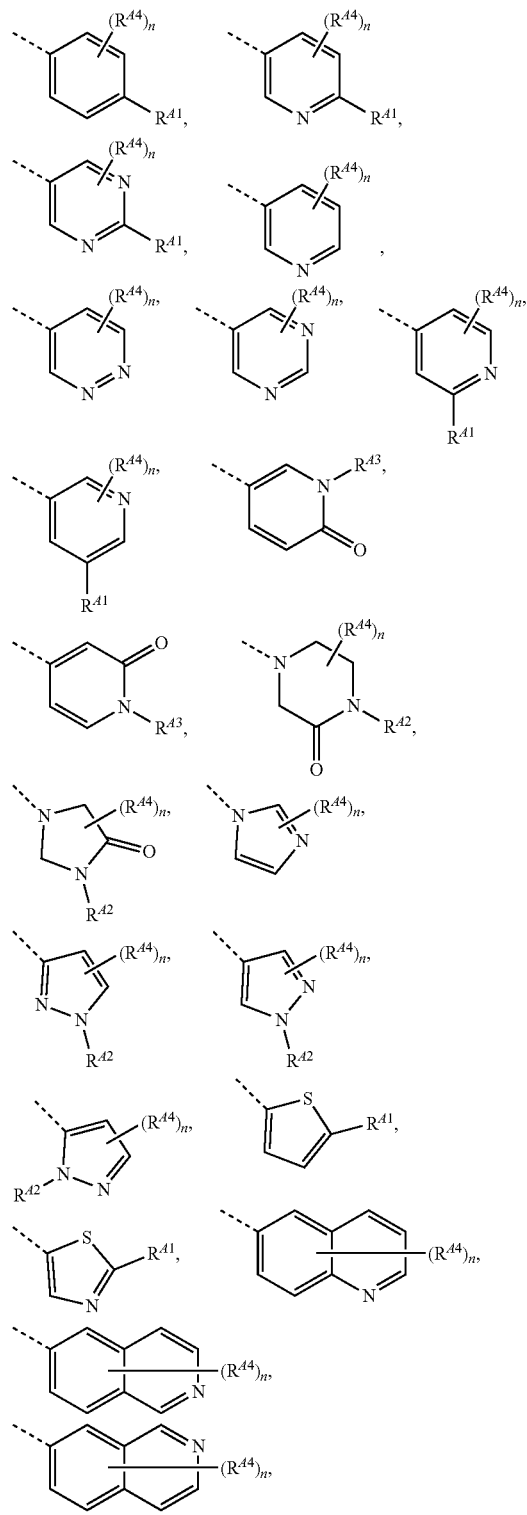
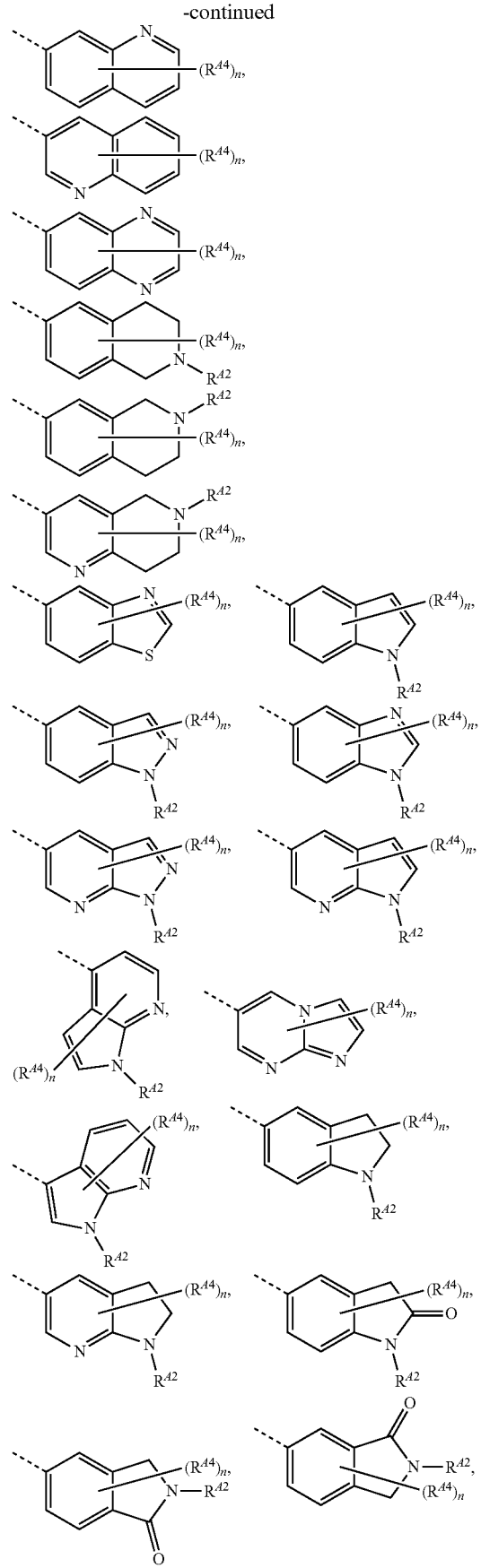

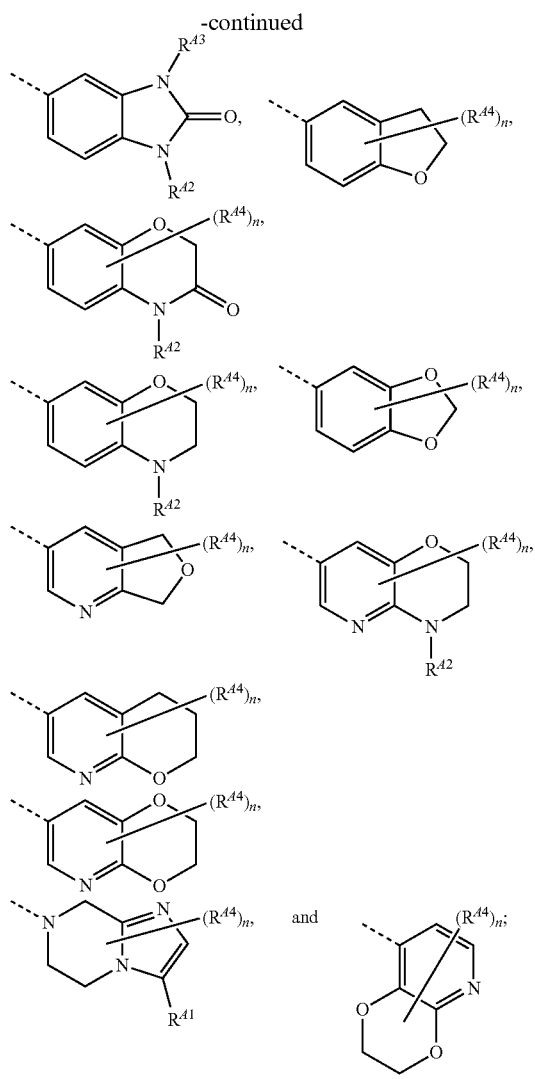

$R^{41}$ is hydrogen, halogen, $C_{1-4}$alkyl, $C_{0-4}$alkyl-$C_{3-6}$cycloalkyl, $C_{0-4}$alkyl-OR$^{41a}$, $C_{0-4}$alkyl-SR$^{41a}$, $C_{0-4}$alkyl-C(O)N(R$^{41a}$)$_2$, $C_{0-4}$alkyl-CN, $C_{0-4}$alkyl-S(O)—$C_{1-4}$alkyl, $C_{0-4}$alkyl-S(O)$_2$—$C_{1-4}$alkyl, $C_{0-4}$alkyl-C(O)OR$^{41b}$, $C_{0-4}$alkyl-C(O)$C_{1-4}$alkyl, $C_{0-4}$alkyl-N(R$^{41b}$)C(O)R$^{41a}$, $C_{0-4}$alkyl-N(R$^{41b}$)S(O)$_2$R$^{41a}$, $C_{0-4}$alkyl-N(R$^{41a}$)$_2$, $C_{0-4}$alkyl-N(R$^{41b}$)(3-6 membered-cycloalkyl), $C_{0-4}$alkyl-N(R$^{41b}$)(4-6 membered-heterocyclyl), N(R$^{41b}$)$C_{2-4}$alkyl-N(R$^{41a}$)$_2$, N(R$^{41b}$)$C_{2-4}$alkyl-OR$^{41a}$, N(R$^{41b}$)$C_{1-4}$alkyl-(5-10 membered heteroaryl), N(R$^{41b}$)$C_{1-4}$alkyl-(4-6 membered heterocyclyl), N(R$^{41b}$)$C_{2-4}$alkyl-N(R$^{41b}$)C(O)R$^{41a}$, $C_{0-4}$alkyl-N(R$^{41b}$)C(O)$C_{1-4}$alkyl, $C_{0-4}$alkyl-N(R$^{41b}$)C(O)O$C_{1-4}$alkyl, $C_{0-4}$alkyl-(phenyl), $C_{0-4}$alkyl-(3-10 membered-heterocyclyl), $C_{0-4}$alkyl-C(O)-(4-6 membered-heterocyclyl), $C_{0-4}$alkyl-O—$C_{0-4}$alkyl-(4-6 membered-heterocyclyl), $C_{0-4}$alkyl-(5-6 membered-heteroaryl), $C_{0-4}$alkyl-C(O)-(5-6 membered-heteroaryl), $C_{0-4}$alkyl-O—$C_{0-4}$alkyl-(5-6 membered-heteroaryl), $C_{0-4}$alkyl-N(R$^{41a}$)(4-6 membered-heterocyclyl), or $C_{0-4}$alkyl-N(R$^{41b}$)(5-6 membered-heteroaryl), wherein each of said R$^{41}$ heterocyclyl is a ring system selected from aziridinyl, oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, tetrahydrothiophenedioxidyl, 1,1-dioxothietanyl, 2-oxa-6-azaspiro[3.4]octanyl, and isoindolinonyl wherein each of said R$^{41}$ heteroaryl is a ring system selected from furanyl, thiophenyl, imidazolyl, benzoimidazolyl, oxazolyl, oxadiazolyl, thiazolyl, pyrazolyl, thiadiazolyl, pyridinyl, pyrimidinyl, pyrazinyl, triazolyl, and tetrazolyl, and wherein each of said R$^{41}$ alkyl, cycloalkyl, phenyl, heterocyclyl, and heteroaryl groups is optionally substituted with up to three F atoms, up to two $C_{1-2}$alkyl groups, a $C_{3-6}$cycloalkyl group, a phenyl group, a benzyl group, an alkenyl-$C_{0-2}$alkyl group, an alkynyl-$C_{0-2}$alkyl group, up to two $C_{0-2}$alkyl-OR$^{41b}$ groups, a $C_{0-2}$alkyl-N(R$^{41b}$)$_2$ group, a S$C_{1-4}$alkyl group, a S(O)$_2C_{1-4}$alkyl group, a C(O)R$^{41b}$ group, a C(O)OR$^{41b}$ group, a C(O)N(R$^{41b}$)$_2$ group, a —CN group, or a $C_{4-6}$heterocyclic ring system selected from oxetanyl, tetrahydrofuranyl, tetrahydropyran, piperidinyl, and morpholinyl;

each R$^{41a}$ is, independently, hydrogen, $C_{1-4}$alkyl, $C_{3-6}$cycloalkyl, $C_{4-6}$heterocyclyl selected from oxetanyl, tetrahydrofuranyl, tetrahydropyran, pyrrolidinyl, and piperidinyl, $C_{5-6}$heteroaryl selected from imidazolyl, triazolyl, tetrazolyl, pyrazolyl, thiophenyl, thiazolyl, pyridinyl, pyrimidinyl, and pyrazinyl, or two R$^{41a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl, wherein each of said R$^{41a}$ alkyl, cycloalkyl, heterocyclyl, and heteroaryl groups is optionally substituted with up to three F atoms, up to three 2H atoms, up to two $C_{1-2}$alkyl groups, a $C_{3-6}$cycloalkyl group, up to two $C_{0-2}$alkyl-OR$^{41b}$ groups, a $C_{0-2}$alkyl-N(R$^{41b}$)$_2$ group, a S$C_{1-4}$alkyl group, a C(O)R$^{41b}$ group, a C(O)OR$^{41b}$ group, a C(O)N(R$^{41b}$)$_2$ group, or a —CN group;

each R$^{41b}$ is, independently, hydrogen, $C_{1-2}$alkyl, or $C_{3-4}$cycloalkyl;

R$^{42}$ is hydrogen, $C_{1-4}$alkyl, $C_{0-4}$alkyl-$C_{3-6}$cycloalkyl, $C_{0-2}$alkyl-(4-6 membered)heterocyclyl, $C_{2-4}$alkyl-OR$^{42a}$, $C_{0-2}$alkyl-C(O)N(R$^{42a}$)$_2$, $C_{0-2}$alkyl-S(O)$_2$—$C_{1-4}$alkyl, $C_{0-2}$alkyl-C(O)O$C_{1-4}$alkyl, $C_{0-2}$alkyl-C(O)-(4-6 membered)heterocyclyl, wherein each of said heterocyclyl is selected from oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, and 1,1-dioxothietanyl, and each of said R$^{42}$ groups except hydrogen is optionally substituted with up to three F atoms, up to two $C_{1-2}$alkyl groups, a $C_{3-6}$cycloalkyl group, an alkenyl-$C_{0-2}$alkyl group, an alkynyl-$C_{0-2}$alkyl group, up to two OR$^{42b}$ groups, a $C_{0-2}$alkyl-N(R$^{42b}$)$_2$ group, a S$C_{1-4}$alkyl group, a S(O)$_2C_{1-4}$alkyl group, a C(O)R$^{42b}$ group, a C(O)OR$^{42b}$ group, a C(O)N(R$^{42b}$)$_2$ group, or a —CN group;

each R$^{42a}$ is, independently, hydrogen, $C_{1-4}$alkyl, a $C_{5-6}$heteroaryl selected from imidazolyl, triazolyl, tetrazolyl, pyrazolyl, thiophenyl, thiazolyl, pyridinyl, pyrimidinyl, and pyrazinyl, or two R$^{42a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl;

each R$^{42b}$ is, independently, hydrogen, $C_{1-4}$alkyl, or $C_{3-4}$cycloalkyl;

R$^{43}$ is hydrogen or $C_{1-2}$alkyl;

each R$^{44}$ is, independently, deuterium, halogen, CN, $C_{1-4}$alkyl, or O$C_{1-4}$alkyl, wherein each R$^{44}$ alkyl is optionally substituted with up to 3 F atoms, two non-geminal OH groups, or one $OC_{1-2}$alkyl, or two $R^{A4}$ together with an intervening saturated carbon atom form a spiro-linked cyclopropyl or cyclobutyl ring;
n is 0-3;
Ring B is a ring system selected from the group consisting of:
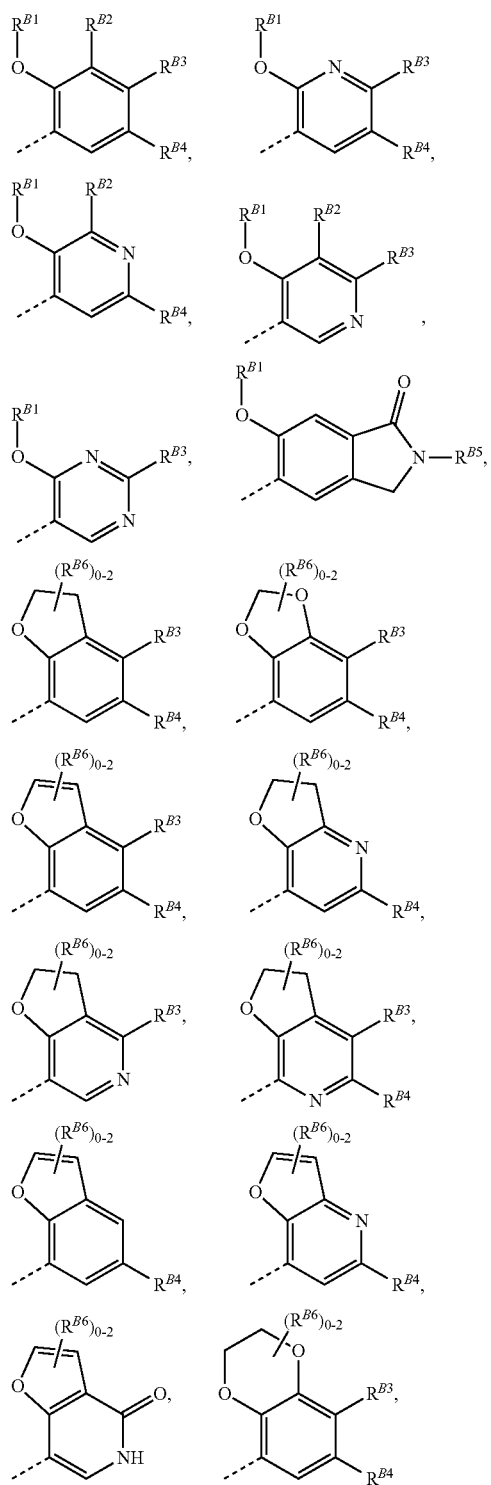
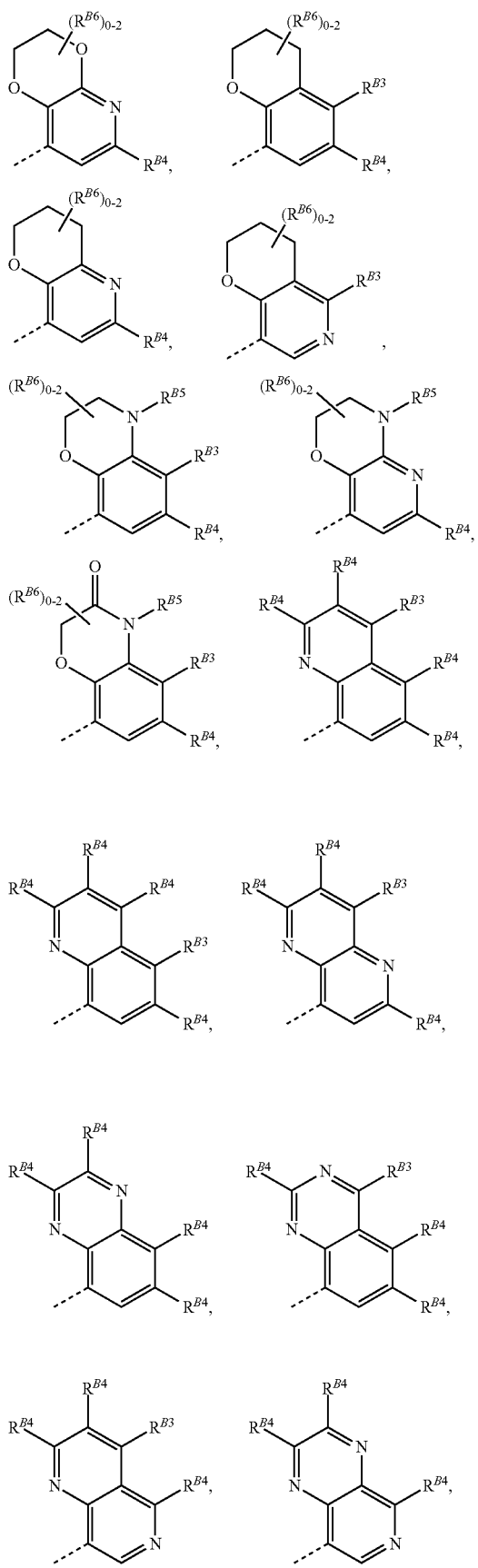

-continued

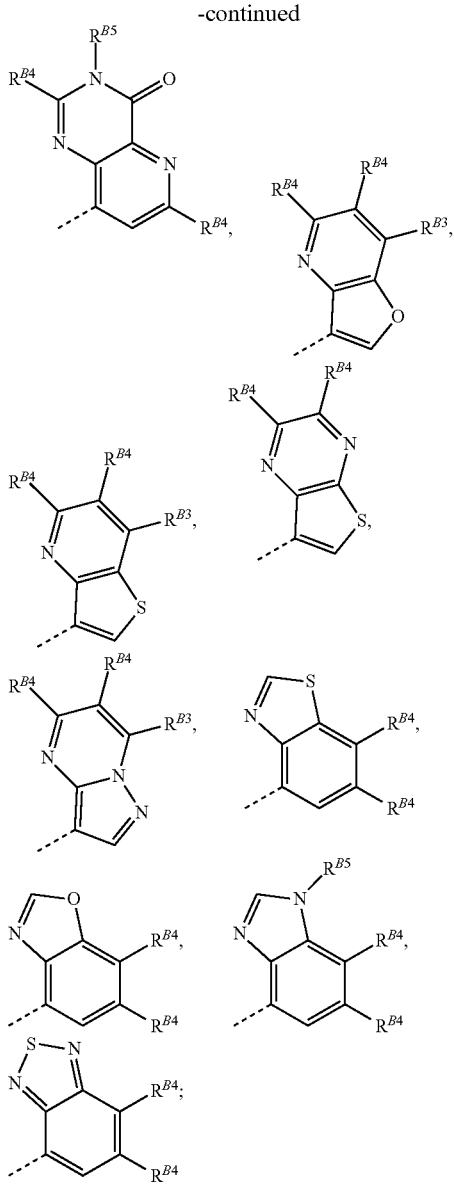

$R^{B1}$ is hydrogen, $C_{1-4}$alkyl, $(CH_2)_{0-1}C_{3-6}$cycloalkyl, $C(O)C_{1-2}$alkyl, $(CH_2)_{0-1}$(4-6 membered)heterocyclyl ring wherein said heterocyclic ring is selected from oxetanyl, tetrahydrofuranyl, tetrahydropyran, dioxanyl, dioxolanyl, and pyrrolidinonyl, or $(CH_2)_{1-2}$(5-6 membered)heteroaryl ring wherein said heteroaryl ring is selected from pyridinyl, imidazolyl, and pyrazolyl, and wherein each of said $R^{B1}$ alkyl, cycloalkyl, phenyl, benzyl, heterocyclyl and heteroaryl groups is optionally substituted with up to 3 F atoms, up to two $C_{1-2}$alkyl groups, two non-geminal OH groups, or one $OC_{1-2}$alkyl;

$R^{B2}$ is hydrogen, $C_{1-4}$alkyl, or $OC_{1-4}$alkyl;

each $R^{B3}$ is, independently, hydrogen, halogen, $C_{1-4}$alkyl, $C_{2-4}$alkenyl, $C_{2-4}$alkynyl, CN, C(O)H, C(O)$C_{1-4}$alkyl, C(O)O$C_{1-4}$alkyl, C(O)$C_{1-4}$alkyl, C(O)NH$_2$, C(O)NH$C_{1-4}$alkyl, C(O)NH$(CH_2)_{0-1}C_{3-6}$cycloalkyl, C(O)NHCH$_2$oxetanyl, C(O)NHCH$_2$tetrahydrofuranyl, C(O)NHCH$_2$tetrahydropyranyl, C(O)NHphenyl, C(O)NHbenzyl, C(O)NHOH, C(O)NHO$C_{1-4}$alkyl, C(O)NHO$(CH_2)_{0-1}C_{3-6}$cycloalkyl, C(O)NHO$(CH_2)_{0-1}$oxetanyl, C(O)NHO$(CH_2)_{0-1}$tetrahydrofuranyl, C(O)NHO$(CH_2)_{0-1}$tetrahydropyranyl, C(O)NHOphenyl, C(O)NHObenzyl, NH$_2$, NHC(O)$C_{1-4}$alkyl, O$C_{1-4}$alkyl, S$C_{1-4}$alkyl, S(O)$C_{1-4}$alkyl, or a 5-membered-heteroaryl ring system selected from furanyl, thiophenyl, imidazolyl, pyrrole, pyrazolyl, and oxadiazolyl, wherein each $R^{B3}$ group except hydrogen or halogen is optionally substituted with Cl, up to three F atoms, up to two non-geminal OH groups, up to two O$C_{1-2}$alkyl, one NH$_2$, one NH$C_{1-2}$alkyl, one NHC(O)$C_{1-2}$alkyl, or one N$(C_{1-2}$alkyl$)_2$;

each $R^{B4}$ is, independently, hydrogen, deuterium, halogen, $C_{1-4}$alkyl, O$C_{1-4}$alkyl, S$C_{1-4}$alkyl, NH$_2$, NH$(C_{1-4}$alkyl), N$(C_{1-4}$alkyl$)_2$, NHC(O)$C_{1-4}$alkyl, C(O)OH, C(O)O$C_{1-4}$alkyl, C(O)NH$_2$, C(O)NH$C_{1-4}$alkyl, C(O)N$(C_{1-4}$alkyl$)_2$, CN, a morpholinyl ring, or an imidazolyl ring, wherein each $R^{B4}$ alkyl is optionally substituted with up to 3 F atoms, two non-geminal OH groups, or one O$C_{1-2}$alkyl;

$R^{B5}$ is hydrogen, $C_{1-4}$alkyl, C(O)$C_{1-4}$alkyl, C(O)O$C_{1-4}$alkyl, C(O)NH$_2$, C(O)NH$C_{1-4}$alkyl, or C(O)N$(C_{1-4}$alkyl$)_2$, wherein said $R^{B5}$ alkyl is optionally substituted with up to 3 F atoms, two non-geminal OH groups, or one O$C_{1-2}$alkyl; and $R^{B6}$ is F or $C_{1-2}$alkyl, or two $R^{B6}$ and an intervening carbon atom form a spirocyclopropyl or spirocyclobutyl ring.

In one embodiment, the DNA-PK inhibitor is a compound of the following formula:

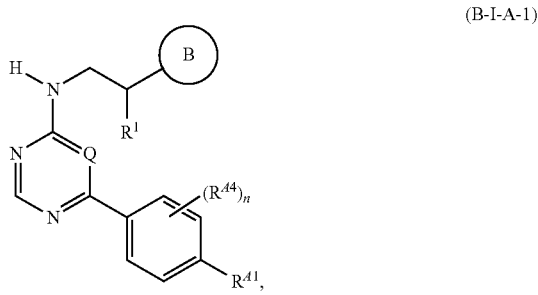

(B-I-A-1)

or a pharmaceutically acceptable salt thereof.

In one embodiment, the DNA-PK inhibitor is a compound of one of the following formulae:

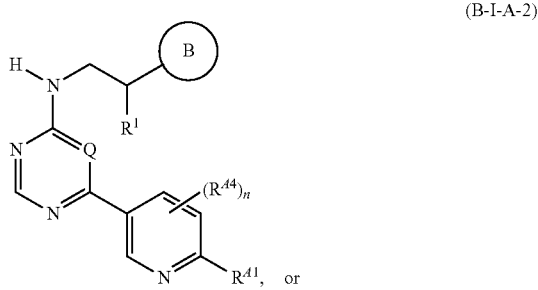

(B-I-A-2)

or (B-I-A-3)
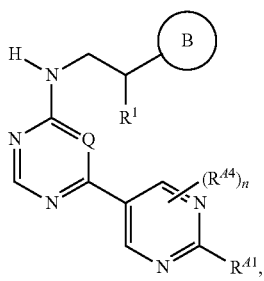

or a pharmaceutically acceptable salt thereof.

In one embodiment, the DNA-PK inhibitor is a compound of one of the following formulae:

(B-I-A-4)
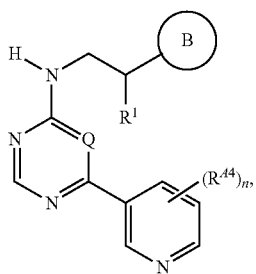

(B-I-A-5)
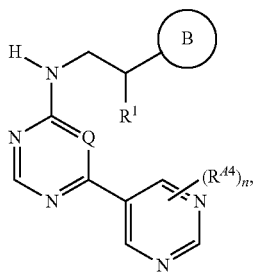

(B-I-A-6)
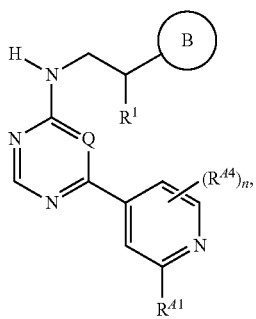

(B-I-A-7)
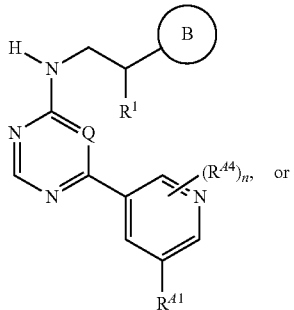

(B-I-A-8)
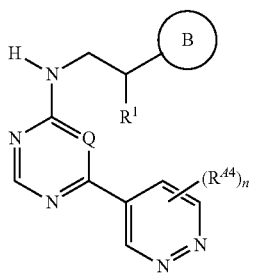

or a pharmaceutically acceptable salt thereof.

In one embodiment, the DNA-PK inhibitor is a compound of one of the following formulae:

(B-I-A-9)
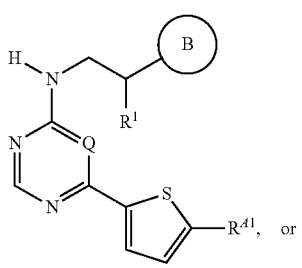

(B-I-A-10)
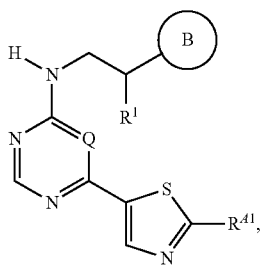

or a pharmaceutically acceptable salt thereof.

In a further embodiment for any compound of formulae B-I-A-1 to B-I-A-3, B-I-A-6 to B-I-A-7, or B-I-A-9 to B-I-A-10, $R^{A1}$ is $C_{1-4}$alkyl, $OC_{1-4}$alkyl, or $N(R^{A1a})_2$, wherein each $R^{A1a}$ is, independently, hydrogen or $C_{1-4}$alkyl, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl, wherein each of said $R^{A1}$ alkyl or heterocyclyl groups is optionally substituted with up to three F atoms, up to three $^2$H atoms, up to two $C_{1-2}$alkyl groups, a $C_{3-6}$cycloalkyl group, up to two $C_{0-2}$alkyl-$OR^{A1b}$ groups, a $C_{0-2}$alkyl-N$(R^{A1b})_2$ group, a $SC_{1-4}$alkyl group, a $C(O)R^{A1b}$ group, a $C(O)OR^{A1b}$ group, a $C(O)N(R^{A1b})_2$ group, or a —CN group, wherein each $R^{A1b}$ is, independently, hydrogen, $C_{1-2}$alkyl, or $C_{3-4}$cycloalkyl.

In one embodiment, the DNA-PK inhibitor is a compound of one of the following formulae:

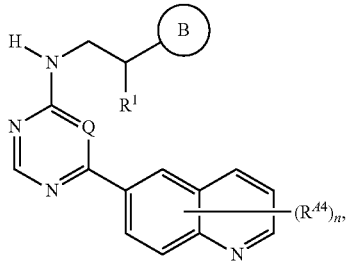
(B-I-A-11)

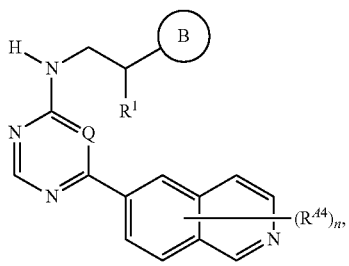
(B-I-A-12)

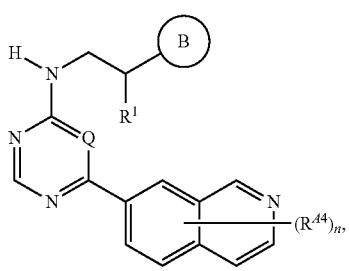
(B-I-A-13)

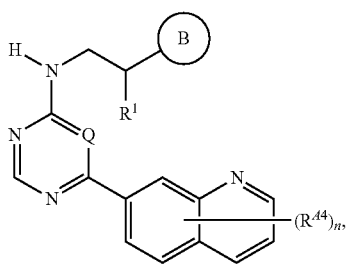
(B-I-A-14)

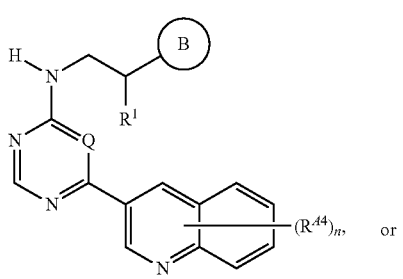
(B-I-A-15) or

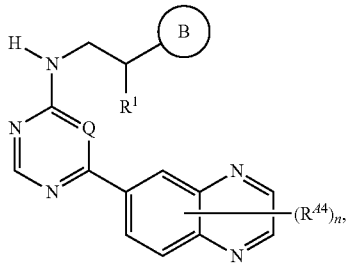
(B-I-A-16)

or a pharmaceutically acceptable salt thereof.

In one embodiment, the DNA-PK inhibitor is a compound of the following formula:

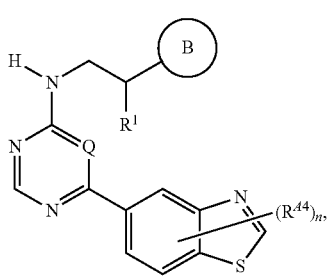
(B-I-A-17)

or a pharmaceutically acceptable salt thereof.

In one embodiment, the DNA-PK inhibitor is a compound of one of the following formulae:

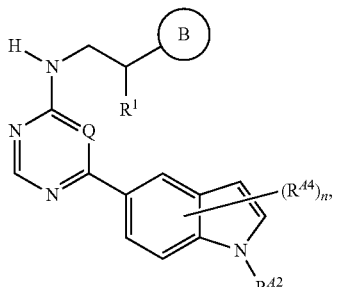
(B-I-A-18)

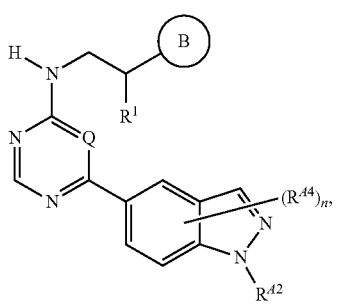
(B-I-A-19)

(B-I-A-20)

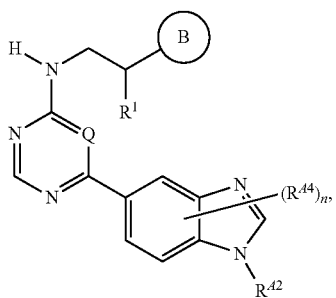

(B-I-A-21)

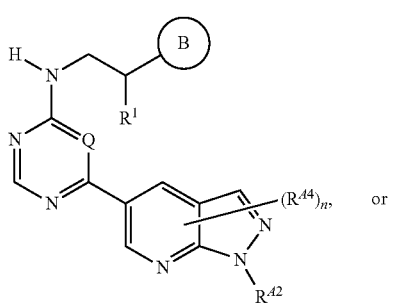

(B-I-A-22)

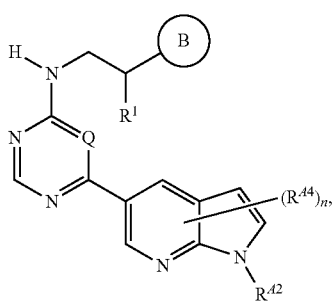

or a pharmaceutically acceptable salt thereof.

In one embodiment, the DNA-PK inhibitor is a compound of one of the following formulae:

(B-I-A-23)

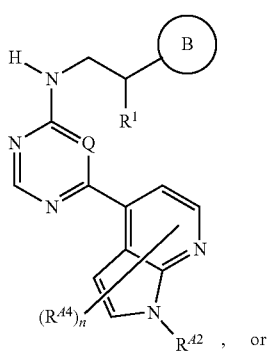

(B-I-A-24)

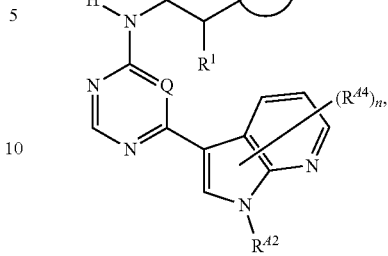

or a pharmaceutically acceptable salt thereof.

In one embodiment, the DNA-PK inhibitor is a compound of the following formula:

(B-I-A-25)

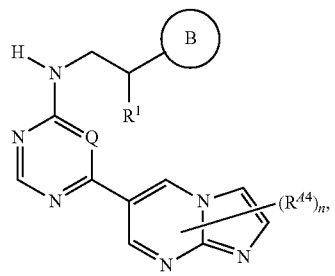

or a pharmaceutically acceptable salt thereof.

In one embodiment, the DNA-PK inhibitor is a compound of one of the following formulae:

(B-I-A-26)

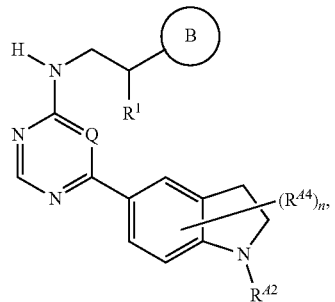

(B-I-A-27)

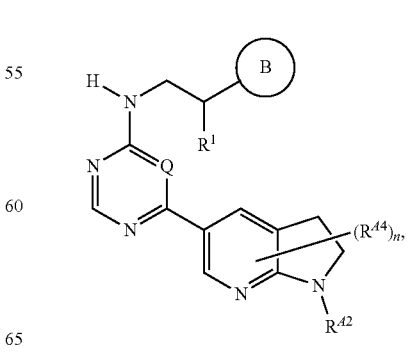

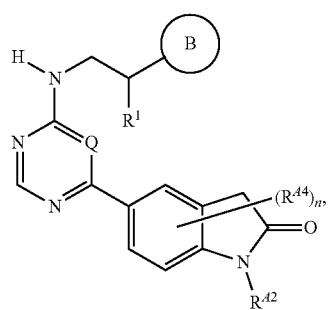 (B-I-A-28)
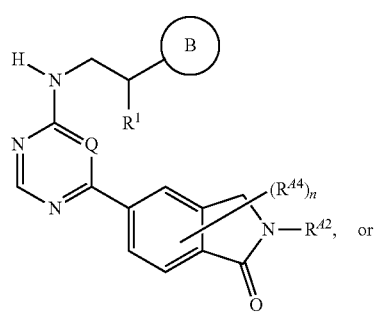 (B-I-A-29)
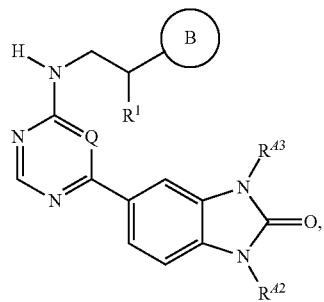 (B-I-A-30)
or a pharmaceutically acceptable salt thereof.
In one embodiment, the DNA-PK inhibitor is a compound of one of the following formulae:
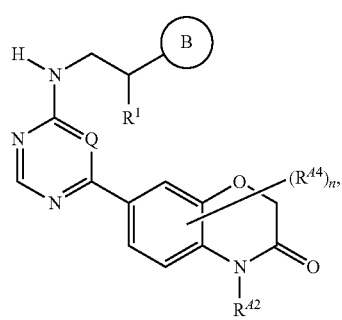 (B-I-A-31)
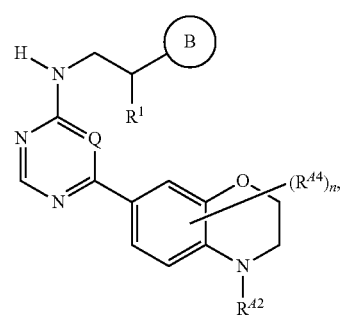 (B-I-A-32)
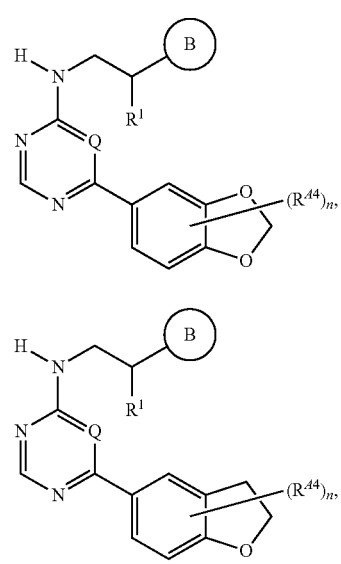 (B-I-A-33)
(B-I-A-34)
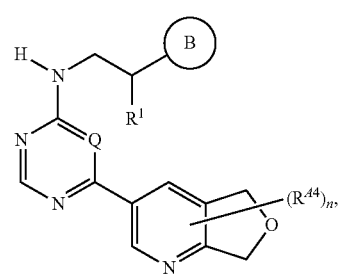 (B-I-A-35)
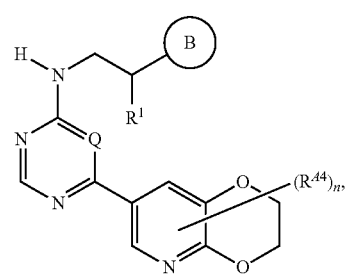 (B-I-A-36)

(B-I-A-37)
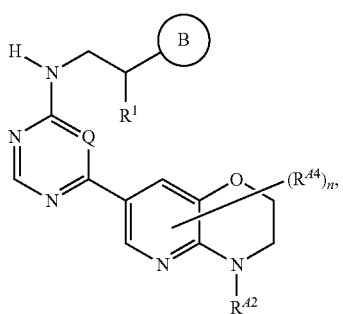
(B-I-A-38)
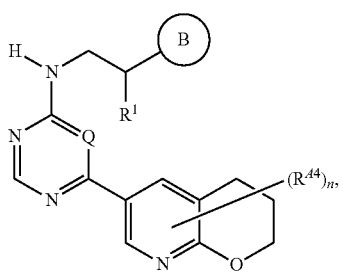
(B-I-A-39)
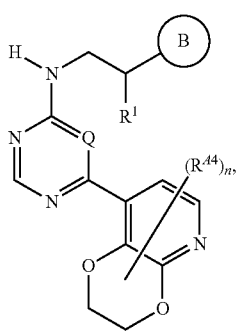
(B-I-A-40)
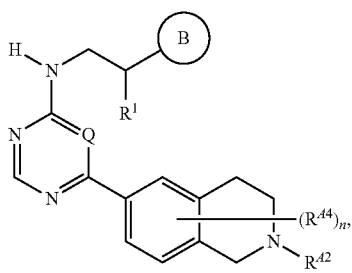
(B-I-A-41)
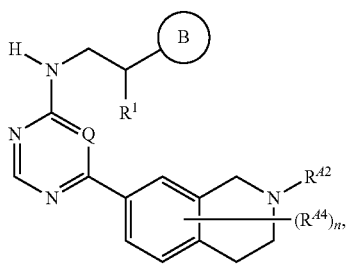
(B-I-A-42)
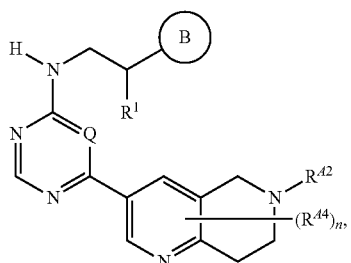
(B-I-A-43)
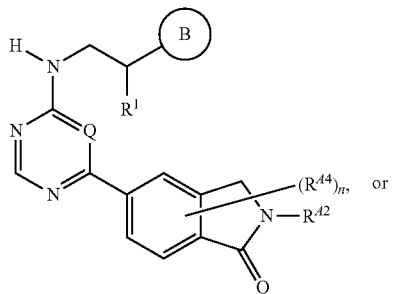
or
(B-I-A-44)
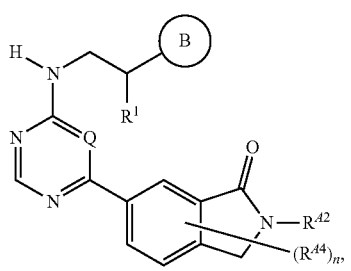
or a pharmaceutically acceptable salt thereof.
In one embodiment, the DNA-PK inhibitor is a compound of one of the following formulae:
(B-I-A-45)
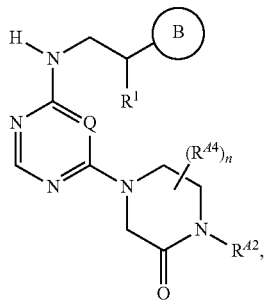
(B-I-A-46)
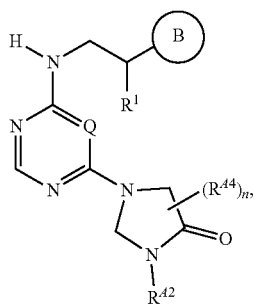

-continued (B-I-A-47)
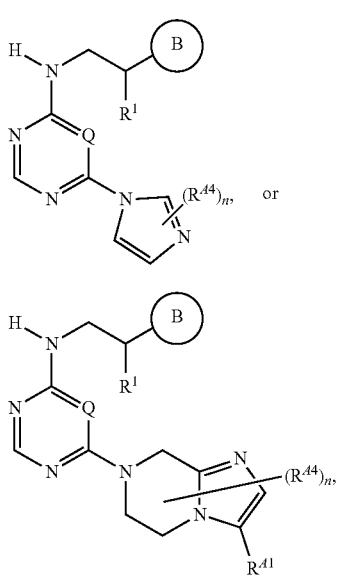

or a pharmaceutically acceptable salt thereof.

In one embodiment, the DNA-PK inhibitor is a compound of one of the following formulae (B-I-A-48)
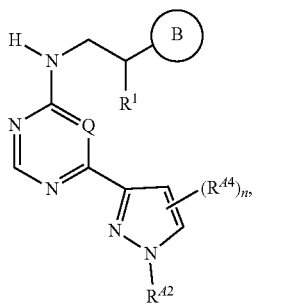

(B-I-A-49)
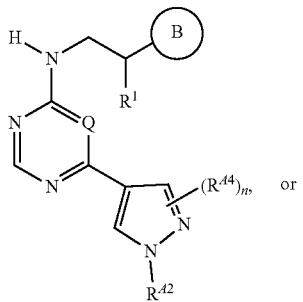

or (B-I-A-50)
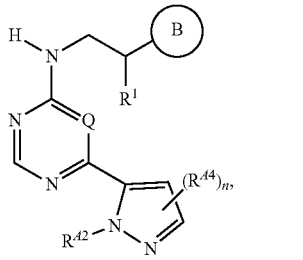

or a pharmaceutically acceptable salt thereof.

In one embodiment, the DNA-PK inhibitor is a compound of the following formula (B-I-B-1)
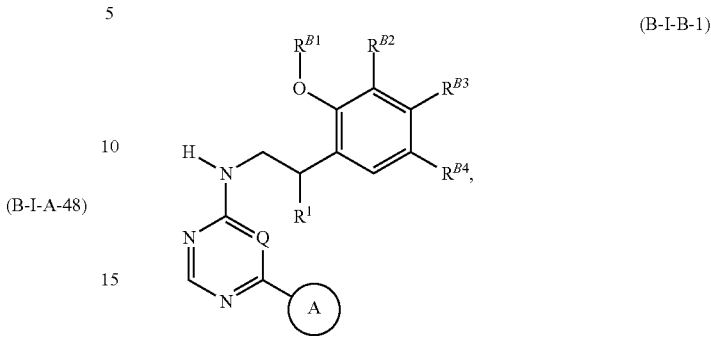

or a pharmaceutically acceptable salt thereof.

In one embodiment, the DNA-PK inhibitor is a compound of one of the following formulae:

(B-I-B-2)
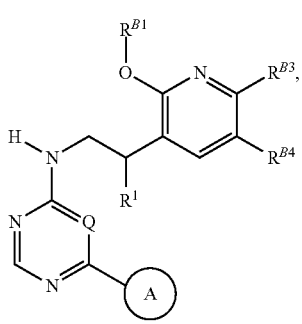

(B-I-B-3)
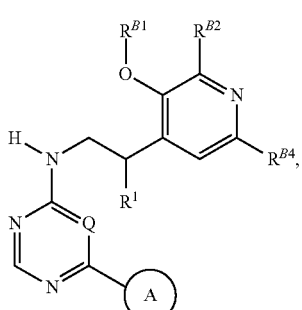

(B-I-B-4)
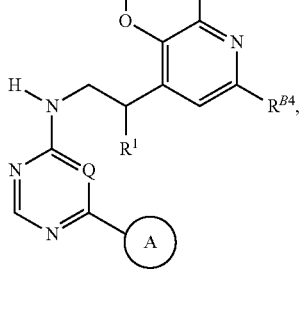

or

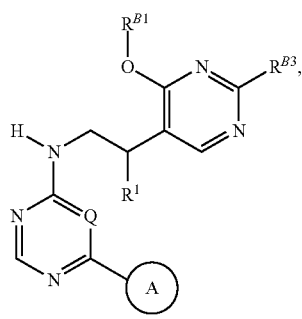

(B-I-B-5)

or a pharmaceutically acceptable salt thereof.

In one embodiment, the DNA-PK inhibitor is a compound of the following formula:

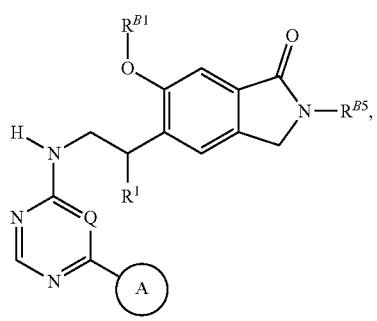

(B-I-B-6)

or a pharmaceutically acceptable salt thereof.

In one embodiment, the DNA-PK inhibitor is a compound of the following formula:

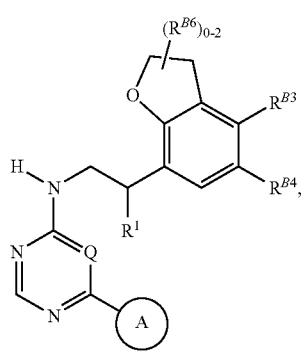

(B-I-B-7)

or a pharmaceutically acceptable salt thereof.

In one embodiment, the DNA-PK inhibitor is a compound of the following formula:

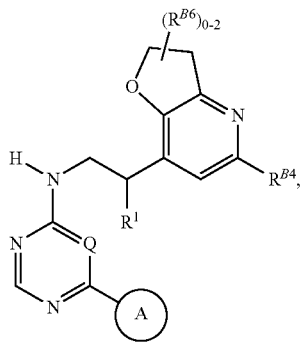

(B-I-B-8)

or a pharmaceutically acceptable salt thereof.

In one embodiment, the DNA-PK inhibitor is a compound of one of the following formulae:

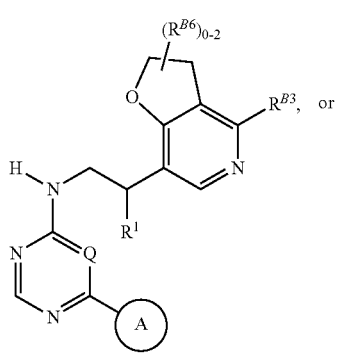

(B-I-B-9)

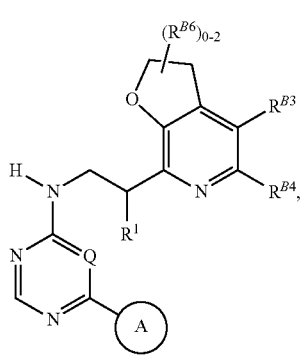

(B-I-B-10)

or a pharmaceutically acceptable salt thereof.

In one embodiment, the DNA-PK inhibitor is a compound of one of the following formulae:

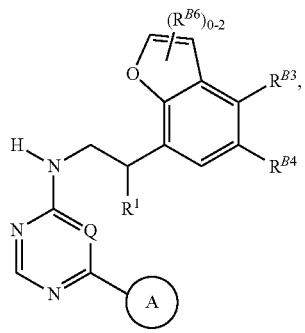
(B-I-B-11)

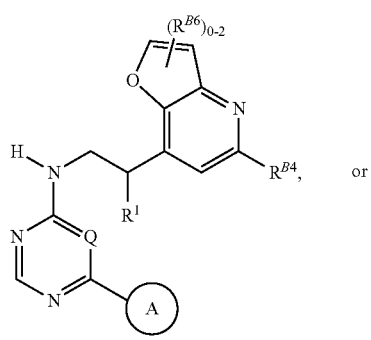
(B-I-B-12)
or

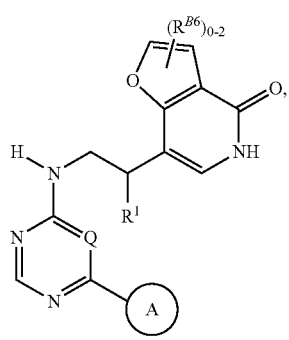
(B-I-B-13)

or a pharmaceutically acceptable salt thereof.

In one embodiment, the DNA-PK inhibitor is a compound of the following formula:

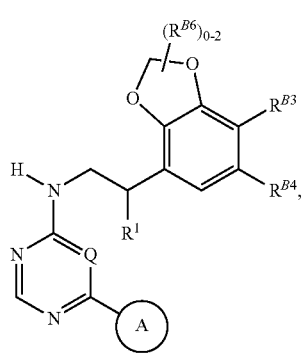
(B-I-B-14)

or a pharmaceutically acceptable salt thereof.

In one embodiment, the DNA-PK inhibitor is a compound of the following formula:

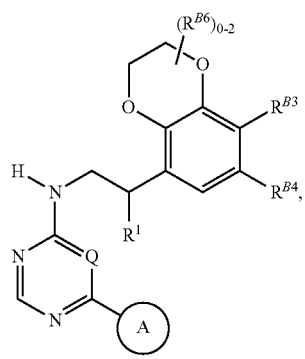
(B-I-B-15)

or a pharmaceutically acceptable salt thereof.

In one embodiment, the DNA-PK inhibitor is a compound of the following formula:

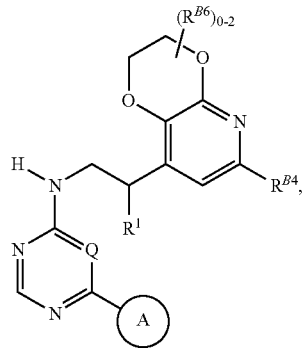
(B-I-B-16)

or a pharmaceutically acceptable salt thereof.

In one embodiment, the DNA-PK inhibitor is a compound of one of the following formulae:

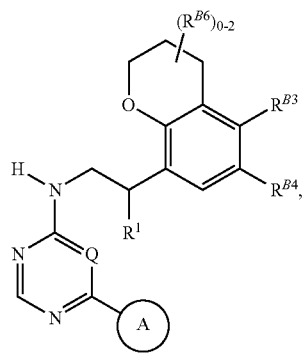
(B-I-B-17)

(B-I-B-18)

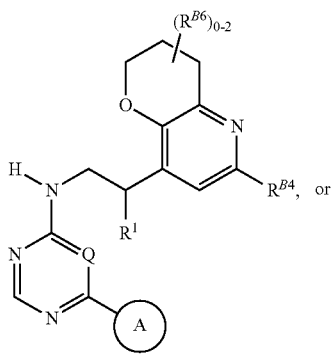

or (B-I-B-19)

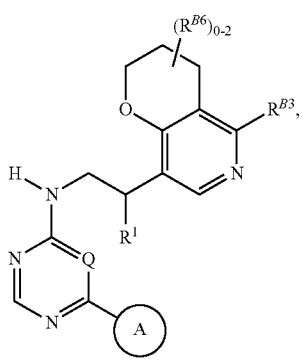

or a pharmaceutically acceptable salt thereof.

In one embodiment, the DNA-PK inhibitor is a compound of one of the following formulae:

(B-I-B-20)

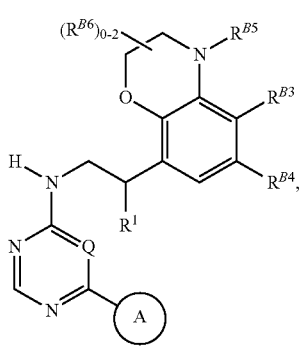

(B-I-B-21)

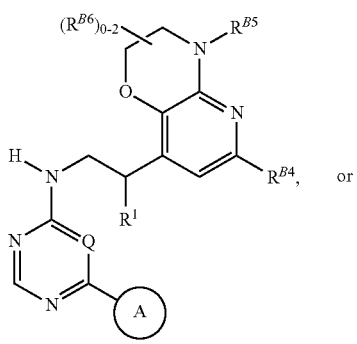

or (B-I-B-22)

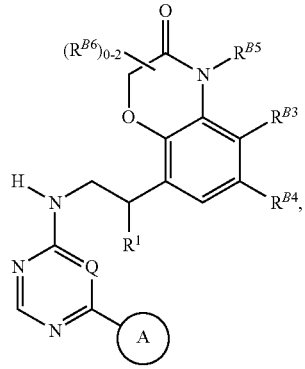

or a pharmaceutically acceptable salt thereof.

In one embodiment, the DNA-PK inhibitor is a compound of the following formula:

(B-I-B-23)

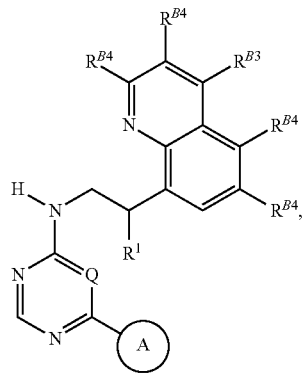

or a pharmaceutically acceptable salt thereof.

In one embodiment, the DNA-PK inhibitor is a compound of one of the following formulae:

(B-I-B-24)

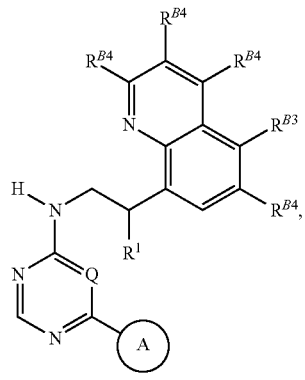

-continued
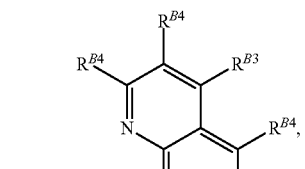
(B-I-B-25)
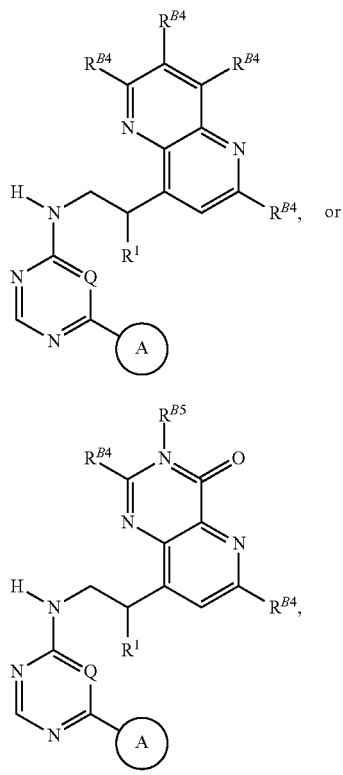
(B-I-B-26)
or a pharmaceutically acceptable salt thereof.
In one embodiment, the DNA-PK inhibitor is a compound of one of the following formulae:
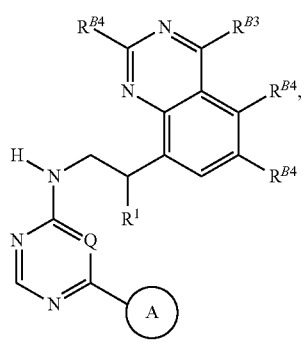
(B-I-B-27)
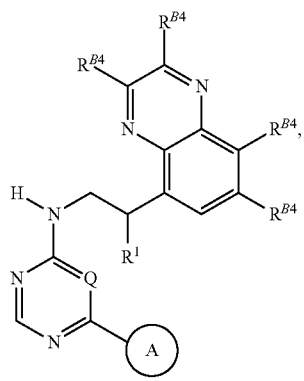
(B-I-B-28)
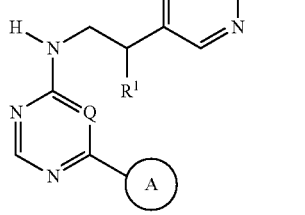
(B-I-B-29)
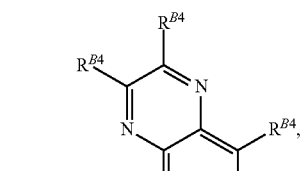
(B-I-B-30)
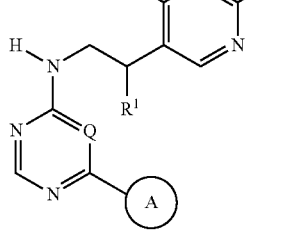
(B-I-B-31)
or a pharmaceutically acceptable salt thereof.
In one embodiment, the DNA-PK inhibitor is a compound of one of the following formulae:
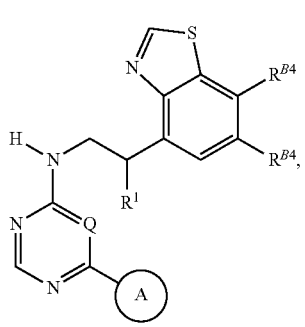
(B-I-B-32)

-continued

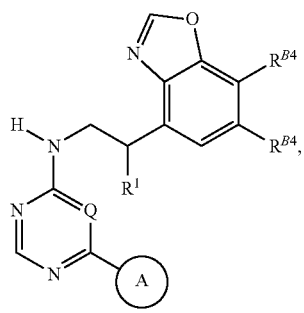
(B-I-B-33)

or a pharmaceutically acceptable salt thereof.

In one embodiment, the DNA-PK inhibitor is a compound of one of the following formulae:

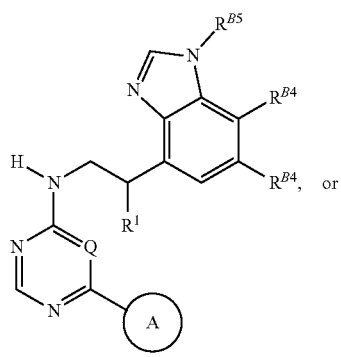
(B-I-B-34)

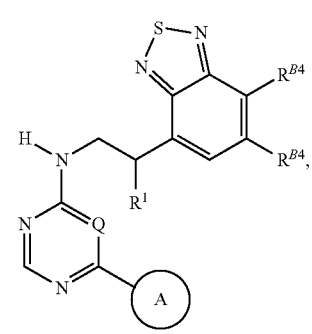
(B-I-B-35)

or a pharmaceutically acceptable salt thereof.

In one embodiment, the DNA-PK inhibitor is a compound of one of the following formulae:

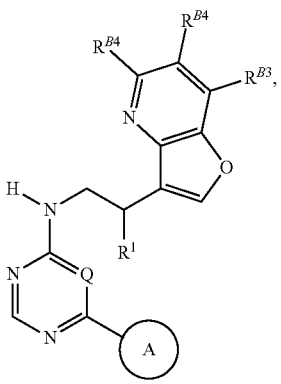
(B-I-B-36)

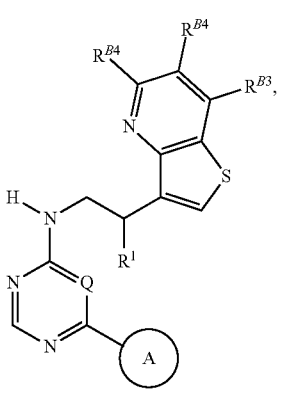
(B-I-B-37)

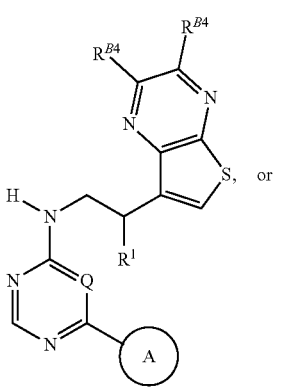
(I-B-38)

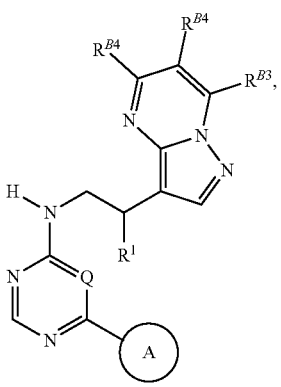
(I-B-39)

or a pharmaceutically acceptable salt thereof.

In one embodiment, the DNA-PK inhibitor is a compound of one of the following formulae:

(B-I-B-40)

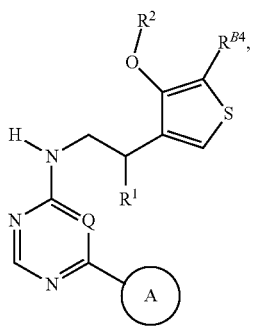

(B-I-B-41)

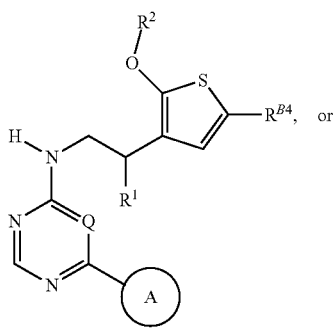

(B-I-B-42)

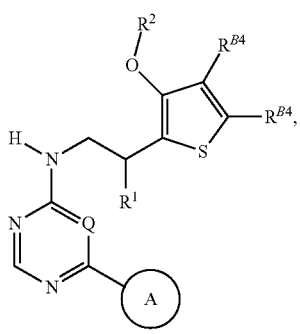

or a pharmaceutically acceptable salt thereof.

In another embodiment, the Ring B of a compound is linked to the remainder of the molecule wherein

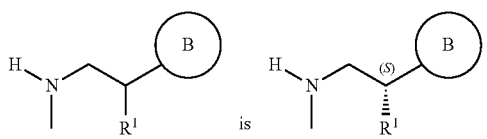

and $R^1$ is $CH_3$; except when Ring B is

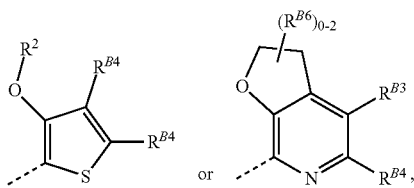

wherein

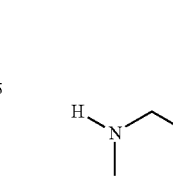 is 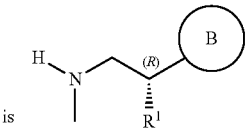

and $R^1$ is $CH_3$.

In another embodiment, Q is CH.

In another embodiment, Ring A comprises a heterocyclyl or heteroaryl ring.

In a further embodiment, Ring A is:

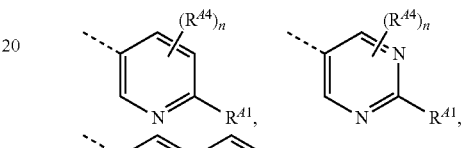

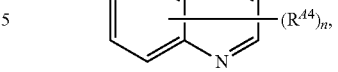

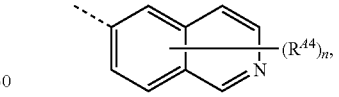

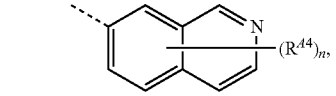

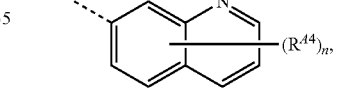

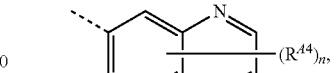

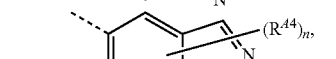

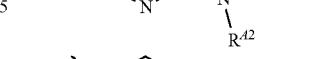

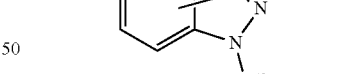

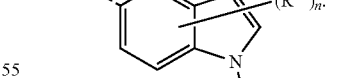

In yet another further embodiment, Ring A is:

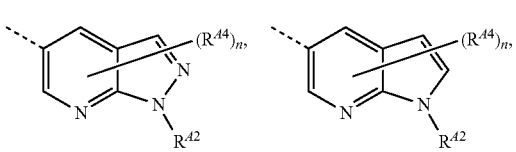

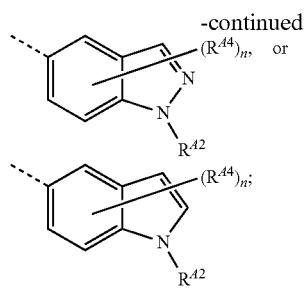

wherein:

$R^{A2}$ is a hydrogen, $C_{1-4}$alkyl, $C_{0-2}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)N(R^{A2a})_2$, $C_{0-2}$alkyl-$S(O)_2$—$C_{1-4}$alkyl, or $C_{0-2}$alkyl-$C(O)OC_{1-4}$alkyl, wherein each of said heterocyclyl is selected from oxetan-2-yl, azetidin-2-yl, piperidin-4-yl, and 1,1-dioxothietan-2-yl, and each of said $R^{A2}$ groups is optionally substituted with up to three F atoms, up to two $C_{1-2}$alkyl groups, up to two $OR^{A2b}$ groups, a $C_{0-2}$alkyl-N$(R^{A2b})_2$ group, a $C(O)R^{A2b}$ group, a $C(O)OR^{A2b}$ group, a $C(O)N(R^{A2b})_2$ group, or a —CN group;

each $R^{A2a}$ is, independently, H, $C_{1-4}$alkyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl;

each $R^{A2b}$ is, independently, H or $C_{1-4}$alkyl; and n is 0.

In yet another further embodiment, Ring A is:

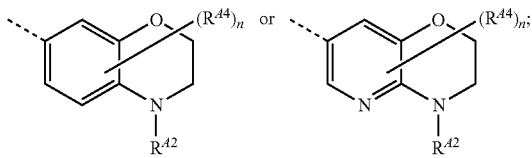

wherein:

$R^{A2}$ is a hydrogen, $C_{1-4}$alkyl, $C_{0-2}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)N(R^{A2a})_2$, $C_{0-2}$alkyl-$S(O)_2$—$C_{1-4}$alkyl, or $C_{0-2}$alkyl-$C(O)OC_{1-4}$alkyl, wherein each of said heterocyclyl is selected from oxetan-2-yl, azetidin-2-yl, piperidin-4-yl, and 1,1-dioxothietan-2-yl, and each of said $R^{A2}$ groups is optionally substituted with up to three F atoms, up to two $C_{1-2}$alkyl groups, up to two $OR^{A2b}$ groups, a $C_{0-2}$alkyl-N$(R^{A2b})_2$ group, a $C(O)R^{A2}$b group, a $C(O)OR^{A2b}$ group, a $C(O)N(R^{A2b})_2$ group, or a —CN group;

each $R^{A2a}$ is, independently, H, $C_{1-4}$alkyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl;

each $R^{A2b}$ is, independently, H or $C_{1-4}$alkyl; and n is 0.

In yet another further embodiment, Ring A is:

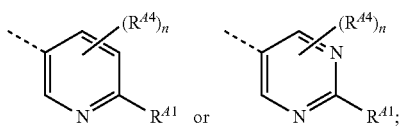

wherein:

$R^{A1}$ is $C_{1-4}$alkyl, $C_{0-4}$alkyl-$C_{3-6}$cycloalkyl, $C_{0-4}$alkyl-$OR^{A1a}$, $C_{0-4}$alkyl-$C_{3-6}$cycloalkyl, $C_{0-4}$alkyl-N$(R^{A1a})_2$, N$(R^{A1a})C_{2-4}$alkyl-N$(R^{A1a})_2$, wherein each of said $R^{A1}$ alkyl and cycloalkyl is optionally substituted with up to three F atoms, up to three $^2$H atoms, or up to two $C_{0-2}$alkyl-$OR^{A1b}$ groups;

each $R^{A1a}$ is, independently, hydrogen, $C_{1-4}$alkyl, a $C(O)R^{A1b}$ group, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl, wherein each of said alkyl and heterocyclyl group of $R^{A1a}$ is optionally substituted with up to three F atoms, up to two $C_{1-2}$alkyl groups, up to two $OR^{A1b}$ groups, or a —CN group;

each $R^{A1b}$ is, independently, hydrogen or $C_{1-2}$alkyl; each $R^{A4}$ is, independently, halogen, $^2$H, $C_{1-4}$alkyl, N$(R^{1a})_2$, or $OC_{1-4}$alkyl, wherein each $R^{A4}$ alkyl is optionally substituted with up to 3 F atoms, up to two non-geminal OH groups, or up to two $OC_{1-2}$alkyl; and n is 0, 1, 2, or 3.

In yet another further embodiment, Ring A is:

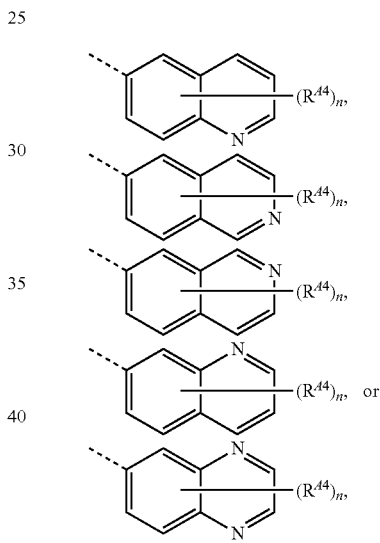

wherein:

each $R^{A4}$ is, independently, halogen, $C_{1-4}$alkyl, or $OC_{1-4}$alkyl, wherein each $R^{A4}$ alkyl is optionally substituted with up to 3 F atoms, up to two non-geminal OH groups, or up to two $OC_{1-2}$alkyl, and n is 0, 1, or 2.

In another embodiment, Ring B comprises a heterocyclyl or heteroaryl ring.

In one embodiment, Ring B is:

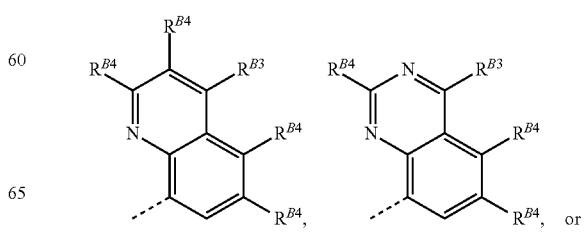

-continued

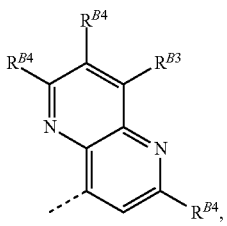

wherein:

$R^{B3}$ is C(O)NHC$_{1-4}$ alkyl, wherein said alkyl is optionally substituted with up to three F atoms, two non-geminal OH groups, or one OC$_{1-2}$alkyl; and each $R^{B4}$ is, independently, hydrogen, $^2$H, F, C$_{1-4}$alkyl, or OC$_{1-4}$alkyl, wherein each $R^{B4}$ alkyl is optionally substituted with up to 3 F atoms, two non-geminal OH groups, or one OC$_{1-2}$alkyl.

In a further embodiment, Ring A is:

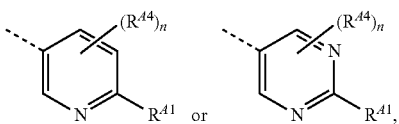

wherein:

$R^{A1}$ is F, C$_{1-4}$alkyl, OC$_{1-4}$alkyl, OC$_{0-4}$alkyl-C$_{3-5}$cycloalkyl, NH$_2$, NHC$_{1-4}$alkyl, NHC$_{0-4}$alkyl-C$_{3-5}$cycloalkyl, or C$_{0-4}$alkyl-heterocyclyl, wherein said heterocyclic ring system is selected from oxetanyl, tetrahydrofuranyl, tetrahydropyranyl, and morpholinyl, and each of said alkyl, cycloalkyl, and heterocyclyl is optionally substituted with up to three F atoms, up to three $^2$H atoms, up to two non-geminal OH groups, or up to two OC$_{1-2}$alkyl;

each $R^{A4}$ is, independently, F, $^2$H, OC$_{1-4}$alkyl, or NH$_2$; and n is 0, 1, or 2.

In another embodiment, Ring B is:

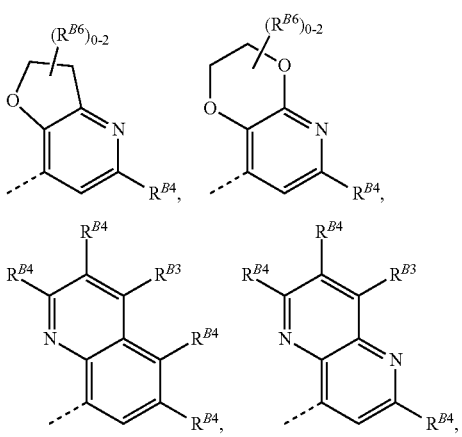

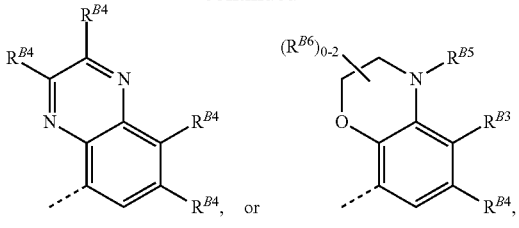

wherein:

each of $R^{B3}$ and $R^{B4}$ is, independently, hydrogen, halogen, or C$_{1-4}$alkyl, wherein each of said $R^{B3}$ and $R^{B4}$ alkyl is optionally substituted with up to 3 F atoms, two non-geminal OH groups, or one OC$_{1-2}$alkyl;

$R^{B5}$ is hydrogen, C$_{1-4}$alkyl, C(O)C$_{1-4}$alkyl, C(O)OC$_{1-4}$alkyl, C(O)NH$_2$, C(O)NHC$_{1-4}$alkyl, or C(O)N(C$_{1-4}$alkyl)$_2$, wherein said $R^{B5}$ alkyl is optionally substituted with up to 3 F atoms, up to two non-geminal OH groups, or up to two OC$_{1-2}$alkyl; and $R^{B6}$ is F or C$_{1-2}$alkyl, or two $R^{B6}$ and an intervening carbon atom from a spirocyclopropyl or spirocyclobutyl ring.

In another aspect, the DNA-PK inhibitor is a compound of Formula (B-II):

B-II

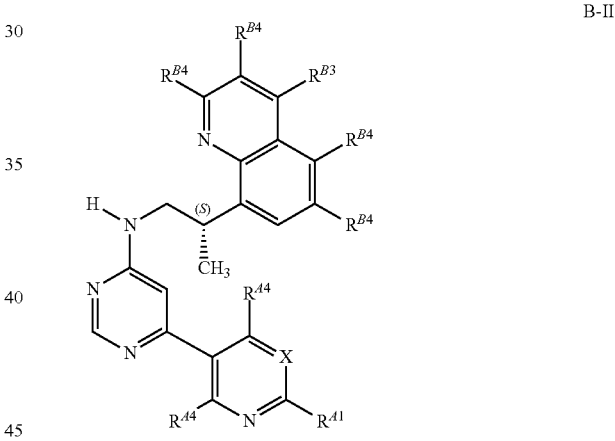

or a pharmaceutically acceptable salt thereof, wherein:

X is N or CR$^{A5}$;

$R^{A1}$ is F, C$_{1-4}$alkyl, C$_{3-5}$cycloalkyl, OC$_{1-4}$alkyl, OC$_{1-4}$alkyl-C$_{3-5}$cycloalkyl, NH$_2$, NHC$_{1-4}$alkyl, NHC$_{1-4}$alkyl-C$_{3-5}$cycloalkyl, or C$_{0-4}$alkyl-heterocyclyl, wherein said heterocyclic ring system is selected from oxetanyl, tetrahydrofuranyl, tetrahydropyran, and morpholinyl, and each of said alkyl, cycloalkyl, and heterocyclyl is optionally substituted with up to three F atoms, up to three $^2$H atoms, up to two non-geminal OH groups, or up to two OC$_{1-2}$alkyl;

each $R^{A4}$ is, independently, H or $^2$H;

$R^{A5}$ is hydrogen, F, C$_{1-4}$alkyl, or OC$_{1-4}$alkyl, wherein each of said alkyl is optionally substituted with up to three F atoms or up to three $^2$H atoms;

$R^{B3}$ is C(O)NHC$_{1-4}$ alkyl, wherein said alkyl is optionally substituted with up to three F atoms, up to three $^2$H atoms, up to two non-geminal OH groups, or up to two OC$_{1-2}$alkyl; and each $R^{B4}$ is, independently, hydrogen, deuterium, F, or C$_{1-4}$alkyl.

In another aspect, the DNA-PK inhibitor is a compound of Formula (B-III):

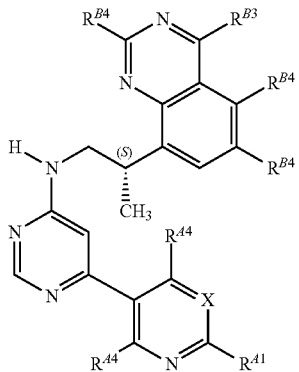

B-III or a pharmaceutically acceptable salt thereof, wherein:

X is N, $CR^{A5}$;

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{0-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyran, and morpholinyl, and each of said alkyl, cycloalkyl, and heterocyclyl is optionally substituted with up to three F atoms, up to three $^2H$ atoms, up to two non-geminal OH groups, or up to two $OC_{1-2}$alkyl;

each $R^{A4}$ is, independently, H or $^2H$;

$R^{A5}$ is hydrogen, F, $C_{1-4}$alkyl, or $OC_{1-4}$alkyl, wherein each of said alkyl is optionally substituted with up to three F atoms or up to three $^2H$ atoms;

$R^{B3}$ is $C(O)NHC_{1-4}$ alkyl, wherein said alkyl is optionally substituted with up to three F atoms, up to three $^2H$ atoms, up to two non-geminal OH groups, or up to two $OC_{1-2}$alkyl; and each $R^{B4}$ is, independently, hydrogen, deuterium, F, or $C_{1-4}$alkyl.

In certain embodiments, the DNA-PK inhibitor is Compound B-1:

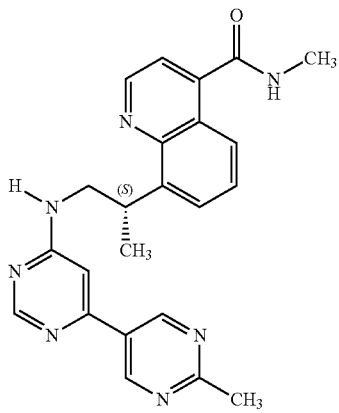

Compound B-1 or a pharmaceutically acceptable salt thereof.

In certain embodiments, the DNA-PK inhibitor is Compound B-2:

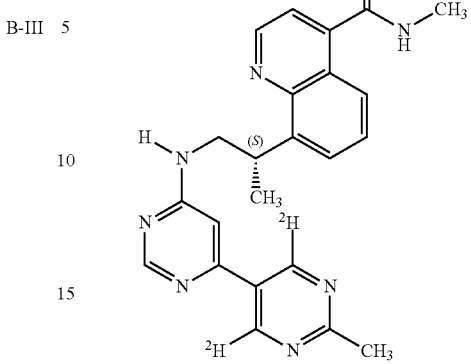

Compound B-2 or a pharmaceutically acceptable salt thereof.

In certain embodiments, the DNA-PK inhibitor is Compound B-3:

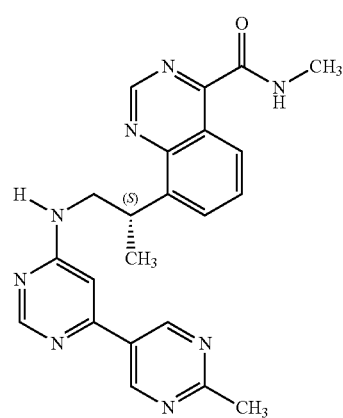

Compound B-3 or a pharmaceutically acceptable salt thereof.

In another embodiment, the DNA-PK inhibitor is selected from a compound described in WO 2013/163190, WO2015/058031, WO2014/159690, and/or WO2015/058067. In certain embodiments, the DNA-PK inhibitor is a compound of Formula (B-I), (B-II), or (B-III). In certain embodiments, the DNA-PK inhibitor is Compound B-1, Compound B-2, or Compound B-3.

In another embodiment, the DNA-PK inhibitor is selected from a compound described in WO 2012/000632 or US 2013/0172337, e.g., such as

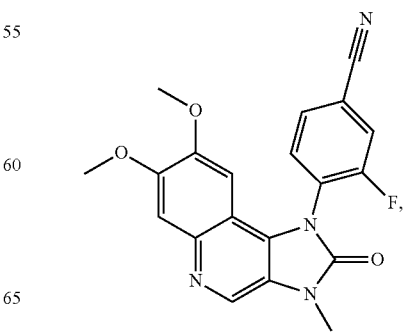

Compound C-1

Compound C-2

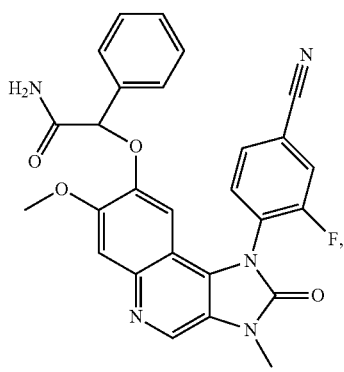

Compound C-3

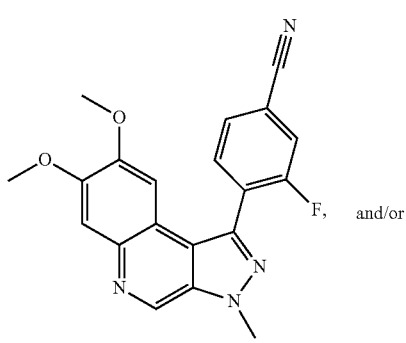
and/or

Compound C-4

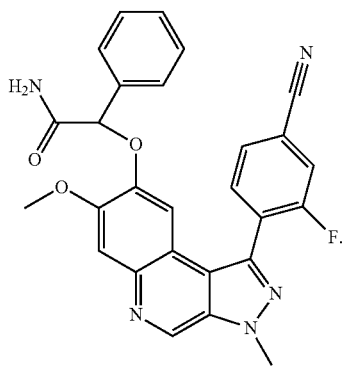

In another embodiment, the DNA-PK inhibitor is CC-115 (5-ethyl-3-[2-methyl-6-(1H-1,2,4-triazol-5-yl)pyridin-3-yl]-7,8-dihydropyrazino[2,3-b]pyrazin-6-one).

For purposes of this application, it will be understood that the terms embodiment, example, and aspect are used interchangeably.

For purposes of this application, it will be understood that the terms DNA-PK, DNA-Pkcs (catalytic subunit of DNA-dependent protein kinase), DNA protein kinase, DNA-dependent protein kinase, and the like, are used interchangeably. DNA-PK inhibitor and a compound that inhibits DNA-PK, and the like, are also used interchangeably.

It will be understood by those skilled in the art that the arrow in →O represents a dative bond.

This application refers to various issued patent, published patent applications, journal articles, and other publications, all of which are incorporated herein by reference.

Compounds include those described generally herein, and are further illustrated by the classes, subclasses, and species disclosed herein. As used herein, the following definitions shall apply unless otherwise indicated. The chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds may optionally be substituted with one or more substituents, such as are illustrated generally herein, or as exemplified by particular classes, subclasses, and species. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example ii below, for instance, $J^1$ can be bonded to the 5-membered ring (on the nitrogen atom, for instance), and to the 6-membered ring.

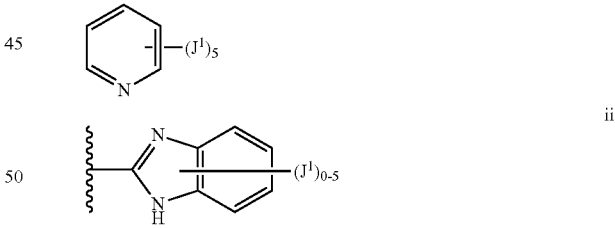

The term "stable", as used herein, refers to compounds that are not substantially altered when patiented to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —$CH_2$-cyclopropyl, —$CH_2CH_2CH(CH_3)$-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, and phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

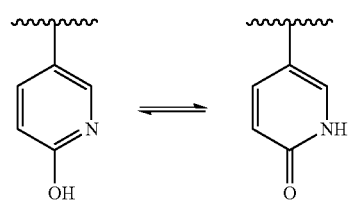 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

"Pegylation" or "pegylated" refers to the process of both covalent and non-covalent attachment or amalgamation of polyethylene glycol (PEG, in pharmacy called macrogol) polymer chains to molecules and macrostructures, such as a drug, therapeutic protein or vesicle/liposome. "Non-pegylation" or "non-pegylated" refers to the absence of PEG.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are contemplated herein. As would be understood to one skilled in the art, a substituent can freely rotate around any rotatable bonds. For example, a substituent drawn as

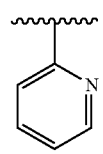

also represents

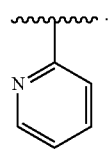

Single stereochemical isomers as well as enantiomeric, diastereomeric, geometric, conformational, and rotational mixtures of the present compounds are contemplated herein.

Unless otherwise indicated, all tautomeric forms of the compounds described are contemplated herein.

In one embodiment, a compound described herein is provided in the form of a single enantiomer at least 95%, at least 97% and at least 99% free of the corresponding enantiomer.

In a further embodiment, a compound described herein is in the form of the (+) enantiomer at least 95% free of the corresponding (−) enantiomer.

In a further embodiment, a compound described herein is in the form of the (+) enantiomer at least 97% free of the corresponding (−) enantiomer.

In a further embodiment, a compound described herein is in the form of the (+) enantiomer at least 99% free of the corresponding (−) enantiomer.

In a further embodiment, a compound described herein is in the form of the (−) enantiomer at least 95% free of the corresponding (+) enantiomer.

In a further embodiment, a compound described herein is in the form of the (−) enantiomer at least 97% free of the corresponding (+) enantiomer.

In a further embodiment, a compound described herein is in the form of the (−) enantiomer at least 99% free of the corresponding (+) enantiomer.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are contemplated herein. Such compounds are useful, for example, as analytical tools or probes in biological assays.

DNA-Damaging Agents

In certain embodiments, the DNA-damaging agent comprises chemotherapy. In certain embodiments, the DNA-PK inhibitor is a compound of Formula (B-I) (e.g., Compound B-1, Compound B-2, or Compound B-3, Compound C-1, Compound C-2, Compound C-3, or Compound C-4, and the DNA-damaging agent is chemotherapy. In certain embodiments, the DNA-PK inhibitor is CC-115 and the DNA-damaging agent is chemotherapy.

As used herein, the term "chemotherapy" does not include radiation therapy, unless where noted. Examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HCl, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capacitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Anthracyclines (e.g., doxorubicin agent, daunorubicin, epirubicin and other derivatives); Anthracenediones (e.g, Mitoxantrone and relatives); *Streptomyces* family (e.g., Bleomycin, Mitomycin C, Actinomycin, Plicamycin); and Ultraviolet light.

In certain embodiments, the DNA-PK inhibitor is a compound of Formula (B-I) (e.g., Compound B-1, Compound B-2, or Compound B-3, Compound C-1, Compound C-2, Compound C-3, or Compound C-4, and the DNA-damaging agent comprises chemotherapy. In certain embodiments, the DNA-PK inhibitor is a compound of Formula (B-I) (e.g., Compound B-1, Compound B-2, or Compound B-3, Compound C-1, Compound C-2, Compound C-3, or Compound C-4, and the DNA-damaging agent is a Topo I inhibitor or a Topo II inhibitor selected from the group consisting of Camptothecin, Topotecan, Irinotecan/SN38, Rubitecan, Belotecan, Etoposide, Daunorubicin, a doxorubicin agent, Aclarubicin, Epirubicin, Idarubicin, Amrubicin, Pirarubicin, Valrubicin, Zorubicin, and Teniposide. In certain embodiments, the DNA-PK inhibitor is a compound of Formula (B-I) (e.g., Compound B-1, Compound B-2, or Compound B-3, Compound C-1, Compound C-2, Compound C-3, or Compound C-4, and the DNA-damaging agent is a doxorubicin agent. In certain embodiments, the DNA-PK inhibitor is a compound of Formula (B-I) (e.g., Compound B-1, Compound B-2, or Compound B-3, Compound C-1, Compound C-2, Compound C-3, or Compound C-4, and the DNA-damaging agent is Doxorubicin HCl liposome (e.g., PLD, DOXIL®). In certain embodiments, the DNA-PK inhibitor is Compound B-1, a pharmaceutically acceptable salt of Compound B-1, Compound B-2, or a pharmaceutically acceptable salt of Compound B-2, and the DNA-damaging agent is Doxorubicin HCl liposome (e.g., PLD, DOXIL®).

In certain embodiments, the DNA-PK inhibitor is CC-115, and the DNA-damaging agent comprises chemotherapy. In certain embodiments, the DNA-PK inhibitor is CC-115, and the DNA-damaging agent is a Topo I inhibitor or a Topo II inhibitor selected from the group consisting of Camptothecin, Topotecan, Irinotecan/SN38, Rubitecan, Belotecan, Etoposide, Daunorubicin, a doxorubicin agent, Aclarubicin, Epirubicin, Idarubicin, Amrubicin, Pirarubicin, Valrubicin, Zorubicin, and Teniposide. In certain embodiments, the DNA-PK inhibitor is CC-115 and the DNA-damaging agent is a doxorubicin agent. In certain embodiments, the DNA-PK inhibitor is CC-115, and the DNA-damaging agent is Doxorubicin HCl liposome injection (e.g., PLD, DOXIL®).

In certain embodiments, the methods described herein can optionally by used in combination with radiation therapy. Examples of radiation therapy include, but are not limited to, ionizing radiation, gamma-radiation, neutron beam radiotherapy, electron beam radiotherapy, proton therapy, brachytherapy, systemic radioactive isotopes and radiosensitizers. Radiosensitizers work in various different ways, including, but not limited to, making cancer cells more sensitive to radiation, working in synergy with radiation to provide an improved synergistic effect, acting additively with radiation, or protecting surrounding healthy cells from damage caused by radiation. As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject. In some embodiments, radiation therapy that is used in combination with the methods described herein is ionizing radiation. In some embodiments, the subject in need thereof is exposed to radiation therapy after administration of the DNA-damaging agent. In some embodiments, the subject in need thereof is exposed to radiation therapy about 10 minutes to about 20 minutes after administration of the DNA-damaging agent. In some embodiments, the subject in need thereof is exposed to radiation therapy about 15 minutes after administration of the DNA-damaging agent.

Dosages of DNA-Damaging Agent and DNA-PK Inhibitor

In general, any effective dose of a DNA-PK inhibitor and DNA-damaging agent may be administered. Various dosing strategies can be used (e.g., a flat-fixed dosing or body surface area based dosing), depending on the pharmacology of the DNA-PK inhibitor and DNA-damaging agent used. In some embodiments, a DNA-PK inhibitor when used in a combination therapy with a DNA-damaging agent, as described herein, is administered at a dosage range of between about 0.5 mg to about 20 mg, between about 20 mg to about 50 mg, between about 50 mg to about 4000 mg, between about 50 mg and about 3000 mg, between about 50 mg and about 2400 mg, between about 60 mg and about 240 mg, between about 60 mg and about 180 mg, between about 60 mg and about 120 mg, between about 80 mg and about 120 mg, between about 90 mg and about 120 mg, between about 80 mg and about 100 mg, or between about 120 mg and about 2000 mg. In some embodiments, the the DNA-PK inhibitor is administered at about 60 mg, 120 mg, 240 mg, or 480 mg. In some embodiments, the various foregoing embodiments are applicable for Compound B-1 or Compound B-2, including salts and co-crystals thereof, in the methods described herein.

In some embodiments, the DNA-PK inhibitor when used in a combination therapy with a DNA-damaging agent, as described herein, is administered at a dosage of between about 50 mg/m$^2$ and about 300 mg/m$^2$, between about 50 mg/m$^2$ and about 240 mg/m$^2$, between about 60 mg/m$^2$ and about 240 mg/m$^2$, between about 60 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, or between about 80 mg/m$^2$ and about 100 mg/m$^2$. In some embodiments, a DNA-PK inhibitor may be administered at a dosage range between about 20 mg/m$^2$ and about 300 mg/m$^2$ (e.g., about 240 mg/m$^2$). In certain embodiments, a DNA-PK inhibitor may be administered at a dosage between about 20 mg/m$^2$ and about 100 mg/m$^2$ (e.g., about 40 or 50 mg/m$^2$). In certain embodiments, a DNA-PK inhibitor may be administered at a dosage between about 20 mg/m$^2$ and about 50 mg/m$^2$ (e.g., about 40 or 50 mg/m$^2$). In certain embodiments, a DNA-PK inhibitor may be administered at a dosage about 30, 40, or 50 mg/m$^2$. In some instances, a DNA-PK inhibitor may be administered at a dosage between about 60 mg/m$^2$ and about 180 mg/m$^2$ (e.g., 120 mg/m$^2$). In certain cases, a DNA-PK inhibitor may be administered at a dosage between about 80 mg/m$^2$ and about 100 mg/m$^2$ (e.g., about 90 mg/m$^2$). In some embodiments, DNA-PK inhibitor may be administered at a dosage of about 90 mg/m$^2$ or about 120 mg/m$^2$.

In some embodiments, a DNA-damaging agent when used in a combination therapy with a DNA-PK inhibitor as described herein, is administered at 50 mg/m$^2$ every 4 weeks for 4 cycles minimal, is administered at 30 mg/m$^2$ every 3 weeks, or is administered 30 mg/m$^2$ on day 4 following bortezomib which is administered at 1.3 mg/m$^2$ on days 1, 4, 8 and 11, every 3 weeks. In some embodiments, a DNA-damaging agent when used in a combination therapy with a DNA-PK inhibitor as described herein, is administered at a dosage range of between about 20 and about 100 mg/m$^2$ (e.g., about 40 or 50 mg/m$^2$). In certain embodiments, a DNA-damaging agent is administered at a dosage between about 20 mg/m$^2$ and about 60 mg/m$^2$ (e.g., about 40 or 50 mg/m$^2$). In certain embodiments, a DNA-damaging agent is administered at a dosage about 30, 40, or 50 mg/m$^2$. In certain embodiments, a DNA-damaging agent is administered at a dosage about 40 mg/m$^2$. In certain embodiments, a DNA-damaging agent is administered at a dosage about 50 mg/m$^2$. In some embodiments, the foregoing embodiments are applicable to doxorubicin agents (e.g., doxorubicin hydrochloride or pegylated liposomal doxorubicin).

In some embodiments, a DNA-damaging agent when used in a combination therapy with a DNA-PK inhibitor as described herein, may be administered at a target AUC of between about 3 and about 6, between about 3.5 and about 6, between about 4 and about 6, between about 4 and about 5.5, or between about 4 and about 5. In some embodiments, a DNA-damaging agent may be administered with at a target AUC of between about 3 and about 6. In certain embodiments, a DNA-damaging agent may be administered with at a target AUC of between about 4 and about 5. As used herein, the term "target AUC" refers the target area under the plasma concentration versus time curve. The dosage of certain DNA-damaging agents may be determined from the drug label information. For example, the dosage in mg of the DNA-damaging agent may be determined from the target AUC based on mathematical formula, which is based on a patient's pre-existing renal function or renal function and desired platelet nadir. The Calvert formula, shown below, is used to calculate dosage in milligrams, based upon a patient's glomerular filtration rate (GFR in mL/min) and carboplatin target area under the concentration versus time curve (AUC in mg/mL·min). GFR may be measured using $^{51}$Cr-EDTA clearance or may be estimated using methods known to ordinary skill in the art.

Total Dose (mg)=(target AUC)×(GFR+25)

It should be understood that all combinations of the above-referenced ranges for dosage of DNA-PK inhibitor and dosage of a DNA-damaging agent for use in a combination therapy, as described herein, may be possible. For instance, in some embodiments, a DNA-damaging agent is administered at a dosage between about 20 to about 50 mg/$^2$ (e.g., about 30, 40, or 50 mg/m$^2$) and a DNA-PK inhibitor is administered with a dosage between about 120 mg and about 4000 mg/m (e.g., between about 60 mg and about 300 mg, between about 120 mg and about 600 mg, between about 240 and about 800 mg). In some embodiments, a DNA-damaging agent may be administered with at a target AUC of between about 3 and about 6 (e.g., between about 4 and about 6, between about 4 and about 5) and a DNA-PK inhibitor may be administered with at a dosage between about 50 mg and about 300 mg (e.g., between about 60 mg and about 180 mg, between about 80 mg and about 100 mg).

In other embodiments, the DNA-PK inhibitor may be administered at a dosage of between about 50 mg/m$^2$ and about 500 mg/m$^2$, between about 100 mg/m$^2$ and about 500 mg/m$^2$, between about 120 mg/m$^2$ and about 500 mg/m$^2$, between about 240 mg/m$^2$ and about 480 mg/m$^2$, between about 50 mg/m$^2$ and about 480 mg/m$^2$, between about 50 mg/m$^2$ and about 300 mg/m$^2$, between about 50 mg/m$^2$ and about 240 mg/m$^2$, or between about 50 mg/m$^2$ and about 120 mg/m$^2$. In some embodiments, DNA-PK inhibitor may be administered at a dosage of about 20 mg/m$^2$, 30 mg/m$^2$, 40 mg/m$^2$, 50 mg/m$^2$, 60 mg/m$^2$, about 120 mg/m$^2$, about 240 mg/m$^2$, or 480 mg/m$^2$. In some embodiments, DNA-PK inhibitor may be administered at a dosage of about 240 mg/m$^2$ or about 480 mg/m$^2$.

Pharmaceutically Acceptable Salts, Solvates, Clathrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. Quaternization of any basic nitrogen-containing groups of the compounds disclosed is also contemplated herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethyl enediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethyl ammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

Mixtures/combinations of different pharmaceutically acceptable salts and also mixtures/combinations of compounds in free form and pharmaceutically acceptable salts are also contemplated herein.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs include, but are not limited to, analogs or derivatives of compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —$NO_2$, —ONO, or —$ONO_2$ moieties. Prodrugs can typically be prepared using well-known methods, such as those described by Burger's Medicial Chemistry and Drug Discovery (1995) 172-178, 949-982 (Manfred E. Wolff ed., 5th ed).

Co-Crystals

Any of the compounds described herein, e.g., the free form, pharmaceutically acceptable salts, solvates, clathrates, prodrugs, and other derivatives, may exist as co-crystals with a co-crystal former (CCF). In the co-crystals, both the compound and the CCF are in the solid state (e.g., crystalline) and are bonded non-covalently (e.g., by hydrogen bonding). Exemplary co-crystal formers (CCF) include, but are not limited to, adipic acid, citric acid, fumaric acid, maleic acid, succinic acid, or benzoic acid. It is understood that compounds, unless explicitly stated, encompass the co-crystal form. For example, reference to Compound B-2 may encompass the co-crystal form, unless stated otherwise.

Methods for preparing and characterizing a co-crystals are well documented in the literature. See, e.g., Trask et al., *Chem. Commun.*, 2004, 890-891; and 0. Almarsson and M. J. Zaworotko, *Chem. Commun.*, 2004, 1889-1896. These methods in general are also suitable for preparing and characterizing co-crystals of compounds described herein.

Examples of preparing co-crystals include hot-melt extrusion, ball-milling, melting in a reaction block, evaporating solvent, slurry conversion, blending, sublimation, or modeling. In the ball-milling method, certain molar ratios of the components of the co-crystal (e.g., a compound of interest and a CCF) are mixed and milled with balls. Optionally, a solvent such as methyl ethyl ketone, chloroform, and/or water can be added to the mixture being ball milled. After milling, the mixture can be dried under vacuum either at the room temperature or in the heated condition, which typically gives a powder product. In the melting method, the components of a co-crystal (e.g., a CCF and a compound of interest) are mixed, optionally with a solvent such as acetonitrile. The mixture is then placed in a reaction block with the lid closed, and then heated to the endotherm. The resulting mixture is then cooled off and solvent, if used, removed. In the solvent-evaporation method, each component of a co-crystal is first dissolved in a solvent (e.g., a solvent mixture, such as methanol/dichloromethane azeotrope, or toluene/acetonitrile (e.g., 50/50 by volume)), and the solutions are then mixed together. The mixture is then allowed to sit and solvent to evaporate to dryness, to yield the co-crystal. In the hot-melt extrusion (HME) method, a new material (the extrudate) is formed by forcing it through an orifice or die (extruder) under controlled conditions, such as temperature, mixing, feed-rate and pressure. An extruder typically comprises a platform that supports a drive system, an extrusion barrel, a rotating screw arranged on a screw shaft and an extrusion die for defining product shape. Alternatively, the extrusion die can be removed and the product can be shaped by other means. Typically, process parameters are controlled via connection to a central electronic control unit. The extrusion drive system generally comprises motor, gearbox, linkage and thrust bearings, whereas the barrel and screw is commonly utilized in a modular configuration. Any suitable HME technologies known in the art, for example, Gavin P. Andrews et al., "Hot-melt extrusion: an emerging drug delivery technology", *Pharmaceutical Technology Europe*, volume 21, Issue 1 (2009), may be used. In one embodiment, the co-crystals are prepared by hot-melt extrusion.

Examples of characterization methods include thermogravimetric analysis (TGA), differential scanning calorimetry (DSC), X-ray powder diffraction (XRPD), solid-state nuclear magnetic resonance spectroscopy (ss-NMR), solubility analyses, dynamic vapor sorption, infrared off-gas analysis, and suspension stability. TGA can be used to investigate the presence of residual solvents in a co-crystal sample and to identify the temperature at which decomposition of each co-crystal sample occurs. DSC can be used to look for thermotransitions occurring in a co-crystal sample as a function of temperature and determine the melting point of each co-crystal sample. XRPD can be used for structural characterization of the co-crystal. Solubility analysis can be performed to reflect the changes in the physical state of each co-crystal sample. Suspension stability analysis can be used to determine the chemical stability of a co-crystal sample in a solvent.

In certain embodiments, the DNA-PK inhibitor is in the form of a co-crystal.

In certain embodiments, the DNA-PK inhibitor is a compound of Formula (B-I) (e.g., Compound B-1, Compound B-2, or Compound B-3, Compound C-1, Compound C-2, Compound C-3, or Compound C-4, which is the form of a co-crystal. In certain embodiments, the DNA-PK inhibitor is Compound B-2, which is the form of a co-crystal. In certain embodiments, the DNA-PK inhibitor is CC-115, which is in the form of a co-crystal.

In certain embodiments, the DNA-PK inhibitor is in the form of a co-crystal with the CCF adipic acid, citric acid, fumaric acid, maleic acid, succinic acid, or benzoic acid, wherein the co-crystal is a solid at the room temperature and the compound and CCF interact by noncovalent bonds. In certain embodiments, the non-covalent bond interactions between the compound and CCF include hydrogen bonding and van der Waals interactions. In one embodiment, the CCF is adipic acid.

In certain embodiments, the DNA-PK inhibitor is a co-crystal comprising a Compound B-1, or a pharmaceutically acceptable salt thereof, and a co-crystal former (CCF) selected from adipic acid, citric acid, fumaric acid, maleic acid, succinic acid, and benzoic acid. In certain embodiments, the CCF is adipic acid. In certain embodiments, the DNA-PK inhibitor is a co-crystal comprising a Compound B-2, or a pharmaceutically acceptable salt thereof, and a co-crystal former (CCF) selected from adipic acid, citric acid, fumaric acid, maleic acid, succinic acid, and benzoic acid. In certain embodiments, the CCF is adipic acid. Preparation and characterization of co-crystals of Compounds B-1 and B-2 are disclosed in PCT Publication No. WO 2015/058067, incorporated herein by reference in its entirety.

In certain embodiments, the DNA-PK inhibitor is Compound B-2, and the compound is the form of a co-crystal of the formula (Compound B-2)$_n$:(AA)$_m$, wherein n is 1 and m is between 0.4 and 2.1. In one embodiment, n is 1 and m is between 0.9 and 3.1. In certain embodiment, n is about 2 and m is about 1. In certain embodiments, the co-crystal is of Compound B-2 and CCF adipic acid, wherein the molar ratio of Compound B-2 to adipic acid is about 2:1.

In certain embodiments, the co-crystal of Compound B-2 and CCF adipic acid is in polymorphic Form A or B. Polymorphic Forms A and B are two conformational polymorphs of the adipic acid co-crystal of Compound B-2.

In a specific embodiment, the polymorphic Form A is characterized by $^{13}$C solid state nuclear magnetic resonance spectroscopy peaks at about 117.1, 96.8, 95.7, 27.6, 14.8 ppm. In another specific embodiment, the polymorphic Form A is characterized by $^{13}$C solid state nuclear magnetic resonance spectroscopy peaks at about 161.6, 154.5, 117.1, 96.8, 95.7, 51.5, 50.2, 27.6, 25.6, 18.5, and 14.8 ppm. In yet another specific embodiment, the polymorphic Form A is characterized by $^{13}$C solid state nuclear magnetic resonance spectroscopy peaks at about 179.4, 168.4, 161.6, 158.3, 154.5, 147.8, 145.7, 143.2, 141.8, 124.6, 117.1, 96.8, 95.7, 51.5, 50.2, 31.2, 30.1, 27.6, 25.6, 18.5, and 14.8 ppm.

In a specific embodiment, the polymorphic Form B is characterized by $^{13}$C solid state nuclear magnetic resonance spectroscopy peaks at about 117.9, 97.3, 94.0, 26.7, and 15.7 ppm. In another specific embodiment, the polymorphic Form B is characterized by $^{13}$C solid state nuclear magnetic resonance spectroscopy peaks at about 161.7, 153.8, 117.9, 97.3, 94.0, 50.7, 25.3, 26.7, 18.8, and 15.7 ppm. In yet another specific embodiment, the polymorphic Form B is characterized by $^{13}$C solid state nuclear magnetic resonance spectroscopy peaks at about 179.1, 168.3, 158.1, 147.2, 142.4, 125.8, 124.5, 117.9, 97.3, 94.0, 32.3, 30.1, 26.7, and 15.7 ppm.

In yet another embodiment, the co-crystal of Compound B-2 and CCF adipic acid is in a mixture of polymorphic Forms A and B.

Co-crystals of a compound and CCF may be in an isolated, pure form, or in a mixture as a solid composition when admixed with other materials, for example, free form of a compound or free CCF. In one embodiment, provided are pharmaceutically acceptable compositions comprising the co-crystals of a compound and the CCF described above and an additional free CCF. In a specific embodiment, the compositions comprise the co-crystals of Compound B-2 and CCF adipic acid described above and additional adipic acid. In some specific embodiments, the overall molar ratio of the compound to CCF (both part of the co-crystals and free CCF, e.g., adpic acid in the co-crystals and free adipic acid) in such compositions is in a range from about 1:0.55 to about 1:100. In other specific embodiments, the overall molar ratio of the compound to CCF in such compositions is in a range from about 1:0.55 to about 1:50. In other specific embodiments, the overall molar ratio of the compound to CCF in such compositions is in a range from about 1:0.55 to about 1:10. In some specific embodiments, the overall weight ratio of the compound to CCF in such compositions is in a range from about 85 wt %:15 wt % to about 60 wt %:40 wt %. In other specific embodiments, the overall weight ratio of the compound to CCF is in a range from about 70 wt %:30 wt % to about 60 wt %:40 wt %. In yet other embodiments, the overall weight ratio of the compound to CCF is about 65 wt %:35 wt %.

In another embodiment, provided are eutectic solid compositions comprising: (a) a co-crystal comprising a compound and a CCF which is adipic acid, and wherein the molar ratio of the compound to adipic acid is about 2 to 1; and (b) adipic acid. As used herein, the term "eutectic solid" means a solid material resulting from a eutectic reaction known in the art. Without being bound to a particular theory, an eutectic reaction is defined as follows:

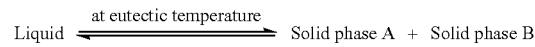

In the euctection reaction, a single liquid phase and two solid phases all co-exist at the same time and are in chemical equilibrium. It forms a super-lattice or microstructure on cooling which releases at once all its components into a liquid mixture (melts) at a specific temperature (the eutectic temperature).

In one embodiment, the overall weight ratio of the compound to adipic acid in the eutectic solid compositions is in a range from about 70 wt %:30 wt % to about 60 wt %:40 wt %. In yet another embodiment, the overall weight ratio of the compound to adipic acid is in a range from about 65 wt %:35 wt %. In yet another embodiment, the molar ratio of the co-crystal of a compound to adipic acid is about 1 to 1.03.

The pure form means that the particular co-crystal or polymorphic form comprises over 95% (w/w), for example, over 98% (w/w), over 99% (w/w %), over 99.5% (w/w), or over 99.9% (w/w).

More specifically, provided are pharmaceutically acceptable compositions where each of the co-crystals or polymorphic forms are in the form of a composition or a mixture of the polymorphic form with one or more other crystalline, solvate, amorphous, or other polymorphic forms or their combinations thereof. For example, in one embodiment, the compositions comprise Form A of the adipic acid co-crystal of Compound B-2 along with one or more other polymorphic forms of Compound B-2, such as amorphous form, hydrates, solvates, and/or other forms or their combinations thereof. In a specific embodiment, the compositions comprise Form A of the adipic acid co-crystal of Compound B-2 along with Form B of the adipic acid co-crystal of Compound B-2. More specifically, the composition may comprise from trace amounts up to 100% of the specific polymorphic form or any amount, for example, in a range of 0.1%-0.5%, 0.1%-1%, 0.1%-2%, 0.1%-5%, 0.1%-10%, 0.1%-20%, 0.1%-30%, 0.1%-40%, 0.1%-50%, 1%-50%, or 10%-50% by weight based on the total amount of the compound in the composition. Alternatively, the composition may comprise at least 50%, 60%, 70%, 80%, 90%, 95%, 97%, 98%, 99%, 99.5% or 99.9% by weight of specific polymorphic form based on the total amount of the compound in the composition.

In certain embodiments, the the co-crystal is administered in a range of about 50 mg to about 200 mg per day, inclusive; a range of about 50 mg to about 2000 mg per day, inclusive; or a range of about 100 mg to about 1500 mg per day, inclusive.

Therapeutic Uses

The present disclosure provides a method of treating diseases, disorders, and conditions characterized by excessive or abnormal cell proliferation, including proliferative or hyperproliferative diseases, in a subject. A "proliferative disease" refers to a disease that occurs due to abnormal growth or extension by the multiplication of cells. See, e.g., Walker, *Cambridge Dictionary of Biology*; Cambridge University Press: Cambridge, UK, 1990. A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include, but are not limited to, cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL)), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familial hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the term "cancer" includes, but is not limited to the following types of cancers: oral, lung, gastrointestinal, genitourinary tract, liver, bone, nervous system, gynecological, skin, thyroid gland, or adrenal gland. More specifically, "cancer" includes, but is not limited to the following cancers: oral cancer: buccal cavity cancer, lip cancer, tongue cancer, mouth cancer, pharynx cancer; cardiac cancer: sarcoma (angiosarcoma, fibrosarcoma, rhabdomyosarcoma, liposarcoma), myxoma, rhabdomyoma, fibroma, lipoma or teratoma; lung cancer: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, or mesothelioma; gastrointestinal cancer: esophageal cancer (squamous cell carcinoma, larynx, adenocarcinoma, leiomyosarcoma, lymphoma), stomach cancer (carcinoma, lymphoma, leiomyosarcoma), pancreatic cancer (ductal adenocarcinoma, insulinoma, glucagonoma, gastrinoma, carcinoid tumors, vipoma), small bowel or small intestinal cancer (adenocarcinoma, lymphoma, carcinoid tumors, Karposi's sarcoma, leiomyoma, hemangioma, lipoma, neurofibroma, fibroma), large bowel or large intestinal cancer (adenocarcinoma, tubular adenoma, villous adenoma, hamartoma, leiomyoma), colon cancer, colon-rectum cancer, colorectal cancer, or rectal cancer; genitourinary tract cancer: kidney cancer (adenocarcinoma, Wilm's tumor [nephroblastoma], lymphoma), bladder cancer and urethral cancer (squamous cell carcinoma, transitional cell carcinoma, adenocarcinoma), prostate (adenocarcinoma, sarcoma), testicular cancer (seminoma, teratoma, embryonal carcinoma, teratocarcinoma, choriocarcinoma, sarcoma, interstitial cell carcinoma, fibroma, fibroadenoma, adenomatoid tumors, lipoma); liver cancer: hepatoma (hepatocellular carcinoma), cholangiocarcinoma, hepatoblastoma, angiosarcoma, hepatocellular adenoma, hemangioma, or biliary passages cancer; bone cancer: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma or giant cell tumors; nervous system cancer: skull cancer (osteoma, hemangioma, granuloma, xanthoma, osteitis deformans), meninges cancer (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, or meningioma, glioma, sarcoma); gynecological cancer: uterine cancer (endometrial carcinoma), cervical cancer (cervical carcinoma, pre-tumor cervical dysplasia), ovarian cancer (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulval cancer (squamous cell carcinoma, intraepithelial carcinoma, adenocarcinoma, fibrosarcoma, melanoma), vaginal cancer (clear cell carcinoma, squamous cell carcinoma, botryoid sarcoma (embryonal rhabdomyosarcoma), fallopian tube cancer (carcinoma), or breast cancer; skin cancer: malignant melanoma, basal cell carcinoma, squamous cell carcinoma, Karposi's sarcoma, keratoacanthoma, moles dysplastic nevi, lipoma, angioma, dermatofibroma, or keloids; thyroid gland cancer: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, or paraganglioma; or adrenal glands cancer: neuroblastoma.

In other embodiments, the cancer is lung cancer (e.g., non-small cell lung cancer, small cell lung cancer), head and neck cancer, pancreatic cancer, breast cancer (e.g., triple negative breast cancer), gastric cancer, brain cancer, endometrial cancer, pancreatic cancer, biliary tract cancer, bladder cancer, colorectal cancer, glioblastoma, esophageal cancer, hepatocellular carcinoma, or ovarian cancer.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

As generally described herein, the method comprises administering to a subject in need thereof a DNA-damaging agent, and between about 8 and about 48 hours later administering to the subject a DNA-PK inhibitor. In some embodiments, the DNA-PK inhibitor is administered between about 8 and about 30 hours after administration of the DNA damaging agent. In some embodiments, the DNA-PK inhibitor is administered between about 8 and about 20 hours after administration of the DNA damaging agent. In some embodiments, the DNA-PK inhibitor is administered between about 10 and about 20 hours after administration of the DNA damaging agent. In some embodiments, the DNA-PK inhibitor is administered between about 12 and about 18 hours after administration of the DNA damaging agent. In some embodiments, the DNA-PK inhibitor is administered between about 14 and about 18 hours after administration of the DNA damaging agent. In some embodiments, the DNA-PK inhibitor is administered about 14 and about 16 hours after administration of the DNA damaging agent. In some embodiments, the DNA-PK inhibitor is administered about 16 hours after administration of the DNA damaging agent. In some embodiments, the DNA-damaging agent is chemotherapy.

A "subject" to which administration is contemplated includes, but is not limited to, humans; commercially relevant mammals such as cattle, pigs, horses, sheep, goats, cats, and/or dogs) and birds (e.g., commercially relevant birds such as chickens, ducks, geese, and/or turkeys). A subject in need of treatment is a subject identified as having a proliferative disorder i.e., the subject has been diagnosed by a physician (e.g., using methods well known in the art) as having a proliferative disorder (e.g., a cancer). In some embodiments, the subject in need of treatment is a subject suspected of having or developing a proliferative disorder, such as a subject presenting one or more symptoms indicative of a proliferative disorder. The term "subject in need of treatment" further includes people who once had a proliferative disorder but whose symptoms have ameliorated. For cancer, the one or more symptoms or clinical features depend on the type and location of the tumor. For example, lung tumors may cause coughing, shortness of breath, or chest pain. Tumors of the colon can cause weight loss, diarrhea, constipation, iron deficiency anemia, and blood in the stool. The following symptoms occur with most tumors: chills, fatigue, fever, loss of appetite, malaise, night sweats, and weight loss.

The terms "administer," "administering," or "administration," as used herein refers to implanting, absorbing, ingesting, injecting, or inhaling the one or more therapeutic agents.

As used herein, the terms "treatment," "treat," and "treating" refer to reversing, alleviating, delaying the onset of, or inhibiting the progress of proliferative disorder. In some embodiments, treatment may be administered after one or more signs or symptoms have developed or have been observed. In other embodiments, treatment may be administered in the absence of signs or symptoms of the proliferative disorder. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "tumor burden" has its ordinary meaning in the art and may refer to the number of cancer cells, the size of a tumor, or the amount of cancer in the body.

As used herein, the terms "about" has its ordinary meaning in the art. In some embodiments with respect to time, about may be within 50 minutes, within 40 minutes, within 30 minutes, within 20 minutes, within 10 minutes, within 5 minutes, or within 1 minute of (before and/or after) the specified time. In some embodiments with respect to dosage, about may be within 20%, within 15%, within 10%, within 5%, or within 1% of (under and/or above) the specified dosage.

A "therapeutically effective amount" refers to an amount sufficient to elicit the desired biological response, i.e., treating the proliferative disorder. "Effective amount" and "therapeutically effective amount" are used synonymously herein. As will be appreciated by those of ordinary skill in this art, the effective amount of the compounds described herein may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with neoplasia. For example, in the treatment of cancer, such terms may refer to a reduction in the size of the tumor.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

The compounds provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve a therapeutically effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, a therapeutically effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds provided herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Biological Samples

As inhibitors of the DNA-PK pathway, the compounds and compositions are also useful in biological samples. One aspect relates to inducing DNA damage and inhibiting DNA-PK in a biological sample, which method comprises contacting said biological sample with a DNA-damaging agent followed by contacting the sample about 8-48 hours later with a compound that inhibits DNA-PK activity. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inducing DNA damage followed by inhibition of DNA-PK activity in a biological sample is useful for a variety of purposes that are known to one of skill in the art. Examples of such purposes include, but are not limited to, blood transfusion, organ-transplantation, and biological specimen storage.

EXAMPLES

In light of the foregoing description, the specific non-limiting examples presented below are for illustrative purposes and not intended to limit the scope of the disclosure in any way.

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations which may be used herein:

| Abbreviation | Term |
|---|---|
| APCI | Atmospheric Pressure Chemical Ionization |
| ATCC | American Type Culture Collection |
| ATM | Ataxia telangiectasia mutated kinase |
| ATR | Ataxia telangiectasia and Rad3-related kinase |
| AUC | Area under the concentration versus time curve |
| bid | Twice a day |
| BQL | Below quantitation limit |
| DBS | Dried blood spot |
| ΔC | Change of tumor volume in control group |
| ΔT | Change of tumor volume in treatment group |
| DNA | Deoxyribonucleic acid |
| DNA-PK | DNA dependent protein kinase |
| DNA-PKcs | DNA dependent protein kinase catalytic subunit |
| DSB | Double stranded DNA break |
| HR | Homologous recombination |
| IR | Ionizing radiation |
| IP | Intraperitoneal |
| IV | Intravenous |
| LC/MS/MS | Liquid chromatography-mass spectrometry and liquid |

| Abbreviation | Term |
|---|---|
| | chromatography-tandem mass spectrometry |
| LLOQ | Lower limit of quantification |
| MRM | Multiple reaction monitoring |
| mTOR | Mammalian target of rapamycin |
| NHEJ | Non-homologous end joining |
| PLD | Pegylated liposomal doxorubicin (DOXIL ®) |
| PIKK | Phosphatidylinositol 3-kinase-related kinase |
| PO | Oral dose |
| qd | Once a day |
| SEM | Standard error of the mean |
| Ti | Tumor volume on treatment day |
| DMSO | Dimethyl sulfoxide |
| DMEM | Dulbecco's Modified Eagle Medium |
| pen/strep | Penicillin Streptomycin |
| NSCLC | Non-small cell lung cancer |
| SCLC | Small cell lung cancer |
| HEPES | 4-(2-hydroxyethyl)-1-piperazineethanesulfonic acid |
| L | Longest dimension of tumor |
| W | Shortest dimension of tumor |
| MC | Methylcellulose |
| ANOVA | One-Way Analysis of Variance |
| DOX | Doxorubicin |
| EC50 | Half maximal effective concentration |
| BSA | Bovine serum albumin |
| FBS | Fetal bovine serum |
| NA | Not Assessed |
| PC-1 | Primary culture-1 |
| PBS | Phosphate buffered saline |
| RT | Radiotherapy |
| TCA | Tumor chemosensitivity assay |
| CSC | Cancer stem cell |
| HCC | Hepatocellular carcinoma |
| IGRT | Image-guided radiotherapy |
| 5-FU | 5-fluorouracil |
| CR | Complete response |
| MTD | Maximum tolerated dose |
| MTV | Mean tumor volume |
| PR | Partial response |
| QW | Once weekly |
| RPM | Rotations per minute |
| SC | Subcutaneous(ly) |
| TFS | Tumor free survivors |
| TGI | Tumor growth inhibition |
| TV | Tumor volume |

Example 1: Compound B-2 CoX and Pegylated Liposomal Doxorubicin for Dosing

Compound B-2 Adipic Acid Co-Crystal.

Preparation and characterization of Compound B-2 adipic acid co-crystals are disclosed in WO 2015/058067, incorporated herein by reference. Methods of preparation and characterization are also provided below and herein.

Preparation of Compound B-2 CoX.

A 1 liter jacketed vessel (with overhead stirring) was charged with Compound B-2 (1.000 equiv.), adipic acid (2.614 equiv.), 1-propanol (122.564 equiv.) and the slurry stirred at 750 rpm. A seed of the co-crystal (0.5% co-crystal seed) was added and the reaction mixture stirred at 25° C. Co-crystal formation was monitored by removing aliquots and analyzing by Raman spectroscopy. After 114 hours it was determined that co-crystal formation was complete. The slurry was filtered using a 600 mL Medium porosity fritted funnel until the solvent level was even with the wet cake. The mother liquor was isolated, labeled and analyzed for content. The wet cake was then washed with 1-propanol. The wet cake solids were weighed and dried in a vacuum oven at 50° C. HPLC analyses indicated a stoichiometry of about 2:1 for Compound B-2 to adipic acid ("Compound B-2 CoX"). The co-crystal produced by this method generates a mixture of Polymorphic Form A and Form B co-crystal.

Figure 24:
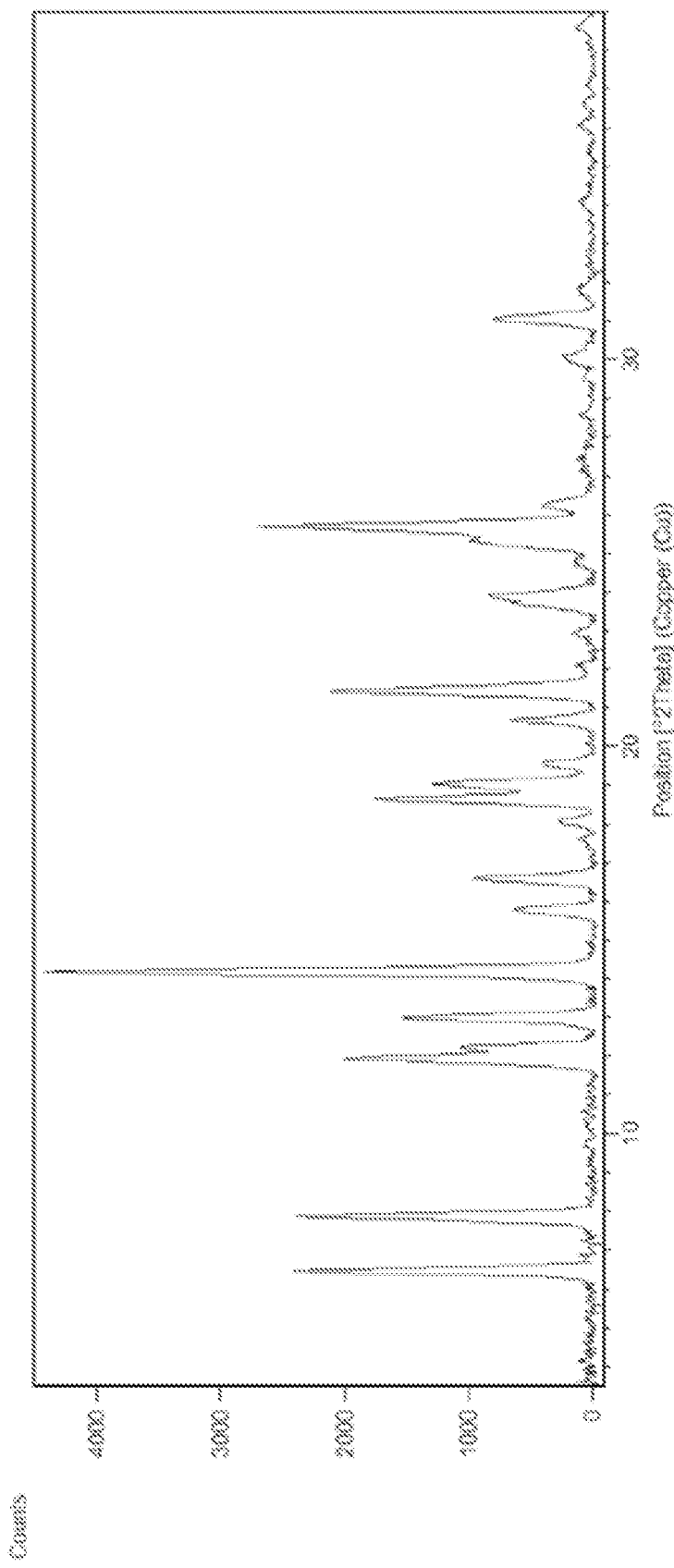

FIG. 24 shows an X-ray powder diffraction (XRPD) pattern of the co-crystal formed between Compound B-2 with adipic acid ("Compound B-2 CoX").

Figure 25:
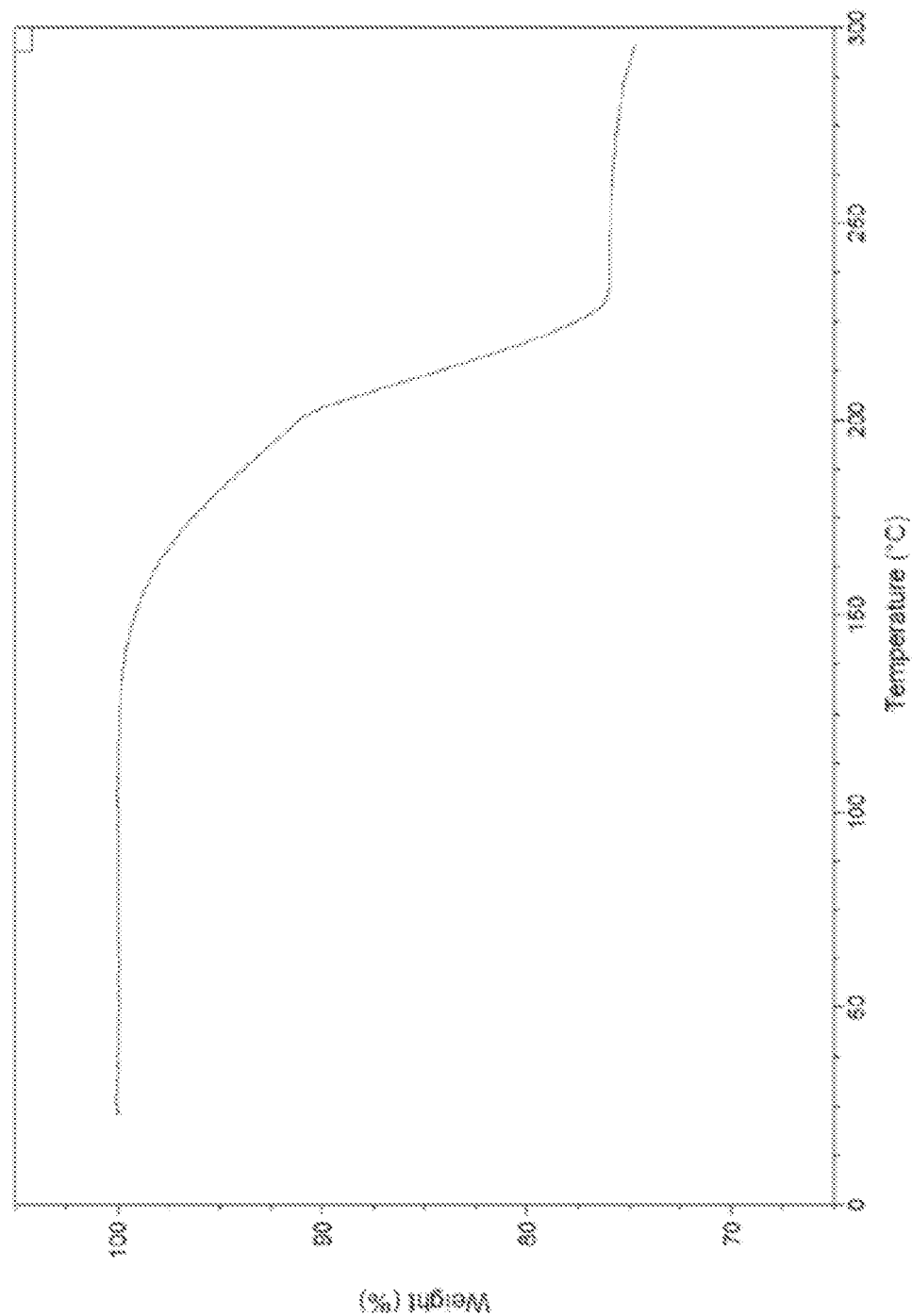
FIG. 25 depicts the thermo gravimetric analysis curves for the co-crystals of adipic acid and Compound B-2.

The thermo gravimetric analysis curves for the co-crystals of adipic acid and Compound B-2 ("Compound B-2 CoX") are shown in FIG. 25. The figures show loss of adipic acid starting at about 150° C. in both co-crystals.

Figure 26:
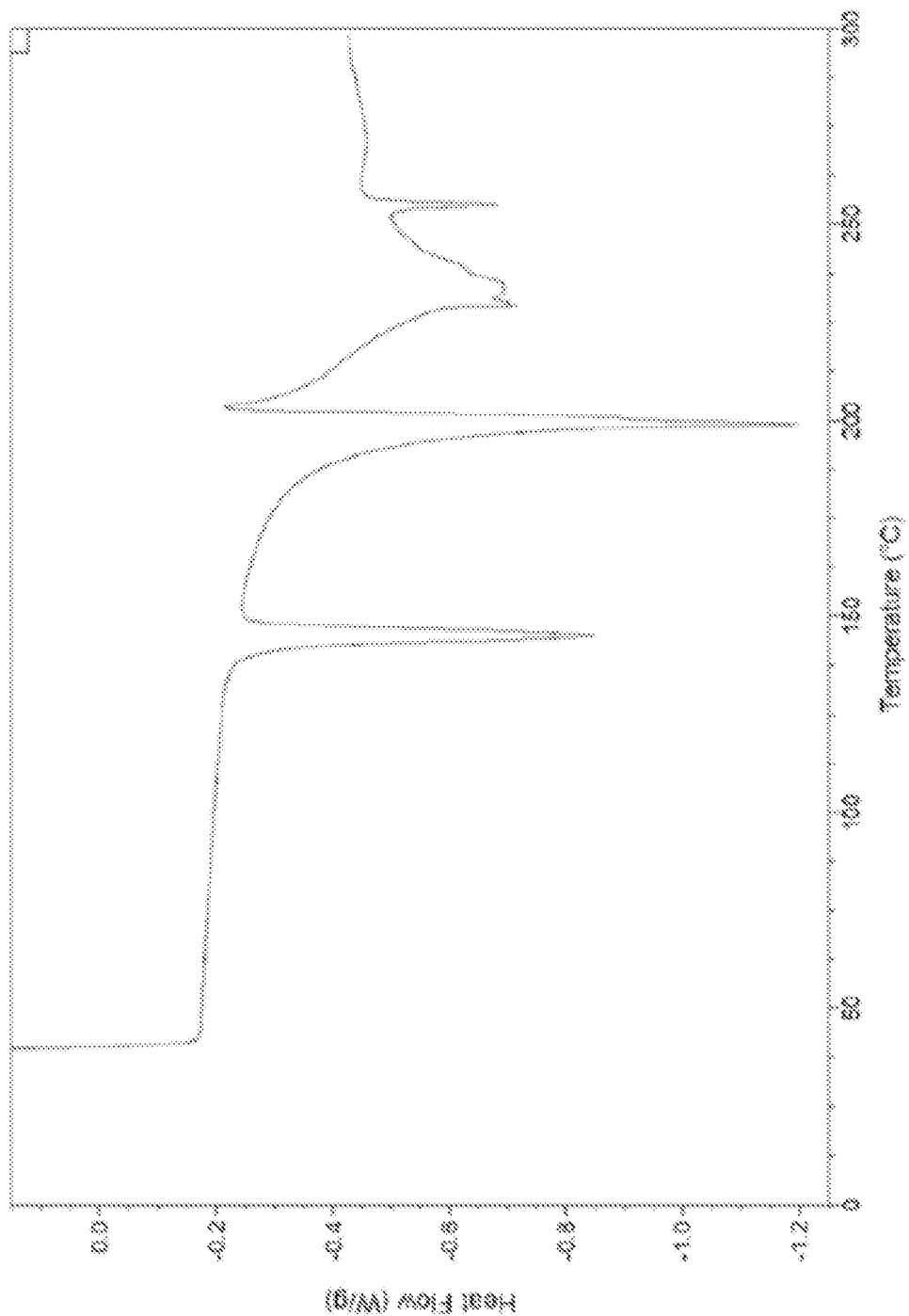
FIG. 26 depicts the differential scanning calorimetry thermogram for the co-crystals of Compound B-2 and adipic acid.

A representative differential scanning calorimetry thermogram is shown in FIG. 26 for the co-crystals of Compound B-2 and adipic acid ("Compound B-2 CoX").

Figure 27:
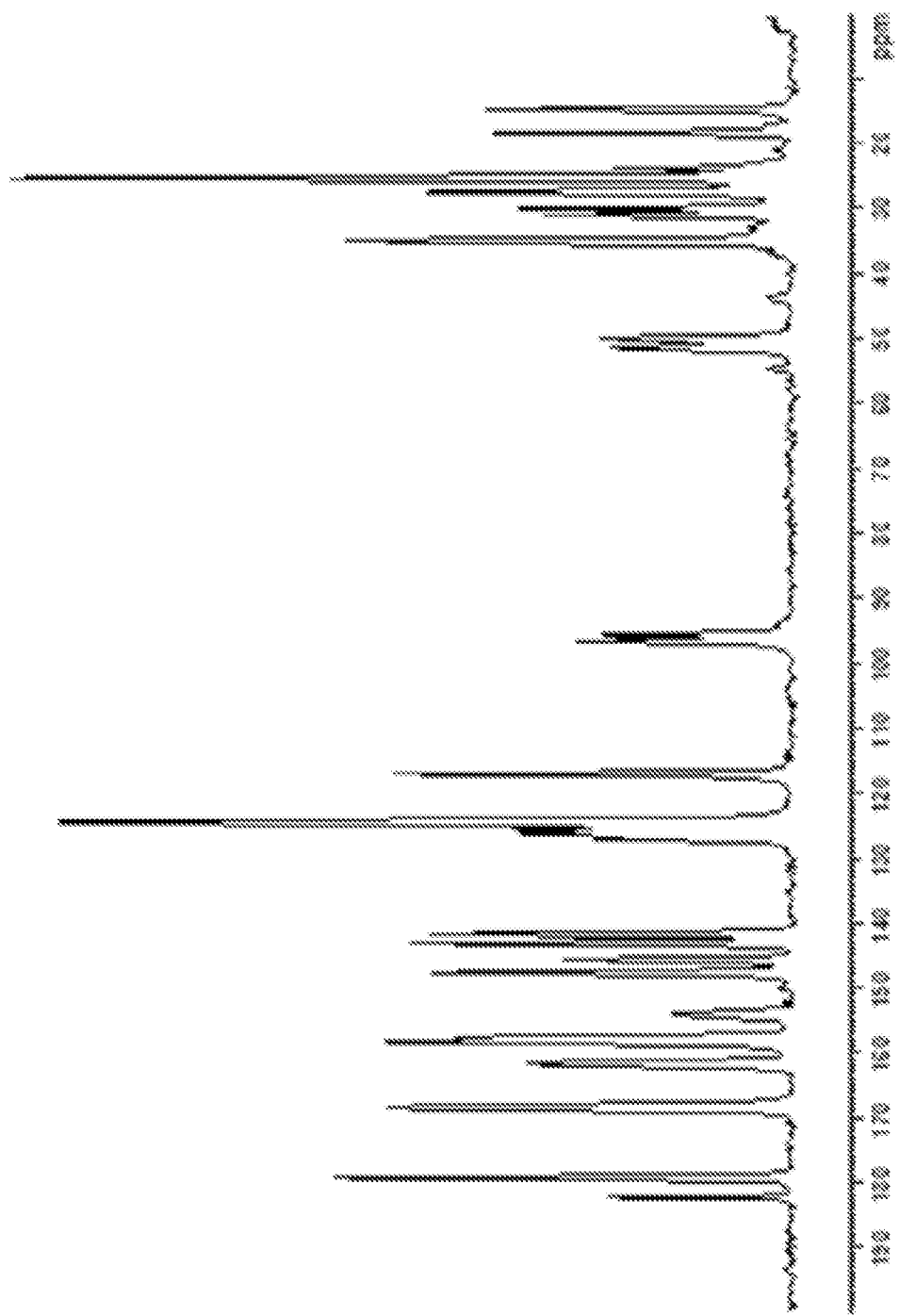
FIG. 27 depicts the solid state NMR spectra (ss-NMR) for co-crystal complexes of Compound B-2 with adipic acid.

Solid state NMR spectra (ss-NMR) were acquired on the Bruker-Biospin 400 MHz Advance III wide-bore spectrometer equipped with Bruker-Biospin 4 mm HFX probe. Approximately 70 mg of each sample was packed into full volume Bruker-Biospin 4 mm ZrO2 rotors. A magic angle spinning (MAS) speed of typically 12.5 kHz was applied. The temperature of the probe head was set to 275° K to minimize the effect of frictional heating during spinning. A relaxation delay of 30 s seconds was used for all experiments. The CP contact time of $^{13}$C CPMAS experiment was set to 2 ms. A CP proton pulse with linear ramp (from 50% to 100%) was employed. The Hartmann-Hahn match was optimized on external reference sample (glycine). SPINAL 64 decoupling was used with the field strength of approximately 100 kHz. The chemical shift was referenced against external standard of adamantane with its upfield resonance set to 29.5 ppm. Following washing with solvent, ss-NMR was used to investigate the co-crystal complexes of Compound B-2 with adipic acid ("Compound B-2 CoX"). See FIG. 27.

Figure 28:
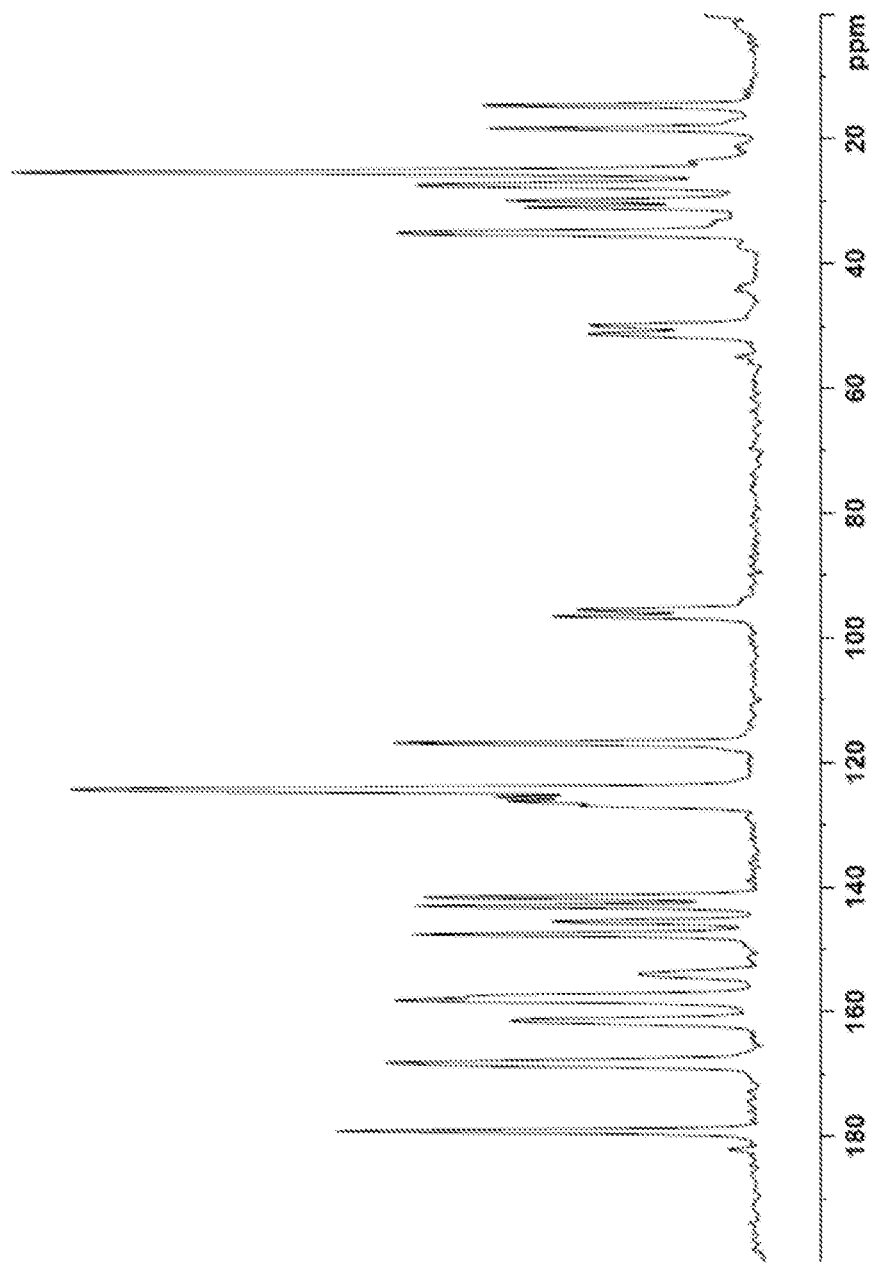
FIG. 28 depicts the $^{13}$C NMR spectrum of Form A of adipic acid co-crystal of Compound B-2.

Preparation of Polymorphic Form A of Adipic Acid Co-Crystal of Compound B-2:

322 mg of a mixture of Form A and Form B Compound B-2 CoX:adipic acid co-crystal prepared as described above and 221 mg of adipic acid were stirred in 9.8 g of acetone at 20 to 30° C. for 30 days. Approximately 50 mg of solid was isolated by filter centrifugation through a 0.45 m membrane filter using a centrifugal filter device and dried in vacuum at 20 to 30° C. for approximately 2 hours. The $^{13}$CNMR spectrum of Form A of adipic acid co-crystal of Compound B-2 is provided in FIG. 28.

Preparation of Polymorphic Form B of Adipic Acid Co-Crystal of Compound B-2:

A solvent mixture for spray drying was prepared by weighing out 50 g of methanol and 117.5 g dichloromehane into a glass bottle and shaking. 500 mg of Compound B-2, 176.2 mg of adipic acid and 19.3 g of the methanol dichloromethane mixture were weighed into a clear glass vial and stirred until all solids were dissolved. This solution was spray dried using a Buchi mini spray drier B-290 using following setting:

| Parameter | Setting |
|---|---|
| Inlet Temp | 99° C. |
| Aspirator | 100% |
| Pump | 40% |
| Condenser | −5° C. |
| Nozzle | 1 mm |
| Atomizer | 35 mm |
| Filter Pressure | −60 mbar |

Figure 29:
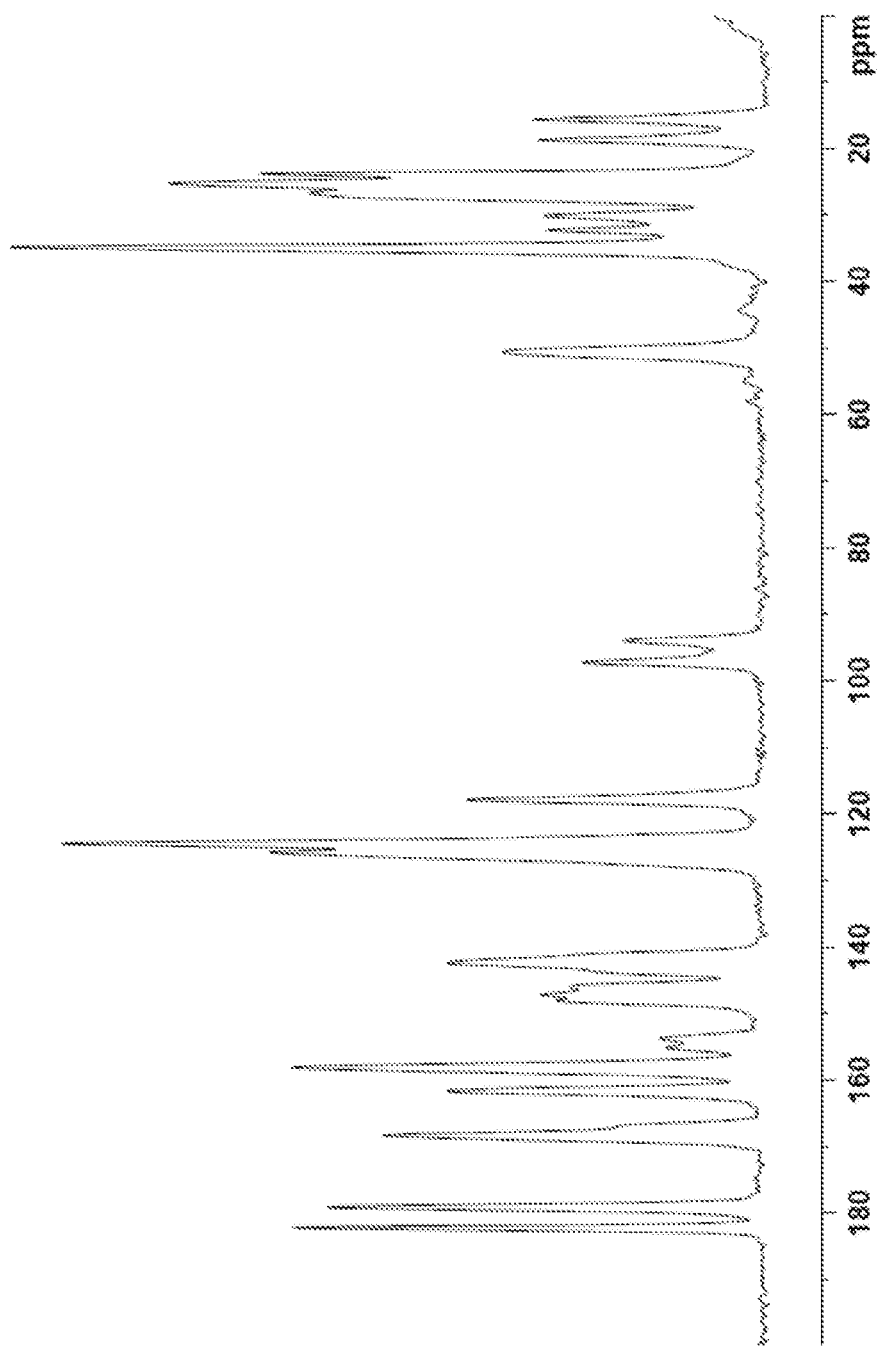
FIG. 29 depicts the $^{13}$C NMR spectrum of Form B of adipic acid co-crystal of Compound B-2.

The isolated material completely recrystallized at room temperature to Compound B-2:adipic acid co-crystal Form B over 2 months. The $^{13}$CNMR spectrum of Form B of adipic acid co-crystal of Compound B-2 is shown in FIG. 29.

Compound B-2 Adipic Acid Co-Crystal Suspension:

A unit dose suspension kit was prepared with "Compound B-2 CoX" (which is a 2:1 molar ratio of Compound B-2: adipic acid co-crystal, mixture of Form A and Form B) powder and vehicle, dose-adjusted to 8 mg/ml (doses <300 mg) or 50 mg/ml (doses ≥300 mg). Vehicle contains 0.5% methylcellulose (weight/volume [w/v]), 0.1% sodium benzoate, 0.1% benzoic acid. Polypropylene bottles with polyethylene caps were used for dispensing of both powder and vehicle. Compound B-2 CoX powder was supplied, with additional adipic acid stabilizer, as powder in containers, with two aliquots of dosing vehicle (0.5% methylcellulose, 0.1% sodium benzoate, 0.1% benzoic acid). One vehicle aliquot was added to the powder container, and the mixture was shaken to suspend. The additional aliquot of the vehicle was used to rinse the containers once more.

Pegylated Liposomal Doxorubicin (PLD):

PLD, supplied as single use vial: 20 mg/10 mL. Diluted PLD was refrigerated at 2 to 8° C.

Example 2: Effect of Duration and Timing of Compound B-2 Exposure of Sensitization of A549 Lung Cancer Cells to Doxorubicin Hydrochloride Cell Lines, Reagents, Equipment, Software:

The human cancer cell line A549 (CCL-185) was obtained from American Type Culture Collection (ATCC; Manassas, Va.). Compound B-2 used in these experiments was not prepared as a co-crystal. A 10 mM stock solution of Compound B-2 was prepared in DMSO (ATCC catalog #4-X) and stored at −20° C. Doxorubicin hydrochloride (dox) was obtained from Sigma (St. Louis, Mo.) (catalog #D1515), dissolved in DMSO to a 10 mM concentration and stored at −20° C.

Cell Culture:

The A549 human lung cancer cell line was cultured in DMEM (Life Technologies, catalog #11995) supplemented with 10% fetal bovine serum (Hyclone, catalog #SH30071.03), 1× GlutaMAX (Life Technologies, catalog #35050-061), pyruvate (Life Technologies, catalog #11360-070) and 1× Penicillin/Streptomycin (Life Technologies, catalog #15070) (complete medium). Cells were maintained at a sub-confluent state by passaging every 3-4 days. Cells were plated at 1000 cells per well in a 96-well, clear-bottomed microplate (Corning, catalog #3904), and incubated in a 37° C., 5% $CO_2$ incubator attach overnight prior to compound addition.

Treatment with Compound B-2 and Doxorubicin Hydrochloride:

Ten mM stocks of Compound B-2 and doxorubicin hydrochloride were made in DMSO and added in combination to the plated cells using an HP digital dispenser D300 (Tecan, Switzerland). For these experiments, combinations with Compound B-2 at all concentrations were run in singlicate using a combination matrix in which Compound B-2 was added as a titration from 20 µM to 0.1 µM on the X-axis of the plate and doxorubicin hydrochloride added in a 2-fold dilution from 80 nM to 0.125 nM for the 6 day and 24 hour co-incubation experiments and 8 nM to 0.0125 nM for the rest of the experiments on the Y-axis. One row contained only the Compound B-2 titration and one column only the doxorubicin hydrochloride titration. Two columns of cells were used as a no-treatment control from which the fractional survival of the treated cells was determined. Cells were cultured at 37° C., 5% $CO_2$, 95% air and 100% relative humidity. The timing of compound addition, the washout of the compounds from the wells of the plates and re-addition of doxorubicin hydrochloride was as detailed in FIG. 1. Briefly, the media from all of the wells in the plate were removed by hand using a multi-pipette, fresh (no compound) media was added, then removed again and then fresh media was added one last time. The re-addition of doxorubicin hydrochloride, where indicated, was performed using the HP D300 as outlined in FIG. 1. After 24 h, all plates were washed as detailed above and fresh medium (no compound) added. The plates were incubated for an additional 5 days (6 days in total).

Cell Viability Analysis:

Six days after initial compound addition, 50 µL of Cell-TiterGlo (prepared according to manufacturer's protocol) was added to each well of the compound titration plates. Luminescence was read on a Pherastar FS luminescence reader (BMG Labtech, Offenberg, Germany) and these values were used for all further analyses.

Computational Methods:

Cell viabilities were evaluated for a matrix of doxorubicin hydrochloride and Compound B-2 concentrations in a series of experiments testing different times of Compound B-2 addition and durations of Compound B-2 exposure. The data from each of these experiments were analyzed separately. The steps in the analysis of each experiment are described below.

1. For each Compound B-2 concentration, the $EC_{50}$ of doxorubicin hydrochloride was calculated using Prism software. The concentration in the matrix of doxorubicin hydrochloride concentrations closest to the $EC_{50}$ was then identified.

2. The fraction inhibition expected using an additive model was calculated for each combination of Compound B-2 concentration and the doxorubicin hydrochloride concentration closest to the corresponding doxorubicin EC50 (from step #1) using the following formula (Bliss C I (1939) The toxicity of poisons applied jointly. *Ann Appl Boil* 26:585-615):

$$I_{add}=I_x+I_y-I_x*I_y$$

where $I_x$ is the fraction inhibition by incubating cells with Compound B-2 alone, $I_y$ is the fraction inhibition by incubating cells with doxorubicin hydrochloride alone and $I_{add}$ is the predicted fraction inhibition by incubating cells with doxorubicin hydrochloride and Compound B-2 under an additive model. The Bliss independence score was then calculated as the difference between the observed inhibition and the inhibition using the additive model.

3. A plot of the bliss independence score vs. Compound B-2 concentration was constructed and the overall Bliss area under the curve (AUC) was calculated.

The Bliss AUCs were calculated at the doxorubicin hydrochloride EC50 because it is expected that efficacy of doxorubicin hydrochloride should be maximally affected by Compound B-2 near this concentration. $EC_{50}$ values for the experiments with Compound B-2 exposure for 4 hours could not be calculated reliably because of low fraction inhibition for these experiments and therefore Bliss AUCs are not reported for these experiments.

Results of Treatment of A549 Cells with Doxorubicin Hydrochloride for 24 Hours and Compound B-2 for 4, 8, 12 or 16 Hour:

The Bliss AUCs were calculated as described above. The results are shown in Table 1. Similar scores were obtained by adding Compound B-2 at the same time as doxorubicin hydrochloride and exposing cells to Compound B-2 for 24 hours (Experiment A in Table 1) or adding Compound B-2 8 or 12 hours after the addition of doxorubicin hydrochloride (Experiments C) and exposing cells to Compound B-2 for 16 hours. Synergy was also observed with 12-hour or 8-hour duration of Compound B-2 exposure, respectively (Experiment G, L) when Compound B-2 was added 12 or 16 hours after addition of doxorubicin hydrochloride. In contrast, exposure to Compound B-2 for 16 hours following doxorubicin hydrochloride addition resulted in much lower Bliss AUCs (Experiment B). These results show that Compound B-2 exposure for as little as 8 hours during the latter half of the 24-hour doxorubicin hydrochloride treatment is sufficient for synergy between doxorubicin hydrochloride and Compound B-2.

TABLE 1

Results of Bliss analysis

| Time of addition (hours) | Duration of exposure (hours) | Bliss AUC | Experiment* |
|---|---|---|---|
| 0 | 24 | 728 | A |
| 0 | 16 | 101 | B |
| 8 | 16 | 710 | C |
| 0 | 12 | ND | D |
| 4 | 12 | 266 | E |
| 8 | 12 | ND | F |
| 12 | 12 | 415 | G |
| 0 | 8 | 71 | H |
| 4 | 8 | 49 | I |
| 8 | 8 | 12 | J |
| 12 | 8 | 124 | K |
| 16 | 8 | 323 | L |
| 0 | 4 | ND | M |
| 4 | 4 | ND | N |
| 8 | 4 | ND | O |
| 12 | 4 | ND | P |
| 16 | 4 | ND | Q |

ND is not determined;
*see FIG. 1

Summary and Conclusions:

This study evaluated the in vitro viability of A549 lung cancer cells exposed to Compound B-2 for between 0 and 24 hours and doxorubicin hydrochloride for 24 hours. The data in this study shows that Compound B-2 coverage in the latter half of the 24-hour period and for as little as 8 hours is sufficient for synergy. These data are consistent with the hypothesis that delaying addition of Compound B-2 for up to 12 hours after doxorubicin hydrochloride addition does not decrease the efficacy of the combination.

Example 3: Evaluation of Compound B-2 CoX in Combination with Doxil® in Cell Line Xenograft Models The efficacy of Compound B-2 CoX in combination with DOXIL® (doxorubicin hydrochloride liposome injection) in Female nu/nu nude mice (Charles River Laboratories, Wilmington, Mass. or Beijing Vital River Lab Animal Technology Company Limited, Beijing, China), implanted with HT-29, HCT 116, OVCAR-3, NCI-H1048, or NCI-H2126 cells were evaluated. As described below in detail, when tumors reached approximately 200 mm³, mice were treated with DOXIL® (1.5, 3, 6 or 12 mg/kg) alone or in combination with at different dose levels and schedules. The % T/C values improved for all combinations of DOXIL® (at 1.5, 3, 6 and 12 mg/kg) with all doses and schedules of Compound B-2 CoX. Multiple days of qd dosing was equivalent or superior to a single day of bid dosing across all studies and there was no difference between dosing qd for 2, 3, or 4 days.

Cell Lines:

Cell lines used in this study are listed in Table 2 and represent a range of tumor origins including colorectal, ovarian, non-small cell lung cancer (NSCLC), and small cell lung cancer (SCLC). Cell lines were obtained from American Type Culture Collection (ATCC).

TABLE 2

Cell Lines

| Cell Line | Origin | Source | Catalog Number |
|---|---|---|---|
| HCT116 | Colorectal | ATCC | CCL-247 |
| HT-29 | Colorectal | ATCC | HTB-38 |
| OVCAR-3 | Ovarian | ATCC | HTB-161 |
| NCI-H2126 | NSCLC | ATCC | CCL-256 |
| NCI-H1048 | SCLC | ATCC | CRL-5853 |

Compound and Formulations:

Compound B-2 CoX was formulated in vehicle containing 0.5% methylcellulose as a homogeneous suspension by stirring at room temperature for 30 minutes. The concentration was 10 mg/mL and it administered to mice orally within 12 hours of preparation at a dosing volume of 10 mL/kg.

Cell Line Xenograft Implantation and Treatment:

HCT 116, HT-29, and OVCAR-3 cell lines were cultured in DMEM (Invitrogen #11995)+2 mM Glutamine (GlutaMAX, Invitrogen #35050-061)+10% Fetal Bovine Serum (Hyclone #SH30071-03), pyruvate (Invitrogen #11360-070) and pen/strep (Invitrogen #15070-063). The NCI-H1048 and NCI-H2126 cell lines were cultured in DMEM/F12 media (Invitrogen #11320-033) supplemented with 1% insulin-transferrin-selenium (Invitrogen #51500-056), 10 nM hydrocortisone (Sigma CAS 50-23-7), 10 nM 3-estradiol (Sigma CAS #50-28-2), 1% glucose (Invitrogen #35050-061), 1.5% HEPES (Invitrogen #15630-080), 10% fetal bovine serum (Invitrogen #10090-141), and 1% pen/strep (Invitrogen #15140-122). Cells were expanded in T150 flasks, split at 80-90% confluency with 0.25% TrypLE Express (Invitrogen #12605-010) until the cells were detached, neutralized with complete media and centrifuged at 1,000×g. Cells were washed once with phosphate buffered saline, centrifuged at 1,000×g and resuspended in a 1:1 mixture of phosphate buffered saline:Matrigel Collagen HC (Becton Dickinson #354248) at a concentration of 20 million cells/mL. The mixture (100 μL) was injected subcutaneously into the dorsal lateral mammary pad of nu/nu nude mice. Mice were randomized into groups prior to study initiation when the average tumor volume was approximately 200 mm³. Treatment groups (n=10) typically consisted of a vehicle control, DOXIL® alone, and DOXIL® in combination with Compound B-2 CoX. On the days of treatment, each animal received DOXIL® IV 16 hr prior to Compound B-2 CoX. Compound B-2 CoX (PO) was then administered either bid at 0 and 4 hr (Regimen A) or qd at 0 hr (Regimen B). In some studies, Compound B-2 CoX was dosed for 2 days (qd×2) or for 4 days (qd×4), 24 hr apart. These cycles were repeated once per week for two weeks. DOXIL® was administered either IV or IP and Compound B-2 CoX was administered PO.

Treatment was conducted for two cycles, one week apart, unless otherwise noted. Dose concentrations for each study are indicated in the results section. Mice were weighed and tumors were measured with calipers twice weekly. Tumor volume, expressed in mm³, was calculated using the equation Volume=0.5×L×W² where L and W were the longest and shortest dimensions of the tumor, respectively. Anti-tumor efficacy is expressed as % T/C (change in tumor volume of treated/change in tumor volume of control× 100%) while regression is expressed as % T/Ti (final tumor volume/initial tumor volume×100%). Data were collected using Gage Wedge (TAL Technologies, Inc.). Blood samples were collected on dried blood spot (DBS) cards (Perkin Elmer).

Body Weight:

Body weights were recorded twice per week at the time of tumor measurements.

Exclusion Criteria:

Animals that died as a result of non-treatment related causes were excluded from all analyses. In addition, any moribund animals or animals with ruptured/ulcerated tumors were euthanized prior to study termination.

Data Analysis:

Percent treatment/control (% T/C) values were calculated using the following formula: % T/C=100×ΔT/ΔC (a measure of tumor growth inhibition), where: T=mean tumor volume of the drug treated group on the day the vehicle group was terminated; ΔT=(mean tumor volume of the drug treated group on the day the vehicle group was terminated)−(mean tumor volume of the drug treated group on treatment Day 0); C=mean tumor volume of the control group on the day the vehicle group was terminated; ΔC=(mean tumor volume of the control group on the day the vehicle group was terminated)−(mean tumor volume of the control group on treatment Day 0). The percent tumor final/tumor initial (% T/Ti) was calculated using the following formula: final tumor volume/initial tumor volume×100%, wherein: T=final tumor volume (mean tumor volume of the drug treated group on the day the vehicle group was terminated); Ti=initial tumor volume (mean tumor volume at study initiation).

Statistical Analysis:

An unpaired, two-tailed, nonparametric t-test (Mann-Whitney test) was conducted using GraphPad Prism software on the day that the vehicle group was euthanized. Statistical significance was defined as P<0.05.

Results of Efficacy of Compound B-2 CoX in Combination with DOXIL® in HT-29 Xenograft Tumors:

The HT-29 cell line xenograft model was used to evaluate the efficacy of Compound B-2 CoX, in combination with DOXIL®. Female nu/nu nude mice implanted with HT-29 cells were randomized when the tumors reached approximately 200 mm³. Treatment groups (n=10) consisted of vehicle control, 3 mg/kg DOXIL®, 3 mg/kg DOXIL®+100 mg/kg Compound B-2 CoX qd×4, 6 mg/kg DOXIL®, 6 mg/kg DOXIL®+100 mg/kg Compound B-2 CoX bid, and 6 mg/kg DOXIL®+100 mg/kg Compound B-2 CoX qd×4. Two cycles of treatment were performed on Day 0 and Day 7.

The effects of the treatments and the calculated % T/C values are given in Table 3. DOXIL® alone inhibited tumor growth; however, there was no statistical difference between the 3 mg/kg and 6 mg/kg DOXIL® dose groups. There was no statistical difference between the 3 mg/kg DOXIL® and 3 mg/kg DOXIL®+100 mg/kg Compound B-2 CoX qd×4 groups (P=0.62), however Compound B-2 CoX enhanced the efficacy of DOXIL® at 6 mg/kg when administered qd×4 (P=0.0068). Although the 6 mg/kg DOXIL®+100 mg/Compound B-2 CoX bid enhanced the efficacy of 6 mg/kg DOXIL® alone as demonstrated by the % T/C values (22.1 and 44.7, respectively), this difference was not statistically significant (P=0.089). The qd×4 dosing schedule of Compound B-2 CoX in combination with DOXIL® was superior to the bid dosing (P=0.023).

TABLE 3

Effect of Compound B-2 CoX in Combination with DOXIL ® on Inhibition of Tumor Growth (% T/C) and Body Weight in an HT-29 Xenograft Tumor Model in Nude Mice

| Treatment | N | % T/C (Day 20) | Max. Body Weight Loss (%) |
|---|---|---|---|
| Vehicle | 10 | | N/A |
| 3 mg/kg DOXIL ® | 10 | 49.9 | N/A |
| 3 mg/kg DOXIL ® + 100 mg/kg Compound B-2 CoX qd × 4 | 10 | 40.0 | N/A |
| 6 mg/kg DOXIL ® | 10 | 44.7 | N/A |
| 6 mg/kg DOXIL ® + 100 mg/kg Compound B-2 CoX bid | 10 | 22.1 | −2.10 (Day 15) |
| 6 mg/kg DOXIL ® + 100 mg/kg Compound B-2 CoX qd × 4 | 10 | 3.6 | −6.41 (Day 15) |

N/A: not applicable.

Body weights were measured twice per week during the course of the study to assess tolerability of the treatments. In general, these dosing regimens were well tolerated in mice with a maximal body weight loss of −6.41% on Day 15 after treatment in the combination group.

Efficacy of Compound B-2 CoX in Combination with DOXIL® in HCT 116 Xenograft Tumors:

The HCT 116 cell line xenograft model was used to evaluate the efficacy of the DNA-PK inhibitor, Compound B-2 CoX, in combination with DOXIL® using the same protocol as that for HT-29 xenograft tumors above.

The efficacy of treatment and calculated % T/C values are shown in Table 4. DOXIL® alone inhibited tumor growth; however, there was no statistical difference between the 3 mg/kg and 6 mg/kg DOXIL® dose groups. There was no statistical difference between the 3 mg/kg DOXIL® and 3 mg/kg DOXIL®+100 mg/kg Compound B-2 CoX qd×4 groups (P=0.72), however Compound B-2 CoX enhanced the efficacy of DOXIL® at 6 mg/kg when dosed qd×4 (P=0.0002). Although the 6 mg/kg DOXIL®+100 mg/kg Compound B-2 CoX bid enhanced the efficacy of 6 mg/kg DOXIL® alone as demonstrated by the % T/C values (24.6 and 36.0, respectively), this difference was not statistically significant (P=0.16).

TABLE 4

Effect of Compound B-2 CoX in Combination with DOXIL ® on Inhibition of Tumor Growth (% T/C) and Body Weight in an HCT 116 Xenograft Tumor Model in Nude Mice

| Treatment | N | % T/C (Day 21) | Max. Body Weight Loss (%) |
|---|---|---|---|
| Vehicle | 10 | | N/A |
| 3 mg/kg DOXIL ® | 10 | 41.1 | N/A |
| 3 mg/kg DOXIL ® + 100 mg/kg Compound B-2 CoX qd × 4 | 10 | 23.3 | −0.77 (Day 13) |
| 6 mg/kg DOXIL ® | 10 | 36.0 | −2.91 (Day 13) |
| 6 mg/kg DOXIL ® + 100 mg/kg Compound B-2 CoX bid | 10 | 24.6 | −0.67 (Day 13) |
| 6 mg/kg DOXIL ® + 100 mg/kg Compound B-2 CoX qd × 4 | 10 | 15.0 | −2.72 (Day 13) |

Body weights were measured twice per week during the course of the study to assess tolerability of the treatments. In general, these dosing regimens were well tolerated in mice with a maximal body weight loss of −2.91% on Day 13 after treatment in the combination group.

Effect of Compound B-2 CoX Schedule in Combination with DOXIL® in HCT 116 Xenograft Tumors:

The HCT 116 xenograft tumor model was selected for further examination of the effect of schedule and dose of Compound B-2 CoX in combination with DOXIL®. In this study, the effect of dosing Compound B-2 CoX qd for 2, 3, and 4 days following DOXIL® was examined.

Female nu/nu nude mice implanted with HCT 116 cells were randomized when the tumors reached approximately 200 mm$^3$. Treatment groups (n=10) consisted of vehicle control, 100 mg/kg Compound B-2 CoX qd×4, 6 mg/kg DOXIL®, 6 mg/kg DOXIL®+100 mg/kg Compound B-2 CoX qd×2, 6 mg/kg DOXIL®+100 mg/kg Compound B-2 CoX qd×3, and 6 mg/kg DOXIL®+100 mg/kg Compound B-2 CoX qd×4. Two cycles of treatment were performed on Day 0 and Day 7.

The effects of the treatments and the calculated % T/C values are given in Table 5. DOXIL® (6 mg/kg) alone inhibited tumor growth, however the combination of 6 mg/kg DOXIL®+Compound B-2 CoX qd×2 further inhibited the growth of the HCT 116 xenograft tumors and this difference was statistically significant (P<0.0007). While the 6 mg/kg DOXIL®+Compound B-2 CoX qd×3, and qd×4 groups were statistically different from the 6 mg/kg DOXIL® group (P<0.02), the extra days of Compound B-2 CoX dosing did not further enhance the efficacy as compared to the qd×2 dosing schedule. In fact, of the three Compound B-2 CoX treatment schedules, the 6 mg/kg DOXIL®+Compound B-2 CoX qd×2 resulted in the best % T/C value (8.3) as compared with the the qd×3 and qd×4 (17.0 and 17.1, respectively). These data suggest that 2 days of Compound B-2 CoX is sufficient to enhance the efficacy of DOXIL®.

TABLE 5

Effect of Compound B-2 CoX in Combination with DOXIL ® on Inhibition of Tumor Growth (% T/C) and Body Weight in an HCT 116 Xenograft Tumor Model in Nude Mice

| Treatment | N | % T/C (Day 19) | Max. Body Weight Loss (%) |
| --- | --- | --- | --- |
| Vehicle | 10 | | N/A |
| 100 mg/kg Compound B-2 CoX qd x 4 | 10 | 106 | N/A |
| 6 mg/kg DOXIL ® | 10 | 40.1 | −0.49 (Day 11) |
| 6 mg/kg DOXIL ® + 100 mg/kg Compound B-2 CoX qd × 2 | 10 | 8.3 | −4.4 (Day 12) |
| 6 mg/kg DOXIL ® + 100 mg/kg Compound B-2 CoX qd × 3 | 10 | 17.0 | −6.49 (Day 12) |
| 6 mg/kg DOXIL ® + 100 mg/kg Compound B-2 CoX qd × 4 | 10 | 17.1 | −5.32 (Day 12) |

N/A: not applicable.

Body weights were measured twice per week during the course of the study to assess tolerability of the treatments. In general, these dosing regimens were well tolerated in mice with a maximal body weight loss of −6.49% on Day 12 after treatment in the combination group.

Dose Response of DOXIL® alone and Dose Response of Compound B-2 CoX in Combination with 6 mg/kg DOXIL® in HCT 116 Xenograft Tumors: Additional investigations were conducted to determine the dose response of DOXIL® alone (1.5-6 mg/kg) in the HCT 116 xenograft tumor model. Further, a dose response of Compound B-2 CoX (25-100 mg/kg) in combination with 6 mg/kg DOXIL® was also assessed. Lastly, the efficacy of 1.5 mg/kg DOXIL® in combination with 200 mg/kg Compound B-2 CoX was also examined.

Female nu/nu nude mice implanted with HCT 116 cells were randomized when the tumors reached approximately 200 mm$^3$. Treatment groups (n=10) consisted of vehicle control, 6 mg/kg DOXIL®, 3 mg/kg DOXIL®, 1.5 mg/kg DOXIL®, 6 mg/kg DOXIL®+100 mg/kg Compound B-2 CoX qd×2, 6 mg/kg DOXIL®+50 mg/kg Compound B-2 CoX qd×2, 6 mg/kg DOXIL®+25 mg/kg Compound B-2 CoX qd×2, and 1.5 mg/kg DOXIL®+200 mg/kg Compound B-2 CoX qd×2. Two cycles of treatment were performed on Day 0 and Day 7.

The calculated % T/C values are given in Table 6. A dose response was observed with the DOXIL® alone with % T/C values of 30, 55.1, and 61.5 for the 6, 3, and 1.5 mg/kg DOXIL® groups, respectively. The 6 mg/kg DOXIL® group was statistically different from the 3 and 1.5 mg/kg groups (P<0.02), but the 3 and 1.5 mg/kg groups were not different (P=0.67). In this study the 6 mg/kg DOXIL® group was not statistically different from any of the three combination groups examined. However, the % T/C values of 20.0, 26.7, and 35.9 for the 100, 50, and 25 mg/kg Compound B-2 CoX+6 mg/kg DOXIL® combination groups indicated a trend which showed enhanced efficacy with higher doses of Compound B-2 CoX. The 1.5 mg/kg DOXIL®+200 mg/kg Compound B-2 CoX inhibited tumor growth more than 1.5 mg/kg DOXIL® as evident by the % T/C values (39.8 and 61.5, respectively), but this difference was not statistically significant (P=0.089).

TABLE 6

Effect of Compound B-2 CoX in Combination with DOXIL ® on Inhibition of Tumor Growth (% T/C) and Body Weight in an HCT 116 Xenograft Tumor Model in Nude Mice

| Treatment | N | % T/C (Day 19) | Max. Body Weight Loss (%) |
| --- | --- | --- | --- |
| Vehicle | 10 | | N/A |
| 6 mg/kg DOXIL ® | 10 | 30 | N/A |
| 3 mg/kg DOXIL ® | 10 | 55.1 | N/A |
| 1.5 mg/kg DOXIL ® | 10 | 61.5 | N/A |
| 6 mg/kg DOXIL ® + 100 mg/kg Compound B-2 CoX qd × 2 | 10 | 20.0 | −1.92 (Day 5) |
| 6 mg/kg DOXIL ® + 50 mg/kg Compound B-2 CoX qd × 2 | 10 | 26.7 | N/A |
| 6 mg/kg DOXIL ® + 25 mg/kg Compound B-2 CoX qd × 2 | 10 | 35.9 | N/A |
| 1.5 mg/kg DOXIL ® + 200 mg/kg Compound B-2 CoX qd × 2 | 10 | 39.8 | N/A |

Body weights were measured twice per week during the course of the study to assess tolerability of the treatments. In general, these dosing regimens were well tolerated in mice with a maximal body weight loss of −1.92% on Day 5 after treatment in the 6 mg/kg DOXIL®+100 mg/kg Compound B-2 CoX combination group. All other groups showed an increase of body weight over the course of the study.

Result of reexamination of Compound B-2 CoX Dose and Schedule in Combination with DOXIL® in an HCT 116 Xenograft Mouse Model. Female nu/nu nude mice implanted with HCT 116 cells were randomized when the tumors reached approximately 200 mm$^3$. Treatment groups (n=10) consisted of vehicle control, 6 mg/kg DOXIL®, 6 mg/kg DOXIL®+100 mg/kg Compound B-2 CoX qd×2, 6 mg/kg DOXIL®+100 mg/kg Compound B-2 CoX qd×4, 6 mg/kg DOXIL®+50 mg/kg Compound B-2 CoX qd×2, 6 mg/kg DOXIL®+50 mg/kg Compound B-2 CoX qd×4, 1.5 mg/kg DOXIL®, 1.5 mg/kg DOXIL®+200 mg/kg Compound B-2 CoX qd×2, and 1.5 mg/kg DOXIL®+100 mg/kg Compound B-2 CoX qd×2. Two cycles of treatment were performed on Day 0 and Day 7.

The effects of the treatments and the calculated % T/C values are given in Table 7. The 6 mg/kg DOXIL®+100 mg/kg Compound B-2 CoX qd×2 and qd×4 combination treatments enhanced the efficacy of, and were statistically different from the 6 mg/kg DOXIL® alone groups (P<0.04). As seen previously there was no difference between the 6 mg/kg DOXIL®+100 mg/kg Compound B-2 CoX qd×2 and qd×4 groups (P=0.57), nor was there a difference between the 6 mg/kg DOXIL®+50 mg/kg Compound B-2 CoX qd×2 and qd×4 groups (P=0.67). Additionally, as seen previously, there was no difference between the 6 mg/kg DOXIL® group and the 6 mg/kg DOXIL®+50 mg/kg Compound B-2 CoX qd×2 or qd×4 groups (P>0.28). At 1.5 mg/kg DOXIL®, the combination with 200 mg/kg Compound B-2 CoX demonstrated a statistically significant improvement in the efficacy of DOXIL® alone, however the 100 mg/kg Compound B-2 CoX dose did not. These data confirm previous studies that qd×2 dosing is as efficacious as the qd×4 schedule.

TABLE 7

Effect of Compound B-2 CoX in Combination with DOXIL ® on Inhibition of Tumor Growth (% T/C) and Body Weight in an HCT 116 Xenograft Tumor Model in Nude Mice

| Treatment | N | % T/C (Day 20) | Max. Body Weight Loss (%) |
|---|---|---|---|
| Vehicle | 10 | | N/A |
| 6 mg/kg DOXIL ® | 10 | 28.5 | −2.27 (Day 16) |
| 6 mg/kg DOXIL ® + 100 mg/kg Compound B-2 CoX qd × 2 | 10 | 13.0 | −4.96 (Day 13) |
| 6 mg/kg DOXIL ® + 100 mg/kg Compound B-2 CoX qd × 4 | 10 | 15.4 | −6.18 (Day 13) |
| 6 mg/kg DOXIL ® + 50 mg/kg Compound B-2 CoX qd × 2 | 10 | 23.9 | −6.18 (Day 13) |
| 6 mg/kg DOXIL ® + 50 mg/kg Compound B-2 CoX qd × 4 | 10 | 26.6 | −3.70 (Day 16) |
| 1.5 mg/kg DOXIL ® | 10 | 78.1 | N/A |
| 1.5 mg/kg DOXIL ® + 200 mg/kg Compound B-2 CoX qd × 2 | 10 | 42.2 | N/A |
| 1.5 mg/kg DOXIL ® + 100 mg/kg Compound B-2 CoX qd × 2 | 10 | 62.8 | N/A |

Body weights were measured twice per week during the course of the study to assess tolerability of the treatments. In general, these dosing regimens were well tolerated in mice with a maximal body weight loss of −6.18% on Day 13 after treatment in the combination groups.

Examination of the Effect of Compound B-2 CoX Dose in Combination with 3 mg/kg DOXIL® in an HCT 116 Xenograft Tumor Model:

A 3 mg/kg DOXIL® dose was examined in combination with a range of doses of Compound B-2 CoX (50-200 mg/kg) to identify the response of HCT 116 xenograft tumors to these combinations.

Female nu/nu nude mice implanted with HCT 116 cells were randomized when the tumors reached approximately 200 mm³. Treatment groups (n=10) consisted of vehicle control, 3 mg/kg DOXIL®, 3 mg/kg DOXIL®+50 mg/kg Compound B-2 CoX qd×2, 3 mg/kg DOXIL®+100 mg/kg Compound B-2 CoX qd×2, 3 mg/kg DOXIL®+200 mg/kg Compound B-2 CoX qd×2 and 6 mg/kg DOXIL®+200 mg/kg Compound B-2 CoX qd×2. Two cycles of treatment were performed on Day 0 and Day 7.

The effects of the treatments and the calculated % T/C values are given in Table 8. DOXIL® (3 mg/kg) alone inhibited tumor growth. The 50 and 100 mg/kg Compound B-2 CoX combination groups did not significantly enhance the effects of DOXIL® alone (P>0.84); however, at 200 mg/kg a statistically significant enhancement of DOXIL® was observed (P=0.019). The efficacy of 3 mg/kg DOXIL®+200 mg/kg Compound B-2 CoX qd×2 was comparable to that observed with 6 mg/kg DOXIL®+100 mg/kg Compound B-2 CoX qd×2 as evidenced by the % T/C values of 16.6, and 20.9, respectively.

TABLE 8

Effect of Compound B-2 CoX to in Combination with DOXIL ® on Inhibition of Tumor Growth (% T/C) and Body Weight in an HCT 116 Xenograft Tumor Model in Nude Mice

| Treatment | N | % T/C (Day 19) | Max. Body Weight Loss (%) |
|---|---|---|---|
| Vehicle | 10 | | Gain |
| 3 mg/kg DOXIL ® | 10 | 34.8 | −3.55 (Day 8) |
| 3 mg/kg DOXIL ® + 50 mg/kg Compound B-2 CoX qd × 2 | 10 | 33.9 | −3.56 (Day 8) |
| 3 mg/kg DOXIL ® + 100 mg/kg Compound B-2 CoX qd × 2 | 10 | 35.1 | −2.84 (Day 8) |
| 3 mg/kg DOXIL ® + 200 mg/kg Compound B-2 CoX qd × 2 | 10 | 16.6 | −4.43 (Day 8) |
| 6 mg/kg DOXIL ® + 100 mg/kg Compound B-2 CoX qd × 2 | 10 | 20.9 | −5.29 (Day 12) |

Body weights were measured twice per week during the course of the study to assess tolerability of the treatments. In general, these dosing regimens were well tolerated in mice with a maximal body weight loss of −5.29% on Day 12 after treatment in the combination group.

Result of Examination of the Effect of Compound B-2 CoX Dose in Combination with 12 mg/kg DOXIL® in an HCT 116 Xenograft Tumor Model: DOXIL® at a dose of 12 mg/kg (36 mg/m²) was examined in combination with 25 or 50 mg/kg Compound B-2 CoX to identify the response of HCT 116 xenograft tumors to these combinations.

The HCT 116 cell line xenograft model was used to evaluate the efficacy of Compound B-2 CoX in combination with DOXIL®. Female nu/nu nude mice implanted with HCT 116 cells were randomized when the tumors reached approximately 200 mm³. Treatment groups (n=10) consisted of vehicle control, 12 mg/kg DOXIL®, 12 mg/kg DOXIL®+25 mg/kg Compound B-2 CoX qd×2, 12 mg/kg DOXIL®+50 mg/kg Compound B-2 CoX qd×2, 6 mg/kg DOXIL®, and 6 mg/kg DOXIL®+100 mg/kg Compound B-2 CoX mice in all 12 mg/kg DOXIL® groups lost 6-7% body weight on average by Day 2. As a result, HydroGel (approximately 0.5 ounces per cage) was given ad libitum to all study groups on Days 2, 7, and 9.

The calculated % T/C values are given in Table 9. DOXIL® alone (6 and 12 mg/kg) inhibited tumor growth. Compound B-2 CoX at 50 mg/kg, but not 25 mg/kg, significantly enhanced the effects of 12 mg/kg DOXIL® alone (P=0.028, 0.57, respectively). The efficacy of 6 mg/kg DOXIL®+100 mg/kg Compound B-2 CoX qd×2 was comparable to that observed in previous studies and demonstrated a statistically significant difference than 6 mg/kg DOXIL® alone (P=0.023).

TABLE 9

Effect of Compound B-2 CoX in Combination with DOXIL ® on Inhibition of Tumor Growth (% T/C) and Body Weight in an HCT 116 Xenograft Tumor Model in Nude Mice

| Treatment | N | % T/C (Day 19) | Max. Body Weight Loss (%) |
|---|---|---|---|
| Vehicle | 10 | N/A | −4.2 (Day 2) |
| 12 mg/kg DOXIL ® | 10 | 21.3 | −9.4 (Day 8) |
| 12 mg/kg DOXIL ® + 25 mg/kg Compound B-2 CoX qd × 2 | 10 | 19.3 | −6.5 (Day 8) |
| 12 mg/kg DOXIL ® + 50 mg/kg Compound B-2 CoX qd × 2 | 10 | 10.8 | −7.4 (Day 8) |
| 6 mg/kg DOXIL ® | 10 | 31.7 | −4.8 (Day 8) |
| 6 mg/kg DOXIL ® + 100 mg/kg Compound B-2 CoX qd × 2 | 10 | 18.5 | −5.9 (Day 2) |

Body weights were measured twice per week during the course of the study to assess tolerability of the treatments. In general, these dosing regimens were well tolerated in mice. However, HydroGel was used to minimize weight loss particularly in the 12 mg/kg DOXIL® groups. Importantly, no increase in body weight loss was observed when Compound B-2 CoX was combined with 12 mg/kg DOXIL®. The 12 mg/kg DOXIL® alone group demonstrated the greatest weight loss of all groups (−9.4% on Day 8).

Efficacy of Compound B-2 CoX in Combination with DOXIL® in OVCAR-3 Xenograft Tumors:

The OVCAR-3 cell line xenograft model was used to evaluate the efficacy of Compound B-2 CoX, in combination with DOXIL®. Female nu/nu nude mice implanted with OVCAR-3 cells were randomized when the tumors reached approximately 200 mm³. Treatment groups (n=10) consisted of vehicle control, 100 mg/kg Compound B-2 CoX qd×4, 6 mg/kg DOXIL®, 6 mg/kg DOXIL®+100 mg/kg Compound B-2 CoX qd×2, 6 mg/kg DOXIL®+100 mg/kg Compound B-2 CoX qd×4, 1.5 mg/kg DOXIL® for 3 cycles, 1.5 mg/kg DOXIL®+200 mg/kg Compound B-2 CoX qd×2, and 1.5 mg/kg DOXIL®+200 mg/kg Compound B-2 CoX qd×2 (three cycles). Two cycles of treatment were performed on Day 0 and Day 7 unless indicated (a third cycle was initiated on Day 14 for one of the 1.5 mg/kg DOXIL®+200 mg/kg Compound B-2 CoX qd×2 groups).

The effects of the treatments and the calculated % T/C values are given in Table 10. DOXIL® (6 mg/kg) alone inhibited tumor growth, and the addition of 100 mg/kg Compound B-2 CoX administered for 2 days or 4 days further suppressed tumor growth. There was no statistical difference between the qd×2 and qd×4 groups (P=0.19). Tumor growth was also inhibited at 1.5 mg/kg DOXIL® for three cycles and was statistically different than the vehicle group (P=0.0007). The addition of 200 mg/kg Compound B-2 CoX further suppressed tumor growth when administered for two or three cycles, as evidenced by the % T/C of 33.6 and 20.0, respectively.

TABLE 10

Effect of Compound B-2 CoX in Combination with DOXIL ® on Inhibition of Tumor Growth (% T/C) and Body Weight in an OVCAR3 Xenograft Tumor Model in Nude Mice

| Treatment | N | % T/C (Day 43) | Max. Body Weight Loss (%) |
|---|---|---|---|
| Vehicle | 10 | | N/A |
| 100 mg/kg Compound B-2 CoX qd ×2 | 10 | 83.2 | N/A |
| 6 mg/kg DOXIL ® | 10 | 26.0 | N/A |
| 6 mg/kg DOXIL ® + 100 mg/kg Compound B-2 CoX qd × 2 | 10 | 10.2 | N/A |
| 6 mg/kg DOXIL ® + 100 mg/kg Compound B-2 CoX qd × 4 | 10 | 13.3 | −0.3 (Day 13) |
| 1.5 mg/kg DOXIL ® (three cycles) | 10 | 43.7 | N/A |
| 1.5 mg/kg DOXIL ® + 200 mg/kg Compound B-2 CoX qd × 2 | 10 | 33.6 | N/A |
| 1.5 mg/kg DOXIL ® + 200 mg/kg Compound B-2 CoX qd × 2 (three cycles) | 10 | 20.0 | N/A |

Body weights were measured twice per week during the course of the study to assess tolerability of the treatments. In general, these dosing regimens were well tolerated in mice with a maximal body weight loss of −0.3% on Day 13 after treatment in the combination group.

Efficacy of Compound B-2 CoX in Combination with DOXIL® in NCI-H1048 Xenograft Tumors:

Female nu/nu nude mice implanted with NCI-H1048 cells were randomized when the tumors reached approximately 200 mm³. Treatment groups (n=10) consisted of vehicle control, 3 mg/kg DOXIL®, 3 mg/kg DOXIL®+100 mg/kg Compound B-2 CoX qd×4, 6 mg/kg DOXIL®, 6 mg/kg DOXIL®+100 mg/kg Compound B-2 CoX bid, and 6 mg/kg DOXIL®+100 mg/kg Compound B-2 CoX qd×4. Two cycles of treatment were performed on Day 0 and Day 7.

The effects of the treatments and the calculated % T/C values are given in Table 11. DOXIL® alone inhibited tumor growth in a dose dependent manner. There was no statistical difference between the 3 mg/kg DOXIL® and 3 mg/kg DOXIL®+100 mg/kg Compound B-2 CoX qd×4 groups (P=0.075), however Compound B-2 CoX enhanced the efficacy of DOXIL® at 6 mg/kg when dosed qd×4 (P=0.0002). The 6 mg/kg DOXIL®+100 mg/kg Compound B-2 CoX bid regimen did not enhance the efficacy of 6 mg/kg DOXIL® alone as demonstrated by the % T/C values (20.0 and 21.7, respectively) and the lack of statistical difference (P=0.67). The qd×4 dosing schedule of Compound B-2 CoX in combination with DOXIL® was superior to the bid dosing (P=0.0001).

TABLE 11

Effect of Compound B-2 CoX in Combination with DOXIL ® on Inhibition of Tumor Growth (% T/C) and Body Weight in an NCI-H1048 Xenograft Tumor Model in Nude Mice

| Treatment | N | % T/C (Day 15) | Max. Body Weight Loss (%) |
|---|---|---|---|
| Vehicle | 10 | | N/A |
| 3 mg/kg DOXIL ® | 10 | 45.5 | −2.23 (Day 4) |
| 3 mg/kg DOXIL ® + 100 mg/kg Compound B-2 CoX qd × 4 | 10 | 32.0 | −1.26 (Day 9) |
| 6 mg/kg DOXIL ® | 10 | 21.7 | −1.62 (Day 4) |
| 6 mg/kg DOXIL ® + 100 mg/kg Compound B-2 CoX bid | 10 | 20.0 | −4.58 (Day 4) |
| 6 mg/kg DOXIL ® + 100 mg/kg Compound B-2 CoX qd × 4 | 10 | 2.3 | −7.55 (Day 12) |

N/A = not applicable.

Body weights were measured twice per week during the course of the study to assess tolerability of the treatments. In general, these dosing regimens were well tolerated in mice with a maximal body weight loss of −7.55% on Day 12 after treatment in the combination groups.

Efficacy of Compound B-2 CoX in Combination with DOXIL® in NCI-H2126 Xenograft Tumors:

Female nu/nu nude mice implanted with NCI-H2126 cells were randomized when the tumors reached approximately 200 mm$^3$. Treatment groups (n=10) consisted of vehicle control, 3 mg/kg DOXIL®, 3 mg/kg DOXIL®+100 mg/kg Compound B-2 CoX qd×4, 6 mg/kg DOXIL®, 6 mg/kg DOXIL®+100 mg/kg Compound B-2 CoX bid, and 6 mg/kg DOXIL®+100 mg/kg Compound B-2 CoX qd×4. Two cycles of treatment were performed on Day 0 and Day 7.

The effects of the treatments and the calculated % T/C values are given in Table 12. DOXIL® alone inhibited tumor growth; however, there was no statistical difference between the 3 and 6 mg/kg dose groups (P=0.063). Compound B-2 CoX (100 mg/kg qd×4) enhanced the efficacy of 3 mg/kg DOXIL® as evident by the % T/C (37.8 and 65.7, respectively) and this difference was statistically significant (P=0.0052). The % T/C of 6 mg/kg DOXIL®+100 mg/kg Compound B-2 CoX bid and qd×4 (27.8 and 28.8, respectively) improved as compared to 6 mg/kg DOXIL® alone (% T/C=43.3), however, neither of these combinations were statistically different from the DOXIL® alone group.

TABLE 12

Effect of Compound B-2 CoX in Combination with DOXIL® on Inhibition of Tumor Growth (% T/C) and Body Weight in an NCI-H2126 Xenograft Tumor Model in Nude Mice

| Treatment | N | % T/C (Day 26) | Max. Body Weight Loss (%) |
|---|---|---|---|
| Vehicle | 10 | | −0.97 (Day 1) |
| 3 mg/kg DOXIL® | 10 | 65.7 | −0.58 (Day 4) |
| 3 mg/kg DOXIL® + 100 mg/kg Compound B-2 CoXqd × 4 | 10 | 37.8 | N/A |
| 6 mg/kg DOXIL® | 10 | 43.3 | −0.70 (Day 11) |
| 6 mg/kg DOXIL® + 100 mg/kg Compound B-2 CoXbid | 10 | 27.8 | −0.41 (Day 11) |
| 6 mg/kg DOXIL® + 100 mg/kg Compound B-2 CoXqd × 4 | 10 | 28.8 | −1.75 (Day 11) |

N/A: not applicable.

Body weights were measured twice per week during the course of the study to assess tolerability of the treatments. In general, these dosing regimens were well tolerated in mice with a maximal body weight loss of −1.75% on Day 11 after treatment in the combination groups.

Discussion:

The anti-tumor efficacy of Compound B-2 CoX in combination with DOXIL® was evaluated in the HT-29, HCT 116, OVCAR-3, NCI-H1048, and NCI-H2126 cell lines. The % T/C values for DOXIL® alone ranged from 10.8-78.1 depending on dose and individual cell line sensitivity. The % T/C values improved for all combinations of DOXIL® (at 1.5, 3, 6 and 12 mg/kg) with all doses and schedules of Compound B-2 CoX, although not all combinations were statistically different when compared to the DOXIL® alone group. Multiple days of qd administration was as good or superior to a single day of bid dosing across all studies and there was no difference between dosing qd for 2, 3, or 4 days. Results generated from these studies demonstrate that Compound B-2 CoX enhances the efficacy of DOXIL®.

These cell line xenograft studies demonstrate that Compound B-2 CoX enhanced the efficacy of DOXIL® in 5 cell lines across a range of tumor origins and these combination treatment regimens were well tolerated.

Example 4: Impact of Compound B-2 CoX on the Sensitivity of a Panel of Primary Ovarian Tumors to PLD Materials:

DOXIL® (Doxorubicin HCl Liposome Injection) is a sterile, translucent, red liposomal dispersion in glass vial at a concentration of 2 mg/mL and stored at 2-8° C. (Janssen Products, LP, Horsham, Pa.). Methylcellulose (MC), 400 cP, is a white powder purchased from Sigma-Aldrich (St. Louis, Mo.) and stored at ambient temperature. Compound B-2 CoX is a white to off white powder provided by Vertex Pharmaceuticals. Compound B-2 CoX has a parent Molecular Weight of 415.39 with a co-crystal (CoX) correction factor of 1.27. Compound B-2 CoX was stored at ambient temperature and protected from light.

The vehicle 0.5% MC was prepared and stored at 2-8° C. and used within 8 days of preparation. Prior to formulating, the 0.5% MC was removed from storage and stirred at ambient temperature for 30 minutes. Appropriate amount of 0.5% MC was added to weighed amount of Compound B-2 CoX and stirred at ambient temperature. The suspension was then homogenized for 15 minutes at 5,000 rpm and the tip of the homogenizer was rinsed with 20% of the final volume of the vehicle in a syringe. The suspension was stirred for another 30 minutes before dosing. The remaining formulation was stored at 4-8° C. for up to eight days and it was stirred at ambient temperature for 30 minutes before dosing.

The NCr nude mice are *Mus musculus* and from Taconic Laboratories (Hudson, N.Y., USA).

Efficacy Study:

The in vivo anti-tumor activity of Compound B-2 CoX in combination with DOXIL® was assessed in a screening panel of 5 primary ovarian cancer subcutaneous xenograft models (CTG-0253, CTG-0486, CTG-0964, CTG-1166, and CTG-1423). These studies were conducted to assess the ability of the selective DNA-PK inhibitor, Compound B-2 CoX, to enhance the anti-tumor effects of DOXIL®. Compound B-2 CoX was administered alone or in combination with DOXIL®. Two cycles of treatment were administered and tumor volumes and body weights were recorded twice weekly.

The ovarian cancer xenograft tumor models were originally established from surgically resected clinical samples. Female athymic NCr nude mice were implanted subcutaneously on the left flank with CTG-0253, CTG-0486, CTG-0964, CTG-1166, or CTG-1423 tumor fragments.

Figure 2:
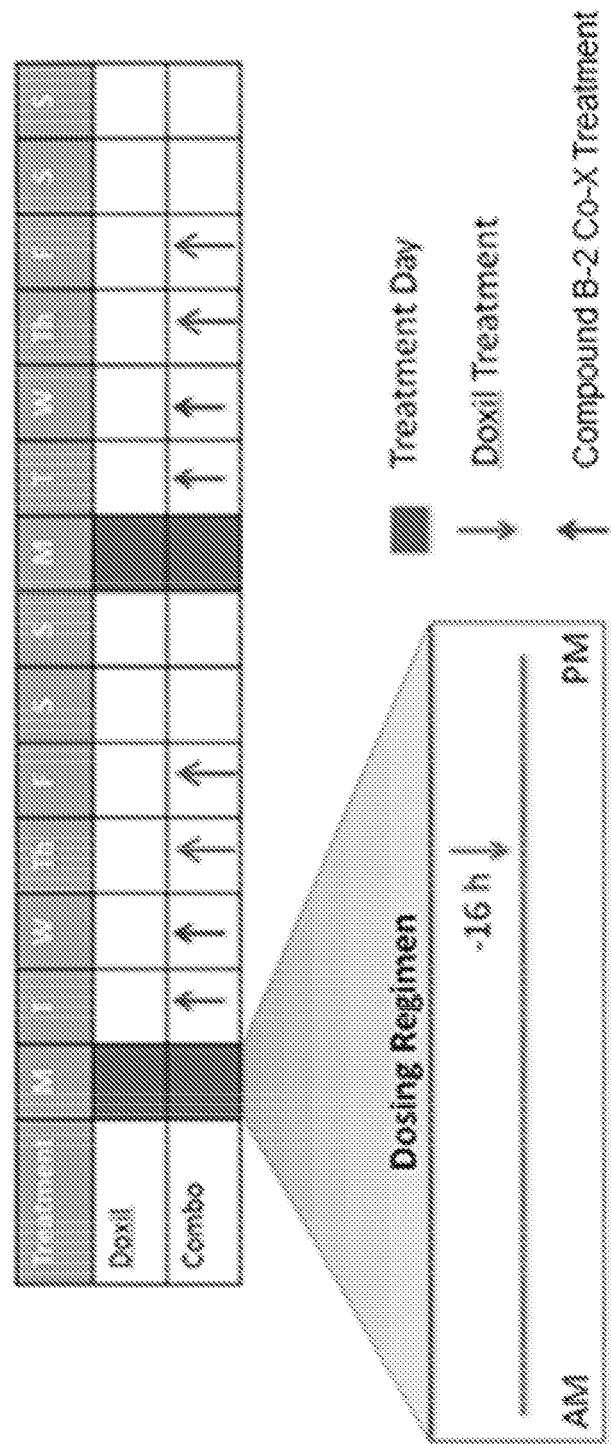
FIG. 2 shows the dosing regimens for Compound B-2 adipic acid co-crystal (2:1 molar ratio of Compound B-2: adipic acid; as used herein "Compound B-2 CoX") in combination with DOXIL®. On the first day of treatment, each animal received DOXIL® IV 16 hr prior to Compound B-2 Co-X. Compound B-2 Co-X (PO) was then administered qd at 0, 24, 48, and 72 h (indicated with the arrows pointing upwards showing when the Compound B-2 Co-X treatment was administered). This cycle was repeated once per week for two weeks.
Figure 7:
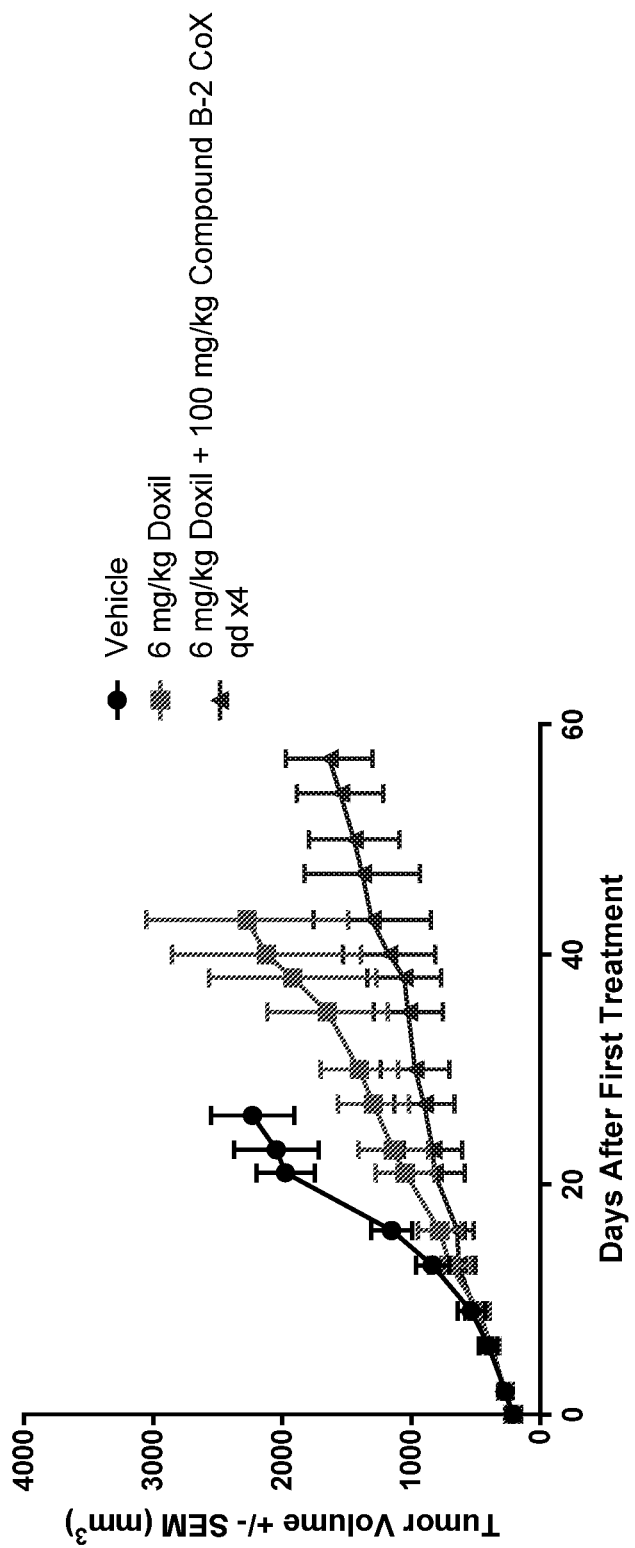
FIG. 7 shows the effect of Compound B-2 Co-X in Combination with DOXIL® on Tumor Volume in the CTG-0964 Primary Patient Derived Xenograft Tumor Model in Nude Mice. Mice were dosed with DOXIL® or the combination of DOXIL® and Compound B-2 Co-X to assess efficacy as described in FIG. 2 (n=4/group).
Figure 8:
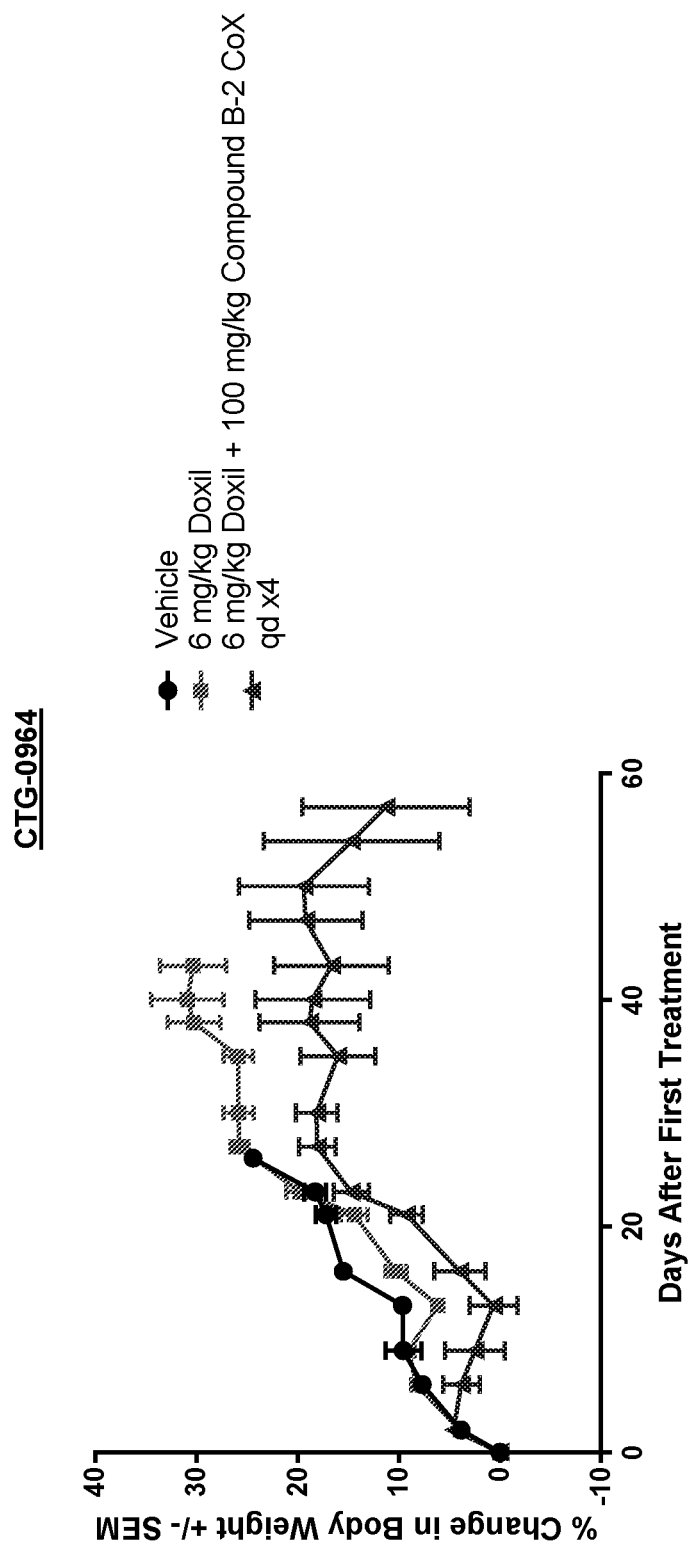
FIG. 8 shows the Effect of DOXIL® or Compound B-2 Co-X in Combination with DOXIL® on Body Weight in the CTG 0964 Primary Patient Derived Xenograft Nude Mouse Model (n=4/group).

This panel of 5 ovarian tumors was examined to identify responders. 03051 Three groups of mice were used, in which mice (n=4/group) were treated with vehicle, 6 mg/kg/dose DOXIL® IV QW, or 6 mg/kg/dose DOXIL®+100 mg/kg/dose Compound B-2 CoX as depicted in FIG. 2. DOXIL® was administered intravenously (IV) and 16 hours later, Compound B-2 CoX was administered orally (PO) for 4 consecutive days, 24 hr apart. This cycle was repeated twice, one week apart. Tumors were measured with calipers and mouse body weights were recorded twice per week. Tumor volume, expressed in mm$^3$, was calculated using the equation Volume=0.52×L×W$^2$ where L and W were the longest and shortest dimensions of the tumor, respectively. Anti-tumor efficacy is expressed as % T/C (change in tumor volume of treated/change in tumor volume of control× 100%) while regression is expressed as % T/Ti (final tumor volume/initial tumor volume×100%). An unpaired, two-tailed, nonparametric t-test (Mann-Whitney test) was conducted using GraphPad Prism software on the day that the vehicle group was euthanized. Additionally, statistical analyses were performed using data up to the last day that tumor volumes were measured for all 3 groups. Statistical comparisons of tumor volumes were conducted using a One-Way Analysis of Variance (ANOVA) was conducted with Dunnett's multiple comparison tests. Statistical significance was identified when P<0.05.

combined with 100 mg/kg Compound B-2 CoX (% T/C 34.1; FIG. 7; Table 14). On Day 26, when the vehicle group was terminated, the combination group was statistically different from the vehicle group (P=0.029), but not the DOXIL® alone group (P=0.49). For all dose groups, treatment was well tolerated as mice in all treatment groups gained weight over the course of the study (FIG. 8, Table 14).

TABLE 13

Design of Efficacy Study in Tumor Bearing NCr Mice for Models CTG-0253, 0486, 0964, 1166 and 1423

| Group | n | Agent | Dose* (mg/kg) | Dose Volume (mL/kg) | Route | Dosing Schedule | Total # of Doses |
|---|---|---|---|---|---|---|---|
| 1 | 4 | 0.5% MC | 0 | 10 | PO | (QD × 4/wk) × 2 | 8 |
| 2 | 4 | DOXIL ® | 6 | 10 | IV | QW × 2 | 2 |
| 3 | 4 | DOXIL ® + | 6 | 10 | IV | QW × 2 | 2 |
|   |   | Compound B-2 CoX | 100 | 10 | PO | (QD × 4/wk) × 2 | 8 |

*Both DOXIL ® doses were administered 16 hours before the subsequent Compound B-2 CoX dose.

Figure 3:
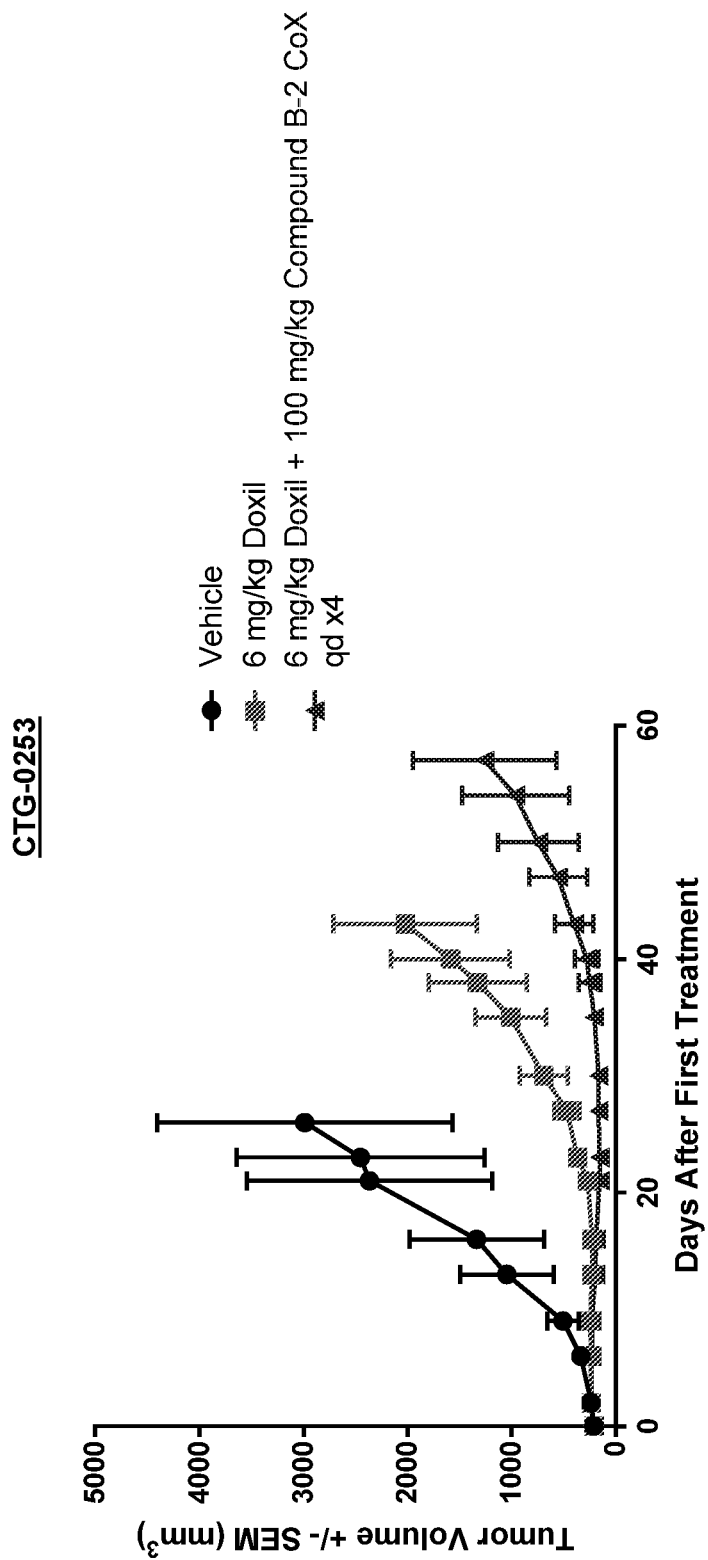
FIG. 3 shows the effect of Compound B-2 Co-X in combination with DOXIL® on tumor volume in the CTG-0253 primary patient derived xenograft tumor model in nude mice. Mice were dosed with DOXIL® or the combination of DOXIL® and Compound B-2 Co-X to assess efficacy as described in FIG. 2 (n=4/group).
Figure 4:
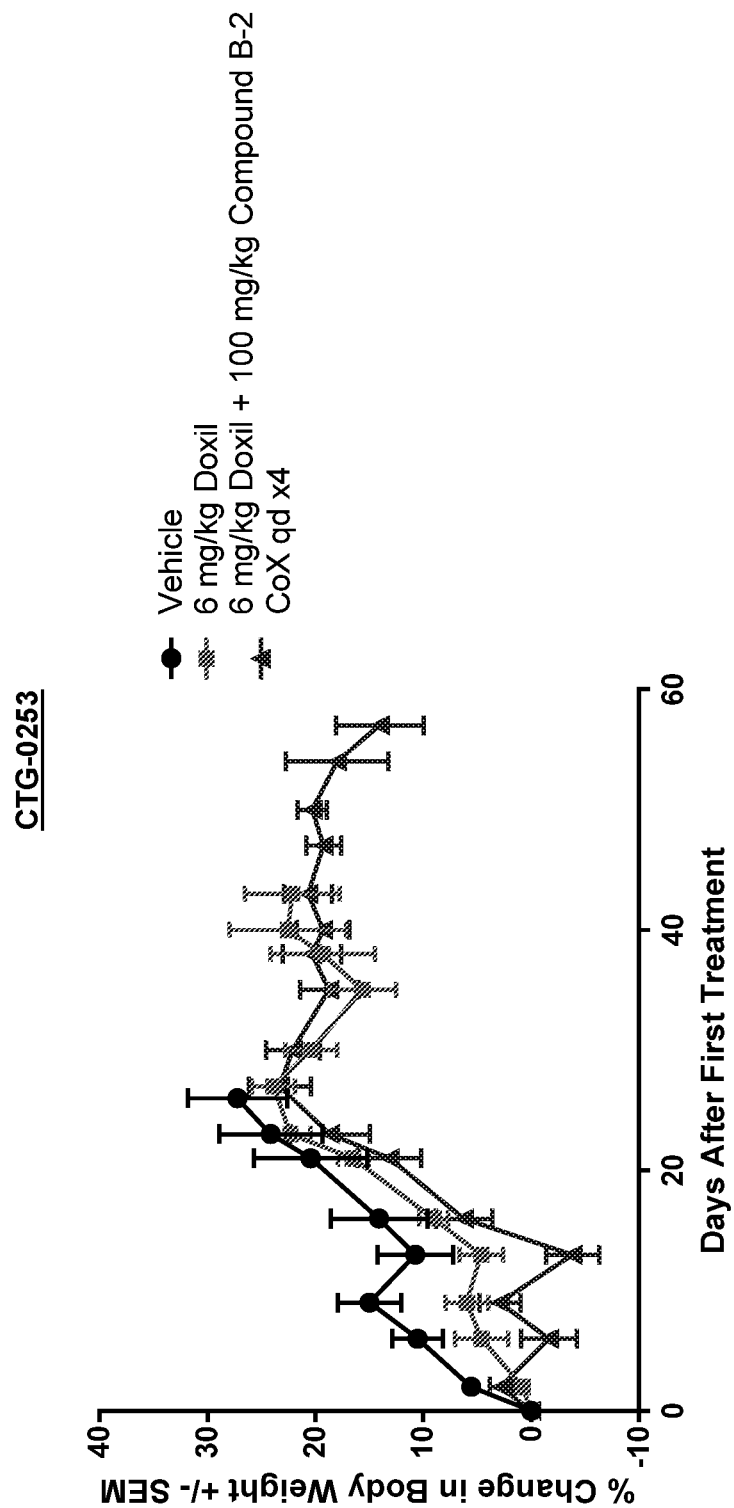
FIG. 4 shows the effect of DOXIL® or Compound B-2 Co-X in combination with DOXIL® on body weight in the CTG-0253 Primary Patient Derived Xenograft Nude Mouse Model (n=4/group).

Efficacy of Compound B-2 CoX in Combination with DOXIL® in the CTG-0253 Primary Ovarian Cancer Xenograft Model:

In the CTG-0253 model, DOXIL® delayed tumor growth (% T/C of 6.9) and this growth delay was enhanced when combined with 100 mg/kg Compound B-2 CoX (% T/Ti 69.1; FIG. 3; Table 14). For all dose groups, treatment was well tolerated as evidenced by maximum body weight loss in the combination group of −3.8% on Day 13 (FIG. 4, Table 14).

Figure 5:
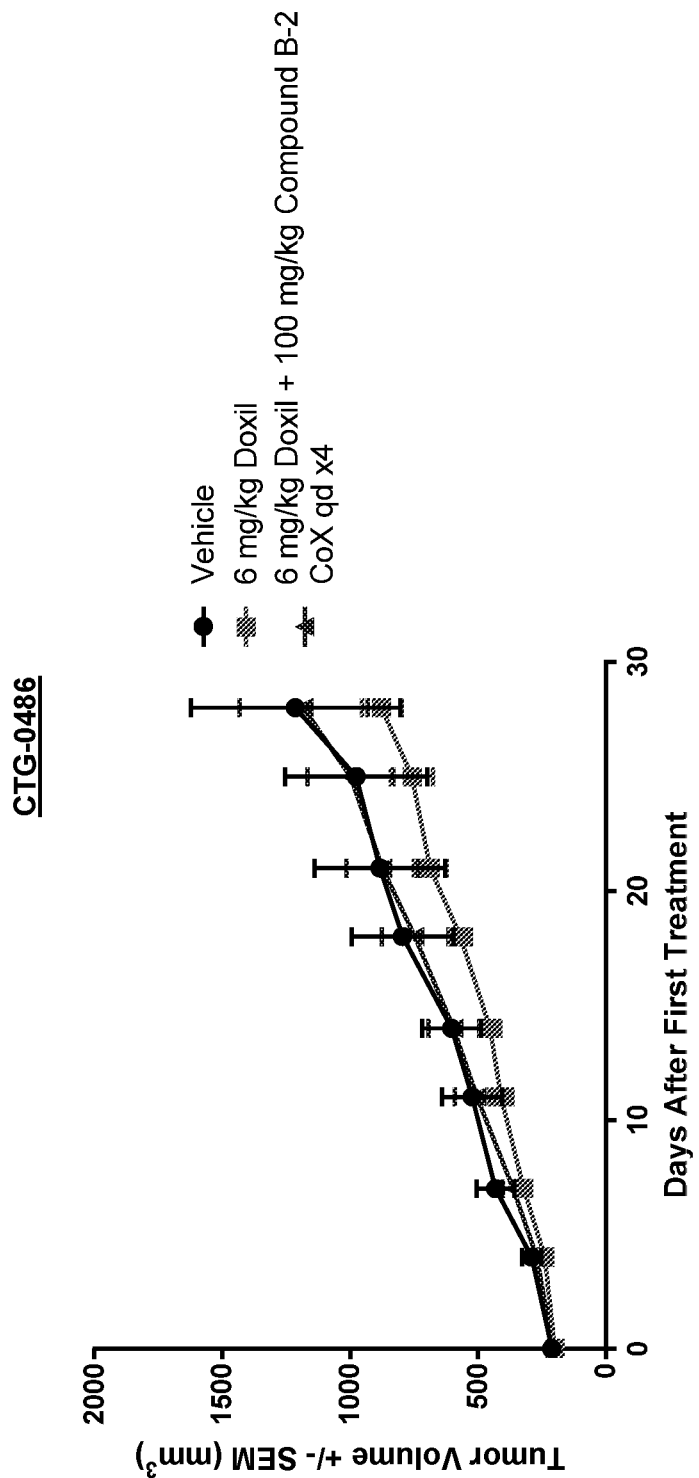
FIG. 5 shows the effect of Compound B-2 Co-X in Combination with DOXIL® on Tumor Volume in the CTG-0486 Primary Patient Derived Xenograft Tumor Model in Nude Mice. Mice were dosed with DOXIL® or the combination of DOXIL® and Compound B-2 Co-X to assess efficacy as described in FIG. 2 (n=4/group).
Figure 6:
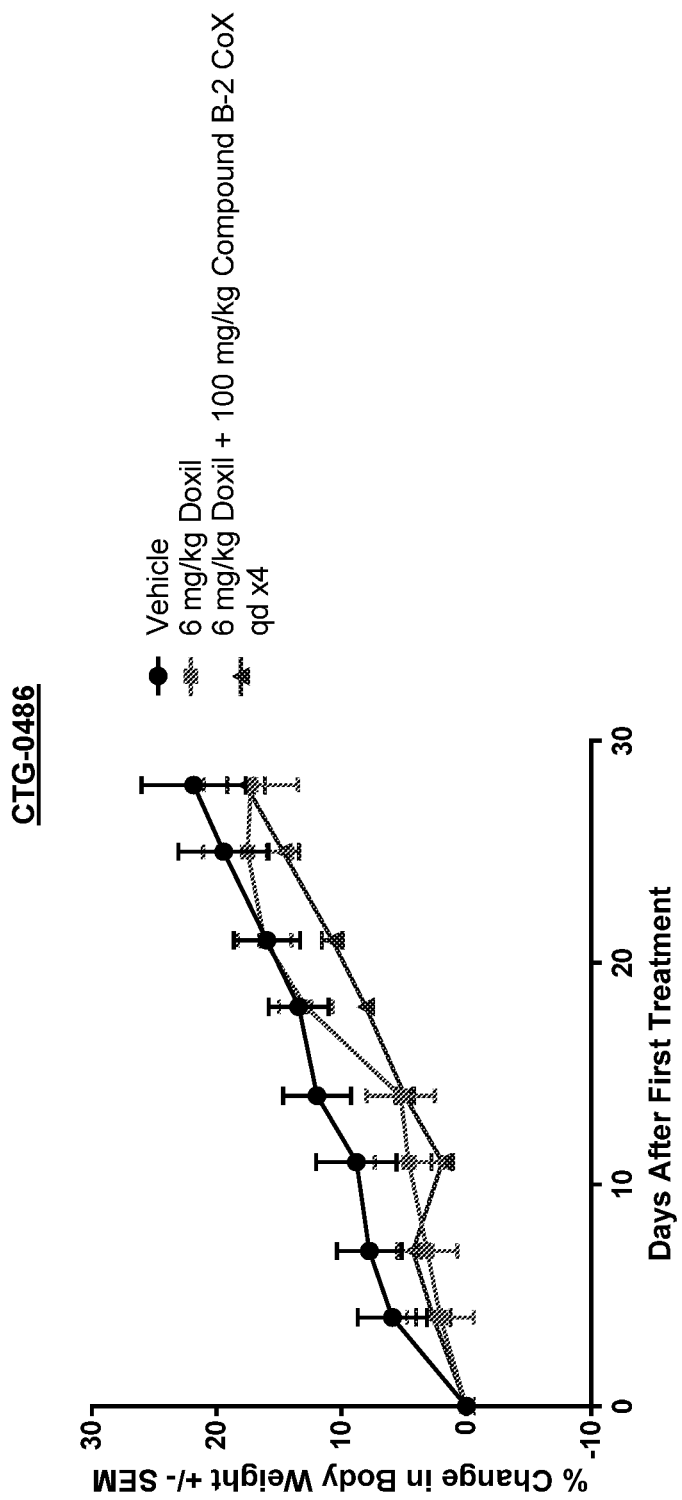
FIG. 6 shows the effect of DOXIL® or Compound B-2 Co-X in Combination with DOXIL® on Body Weight in the CTG 0486 Primary Patient Derived Xenograft Nude Mouse Model (n=4/group).

Efficacy of Compound B-2 CoX in Combination with DOXIL® in the CTG-0486 Primary Ovarian Cancer Xenograft Model:

In the CTG-0486 model, DOXIL® minimally affected tumor growth alone (% T/C of 72.3) or when combined with 100 mg/kg Compound B-2 CoX (% T/C 97.4; FIG. 5; Table 14). For all dose groups, treatment was well tolerated as mice in all treatment groups gained weight over the course of the study (FIG. 6, Table 14).

Figure 9:
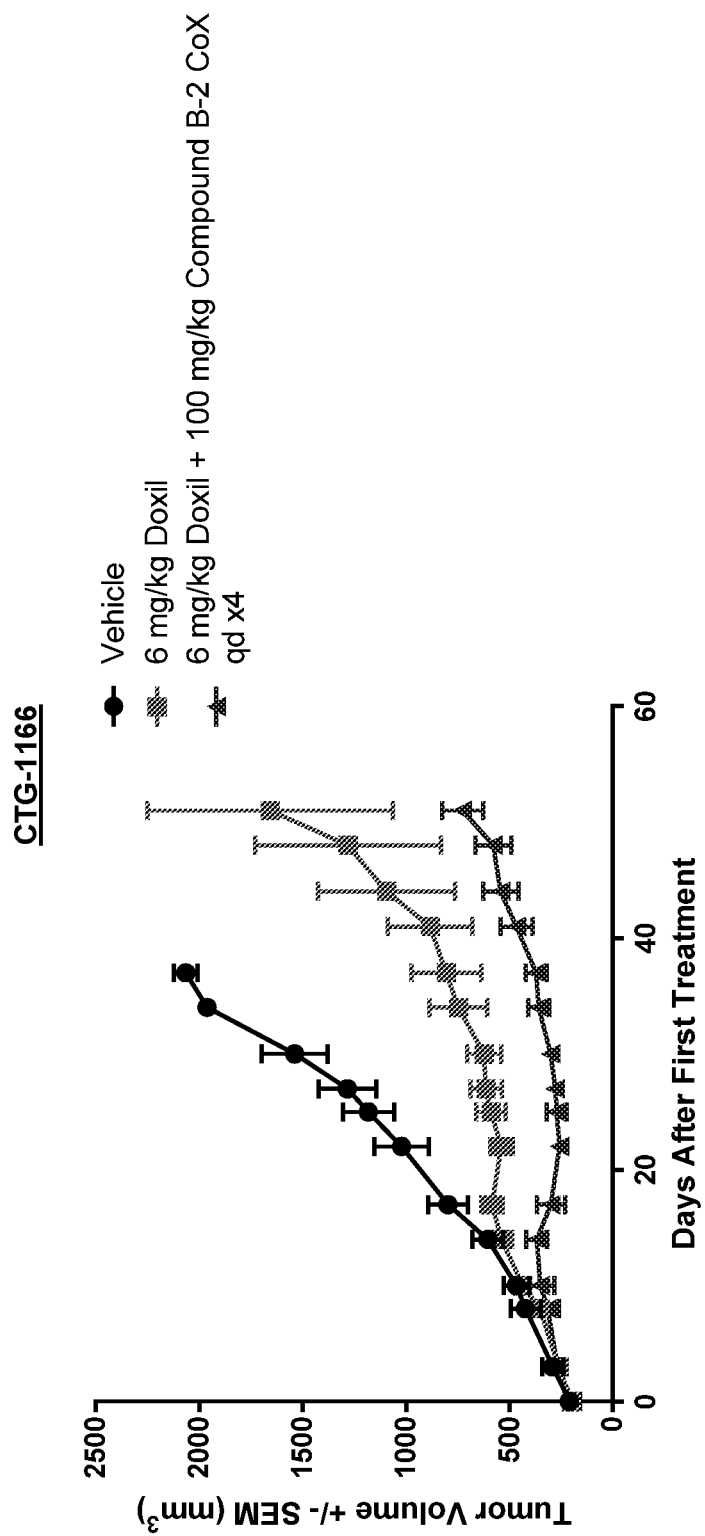
FIG. 9 shows the Effect of Compound B-2 Co-X in Combination with DOXIL® on Tumor Volume in the CTG 1166 Primary Patient Derived Xenograft Tumor Model in Nude Mice. Mice were dosed with DOXIL® or the combination of DOXIL® and Compound B-2 Co-X to assess efficacy as described in FIG. 2 (n=4/group).
Figure 10:
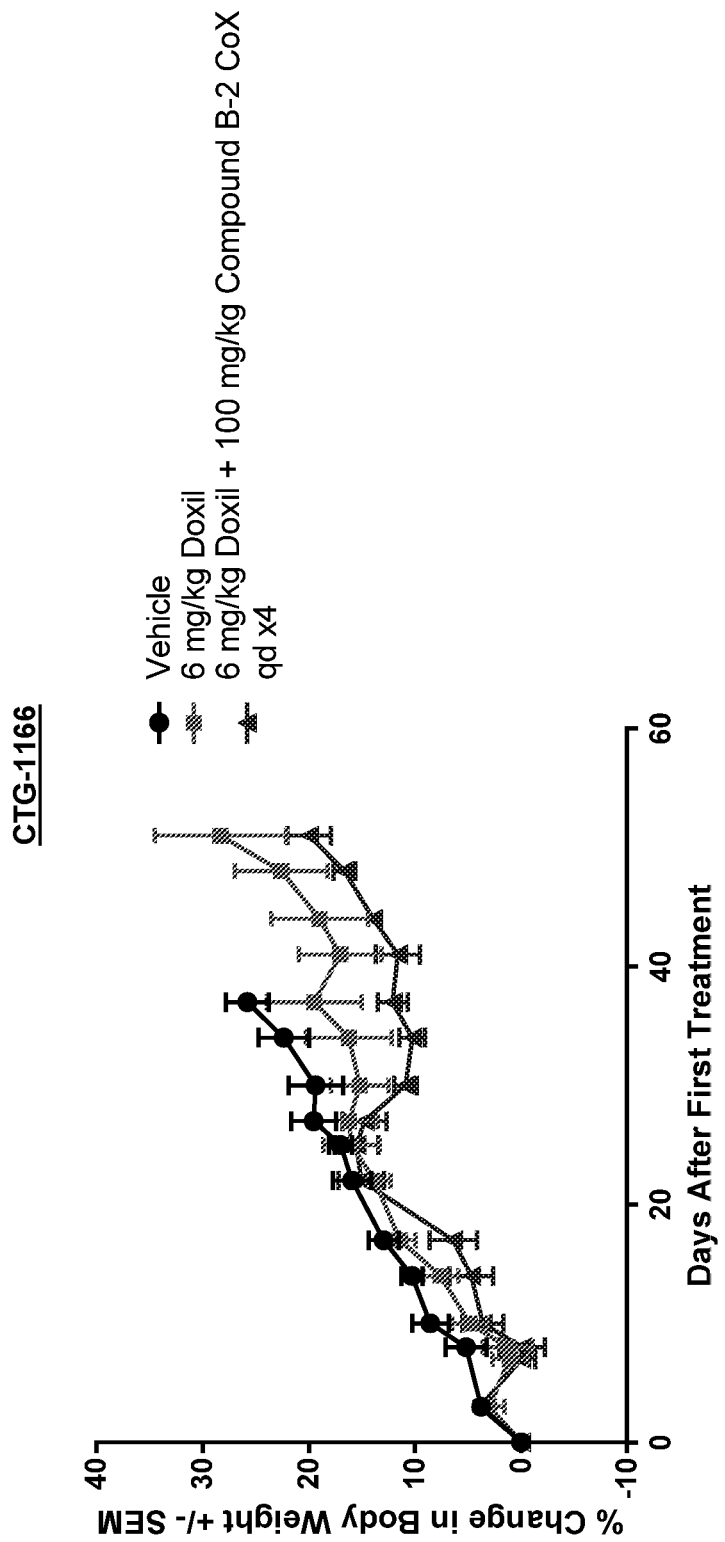
FIG. 10 shows the Effect of DOXIL® or Compound B-2 Co-X in Combination with DOXIL® on Body Weight in the CTG 1166 Primary Patient Derived Xenograft Nude Mouse Model (n=4/group).

Efficacy of Compound B-2 CoX in Combination with DOXIL® in the CTG-0964 Primary Ovarian Cancer Xenograft Model:

In the CTG-0964 model, DOXIL® delayed tumor growth (% T/C of 50.1) and this growth delay was enhanced when Efficacy of Compound B-2 CoX in Combination with DOXIL® in the CTG-1166 Primary Ovarian Cancer Xenograft Model:

The first two doses of Compound B-2 CoX during the second cycle of DOXIL® treatment were not given in the CTG-1166 model. Nonetheless, DOXIL® delayed tumor growth (% T/C of 32.7) and this growth delay was enhanced when combined with 100 mg/kg Compound B-2 CoX (% T/C 9.4; FIG. 9; Table 14). On Day 37, when the vehicle group was terminated, the treatment groups were statistically different from the vehicle group (P=0.029). For all dose groups, treatment was well tolerated as evidenced by maximum body weight loss in the combination group of −0.01% on Day 8 (FIG. 10, Table 14).

Figure 11:
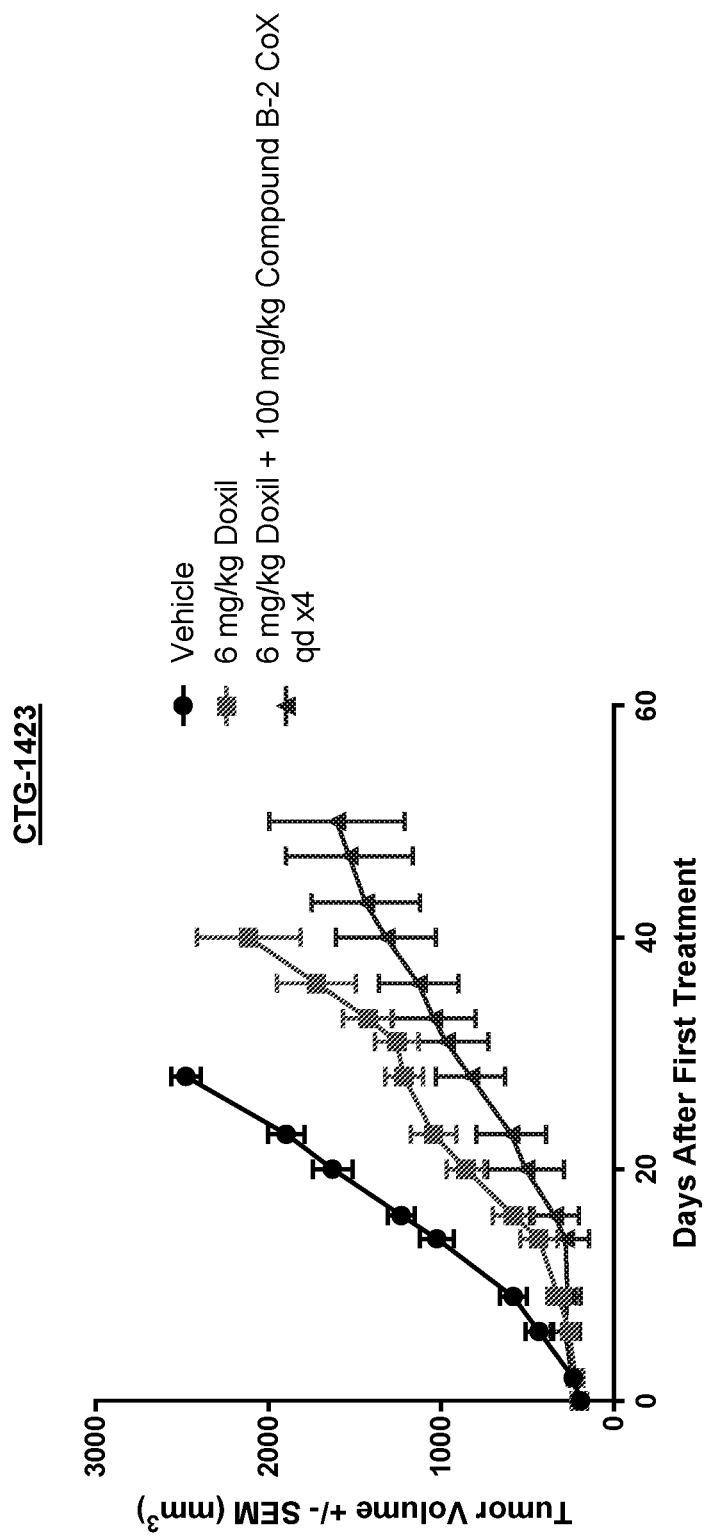
FIG. 11 shows the Effect of Compound B-2 Co-X in Combination with DOXIL® on Tumor Volume in the CTG 1423 Primary Patient Derived Xenograft Tumor Model in Nude Mice. Mice were dosed with DOXIL® or the combination of DOXIL® and Compound B-2 Co-X to assess efficacy as described in FIG. 2 (n=4/group).
Figure 12:
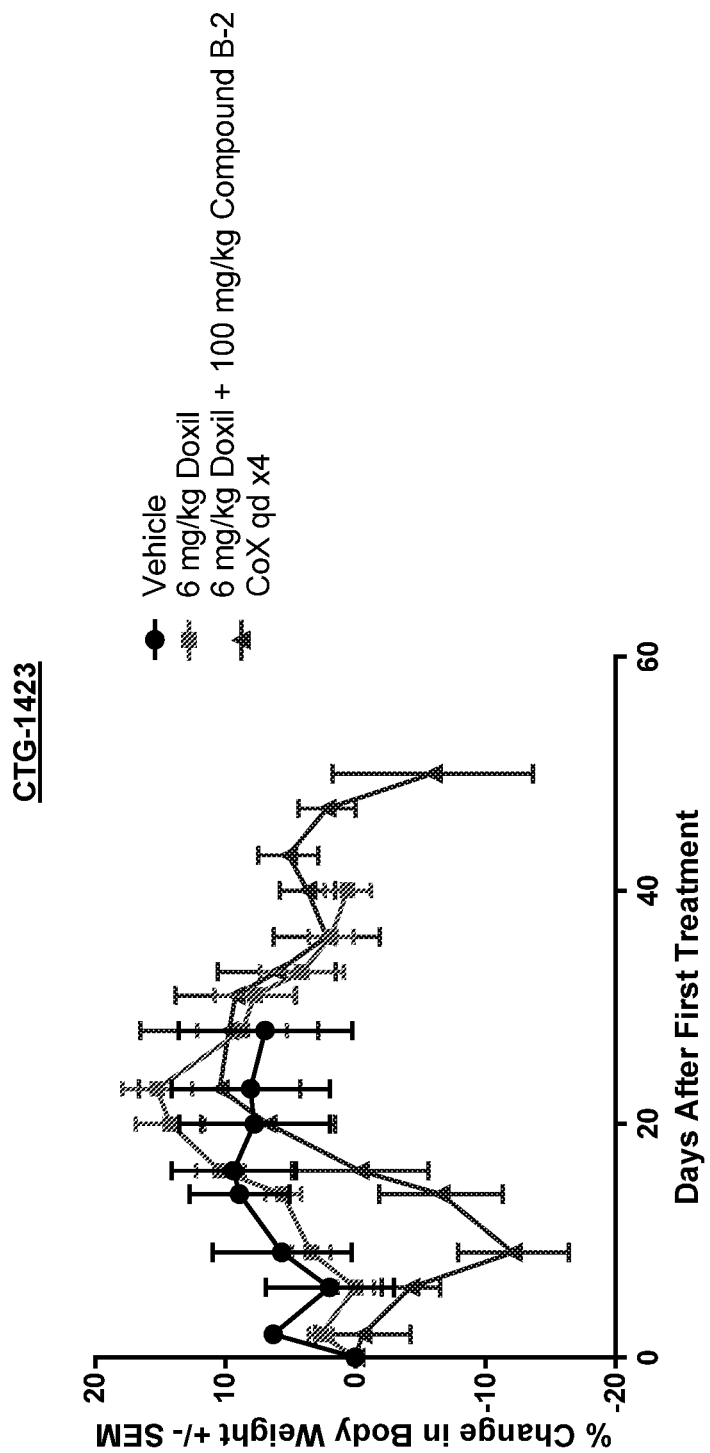
FIG. 12 shows Effect of DOXIL® or Compound B-2 Co-X in Combination with DOXIL® on Body Weight in the CTG 1423 Primary Patient Derived Xenograft Nude Mouse Model (n=4/group).

Efficacy of Compound B-2 CoX in Combination with DOXIL® in the CTG-1423 Primary Ovarian Cancer Xenograft Model:

In the CTG-1423 model, DOXIL® delayed tumor growth (% T/C of 44.5) and this growth delay was enhanced when combined with 100 mg/kg Compound B-2 CoX (% T/C 27.6; FIG. 11; Table 14). On Day 28, when the vehicle group was terminated, the treatment groups were statistically different from the vehicle group (P=0.029). For all dose groups, treatment was tolerated as evidenced by maximum body weight loss in the combination group of −12.1% on Day 9 (FIG. 12, Table 14).

TABLE 14

Effect of Compound B-2 CoX in Combination with DOXIL ® on Inhibition of Tumor Growth (% T/C or % T/Ti) and Body Weight in the Primary Ovarian Cancer Xenograft Tumor Model in Nude Mice

| Xenograft Tumor Model (Day vehicle group terminated) | Treatment | N | % T/C | % T/Ti | Max. Body Weight Loss (%) |
|---|---|---|---|---|---|
| CTG-0253 | Vehicle | 4 | — | — | N/A (not applicable) |
| (Day 23) | 6 mg/kg DOXIL ® | 4 | 6.9 | — | N/A |
|   | 6 mg/kg DOXIL ® + 100 mg/kg Compound B-2 CoX qd x4 | 4 | — | 69.1 | −3.8 (Day 13) |
| CTG-0486 | Vehicle | 4 | — | — | N/A |
| (Day 28) | 6 mg/kg DOXIL ® | 4 | 72.3 | — | N/A |
|   | 6 mg/kg DOXIL ® + 100 mg/kg Compound B-2 CoX qd x4 | 4 | 97.4 | — | N/A |

TABLE 14-continued

Effect of Compound B-2 CoX in Combination with DOXIL ® on Inhibition of
Tumor Growth (% T/C or % T/Ti) and Body Weight in the Primary Ovarian Cancer
Xenograft Tumor Model in Nude Mice

| Xenograft Tumor Model (Day vehicle group terminated) | Treatment | N | % T/C | % T/Ti | Max. Body Weight Loss (%) |
|---|---|---|---|---|---|
| CTG-0964 (Day 26) | Vehicle | 4 | — | — | N/A |
|  | 6 mg/kg DOXIL ® | 4 | 50.1 | — | N/A |
|  | 6 mg/kg DOXIL ® + 100 mg/kg Compound B-2 CoX qd x4 | 4 | 34.1 | — | N/A |
| CTG-1166 (Day 37) | Vehicle | 4 | — | — | N/A |
|  | 6 mg/kg DOXIL ® | 4 | 32.7 | — | N/A |
|  | 6 mg/kg DOXIL ® + 100 mg/kg Compound B-2 CoX qd x4 | 4 | 9.4 | — | −0.01 (Day 8) |
| CTG-1423 (Day 28) | Vehicle | 4 | — | — | N/A |
|  | 6 mg/kg DOXIL ® | 4 | 44.5 | — | −0.02 (Day 6) |
|  | 6 mg/kg DOXIL ® + 100 mg/kg Compound B-2 CoX qd x4 | 4 | 27.6 | — | −12.1 (Day 9) |

Discussion:

Compound B-2 CoX at 100 mg/kg in combination with DOXIL® was well tolerated and treatments resulted in an enhancement in anti-tumor activity as evidenced by the improvement in % T/C values in 4 of the 5 above-described models examined compared to DOXIL® only. Compound B-2 CoX in combination with DOXIL® demonstrated statistically significant (one-way ANOVA) anti-tumor activity over the course of the study when compared to DOXIL® alone in 2 of the 5 models (CTG-0253 and CTG-1166) examined These data support the further examination of Compound B-2 CoX in combination with DOXIL® for the treatment of solid tumors.

Figure 13:
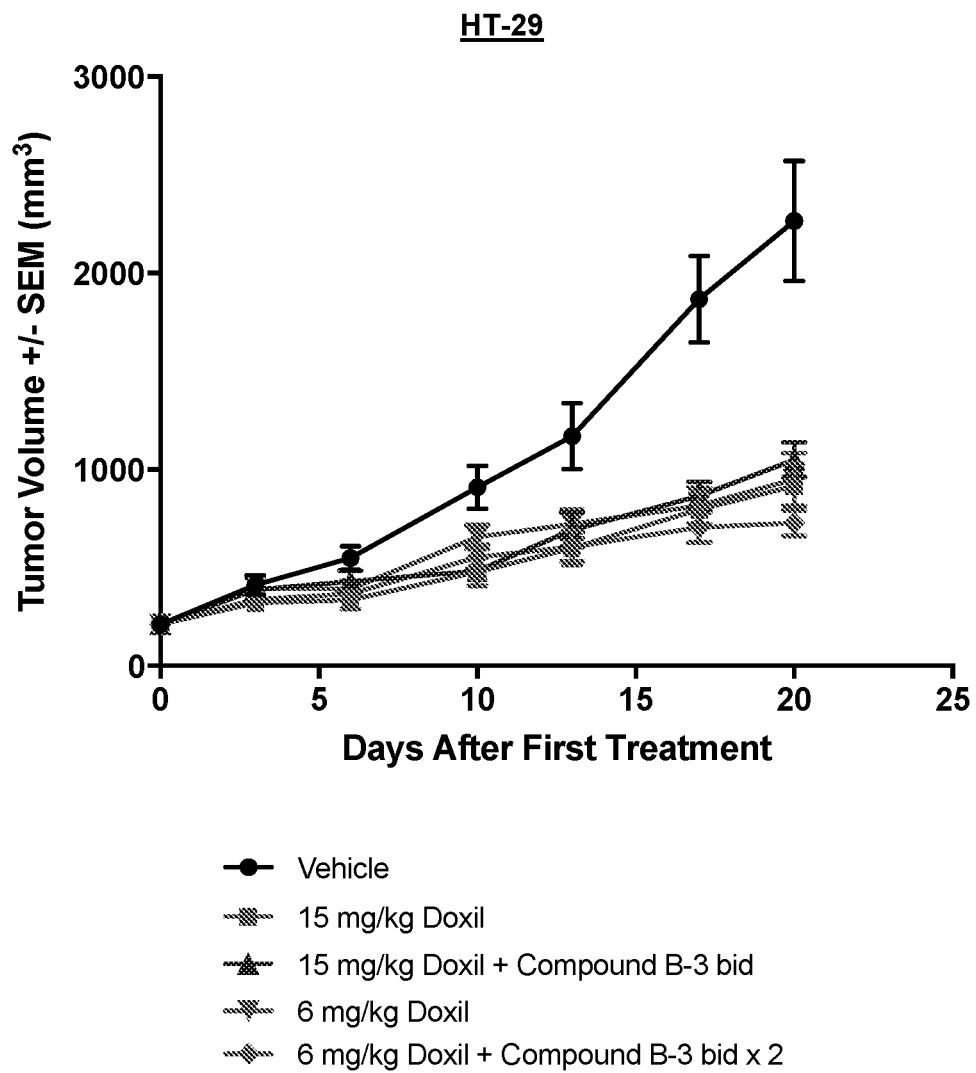
FIG. 13 shows the effect of Compound B-3 in combination with DOXIL® on tumor volume in the HT-29 cell line xenograft model. Mice were dosed with DOXIL® or the combination of DOXIL® and Compound B-3 to assess efficacy as described herein.
Figure 14:
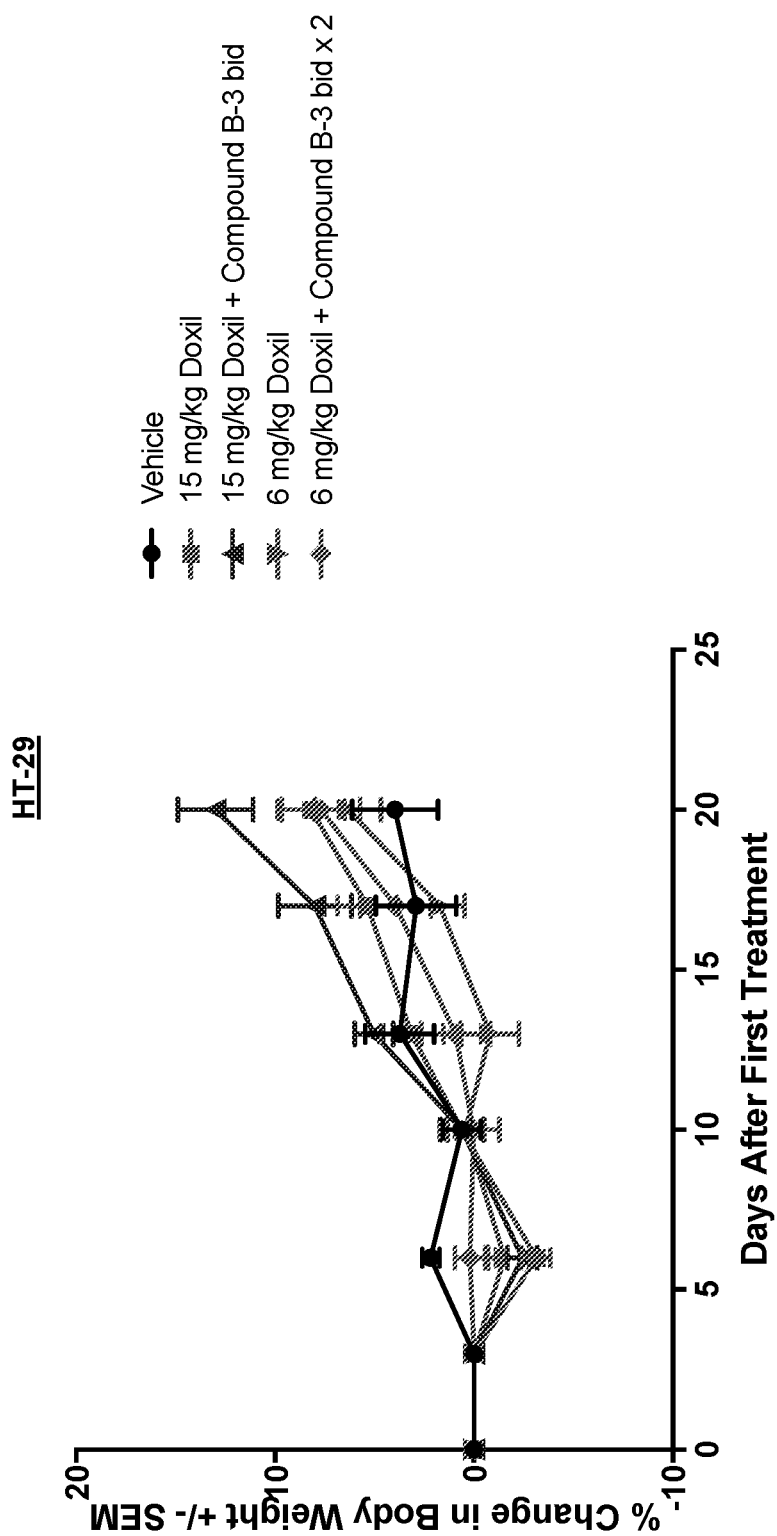
FIG. 14 shows the effect of Compound B-3 in combination with DOXIL® on body weight in the HT-29 cell line xenograft model.

Example 5: Efficacy of DOXIL® with and without Compound B-3 in HCT 116 Xenografts Similar to the xenograft methods described in previous examples, the HT-29 cell line xenograft model was used to evaluate the efficacy of Compound B-3, in combination with DOXIL®. Compound B-3 used in these experiments was not prepared as a co-crystal. Treatment groups (n=5) consisted of vehicle control, 15 mg/kg DOXIL®, 15 mg/kg DOXIL®+100 mg/kg Compound B-3 bid, 6 mg/kg DOXIL® once per week for 2 cycles, and 6 mg/kg DOXIL®+100 mg/kg Compound B-3 bid once/week for 2 cycles. On the days of treatment, each mouse received DOXIL® 16 hr prior to Compound B-3. FIG. 13 and FIG. 14 show the tumor volume and the change in body weight, respectively.

Example 6: Efficacy of DOXIL® and Compound B-2 Administered in H460 Xenografts

Figure 15:
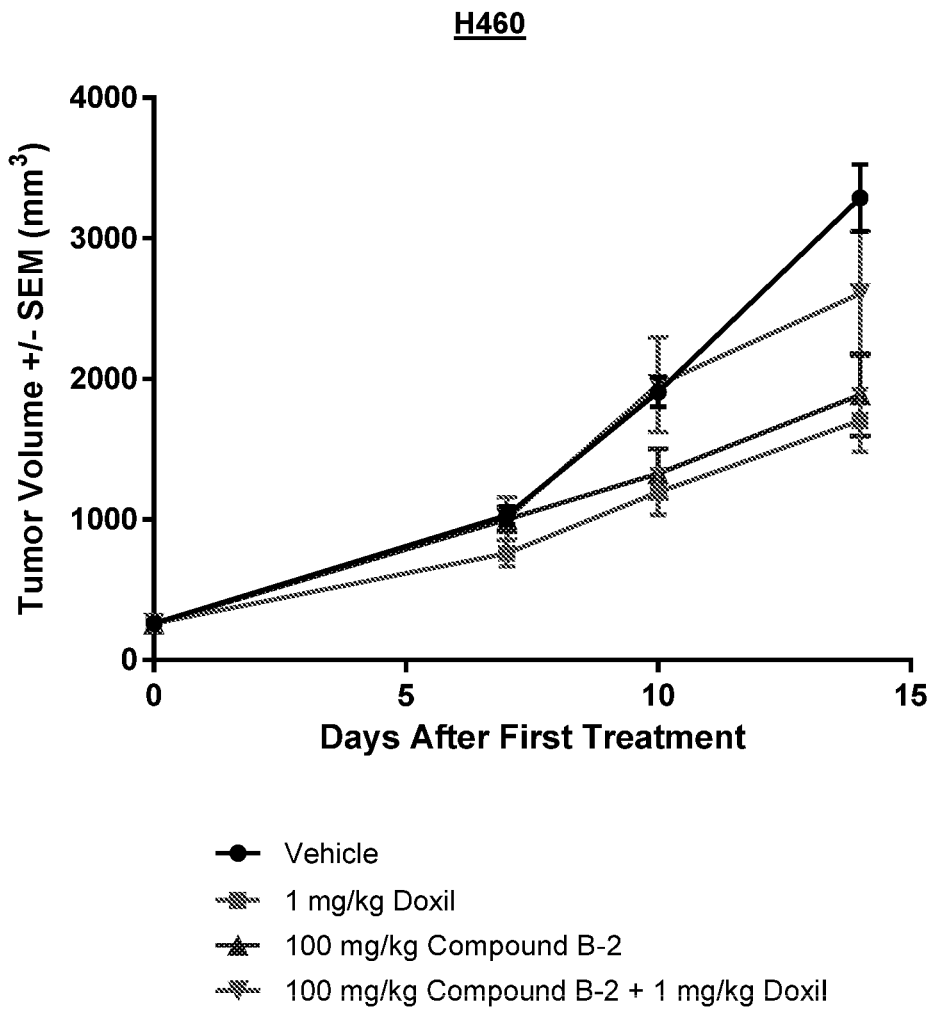
FIG. 15 shows the effect of Compound B-2 in combination with DOXIL® on tumor volume. DOXIL® and Compound B-2 were administered on the same day in a H460 xenograft model.
Figure 16:
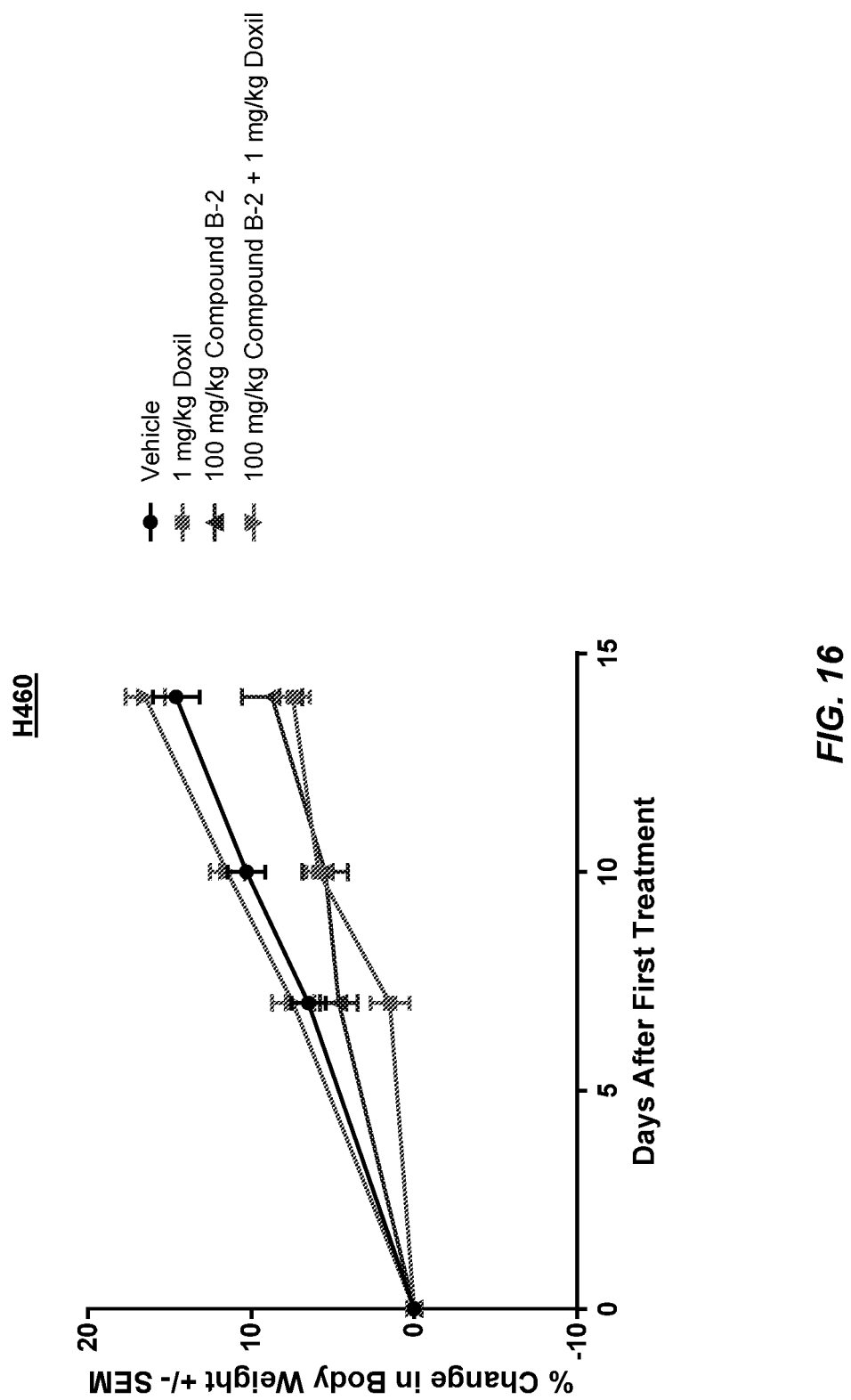
FIG. 16 shows the effect of Compound B-2 in combination with DOXIL® on change in body weight. DOXIL® and Compound B-2 were administered on the same day in a H460 xenograft model.

Similar to the xenograft methods described in previous examples, the H460 xenograft model was used to evaluate the efficacy of Compound B-2, in combination with DOXIL®. Compound B-2 used in these experiments was not prepared as a co-crystal. Four groups (vehicle, 1 mg/kg DOXIL® (IP administration), 100 mg/kg Compound B-2 (PO administration), 1 mg/kg DOXIL®+100 mg/kg Compound B-2) were examined in H460 xenografts. Compound B-2 was administered at about 0 hr and at about 4 hours and DOXIL® at about 15 minutes. The regimen was provided twice a week on Days 1 and 4. Tumor volume and body weights were measured similar to methods described in other examples. Blood was collected by cheek bleeds and put onto dried blood spot cards for PK analysis. FIGS. 15 and 16 show the effect of Compound B-2 in co-administered simultaneously on the same day with DOXIL® on tumor volume and on body weight of a xenograft mouse model.

Example 7: Evaluation of Compound B-2 Co-X in Combination with DOXIL® in a Primary Endometrial and Ovarian Tumor Xenograft Models The objective of this study was to evaluate the efficacy of the DNA-PK inhibitor, Compound B-2 Co-X, in combination with pegylated liposomal doxorubicin (PLD, DOXIL®) in Female NCr nude mice implanted with a primary endometrial tumor CTG-1280 and a primary ovarian tumor (CTG-0259).

When tumors reached approximately 200 mm$^3$ (for CTG-1280) or 180 mm$^3$ (for CTG-0259), mice were treated with PLD (6 mg/kg) q7d alone or in combination with Compound B-2 CoX at 100 mg/kg qdx2 for 2 cycles. For CTG-1280, the combination of PLD with Compound B-2 CoX resulted in tumor regression (% T/Ti −51.5) while PLD treatment alone caused tumor growth inhibition (% T/C 21.7). For CTG-0259, the combination of PLD with Compound B-2 CoX resulted in tumor growth inhibition (% T/C 19.2) which was significantly different (P<0.0355) from PLD treatment alone (% T/C 49). These data support the continued development of Compound B-2 CoX in combination with PLD for the treatment of solid tumors.

Formulation:

Compound B-2 CoX was formulated in vehicle containing 0.5% methylcellulose as a homogeneous suspension by stirring at room temperature for 30 minutes. Compound B-2 CoX was prepared at a concentration of 10 mg/mL and administered to mice orally at a dosing volume of 10 mL/kg.

Figure 17:
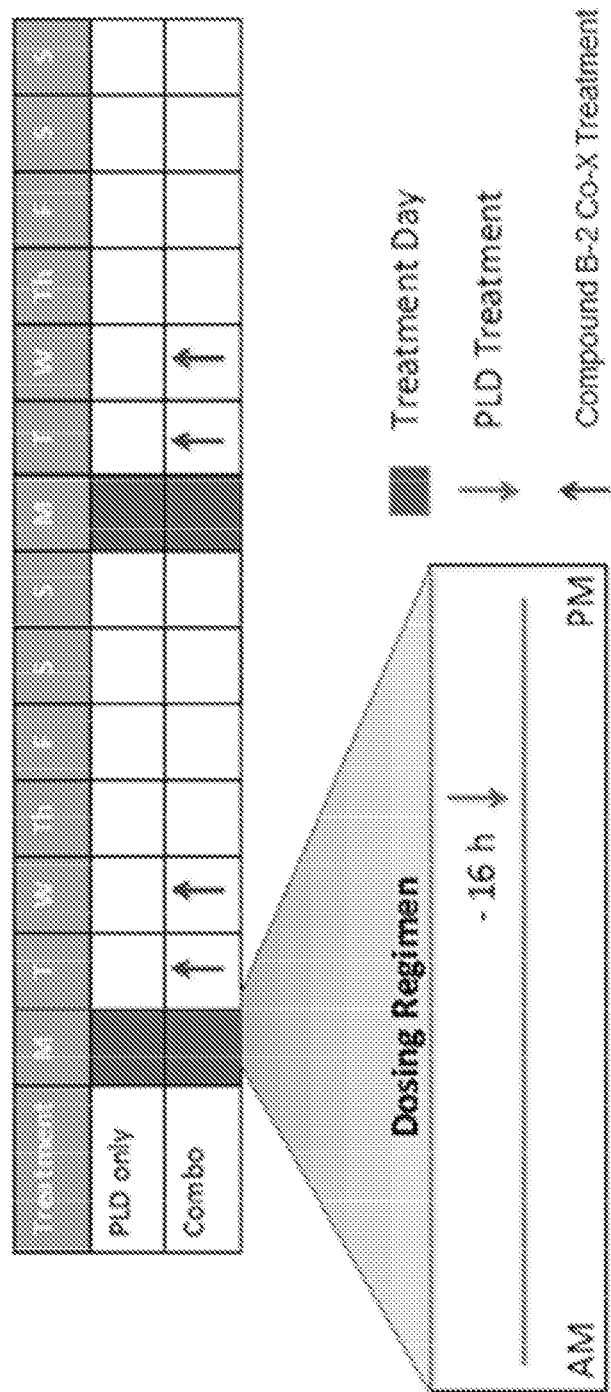
FIG. 17 shows the dosing regimen for Compound B-2 CoX in combination with PLD (DOXIL®). On the days of treatment, each animal received PLD (IV) 16 hr prior to Compound B-2 CoX. Compound B-2 CoX (PO) was then administered qd at 0 hr for two days. These cycles were repeated once per week for two weeks.
Figure 18A:
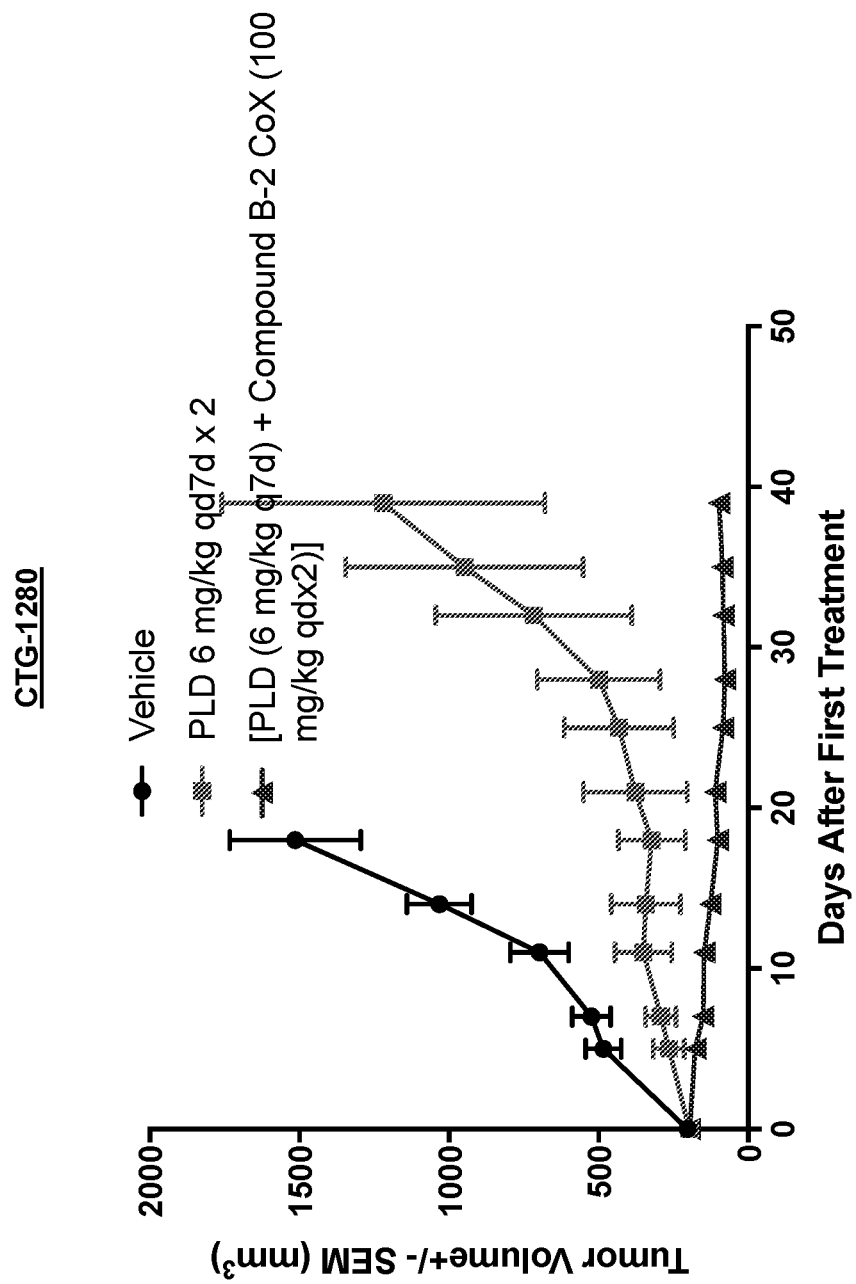
FIG. 18A and FIG. 18B show the results from the efficacy and tolerability study of PLD with and without Compound B-2 CoX.
Figure 18B:
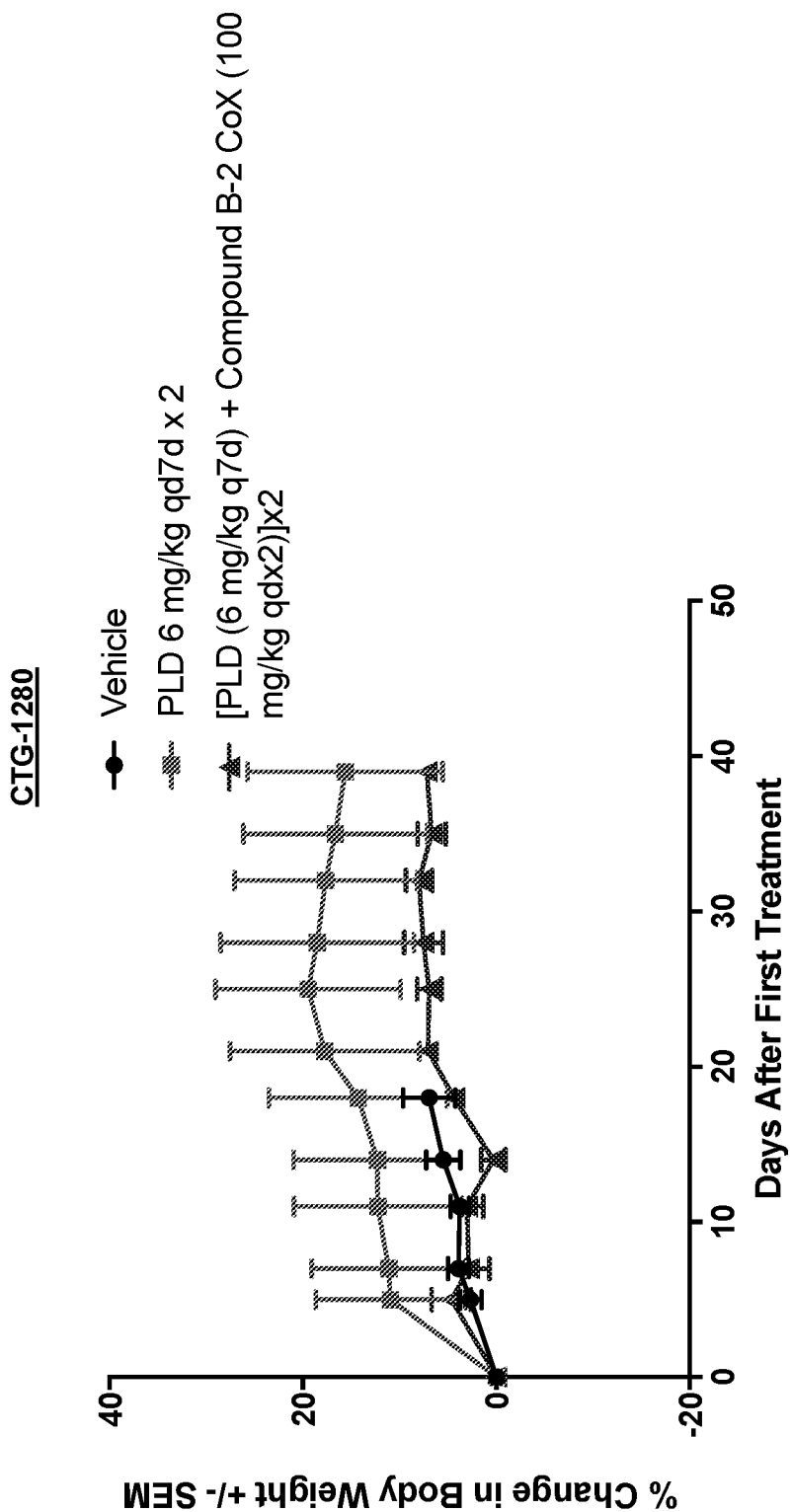

Methods:

The endometrial cancer xenograft tumor models were originally established from surgically resected clinical samples. Female athymic NCr nude mice were implanted subcutaneously on the left flank with CTG-1280 tumor fragments. Mice (n=5/group) were treated with vehicle, 6 mg/kg PLD, or 6 mg/kg PLD+100 mg/kg Compound B-2 CoX as depicted in FIG. 17 and FIGS. 18A-18B. PLD was administered IV and 16 hours later, Compound B-2 CoX was administered PO for 2 consecutive days, 24 hr apart. This cycle was repeated twice, one week apart. Tumors were measured with calipers and mouse body weights were recorded twice per week. Tumor volume, expressed in mm$^3$, was calculated using the equation Volume=$0.52 \times L \times W^2$ where L and W were the longest and shortest dimensions of the tumor, respectively. Anti-tumor efficacy is expressed as % T/C (change in tumor volume of treated/change in tumor volume of control×100%) while regression is expressed as % T/Ti (final tumor volume/initial tumor volume×100%). An unpaired, two-tailed, nonparametric t-test (Mann-Whitney test) was conducted using GraphPad Prism software on the day that the vehicle group was euthanized.

Figure 19A:
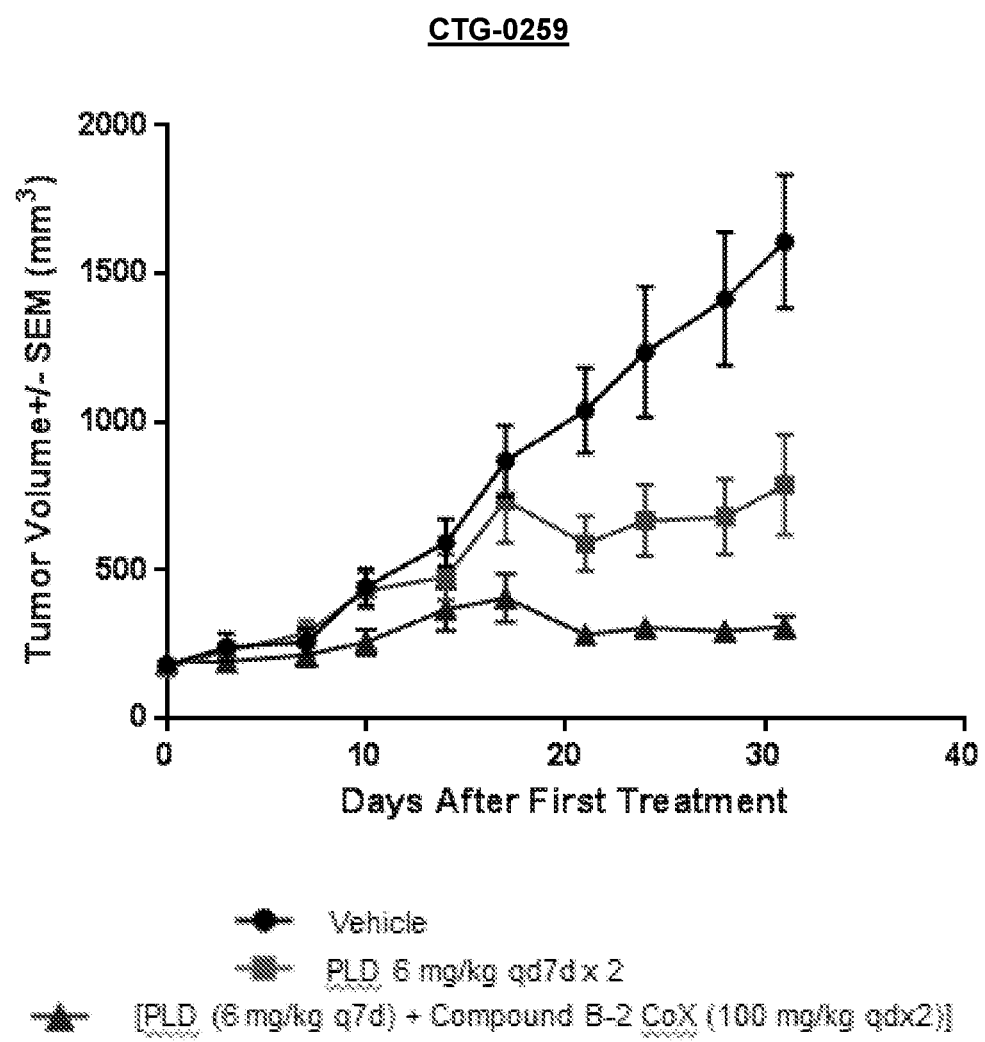
FIG. 19A and FIG. 19B show the effect of Compound B-2 CoX in combination with PLD (DOXIL®) on tumor volume (FIG. 19A) and body weight FIG. 19B) in the ovarian CTG-0259 xenograft tumor model in nude mice.
Figure 19B:
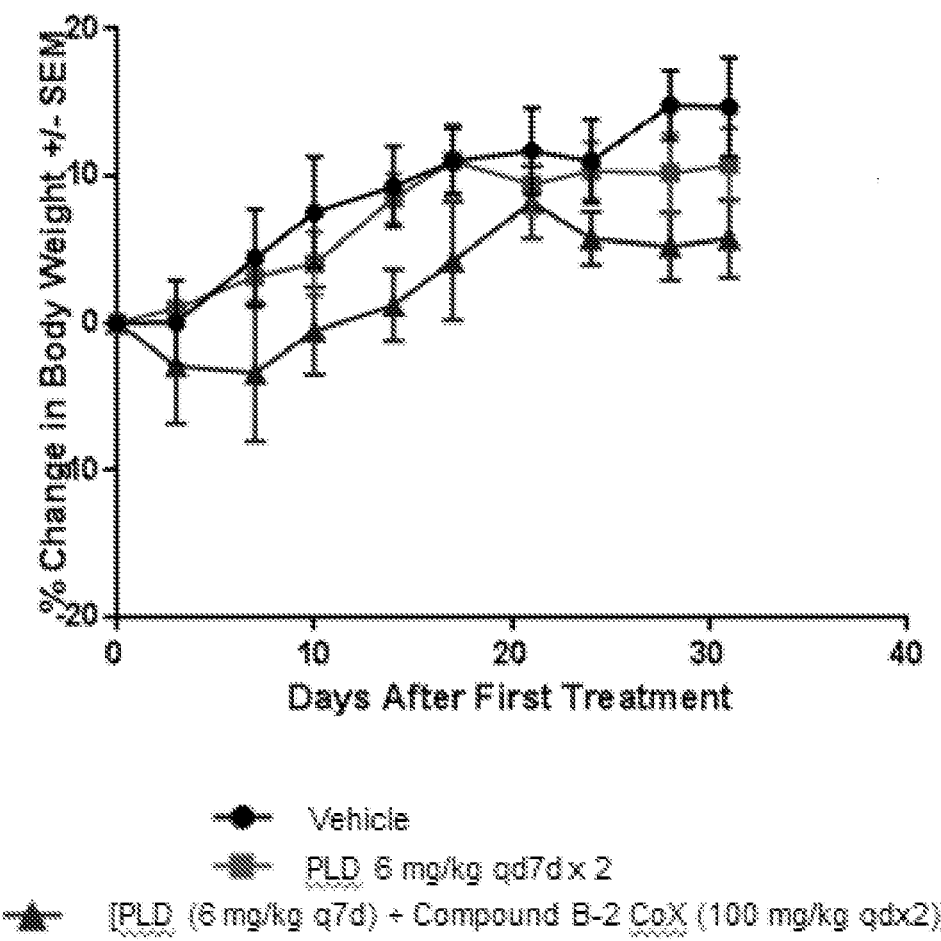

The ovarian cancer xenograft tumor models were originally established from surgically resected clinical samples. Female athymic NCr nude mice were implanted subcutaneously on the left flank with CTG-0259 tumor fragments. Mice (n=5/group) were treated with vehicle, 6 mg/kg PLD, or 6 mg/kg PLD+100 mg/kg Compound B-2 CoX as depicted in FIGS. 19A-19B. PLD was administered IV and 16 hours later, Compound B-2 CoX was administered PO for 2 consecutive days, 24 hr apart. This cycle was repeated twice, one week apart. Tumors were measured with calipers and mouse body weights were recorded twice per week. Tumor volume, expressed in mm3, was calculated using the equation Volume=0.52×L×W2 where L and W were the longest and shortest dimensions of the tumor, respectively. Anti-tumor efficacy is expressed as % T/C (change in tumor volume of treated/change in tumor volume of control× 100%) while regression is expressed as % T/Ti (final tumor volume/initial tumor volume×100%). An unpaired, two tailed, nonparametric t-test (Mann-Whitney test) was conducted using GraphPad Prism software on the day that the vehicle group was euthanized.

Results of Efficacy of Compound B-2 CoX in Combination with PLD in CTG-1280 Endometrial Patient-Derived Xenograft Tumors:

The CTG-1280 xenograft model was used to evaluate the efficacy of the Compound B-2 CoX in combination with PLD. Female NCr nude mice implanted with CTG-1280 fragments were randomized when the tumors reached approximately 200 mm$^3$. Treatment groups (n=5) consisted of vehicle control, 6 mg/kg PLD, 6 mg/kg PLD+100 mg/kg Compound B-2 CoX qd×2. Two cycles of treatment were performed on Day 0 and Day 7.

The effects of the treatments are shown in FIG. 18A (top graph) and the calculated % T/C or % T/Ti values are given in Table 15A. PLD treatment alone resulted in statistically significant tumor growth inhibition compared with the Vehicle group (P=0.0079). Compound B-2 CoX enhanced the efficacy of PLD at 6 mg/kg when administered qd×2 (% T/Ti −51.5, P<0.016) and resulted in tumor regression. Body weights were measured twice per week during the course of the study to assess tolerability of the treatments. In general, these dosing regimens in mice resulted in a maximal body weight change of −4.3% on Day 14 after treatment in one animal in the combination group (FIG. 18B, bottom graph).

TABLE 15A

Effect of Compound B-2 CoX in Combination with PLD on Inhibition of Tumor Growth (% T/C) and Body Weight in an CM-1280 Xenograft Tumor Model in Nude Mice

| Treatment | N | % T/C (Day 18) | % T/Ti (Day 18) | Mean Max. Body Weight Loss (%) |
|---|---|---|---|---|
| Vehicle | 5 | N/A | N/A | N/A |
| 6 mg/kg PLD | 5 | 21.7 | N/A | N/A |
| 6 mg/kg PLD + 100 mg/kg Compound B-2 CoX qd x2 | 5 | N/A | −51.5 | N/A* |

N/A: not applicable.
*Note: one animal in the combination group had a maximal body weight change of −4.3%.

Results of Efficacy of Compound B-2 CoX in Combination with PLD in CTG-0259 Ovarian Patient-Derived Xenograft Tumors:

The CTG-0259 xenograft model was used to evaluate the efficacy of the DNA-PK inhibitor, Compound B-2 CoX, in combination with PLD. Female NCr nude mice implanted with CTG 0259 fragments were randomized when the tumors reached approximately 180 mm$^3$. Treatment groups (n=5) consisted of vehicle control, 6 mg/kg PLD, 6 mg/kg PLD+100 mg/kg Compound B-2 CoX qd×2. Two cycles of treatment were performed on Day 0 and Day 7.

The effects of the treatments are shown in FIGS. 19A-19B, and the calculated % T/C or % T/Ti values are given in Table 15B. PLD treatment alone resulted in statistically significant tumor growth inhibition compared with the Vehicle group. Compound B-2 CoX enhanced the efficacy of PLD at 6 mg/kg when administered qd×2 (% T/C −19.2, P<0.0355).

Body weights were measured twice per week during the course of the study to assess tolerability of the treatments. In general, these dosing regimens were well tolerated in mice with a mean maximal body weight loss of 3.4% on Day 7 after treatment; however, in one animal in the combination group the maximal body weight loss was 22%, which recovered over time (FIG. 19B).

TABLE 15B

Effect of Compound B-2 CoX in Combination with PLD on Inhibition of Tumor Growth (% T/C) and Body Weight in an CTG-0259 Xenograft Tumor Model in Nude Mice

| Treatment | N | % T/C (Day 31) | % T/Ti (Day 31) | Mean Max. Body Weight Loss (%) |
|---|---|---|---|---|
| Vehicle | 5 | 100 | N/A | Weight gain |
| 6 mg/kg PLD | 5 | 49 | N/A | Weight gain |
| 6 mg/kg PLD + 100 mg/kg Compound B-2 CoX qd x2 | 5 | 19 | N/A | 3.4 |

N/A: not applicable.
*Note: one animal in the combination group had a maximal body weight loss of 22%.

Discussion:

The anti-tumor efficacy of Compound B-2 CoX in combination with PLD was evaluated in the CTG-1280 patient-derived xenograft model. The % T/C value for PLD alone was 21.7. Regression was seen (% T/Ti −51.5) for the combination of PLD (at 6 mg/kg) with Compound B-2 CoX (at 100 mg/kg). Results generated from these studies demonstrate that Compound B-2 CoX enhances the efficacy of PLD.

The anti-tumor efficacy of Compound B-2 CoX in combination with PLD was also evaluated in the CTG-0259 patient-derived xenograft model. The % T/C value for PLD alone was 49. Significant tumor growth inhibition was seen (% T/C 19.2) for the combination of PLD (at 6 mg/kg) with Compound B-2 CoX (at 100 mg/kg). Results generated from these studies demonstrate that Compound B-2 CoX enhances the efficacy of PLD.

Example 8: Effect of Compound B-1 or Compound B-2 on the Sensitivity of Primary Tumor Cells to Chemotherapeutics In Vitro Primary human tumors tested in vitro may provide additional indication of clinical efficacy than immortalized cancer cell lines due to their increased heterogeneity and closer proximity to the patient tumor from which they were derived. The objective of the following two studies was to assess the response rate of primary patient tumor samples in vitro to a combination of a DNA-dependent protein kinase (DNA-PK) selective inhibitor (either Compound B-1 or Compound B-2) and chemotherapeutic agents. Compound B-1 and Compound B-2 used in these experiments were not prepared as co-crystals.

Specifically, one study described the combination of Compound B-2 and doxorubicin hydrochloride. In this study, a panel of primary human ovarian and endometrial tumors was dissociated and treated with Compound B-2 to determine the effectiveness of this selective DNA-PK inhibitor to enhance the activity of doxorubicin.

Another study described the combination of Compound B-1 with either radiation, bleomycin, cisplatin, doxorubicin hydrochloride, gemcitabine, etoposide, carboplatin, paclitaxel, or 5-fluorouracil (5-FU). In this study, a panel of primary human tumors (non-small cell lung cancer (NSCLC), small-cell lung cancer (SCLC), pancreatic, hepatocellular carcinoma (HCC), gastric, esophageal) was dissociated and treated with Compound B-1 to determine the effectiveness of a selective DNA-PK inhibitor to enhance the activities of standard of care treatments that cause DNA damage including radiation, bleomycin sulfate, cisplatin, doxorubicin hydrochloride, gemcitabine, etoposide, carboplatin, paclitaxel, and 5-fluorouracil (5-FU).

In both studies, cell viability was assessed after 6 days in culture. Statistical analysis of the combination matrix was performed to assess whether synergy, additivity, or antagonism of the combination treatments were observed.

Materials:

Primary patient samples (See Tables 16 and 17, below) were excised from mice when they reached 500 mg to 1000 mg in size and processed immediately, or after overnight shipment. Tumors were serially passaged by subcutantous implantation of 50 mg to 150 mg fragments into the flanks of immunocompromised (nude) mice. Tumors were used within the first 5 or 7 passages.

TABLE 16

Primary Tumor Information

| Tumor identifier | Tumor type | Histological subtype | Histological grade |
|---|---|---|---|
| OD26131 | Lung-NSCLC | Squamous cell carcinoma | Poorly Differentiated |
| OD33966 | Lung-NSCLC | Adenocarcinoma | Moderately to poorly differentiated |
| OD26749 | Lung-NSCLC | Adenocarcinoma | Poorly differentiated |
| OD29498 | Lung-NSCLC | Bulky non-small cell carcinoma | Poorly differentiated |
| OD35982 | Lung-NSCLC | Squamous cell carcinoma | Poorly differentiated |
| YAS111611 | Lung-NSCLC | N/A | N/A |
| OD36088 | Lung-NSCLC | Squamous cell carcinoma | Poorly differentiated |
| TS110310 | Lung-NSCLC | N/A | N/A |
| OD33117 | Lung-NSCLC | Squamous carcinoma | Poorly differentiated |
| LUX031 | Lung-SCLC | Small-cell neuroendocrine carcinoma | N/A |
| LUX013 | Lung-SCLC | Squamous cell carcinoma (small cell subtype) | N/A |
| P110408 | Pancreatic | Ductal adenocarcinoma | Moderately differentiated |
| P110603 | Pancreatic | Ductal adenocarcinoma | Moderately differentiated |
| P110504 | Pancreatic | Ductal adenocarcinoma | Poorly to moderately differentiated |
| P110325 | Pancreatic | Ductal adenocarcinoma | Poorly to moderately differentiated |
| P110413 | Pancreatic | Ductal adenocarcinoma | Poorly differentiated |
| P110323 | Pancreatic | Ductal adenocarcinoma | Moderately differentiated |
| L090923 | Liver-HCC | Hepatocellular carcinoma | Poorly differentiated |
| GAX001 | Gastric | Adenocarcinoma | Moderately differentiated |
| GAX007 | Gastric | Adenocarcinoma | Moderately differentiated |
| GAX027 | Gastric | Adenocarcinoma | Moderately differentiated |
| ESX005 | Esophageal | Squamous carcinoma | Well differentiated |
| ESX008 | Esophageal | Squamous carcinoma | Moderately differentiated |

TABLE 17

Primary Tumor Information

| Tumor identifier | Tumor type | Histological subtype | Disease stage | Histological grade |
|---|---|---|---|---|
| OVX001 | Ovarian | NA | NA | NA |
| CTG-0992 | Ovarian | Carcinoma | III | NA |
| CTG-1301 | Ovarian | Carcinoma | III | NA |
| CTG-0947 | Ovarian | Epithelial | III | NA |
| CTG-0252 | Ovarian | Papilary serous adenocarcinoma | NA | NA |
| CTG-0258 | Ovarian | Carcinoma | NA | Poorly differentiated |
| CTG-0791 | Ovarian | Papilary serous adenocarcinoma | IIIC | Poorly differentiated |
| CTG-1423 | Ovarian | Mixed epithelial carcinoma | II | Poorly differentiated |
| CTG-0253 | Ovarian | Papilary serous adenocarcinoma | NA | Poorly differentiated |

TABLE 17-continued

Primary Tumor Information

| Tumor identifier | Tumor type | Histological subtype | Disease stage | Histological grade |
|---|---|---|---|---|
| CTG-0486 | Ovarian | Papilary serous adenocarcinoma | III | NA |
| CTG-1166 | Ovarian | Papilary serous adenocarcinoma | IV | Poorly differentiated |
| ENX005 | Endometrial | NA | NA | NA |
| ENX001 | Endometrial | NA | NA | NA |

Tumor Chemosensitivity Assay (TCA):

Primary tumor samples were grown and serially passaged in immunocompromised mice. Tumors were mechanically dissociated into small fragments (1 mm to 2 mm) with scalpels in phosphate buffered saline (PBS or RPMI) and centrifuged at 200×g for 5 minutes at room temperature in 50 mL centrifuge tubes. Samples were resuspended in 10 mL of cell dissociation reagent and enzymatically digested with mechanical agitation for 1 to 3 hours at 37° C., 5% $CO_2$ to a single cell suspension. Ten mL of complete RPMI-1640 media was added to the cell mixture and pipetted up and down 4 to 5 times. The mixture was then passed through a 70 m or 100 m mesh strainer to remove undigested tumor. The filtrate was then centrifuged 200×g for 5 minutes at room temperature and resuspended in 20 mL complete RPMI-1640. This cell suspension was slowly layered onto 20 mL of room temperature Histopaque and centrifuged at 400×g for 15 minutes at room temperature without a brake. The interface was transferred to a new 50 mL centrifuge tube and 15 mL of complete RPMI-1640 was added. This suspension was centrifuged at 200×g at room temperature, and the resulting pellet was resuspended in 10 mL of complete PC-1 media, except for pancreatic tumors in which case Pancreatic Medium was used. Cells were diluted in Trypan blue, and viable cells that excluded the dye were counted. Only the larger, tumor cells were included in the cell count. Cells were diluted in complete PC-1 or Pancreatic media, as appropriate for the cells, and were plated at 15,000 to 20,000 cells per well in 100-135 µL in ultra-low attachment U-bottom plates.

Compound Addition:

For these studies, a 10 mM stock of the DNA-PK inhibitor (Compound B-1 or Compound B-2) was made in DMSO and used to add to cells from most tumors with HP D300 Digital Dispenser (Tecan US, Morrisville, N.C., USA), or diluted into the appropriate media (PC-1 or pancreatic media) as a 5-10× stock and added to cells (OVX001 and ENX001, 005). PC-1, pancreatic media, and chemotherapeutics were also added so that final well volume was 150 µL. Doxorubicin was made as DMSO stock of 1 or 10 mM and added to cells for most tumors with HP D300 Digital Dispenser, or diluted into PC-1 as 5-10× stock and added to cells (OVX001 and ENX001, 005). Cisplatin (cis-diammine platinum(II), dichloride) was prepared fresh to 10 mM in warm (60° C.) distilled water and diluted in PC-1 as a 5-10× stock. Bleomycin, etoposide, doxorubicin, gemcitabine, carboplatin, paclitaxel, and 5-FU were prepared as DMSO stocks and diluted into PC-1 or Pancreatic media as 5-10× stock and added to cells. Different starting concentrations, dose ranges, and number of doses were used for each experiment based on the response data available at the time.

For doxorubicin hydrochloride experiments, combinations with Compound B-2 at all concentrations were run in triplicate. A 6×3 matrix was designed on each plate: 0.73 µM and 2.2 µM Compound B-2, or 0.37 µM and 4.4 µM Compound B-2 on some tumors where additional cells were available, plus no treatment control, in 3 columns each of 6 wells. Doxorubicin hydrochloride (plus 'no treatment' control) was added to 9 wells in rows of this plate. Doxorubicin hydrochloride starting concentration was variable; for OVX, starting concentration was 1 µM doxorubicin hydrochloride which was diluted 1:3. For the rest of the ovarian tumors, starting concentration was 5 µM doxorubicin hydrochloride which was diluted 1:3, with 5 µM doxorubicin hydrochloride start on one plate, continuing to 0.021 µM doxorubicin hydrochloride start on another plate.

For the ENX tumors, combinations with Compound B-2 at all concentrations were run in singlicate, on each of 3 identical plates. An 8×10 matrix was designed on each plate, such that Compound B-2 was tested at 20 µM starting concentration in one column, and diluted 1.8× across 8 additional columns, with the final column containing DMSO. Doxorubicin was tested starting at 0.032 µM in one row, and diluted 2× in 6 additional rows, with the final row containing DMSO.

In radiation experiments, a range of 1-16 Gy was administered using a cesium-137 source (GammaCell 40 Exactor, MDS Nordion, Ontario, Canada). These experiments were designed as a 6×5 matrix in triplicate. Each point of a 4-point concentration range of 0.15, 0.73, 1.5 and 2.2 µM Compound B-1 plus a 'no treatment' control in triplicate were added to 6 individual plates. The matrix was then assembled by exposure of each plate to 0, 1, 2, 4, 8, or 16 Gy of radiation.

For bleomycin experiments, combinations with Compound B-1 at all concentrations were run in triplicate. A 6×3 matrix was designed on one plate, consisting of a 2-point concentration range of 0.73 µM and 2.2 LM Compound B-1 plus no treatment control, in 3 columns each of 6 wells. Bleomycin (plus 'no treatment' control) was added to 9 wells in rows of this plate. Similar 6×3 matrices were set up for additional agents with different starting concentrations for compound dilutions. For cisplatin experiments the starting concentration was 30 µM which was diluted 1:3. For etoposide experiments the starting concentration was 50 µg/mL etoposide which was diluted 1:2 for NSCLC tumors, or 30 µg/mL that was diluted 1:3 for SCLC tumors. For doxorubicin hydrochloride experiments the starting concentration was 5 µM doxorubicin which was diluted 1:3. For gemcitabine experiments the starting concentration was 5 µM gemcitabine which was diluted 1:3. For carboplatin experiments the starting concentration was 20 µM carboplatin which was diluted 1:3 dilutions. For paclitaxel experiments the starting concentration was 1 LM paclitaxel for GAX027, GAX007, and ESX005, and 20 µM paclitaxel for GAX001 and ESX008 which was diluted 1:3. For 5-FU experiments the starting concentration was 20 µM 5-FU for GAX027, GAX007, and ESX005, and 150 µM 5-FU for GAX001 and ESX008 which was diluted 1:3.

Cells were cultured at 37° C., 5% $CO_2$, 95% air and 100% relative humidity.

Viability Determination:

Six days after compound addition, 75 µL of CellTiterGlo (prepared according to manufacturer's protocol) was added to each well of the compound titration plates. After pipetting up and down 4 to 5 times, 100-200 µL was transferred to a 96-well white or black walled plate. Luminescence was read on either the Wallac 1450 MicroBeta liquid scintillation, Pherastar luminescence reader (BMG Labtech, Offenberg, Germany) or Envision multilabel reader (Perkin Elmer, Waltham, Mass., USA) and these values were used for all further analysis.

Data Analysis:

The Bliss additivism model is a standard statistical method to identify synergies between two compounds (Berenbaum, M C. Criteria for analyzing interactions between biologically active agents. Adv Cancer Res 1981; 35:269-335). The data are transformed in the following manner:

Normalization:

Each individual data point is divided by the average of the negative control (wells with no Standard of Care agent and no Compound B-1 or B2).

Average fraction affected:

The normalized values are subtracted from 1.0. Triplicate values are averaged.

Bliss Additivity:

The combined response C of both agents with individual effects for each concentration or dose of A (either Compound B-1 or B-2) and B (Standard of Care agent) is C=A+B (1−A), where A and B represent the average fraction affected between 0 and 1.

Excess Over Bliss Score:

The combined response C is subtracted from the average fraction affected for each combination. This value (C) is multiplied by 100 to give the Bliss score. Individual Bliss scores greater than 10 are considered strongly synergistic, greater than 5 are considered synergistic, less than −5 are considered antagonistic, and less than −10 are considered strongly antagonistic. Values between 5 and −5 are considered additive.

Average Bliss:

For each combination matrix, the average Bliss score is used to categorize each tumor and treatment as synergistic, antagonistic, or additive as described above.

Results of Compound B-2 in Combination with Doxorubicin:

To evaluate the synergy between doxorubicin and Compound B-2, the Bliss additivism model was used. This model is a statistical method that quantifies the fractional response of two compounds added in combination. The result will be additive (the same as the sum of the two compounds individually), synergistic (one compound potentiates the effect of the other), or antagonistic (one compound inhibits the effect of the other). The average Bliss score for each tumor and treatment was used to categorize synergy, antagonism, or additivity as follows: greater than 10 are considered strongly synergistic, greater than 5 are considered synergistic, less than −5 are considered antagonistic, and less than −10 are considered strongly antagonistic. Values between 5 and −5 are considered additive.

Eleven ovarian tumors were assessed for response to the combination of doxorubicin and Compound B-2 (Table 18). All 11 tumors (100%) showed synergy or additivity. Four of the tumors showed strong synergy (36%). In most cases, synergy was only limited by most of the cells being killed by doxorubicin alone; synergy and strong synergy was observed at sub-optimal concentrations of doxorubicin.

Two endometrial tumors were assessed for response to the combination of doxorubicin and Compound B-2 (Table 18). ENX005 showed strong synergy, and ENX001 showed synergy.

TABLE 18

Summary of Combinations with Compound B-2 and Doxorubicin

| Tumor identifier | Tumor type | Average Bliss score | Synergy/Additivity/Antagonism |
|---|---|---|---|
| OVX001 | Ovarian | 11 | Strongly Synergistic |
| CTG-0992 | Ovarian | 8 | Synergistic |
| CTG-1301 | Ovarian | 8 | Synergistic |
| CTG-0947 | Ovarian | 10 | Synergistic |
| CTG-0252 | Ovarian | 14 | Strongly Synergistic |
| CTG-0258 | Ovarian | 9 | Synergistic |
| CTG-0791 | Ovarian | 14 | Strongly Synergistic |
| CTG-1423 | Ovarian | 12 | Strongly Synergistic |
| CTG-0253 | Ovarian | 6 | Synergistic |
| CTG-0486 | Ovarian | 5 | Additive |
| CTG-1166 | Ovarian | 8 | Synergistic |
| ENX005 | Endometrial | 21 | Strongly Synergistic |
| ENX001 | Endometrial | 6 | Synergistic |

Results of Compound B-1 in Combination with Chemotherapeutics:

Nine NSCLC tumors were assessed for response to the combination of radiation and Compound B-1. All 9 tumors (100%) showed synergy or additivity (Table 19). Three of the tumors showed strong synergy (33%) (Table 19). Twenty tumors (NSCLC, pancreatic, gastric, esophageal) were also assessed for response to the combination of bleomycin and Compound B-1. All 20 tumors showed synergy or additivity (Table 20). Six of those (30%) showed strong synergy (Table 20). The tissue of origin of the tumor did not affect response rates of the combination of bleomycin and Compound B-1.

One hepatocellular carcinoma (HCC) tumor was assessed for response to the combination of doxorubicin and Compound B-1. This tumor demonstrated an additive response (Table 21).

Four pancreatic tumors were assessed for response to the combination of gemcitabine and Compound B-1. Of the 4 tumors, 2 (50%) showed additivity, and the other 2 (50%) showed antagonism (Table 22).

Ten tumors (NSCLC, esophageal, gastric) were assessed for response to the combination of cisplatin and Compound B-1. Nine of the 10 tumors showed additivity or synergy (90%), and one of those showed strong synergy. However, one tumor demonstrated antagonism (10%) (Table 23).

Five tumors were assessed for response to the combination of 5-FU (5-Fluorouracil) and Compound B-1. All 5 tumors (100%) showed synergy or additivity (Table 24).

Five tumors were assessed for response to the combination of Carboplatin and Compound B-1. All 5 tumors (100%) showed synergy or additivity (Table 25).

Five tumors were assessed for response to the combination of paclitaxel and Compound B-1. Four of the 5 tumors (80%) showed additivity, and the remaining tumor (20%) showed antagonism (Table 26).

Four tumors were assessed for response to the combination of Etoposide and Compound B-1. All 3 tumors (100%) showed strong synergy (Table 27).

Overall, 29/68 (46%) of combination treatments with Compound B-1 demonstrated synergy or strong synergy in TCA assays. An additional 29/63 (46%) showed additive effects. Only a very small fraction of tumors (4/63; 6%) showed antagonism. There was no observed bias in response based on the tissue of origin of the tumors with any treatment combination. Radiation, bleomycin, and etoposide combined with Compound B-1 showed the strongest and most consistent synergy across tumor types. Doxorubicin, carboplatin, and 5-FU combinations showed primarily additive responses. Paclitaxel, cisplatin, and gemcitabine also had a preponderance of additive responses, but did show antagonism in a small subset of tumors tested.

TABLE 19

Summary of Combinations with Compound B-1 and Radiation

| Tumor identifier | Tumor origin | Average Bliss score | Synergy/Additivity/Antagonism |
|---|---|---|---|
| YAS111611 | Lung (NSCLC) | 1 | Additive |
| OD35982 | Lung (NSCLC) | 5 | Additive |
| OD29498 | Lung (NSCLC) | 2 | Additive |
| OD36088 | Lung (NSCLC) | 14 | Strongly Synergistic |
| TS110310 | Lung (NSCLC) | 16 | Strongly Synergistic |
| OD26131 | Lung (NSCLC) | 12 | Strongly Synergistic |
| OD33966 | Lung (NSCLC) | 8 | Synergistic |
| OD33117 | Lung (NSCLC) | 9 | Synergistic |
| OD26749 | Lung (NSCLC) | 7 | Synergistic |

TABLE 20

Summary of Combinations with Compound B-1 and Bleomycin

| Tumor identifier | Tumor origin | Average Bliss score | Synergy/Additivity/Antagonism |
|---|---|---|---|
| OD33966 | Lung (NSCLC) | 3 | Additive |
| TS110310 | Lung (NSCLC) | 2 | Additive |
| OD25982 | Lung (NSCLC) | 4 | Additive |
| OD29498 | Lung (NSCLC) | 3 | Additive |
| P110325 | Pancreatic | 0 | Additive |
| GAX027 | Gastric | 11 | Strongly Synergistic |
| GAX001 | Gastric | 14 | Strongly Synergistic |
| OD36088 | Lung (NSCLC) | 14 | Strongly Synergistic |
| OD26749 | Lung (NSCLC) | 10 | Strongly Synergistic |
| P110603 | Pancreatic | 14 | Strongly Synergistic |
| P110323 | Pancreatic | 10 | Strongly Synergistic |
| ESX005 | Esophageal | 6 | Synergistic |
| ESX008 | Esophageal | 7 | Synergistic |
| GAX007 | Gastric | 5 | Synergistic |
| YAS111611 | Lung (NSCLC) | 6 | Synergistic |
| OD33117 | Lung (NSCLC) | 9 | Synergistic |
| OD26131 | Lung (NSCLC) | 9 | Synergistic |
| P110408 | Pancreatic | 7 | Synergistic |
| P110504 | Pancreatic | 8 | Synergistic |
| P110413 | Pancreatic | 6 | Synergistic |

TABLE 21

Summary of Combinations with Compound B-1 and Doxorubicin Hydrochloride

| Tumor identifier | Tumor origin | Average Bliss score | Synergy/Additivity/Antagonism |
|---|---|---|---|
| L090923 | Liver | 4 | Additive |

TABLE 22

Summary of Combinations with Compound B-1 and Gemcitabine

| Tumor identifier | Tumor origin | Average Bliss score | Synergy/Additivity/Antagonism |
|---|---|---|---|
| P110603 | Pancreatic | −2 | Additive |
| P110413 | Pancreatic | −1 | Additive |
| P110325 | Pancreatic | −9 | Antagonistic |
| P110504 | Pancreatic | −6 | Antagonistic |

TABLE 23

Summary of Combinations with Compound B-1 and Cisplatin

| Tumor identifier | Tumor origin | Average Bliss score | Synergy/Additivity/Antagonism |
|---|---|---|---|
| ESX005 | Esophageal | 2 | Additive |
| ESX008 | Esophageal | 1 | Additive |
| GAX007 | Gastric | 2 | Additive |
| GAX027 | Gastric | −3 | Additive |
| OD33966 | Lung (NSCLC) | −1 | Additive |
| TS110310 | Lung (NSCLC) | −3 | Additive |
| YAS111611 | Lung (NSCLC) | −6 | Antagonistic |
| GAX001 | Gastric | 14 | Strongly Synergistic |
| OD36088 | Lung (NSCLC) | 6 | Synergistic |
| OD33117 | Lung (NSCLC) | 6 | Synergistic |

TABLE 24

Summary of Combinations with Compound B-1 and 5-FU

| Tumor identifier | Tumor origin | Average Bliss score | Synergy/Additivity/Antagonism |
|---|---|---|---|
| ESX005 | Esophageal | −1 | Additive |
| ESX008 | Esophageal | −2 | Additive |
| GAX007 | Gastric | 0 | Additive |
| GAX027 | Gastric | 4 | Additive |
| GAX001 | Gastric | 6 | Synergistic |

TABLE 25

Summary of Combinations with Compound B-1 and Carboplatin

| Tumor identifier | Tumor origin | Average Bliss score | Synergy/Additivity/Antagonism |
|---|---|---|---|
| ESX005 | Esophageal | 3 | Additive |
| GAX007 | Gastric | 4 | Additive |
| GAX027 | Gastric | 4 | Additive |
| GAX001 | Gastric | 2 | Additive |
| ESX008 | Esophageal | 5 | Synergistic |

TABLE 26

Summary of Combinations with Compound B-1 and Paclitaxel

| Tumor identifier | Tumor origin | Average Bliss score | Synergy/Additivity/Antagonism |
|---|---|---|---|
| ESX005 | Esophageal | −3 | Additive |
| GAX007 | Gastric | −4 | Additive |
| GAX027 | Gastric | 1 | Additive |
| GAX001 | Gastric | −1 | Additive |
| ESX008 | Esophageal | −5 | Antagonistic |

TABLE 27

Summary of Combinations with Compound B-1 and Etoposide

| Tumor identifier | Tumor origin | Average Bliss score | Synergy/Additivity/Antagonism |
|---|---|---|---|
| OD29498 | Lung (NSCLC) | 13 | Strongly Synergistic |
| OD26749 | Lung (NSCLC) | 19 | Strongly Synergistic |
| LUX031 | Lung (SCLC) | 16 | Strongly Synergistic |
| LUX013 | Lung (SCLC) | 15 | Strongly Synergistic |

Example 9: pH2AX and pKAP1 as Biomarkers for DNA-PK Inhibition

Ionizing radiation (IR) induces a variety of DNA damage of which double strand breaks (DSBs) are the most cytotoxic. See, e.g., Salles B. DNA-PK, a pharmacological target in cancer chemotherapy and radiotherapy? J Cancer Sci Ther 2011; S8:1-11. These DSBs can lead to cell death via apoptosis and/or mitotic catastrophe if not rapidly and completely repaired. In addition to IR, certain chemotherapeutic agents including anthracyclines (doxorubicin), topoisomerase II inhibitors, and bleomycin, also cause DSBs. See, e.g., Helleday T. DNA repair pathways as targets for cancer therapy. Nat Rev Cancer 2008; 8:193-204. These DNA lesions trigger a complex set of signals through the DNA damage response network that function to repair the damaged DNA and maintain cell viability and genomic stability.

In mammalian cells, the predominant repair pathway for DSBs is the Non-Homologous End Joining Pathway (NHEJ). See, e.g., Bolderson E, et al. Recent advances in cancer therapy targeting proteins involved in DNA double-strand break repair. Clin Cancer Res 2009; 15(20):6314-6320. This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated kinase (ATM), ataxia telangiectasia and Rad3-related kinase (ATR), and mammalian target of rapamycin (mTOR). However, while DNA-PKcs is in the same protein kinase family as ATM and ATR, these latter kinases function to repair DNA damage through the Homologous Recombination (HR) pathway and are restricted to the S and $G_2$ phases of the cell cycle. Additionally, while ATM is also recruited to sites of DSBs, ATR is recruited to sites of single stranded DNA breaks. See, e.g., Dobbs, T A, et al. A structural model for regulation of NHEJ by DNA-PKcs autophosphorylation. DNA Repair 2010; 9:1307-1314.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. See, e.g., Bolderson and Dobbs, supra. In some cases DNA polymerase may be required to synthesize new ends prior to the ligation step. The autophosphorylation of DNA-PKcs is believed to induce a conformational change that opens the central DNA binding cavity, releases DNA-PKcs from DNA, and facilitates the ultimate religation of the DNA ends.

In addition to DNA-PK, ATM is also activated by and recruited to the sites of DSBs, phosphorylating multiple substrates including histone H2A variant X (H2AX) on residue Ser139 (pH2AX or gammaH2AX) (See, e.g., Stiff, T. et al. ATM and DNA-PK function redundantly to phosphorylate H2AX after exposure to ionizing radiation. Cancer Res 2004; 64:2390-2396) as well as KAP1 on residue Ser824 (pKAP1) (See, e.g., White D E et al. KAP1, a novel substrate for PIKK family members, colocalizes with numerous damage response factors at DNA lesions. Caner Res 2006; 66:11594-11599). Thus pH2AX and pKAP1 levels could serve as indicators of DSBs and DNA repair. The purpose of this study was to evaluate pH2AX and pKAP1 as biomarkers for DNA-PK inhibition in cultured cancer cells treated with standard chemotherapeutic DNA damaging agents etoposide or doxorubicin alone or in combination with the selective DNA-PK inhibitors Compound B-1 and Compound B-2.

Materials and Methods.

The human cancer cell lines A549 (CCL-185), DU4475 (HTB-123), MDA-MB-436 (HTB-130), and MDA-MB-468 (HTB-132) were obtained from American Type Culture Collection (ATCC; Manassas, Va.). A 10 mM stock solution of Compound B-1 or Compound B-2 was prepared in DMSO and stored at −20° C. Etoposide and doxorubicin were purchased from Sigma-Aldrich (St. Louis, Mo.).

The A549 human lung cancer cell line was purchased from ATCC and was cultured in DMEM supplemented with 10% fetal bovine serum, 1× non-essential amino acids and 1× Penicillin/Streptomycin (complete medium). Cells were maintained at a subconfluent state by passaging every 2-3 days. Human breast cancer cells lines DU4475, MDA-MB-436, and MDA-MB-468 were purchased from ATCC and cultured in DMEM supplemented with 10% fetal bovine serum, 1× Glutamax and Penicillin/Streptomycin. Cells were maintained at a subconfluent state by passaging every 2-3 days.

Compound B-1 and Compound B-2 were prepared as 10 mM stock solutions in DMSO and stored at −20° C.; Etoposide was prepared as 20 mM stock solution in DMSO and stored at −20° C. Compound B-1 and Compound B-2 used in these experiments were not prepared as a co-crystals.

A549 lung cancer cells grown in 12-well (Costar 3513) tissue culture plates to 70-80% confluence were pre-incubated with the indicated concentrations of Compound B-1 or DMSO for 45 min. Etoposide was added to a final concentration of 10 μM from a 4× working stock prepared in culture medium. Cells were then incubated for the indicated amount of time and harvested for analysis.

Breast cancer cell lines grown in 24-well (Costar, catalog #3526) or 6-well (Costar, catalog #3516) tissue culture plates to 70-80% confluence were pre-incubated with 1 μM Compound B-2 or DMSO for 15 min. Doxorubicin was added to a final concentration of either 100 nM or 500 nM from a 1000× stock prepared in DMSO. Cells were then incubated for the indicated amount of time and harvested for analysis.

For wash-out experiments, doxorubicin and Compound B-2-containing medium was removed at indicated times and cells were washed once with 1×PBS, and fresh medium containing 1 μM of Compound B-2 was added. Cells were incubated for 8 h after initial doxorubicin addition and then harvested for analysis.

Cell Lysis and Western Blot Analysis.

Cells treated with Compound B-1 or Compound B-2 in combination with chemotherapeutic agents were washed once with ice-cold PBS and then dissolved in 150 L/well 2×SDS-PAGE sample buffer, transferred to microfuge tubes, and heated in a 105° C. heat block for 5 min for immunoblotting. A 15-μL aliquot of each SDS-PAGE sample was loaded onto 12-lane 4 20% Tris-Glycine gels and the gels were run at 125 v constant voltage until the dye front reached the bottom (approximately 2 h). Following electrophoresis, separated proteins in the gels were transferred to a nitrocellulose membrane. Transfer was carried out for 2 h at 1.5 A constant current in a cold room using a Hoefer transfer apparatus (Model TE42 or TE62, Hoefer Inc, Holliston, Mass.) according to manufacturer's instructions. Following transfer, nitrocellulose membranes were incubated with blocking buffer for 1 h at room temperature. The nitrocellulose membranes were cut and the bottom halves were incubated overnight with 2 primary antibodies, anti-pH2AX (1/1000) and anti-total H2AX (1/1000). After washing, the appropriate fluorescently labeled secondary antibodies were added to the membranes and then imaged with pH2AX on the 800 (green) channel and total H2AX on the 700 (red) channel. The top halves of the membranes were probed sequentially for pKAP1 (1/1000) on the 700 (red) channel and then probed for total KAP1 (1/1000) and GAPDH (1/2500) on the 800 (green) channel. Image acquisition was conducted using an Odyssey fluorescent imaging system (Li-Cor Biosciences; Lincoln, Nebr.).

Compound B-1 and Etoposide Combination in A549 Lung Cells.

Figures 20A, 20B:
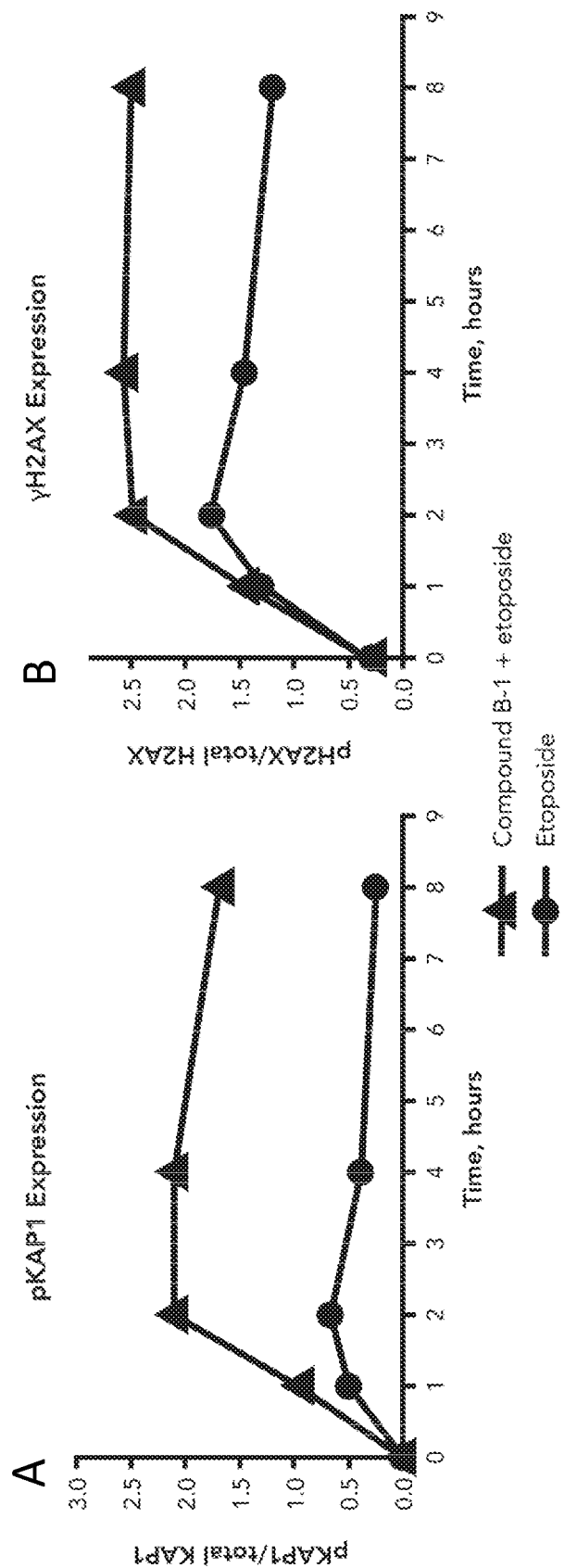
FIG. 20A and FIG. 20B show that Compound B-1 potentiates the DNA damaging effects of etoposide in a lung cancer cell line (A549 cell line). Data indicated with circles is etoposide alone in DMSO vehicle. Data indicated with diamonds is Compound B-1 and etoposide combination. A549 cells were preincubated with 3 μM Compound B-1 or DMSO for 45 minutes. Etoposide was added to a final concentration of 10 μM. Cells were harvested at the indicated time points after etoposide addition and analyzed for the expression of DNA damage markers pKAP1-S824 and γH2AX (pH2AX-S139) by immunoblotting and normalized to total KAP1 (FIG. 20A) and total H2AX (FIG. 20B), respectively.

To examine the effect of DNA-PK inhibition on pKAP1 in vitro, A549 cells were pre incubated with 3 µM Compound B-1 for 45 min and etoposide was then added to a final concentration of 10 µM. Cells were harvested at various time points following etoposide addition and analyzed for levels of pH2AX and pKAP1 by immunoblotting. Results are shown in FIGS. 20A-20B. Etoposide treatment resulted in a gradual increase in both pH2AX and pKAP1 levels over a 2-hour period, indicating induction of DNA damage. The levels of these markers then decreased gradually over the next 6 h, likely reflecting the repair of DNA damage by the DNA damage repair machinery. Co treatment of cells with Compound B-1 and etoposide resulted in a greater increase in both pH2AX (max 2-fold at 8 h) and pKAP1 (max 7-fold at 8 h) levels as compared to etoposide treatment alone, consistent with the hypothesis that inhibition of DNA-PK attenuates the repair of DNA damage induced by etoposide.

Compound B-2 and Doxorubicin Combination in Breast Cancer Cell Lines in Culture.

Figures 21A, 21B:
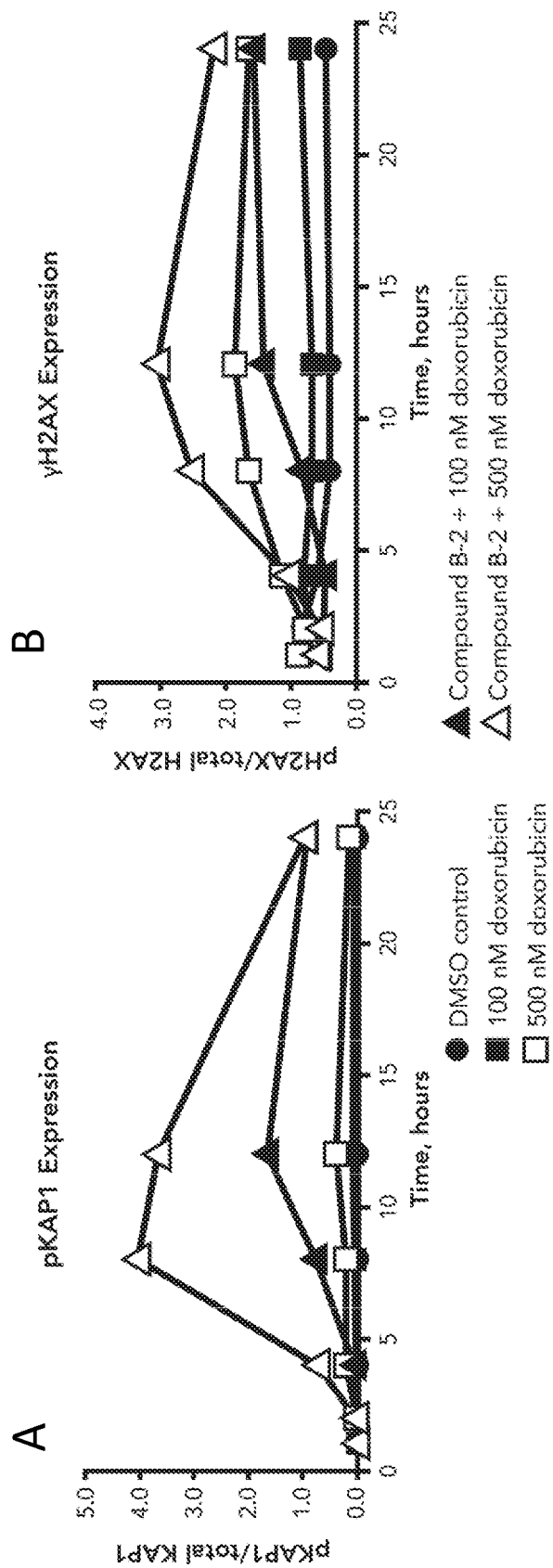
FIG. 21A and FIG. 21B show that Compound B-2 potentiates the DNA damaging effects of doxorubicin in a breast cancer cell line. Data indicated with a circles is DMSO control; data indicated with black squares is 100 nM doxorubicin; data indicated white squares is 500 nM doxorubicin; data indicated with black triangles is Compound B-2/100 nM doxorubicin; data indicated with white triangles is Compound B-2/500 nM doxorubicin. DU4475 cells were pre-incubated with 1 μM Compound B-2 for 15 minutes. Doxorubicin was added to a final concentration of 100 nM or 500 nM. Cells were harvested at the indicated time points after doxorubicin addition and analyzed for the expression of DNA damage markers pKAP1-S824 and γH2AX (pH2AX-S139) by immunoblotting and normalized to total KAP1 (FIG. 21A) and total H2AX (FIG. 21B), respectively.

To examine the effect of DNA-PK inhibition on pKAP1 and pH2AX in vitro, DU4475 breast cancer cells were pre-incubated with 1 µM Compound B-2 for 15 min, followed by addition of 100 nM or 500 nM doxorubicin. Cells were harvested at various time points following doxorubicin addition and analyzed for levels of pKAP1 and pH2AX by immunoblotting. Results are shown in FIGS. 21A-21B. Doxorubicin treatment resulted in an increased level of pKAP1 and pH2AX from 4-8 h and remained elevated up to 24 h in the 500 nM but not in the 100 nM treatment group. Concurrent treatment with 100 nM or 500 nM doxorubicin and Compound B-2 resulted in enhanced levels of pKAP1 (max 37-42-fold at 12-24 h and 19-fold at 8 h for 100 nM and 500 nM doxorubicin, respectively) and pH2AX (max 2-fold at 12 h and 1.6 fold at 12 h for 100 nM and 500 nM doxorubicin, respectively), consistent with the notion that inhibition of DNA-PK attenuates the repair of DNA damage induced by doxorubicin.

Figure 22A:
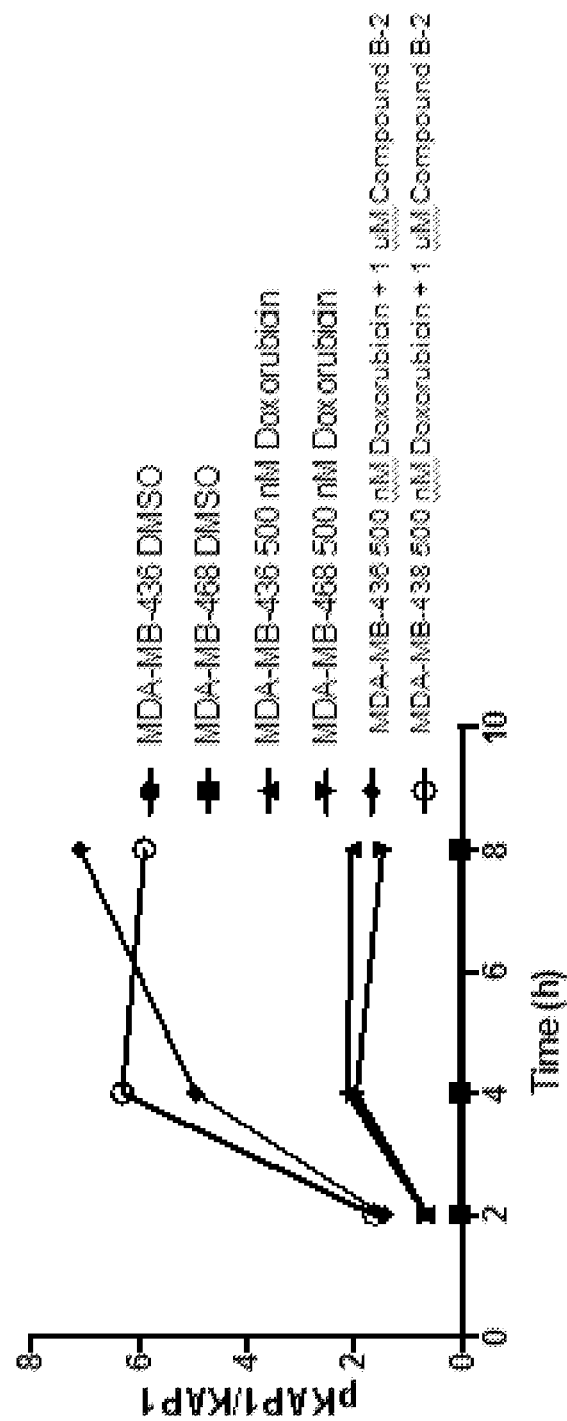
FIG. 22A and FIG. 22B show that Compound B-2 enhances doxorubicin-induced phosphorylation of DNA damage markers KAP1 and H2AX in MDA-MB-436 and MDA MB 468 breast cancer cells. MDA-MB-436 and MDA-MB-468 cells were preincubated with 1 μM Compound B-2 or DMSO for 15 min. Doxorubicin was then added to a final concentration of 500 nM. Cells were harvested at the indicated time points following doxorubicin addition and analyzed for pKAP1 (FIG. 22A) and pH2AX (FIG. 22B).
Figure 22B:
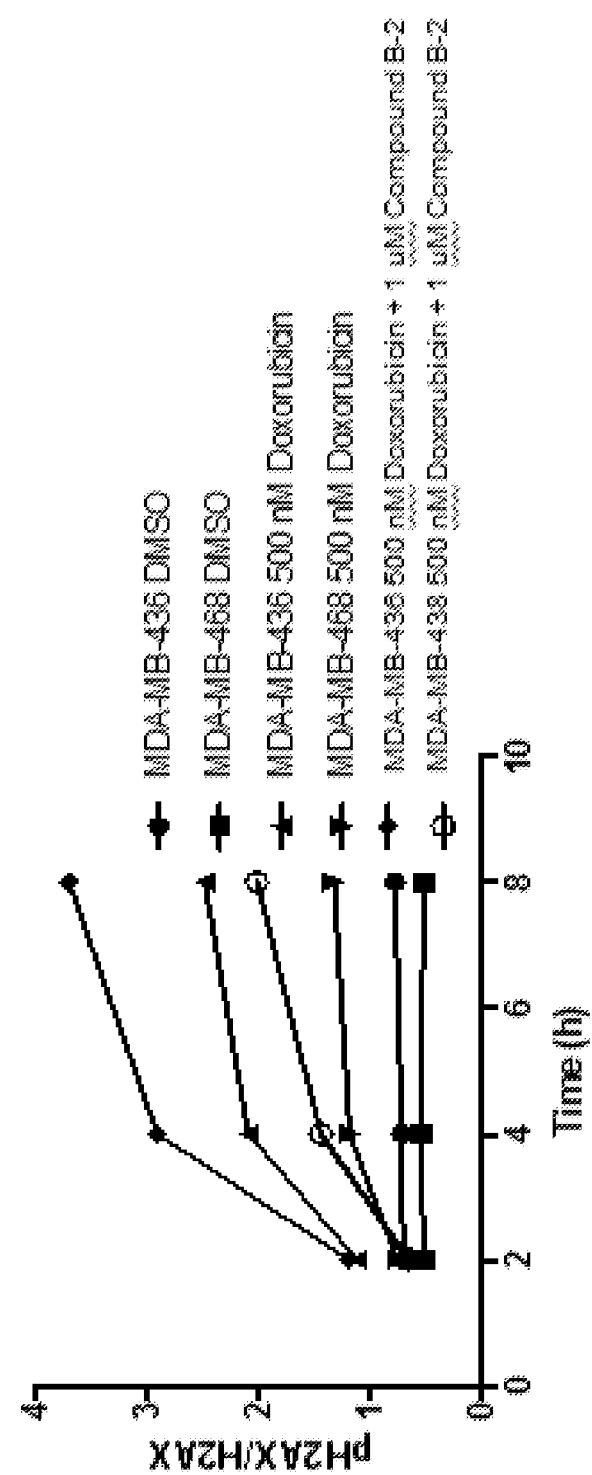

To determine that enhancement of DNA damage by concurrent treatment of cells with Compound B-2 and doxorubicin was not specific to DU4475 cells, two additional breast cancer cell lines, MDA-MB-436 and MDA-MB-468, were also pre-incubated with 1 µM Compound B-2 for 15 min, followed by addition of 500 nM doxorubicin. Cells were harvested at various time points following doxorubicin addition and analyzed for levels of pKAP1 and pH2AX by immunoblotting. See FIGS. 22A-22B. Doxorubicin treatment again resulted in an increased level of pKAP1 and pH2AX at 4 h, which remained elevated even to 8 h. Concurrent treatment with Compound B-2 resulted in enhanced levels of pKAP1 (max 3.5-4-fold at 8 h) and pH2AX (max 1.5-fold at 8 h), consistent with the results in the DU4475 cell line, indicating that this combination treatment is broadly effective in multiple breast cancer cell lines.

Figure 23A:
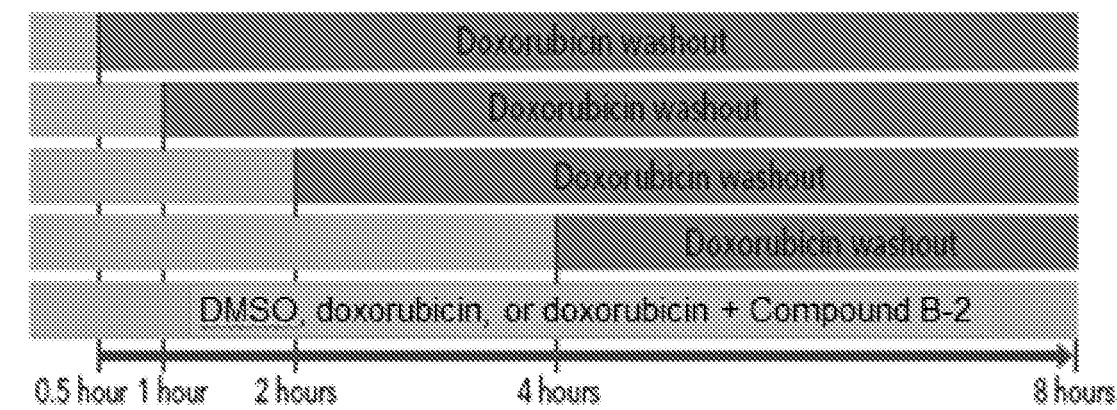
FIG. 23A, FIG. 23B and FIG. 23C show that Compound B-2 enhances short-duration doxorubicin-induced phosphorylation of DNA damage markers KAP1 and H2AX in MDA-MB-468 breast cancer cells. MDA-MB-468 cells were preincubated with 1 μM Compound B-2 or DMSO for 15 min. Doxorubicin was then added to a final concentration of 500 nM. Medium was removed from cells at indicated times and fresh 1 μM Compound B-2 added. The 8 h time point is equivalent to no washout. The washout schedule is depicted in FIG. 23A. Cells were harvested at 8 h following initial doxorubicin addition and analyzed for pKAP1 (FIG. 23B) and pH2AX (FIG. 23C).
Figure 23B:
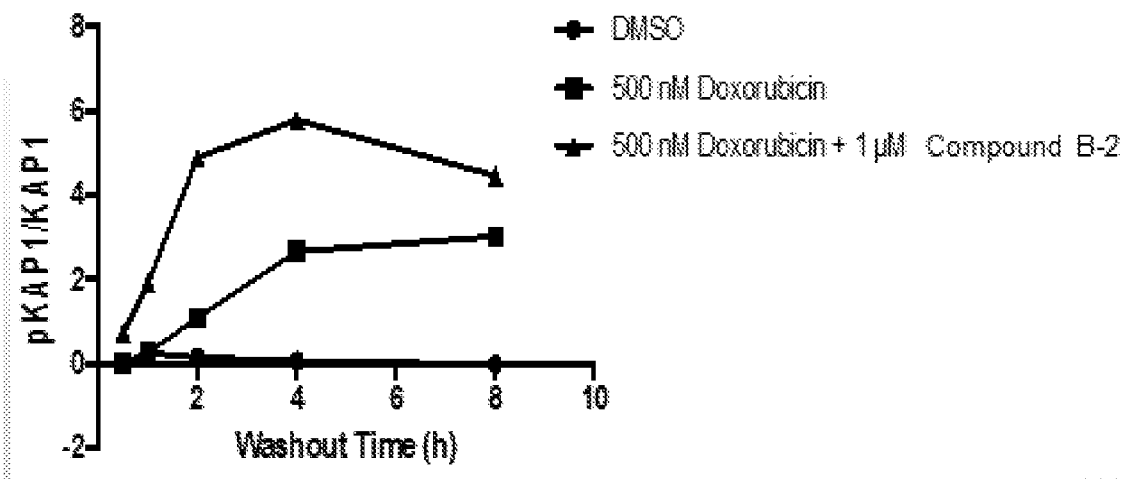
Figure 23C:
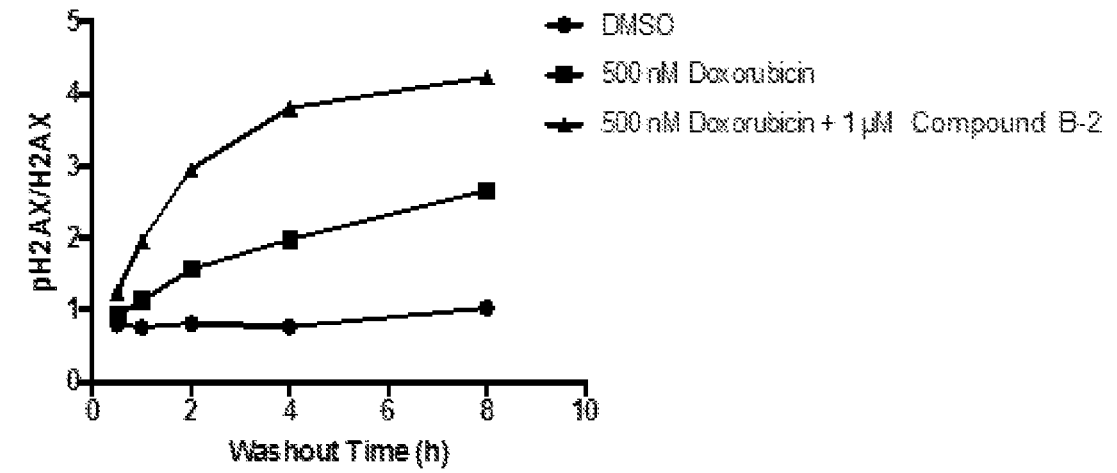

In order to determine the effect of a pulse of doxorubicin in combination with a DNA-PK inhibitor on pKAP1 and pH2AX levels, which would more closely simulate an in vivo administration of doxorubicin, MDA-MB-468 breast cancer cells were pre-incubated with 1 µM Compound B-2 for 15 min, followed by addition of 500 nM doxorubicin. At indicated time points, medium was removed from cells and fresh medium containing only 1 µM Compound B-2 was added. Cells were harvested 8 h from initial doxorubicin exposure, and analyzed for levels of pKAP1 and pH2AX by immunoblotting. Results are shown in FIGS. 23A-23C. Doxorubicin exposure for 1-2 h was sufficient for detection of pKAP1 and pH2AX, which continued to increase until the 8-hour time point. Concurrent treatment with Compound B-2 resulted in enhanced levels of pKAP1 and pH2AX beginning at 1 h doxorubicin exposure, consistent with the hypothesis that even short-duration exposure to doxorubicin is sufficient to cause DNA damage that can be enhanced by concurrent treatment with Compound B-2.

Conclusion.

pH2AX and pKAP1 were evaluated as markers of DNA damage in cancer cells treated with standard DNA damaging chemotherapeutic agents alone and in combination with selective DNA-PK inhibitors Compound B-1 or Compound B-2. Specifically, these markers were evaluated in one lung cancer cell line (A549) treated with etoposide and in 3 breast cancer cell lines treated with doxorubicin. In both types of cancer cells, treatment with chemotherapeutic agent alone resulted in increased pH2AX and pKAP1 levels, consistent with the known mechanism of action of these agents in inducing DNA double strand breaks. Co-treatment of cells with these chemotherapeutics in combination with the selective DNA-PK inhibitors Compound B-1 or Compound B-2 invariably increased the levels of pH2AX and pKAP1 when compared to chemotherapeutic agent alone. These findings are consistent with the hypothesis that DNA-PK inhibition results in enhanced DNA damage and that pKAP1 and pH2AX can serve as markers of DNA damage and of DNA-PK inhibition.

Example 10: Biomarker Analysis In Vivo

DOXIL® or vehicle was administered at 15 mg/kg to nude mice bearing H460 xenograft tumors. Tumors were collected (N=3 per group) from 15 minutes to 72 hours post DOXIL® administration and snap frozen in liquid nitrogen. Frozen samples were processed for Western analysis using an antibody against pKAP1. pKAP1 levels in H460 tumors were increased at 24 and 48 hours after DOXIL® treatment when compared to vehicle controls.

Other Embodiments

All references provided herein are incorporated herein in its entirety by reference.

As used herein, all abbreviations, symbols and conventions are consistent with those used in the contemporary scientific literature.

Although the foregoing has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A method of treating a proliferative disorder in a subject, the method comprising:
    administering to a subject in need thereof a therapeutically effective amount of DNA-damaging agent and
    administering to the subject a therapeutically effective amount of DNA-PK inhibitor between about 8 and about 48 hours after administration of the DNA-damaging agent, wherein the DNA-damaging agent is a doxorubicin agent;
    wherein the proliferative disorder is a cancer selected from the group consisting of non-small cell lung cancer, small cell lung cancer, colorectal cancer, breast cancer, hepatocellular carcinoma, endometrial cancer, and ovarian cancer; and
    wherein the DNA-PK inhibitor is represented by Formula (B-I):

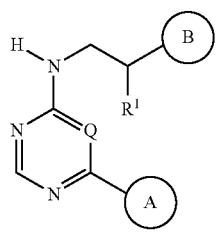

B-I or a pharmaceutically acceptable salt thereof,
wherein:
    Q is N or CH;
    $R^1$ is hydrogen, $CH_3$, or $CH_2CH_3$, or $R^1$ and the carbon to which it is bound form a $C=CH_2$ group;
    Ring A is a ring system selected from the group consisting of:

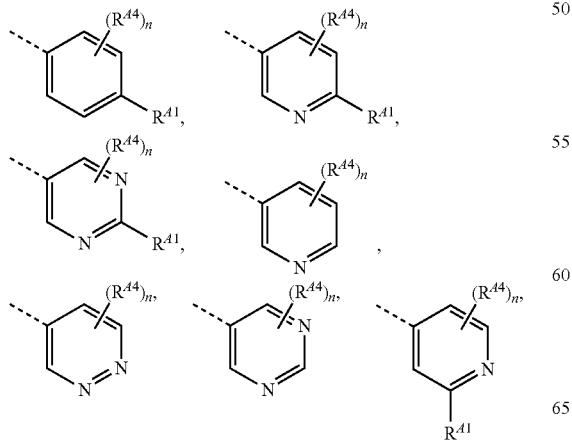

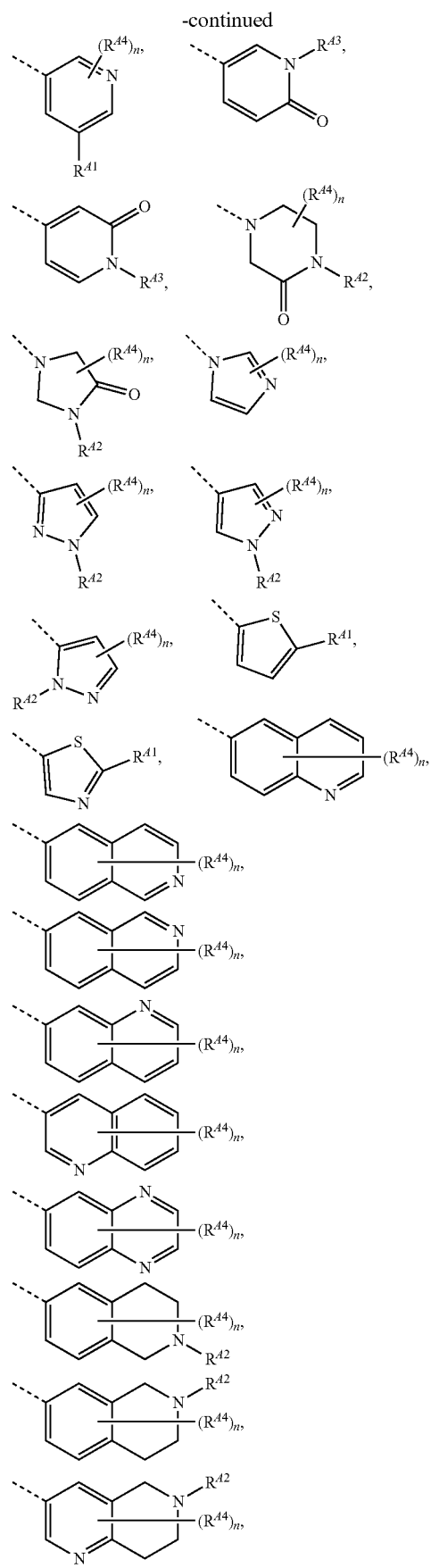

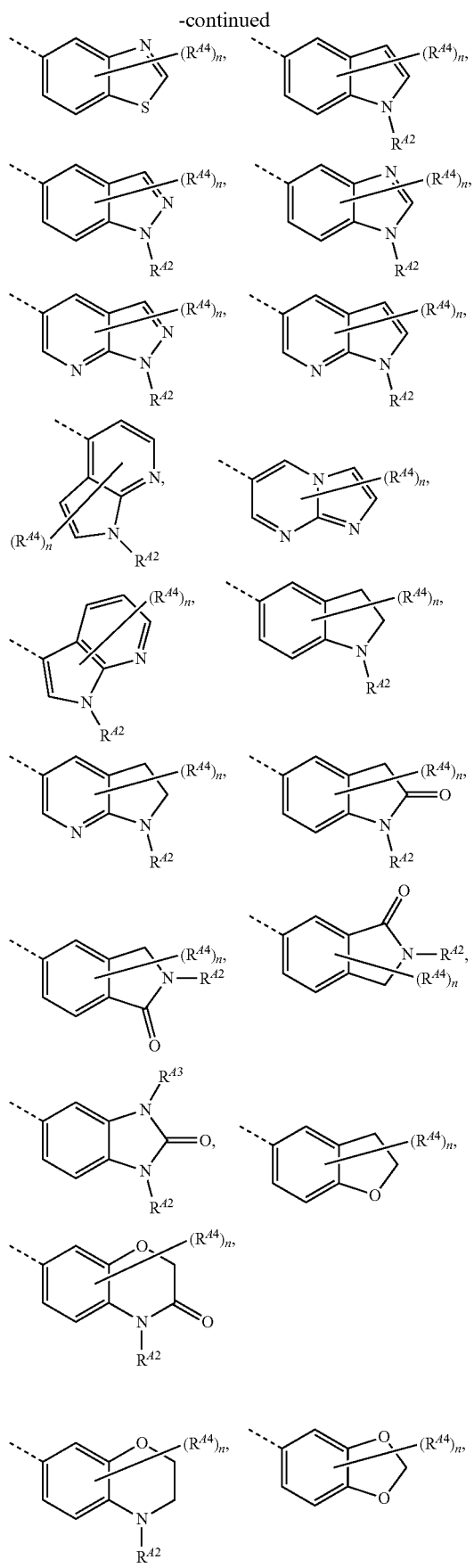
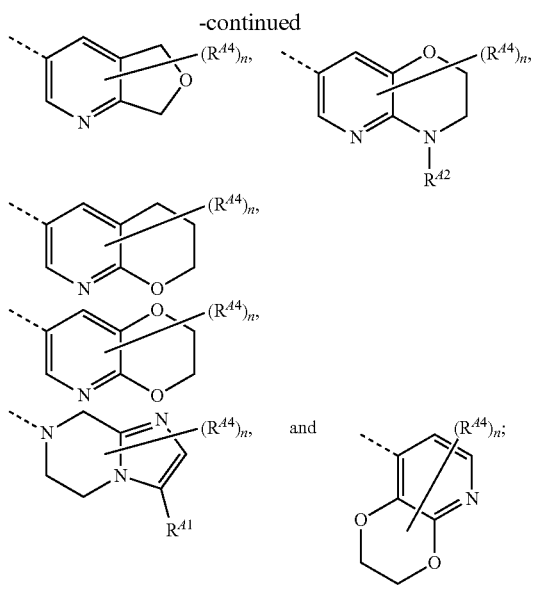

$R^{A1}$ is hydrogen, halogen, $C_{1-4}$alkyl, $C_{0-4}$alkyl-$C_{3-6}$cycloalkyl, $C_{0-4}$alkyl-$OR^{A1a}$, $C_{0-4}$alkyl-$SR^{A1a}$ $C_{0-4}$alkyl-$C(O)N(R^{A1a})_2$, $C_{0-4}$alkyl-CN, $C_{0-4}$alkyl-S(O)—$C_{1-4}$alkyl, $C_{0-4}$alkyl-$S(O)_2$—$C_{1-4}$alkyl, $C_{0-4}$alkyl-C(O)$OR^{A1b}$, $C_{0-4}$alkyl-$C(O)C_{1-4}$alkyl, $C_{0-4}$alkyl-$N(R^{A1b})C(O)R^{A1a}$, $C_{0-4}$alkyl-$N(R^{A1b})S(O)_2R^{A1a}$, $C_{0-4}$alkyl-N$(R^{A1a})_2$, $C_{0-4}$alkyl-$N(R^{A1b})$(3-6 membered-cycloalkyl), $C_{0-4}$alkyl-$N(R^{A1b})$(4-6 membered-heterocyclyl), $N(R^{A1b})C_{2-4}$alkyl-$N(R^{A1a})_2$, $N(R^{A1b})C_{2-4}$alkyl-$OR^{A1a}$, $N(R^{A1b})C_{1-4}$alkyl-(5-10 membered heteroaryl), $N(R^{A1b})C_{1-4}$alkyl-(4-6 membered heterocyclyl), $N(R^{A1b})C_{2-4}$alkyl-$N(R^{A1b})C(O)R^{A1a}$, $C_{0-4}$alkyl-$N(R^{A1b})C(O)C_{1-4}$alkyl, $C_{0-4}$alkyl-$N(R^{A1b})C(O)OC_{1-4}$alkyl, $C_{0-4}$alkyl-(phenyl), $C_{0-4}$alkyl-(3-10 membered-heterocyclyl), $C_{0-4}$alkyl-C(O)-(4-6 membered-heterocyclyl), $C_{0-4}$alkyl-O—$C_{0-4}$alkyl-(4-6 membered-heterocyclyl), $C_{0-4}$alkyl-(5-6 membered-heteroaryl), $C_{0-4}$alkyl-C(O)-(5-6 membered-heteroaryl), $C_{0-4}$alkyl-O—$C_{0-4}$alkyl-(5-6 membered-heteroaryl), $C_{0-4}$alkyl-N$(R^{A1a})$(4-6 membered-heterocyclyl), or $C_{0-4}$alkyl-N$(R^{A1b})$(5-6 membered-heteroaryl), wherein each of said $R^{A1}$ heterocyclyl is a ring system selected from aziridinyl, oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, tetrahydrothiophenedioxidyl, 1,1-dioxothietanyl, 2-oxa-6-azaspiro[3.4]octanyl, and isoindolinonyl wherein each of said $R^{A1}$ heteroaryl is a ring system selected from furanyl, thiophenyl, imidazolyl, benzoimidazolyl, oxazolyl, oxadiazolyl, thiazolyl, pyrazolyl, thiadiazolyl, pyridinyl, pyrimidinyl, pyrazinyl, triazolyl, and tetrazolyl, and wherein each of said $R^{A1}$ alkyl, cycloalkyl, phenyl, heterocyclyl, and heteroaryl groups is optionally substituted with up to three F atoms, up to two $C_{1-2}$alkyl groups, a $C_{3-6}$cycloalkyl group, a phenyl group, a benzyl group, an alkenyl-$C_{0-2}$alkyl group, an alkynyl-$C_{0-2}$alkyl group, up to two $C_{0-2}$alkyl-$OR^{A1b}$ groups, a $C_{0-2}$alkyl-N$(R^{A1b})_2$ group, a $SC_{1-4}$alkyl group, a $S(O)_2C_{1-4}$alkyl group, a $C(O)R^{A1b}$ group, a $C(O)OR^{A1b}$ group, a $C(O)N(R^{A1b})_2$ group, a —CN group, or a $C_{4-6}$heterocyclic ring system selected from oxetanyl, tetrahydrofuranyl, tetrahydropyran, piperidinyl, and morpholinyl;

each $R^{A1a}$ is, independently, hydrogen, $C_{1-4}$alkyl, $C_{3-6}$cycloalkyl, $C_{4-6}$heterocyclyl selected from oxetanyl, tetrahydrofuranyl, tetrahydropyran, pyrrolidinyl, and piperidinyl, $C_{5-6}$heteroaryl selected from imidazolyl, triazolyl, tetrazolyl, pyrazolyl, thiophenyl, thiazolyl, pyridinyl, pyrimidinyl, and pyrazinyl, or two $R^{A1a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl, wherein each of said $R^{A1a}$ alkyl, cycloalkyl, heterocyclyl, and heteroaryl groups is optionally substituted with up to three F atoms, up to three 2H atoms, up to two $C_{1-2}$alkyl groups, a $C_{3-6}$cycloalkyl group, up to two $C_{0-2}$alkyl-$OR^{A1b}$ groups, a $C_{0-2}$alkyl-$N(R^{A1b})_2$ group, a $SC_{1-4}$alkyl group, a $C(O)R^{A1b}$ group, a $C(O)OR^{A1b}$ group, a $C(O)N(R^{A1b})_2$ group, or a —CN group;

each $R^{A1b}$ is, independently, hydrogen, $C_{1-2}$alkyl, or $C_{3-4}$cycloalkyl;

$R^{A2}$ is hydrogen, $C_{1-4}$alkyl, $C_{0-4}$alkyl-$C_{3-6}$cycloalkyl, $C_{0-2}$alkyl-(4-6 membered)heterocyclyl, $C_{2-4}$alkyl-$OR^{A2a}$, $C_{0-2}$alkyl-$C(O)NR^{A2a})_2$, $C_{0-2}$alkyl-$S(O)_2$—$C_{1-4}$ alkyl, $C_{0-2}$alkyl-$C(O)OC_{1-4}$alkyl, $C_{0-2}$alkyl-$C(O)$-(4-6 membered)heterocyclyl, wherein each of said heterocyclyl is selected from oxetanyl, tetrahydropyran, tetrahydrofuranyl, dioxanyl, dioxolanyl, azetidinyl, pyrrolidinyl, pyrrolidinonyl, pyrrolidinedionyl, morpholinyl, piperidinyl, piperazinyl, piperazinonyl, and 1,1-dioxothietanyl, and each of said $R^{A2}$ groups except hydrogen is optionally substituted with up to three F atoms, up to two $C_{1-2}$alkyl groups, a $C_{3-6}$cycloalkyl group, an alkenyl-$C_{0-2}$alkyl group, an alkynyl-$C_{0-2}$alkyl group, up to two $OR^{A2b}$ groups, a $C_{0-2}$alkyl-$N(R^{A2b})_2$ group, a $SC_{1-4}$alkyl group, a $S(O)_2C_{1-4}$alkyl group, a $C(O)R^{A2b}$ group, a $C(O)OR^{A2b}$ group, a $C(O)N(R^{A2b})_2$ group, or a —CN group;

each $R^{A2a}$ is, independently, hydrogen, $C_{1-4}$alkyl, a $C_{5-6}$heteroaryl selected from imidazolyl, triazolyl, tetrazolyl, pyrazolyl, thiophenyl, thiazolyl, pyridinyl, pyrimidinyl, and pyrazinyl, or two $R^{A2a}$ and an intervening nitrogen atom form a 3-6 membered heterocyclic ring selected from aziridinyl, azetidinyl, pyrrolidinyl, pyrrolidinonyl, piperidinyl, piperidinonyl, tetrahydropyridinyl, piperazinyl, and morpholinyl;

each $R^{A2b}$ is, independently, hydrogen, $C_{1-4}$alkyl, or $C_{3-4}$cycloalkyl;

$R^{A3}$ is hydrogen or $C_{1-2}$alkyl;

each $R^{A4}$ is, independently, deuterium, halogen, CN, $C_{1-4}$alkyl, or $OC_{1-4}$alkyl, wherein each $R^{A4}$ alkyl is optionally substituted with up to 3 F atoms, two non-geminal OH groups, or one $OC_{1-2}$alkyl, or two $R^{A4}$ together with an intervening saturated carbon atom form a spiro-linked cyclopropyl or cyclobutyl ring;

n is 0-3;

Ring B is a ring system selected from the group consisting of:

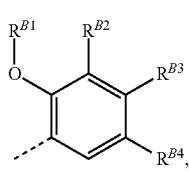

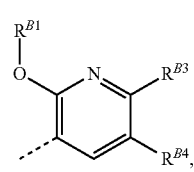

-continued

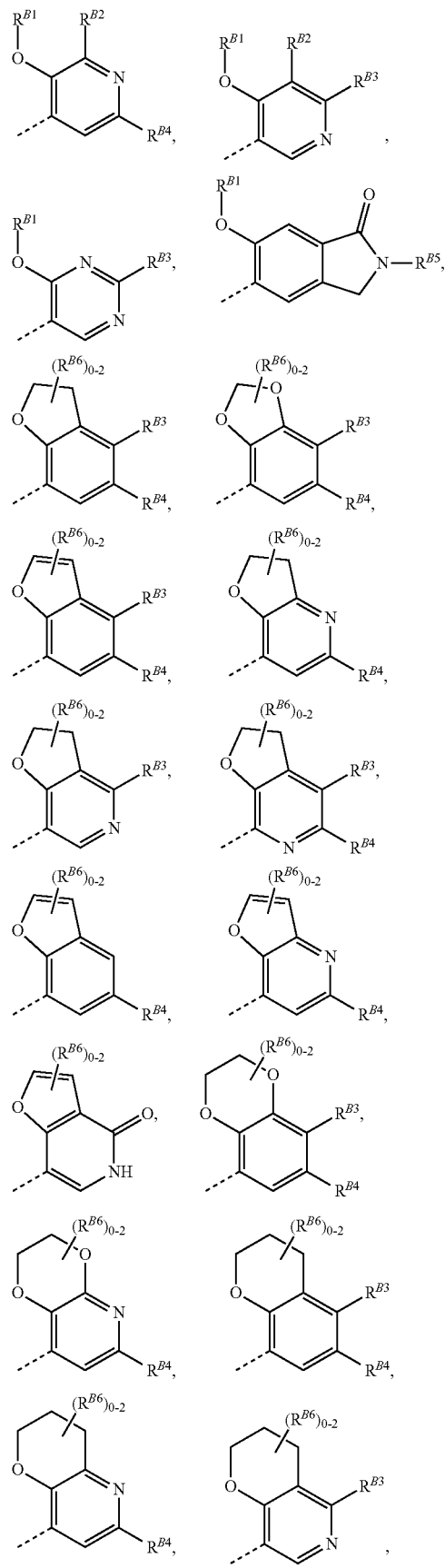

-continued

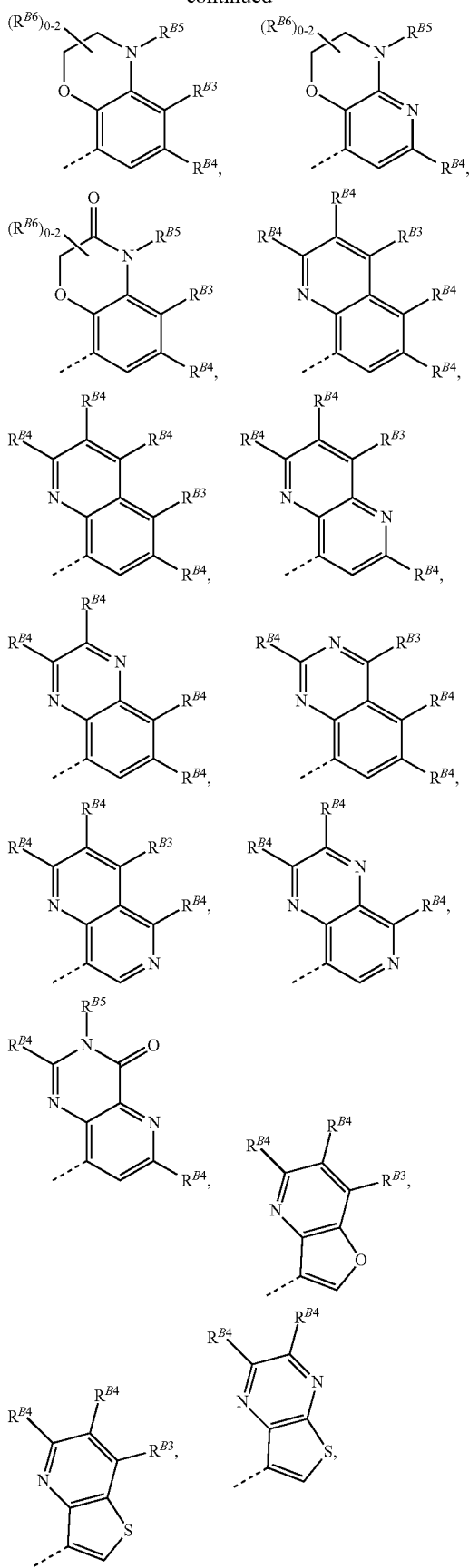
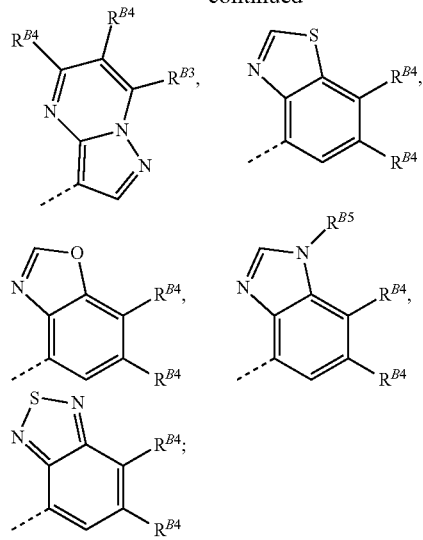

$R^{B1}$ is hydrogen, $C_{1-4}$alkyl, $(CH_2)_{0-1}C_{3-6}$cycloalkyl, C(O)$C_{1-2}$alkyl, $(CH_2)_{0-1}$-(4-6 membered)heterocyclyl ring wherein said heterocyclic ring is selected from oxetanyl, tetrahydrofuranyl, tetrahydropyran, dioxanyl, dioxolanyl, and pyrrolidinonyl, or $(CH_2)_{1-2}$(5-6 membered)heteroaryl ring wherein said heteroaryl ring is selected from pyridinyl, imidazolyl, and pyrazolyl, and wherein each of said $R^{B1}$ alkyl, cycloalkyl, phenyl, benzyl, heterocyclyl and heteroaryl groups is optionally substituted with up to 3 F atoms, up to two $C_{1-2}$alkyl groups, two non-geminal OH groups, or one $OC_{1-2}$alkyl;

$R^{B2}$ is hydrogen, $C_{1-4}$alkyl, $OC_{1-4}$alkyl;

each $R^{B3}$ is, independently, hydrogen, halogen, $C_{1-4}$alkyl, $C_{2-4}$alkenyl, $C_{2-4}$alkynyl, CN, C(O)H, C(O)$C_{1-4}$alkyl, C(O)O$C_{1-4}$alkyl, C(O)$C_{1-4}$alkyl, C(O)$NH_2$, C(O)NH$C_{1-4}$alkyl, C(O)NH$(CH_2)_{0-1}C_{3-6}$cycloalkyl, C(O)NHCH$_2$oxetanyl, C(O)NHCH$_2$tetrahydrofuranyl, C(O)NHCH$_2$tetrahydropyranyl, C(O)NHphenyl, C(O)NHbenzyl, C(O)NHOH, C(O)NHO$C_{1-4}$alkyl, C(O)NHO$(CH_2)_{0-1}C_{3-6}$cycloalkyl, C(O)NHO$(CH_2)_{0-1}$oxetanyl, C(O)NHO$(CH_2)_{0-1}$tetrahydrofuranyl, C(O)NHO$(CH_2)_{0-1}$tetrahydropyranyl, C(O)NHOphenyl, C(O)NHObenzyl, $NH_2$, NHC(O)$C_{1-4}$alkyl, $OC_{1-4}$alkyl, $SC_{1-4}$alkyl, S(O)$C_{1-4}$alkyl, or a 5-membered-heteroaryl ring system selected from furanyl, thiophenyl, imidazolyl, pyrrole, pyrazolyl, and oxadiazolyl, wherein each $R^{B3}$ group except hydrogen or halogen is optionally substituted with Cl, up to three F atoms, up to two non-geminal OH groups, up to two $OC_{1-2}$alkyl, one $NH_2$, one NHC$_{1-4}$alkyl, one NHC(O)$C_{1-2}$alkyl, or one N($C_{1-2}$alkyl)$_2$;

each $R^{B4}$ is, independently, hydrogen, deuterium, halogen, $C_{1-4}$alkyl, $OC_{1-4}$alkyl, $SC_{1-4}$alkyl, $NH_2$, NH($C_{1-4}$alkyl), N($C_{1-4}$alkyl)$_2$, NHC(O)$C_{1-4}$alkyl, C(O)OH, C(O)O$C_{1-4}$alkyl, C(O)$NH_2$, C(O)NH$C_{1-4}$alkyl, C(O)N($C_{1-4}$alkyl)$_2$, CN, a morpholinyl ring, or an imidazolyl ring, wherein each $R^{B4}$ alkyl is optionally substituted with up to 3 F atoms, two non-geminal OH groups, or one $OC_{1-2}$alkyl;

$R^{B5}$ is hydrogen, $C_{1-4}$alkyl, C(O)$C_{1-4}$alkyl, C(O)O$C_{1-4}$alkyl, C(O)$NH_2$, C(O)NH$C_{1-4}$alkyl, or C(O)N($C_{1-4}$alkyl)$_2$, wherein said $R^{B5}$ alkyl is optionally substituted with up to 3 F atoms, two non-geminal OH groups, or one $OC_{1-2}$alkyl and $R^{B6}$ is F or $C_{1-2}$alkyl, or two $R^{B6}$ and an intervening carbon atom form a spirocyclopropyl or spirocyclobutyl ring.

2. The method of claim 1, wherein the DNA-damaging agent is in liposomes.

3. The method of claim 2, wherein the liposomes are pegylated.

4. The method of claim 2, wherein the liposomes are non-pegylated.

5. The method of claim 1, wherein the DNA-damaging agent is doxorubicin hydrochloride.

6. The method of claim 1, wherein the DNA-damaging agent is pegylated liposomal doxorubicin.

7. The method of claim 6, wherein pegylated liposomal doxorubicin is administered in a dosage range of about 14 mg/m$^2$ to about 80 mg/m$^2$, inclusive.

8. The method of claim 7, wherein pegylated liposomal doxorubicin is administered in a dosage range of about 18 mg/m$^2$ to about 72 mg/m$^2$, inclusive.

9. The method of claim 8, wherein pegylated liposomal doxorubicin is administered in a dosage range of about 25 mg/m$^2$ to about 55 mg/m$^2$, inclusive.

10. The method of claim 9, wherein pegylated liposomal doxorubicin is administered in a dosage range of about 30 mg/m$^2$ to about 50 mg/m$^2$, inclusive.

11. The method of claim 10, wherein pegylated liposomal doxorubicin is administered in a dosage of about 40 mg/m$^2$ or 50 mg/m$^2$, inclusive.

12. The method of claim 1, wherein the DNA-PK inhibitor and the DNA-damaging agent are administered for more than one cycle, wherein each cycle is 7-days to 28-days apart, and wherein a cycle comprises administering the DNA-damaging agent once on Day 1, and administering the DNA-PK inhibitor once to up to 5 consecutive times, each consecutive time being about 16 to about 32 hours apart.

13. The method of claim 12, wherein each cycle is about 28-days apart.

14. The method of claim 12, wherein the DNA-PK inhibitor and the DNA-damaging agent are administered for at least 2 cycles, and wherein each cycle is about 28-days apart.

15. The method of claim 12, wherein the DNA-PK inhibitor is administered for 3, 4, or 5 consecutive times per cycle, each of the consecutive times being about 24 hours apart.

16. The method of claim 1, wherein said cancer is selected from the group consisting of ovarian cancer and endometrial cancer.

17. The method of claim 1, wherein the DNA-PK inhibitor is administered about 8 and about 30 hours after administration of the DNA-damaging agent.

18. The method of claim 1, wherein the DNA-PK inhibitor is administered about 12 and about 30 hours after administration of the DNA-damaging agent.

19. The method of claim 1, wherein the DNA-PK inhibitor is administered about 20 and about 28 hours after administration of the DNA-damaging agent.

20. The method of claim 1, wherein the DNA-PK inhibitor is administered about 16 hours after administration of the DNA-damaging agent.

21. The method of claim 1, wherein the DNA-PK inhibitor is administered about 24 hours after administration of the DNA-damaging agent.

22. The method of claim 21, wherein the method comprises dosing the DNA-PK inhibitor and the DNA-damaging agent for at least 2 cycles, and wherein each cycle is 28-days apart, and wherein the DNA-damaging agent is dosed on day 1 and the DNA-PK inhibitor is dosed on days 2, 3, and 4 per cycle.

23. The method of claim 22, wherein the method comprises dosing the DNA-PK inhibitor and the DNA-damaging agent for 2, 3, 4, 5, 6, 7, 8, 9, or 10 cycles.

24. The method of claim 1, wherein the compound that inhibits DNA-PK is of Formula (B-II):

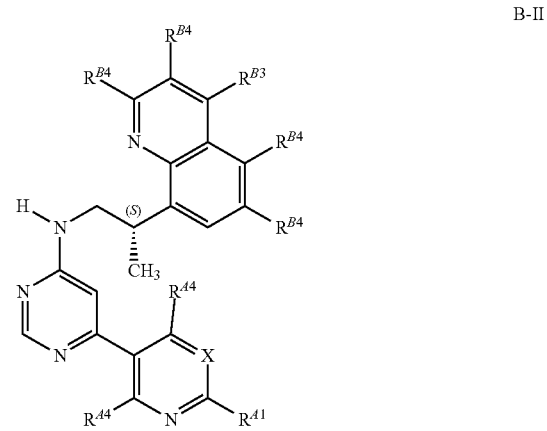

B-II or a pharmaceutically acceptable salt thereof,
wherein:
X is N or $CR^{A5}$;
$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyran, and morpholinyl, and each of said alkyl, cycloalkyl, and heterocyclyl is optionally substituted with up to three F atoms, up to three $^2$H atoms, up to two non-geminal OH groups, or up to two $OC_{1-2}$alkyl;
each $R^{A4}$ is, independently, H or $^2$H;
$R^{A5}$ is hydrogen, F, $C_{1-4}$alkyl, or $OC_{1-4}$alkyl, wherein each of said alkyl is optionally substituted with up to three F atoms or up to three $^2$H atoms;
$R^{B3}$ is $C(O)NHC_{1-4}$ alkyl, wherein said alkyl is optionally substituted with up to three F atoms, up to three $^2$H atoms, up to two non-geminal OH groups, or up to two $OC_{1-2}$alkyl; and
each $R^{B4}$ is, independently, hydrogen, deuterium, F, or $C_{1-4}$alkyl.

25. The method of claim 1, wherein the compound that inhibits DNA-PK is of Formula (B-III):

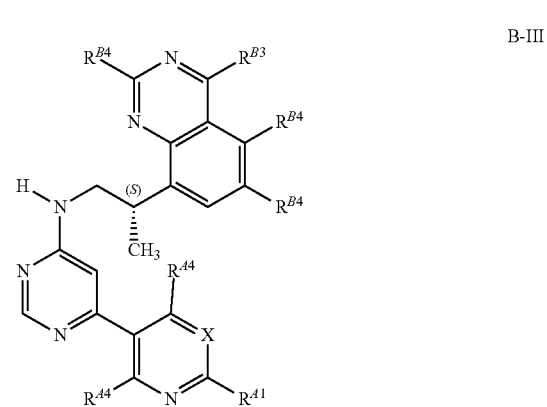

B-III or a pharmaceutically acceptable salt thereof, wherein:

X is N or $CR^{A5}$;

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{0-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyran, and morpholinyl, and each of said alkyl, cycloalkyl, and heterocyclyl is optionally substituted with up to three F atoms, up to three $^2$H atoms, up to two non-geminal OH groups, or up to two $OC_{1-2}$alkyl;

each $R^{A4}$ is, independently, H or $^2$H;

$R^{A5}$ is hydrogen, F, $C_{1-4}$alkyl, or $OC_{1-4}$alkyl, wherein each of said alkyl is optionally substituted with up to three F atoms or up to three $^2$H atoms;

$R^{B3}$ is C(O)NH$C_{1-4}$ alkyl, wherein said alkyl is optionally substituted with up to three F atoms, up to three $^2$H atoms, up to two non-geminal OH groups, or up to two $OC_{1-2}$alkyl; and each $R^{B4}$ is, independently, hydrogen, deuterium, F, or $C_{1-4}$alkyl.

26. The method of claim 1, wherein the compound that inhibits DNA-PK is:

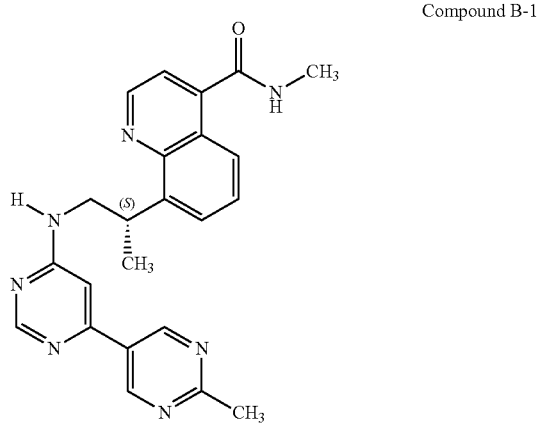

Compound B-1 or a pharmaceutically acceptable salt thereof.

27. The method of claim 1, wherein the compound that inhibits DNA-PK is:

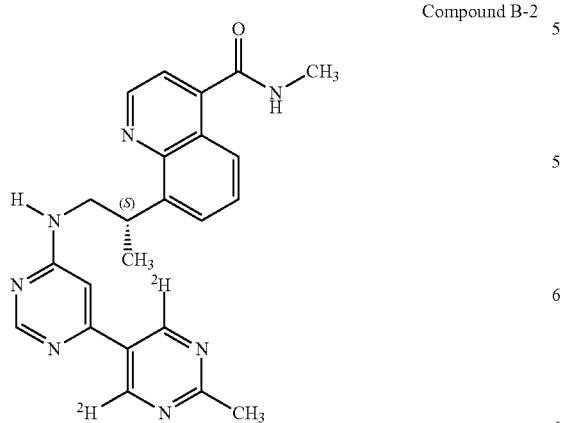

Compound B-2 or a pharmaceutically acceptable salt thereof.

28. The method of claim 1, wherein the DNA-PK inhibitor is a co-crystal comprising Compound B-1 or a pharmaceutically acceptable salt thereof:

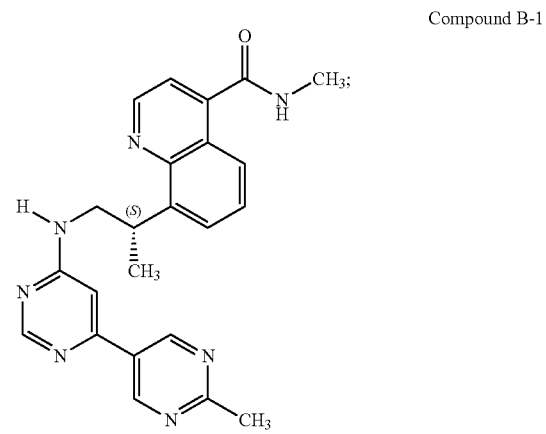

Compound B-1 a co-crystal former selected from adipic acid, citric acid, fumaric acid, maleic acid, succinic acid, and benzoic acid.

29. The method of claim 28, wherein the co-crystal former is adipic acid.

30. The method of claim 29, wherein the molar ratio of adipic acid to Compound B-1 is about 1 to 2.

31. The method of claim 1, wherein the DNA-PK inhibitor is a co-crystal comprising Compound B-2 or a pharmaceutically acceptable salt thereof:

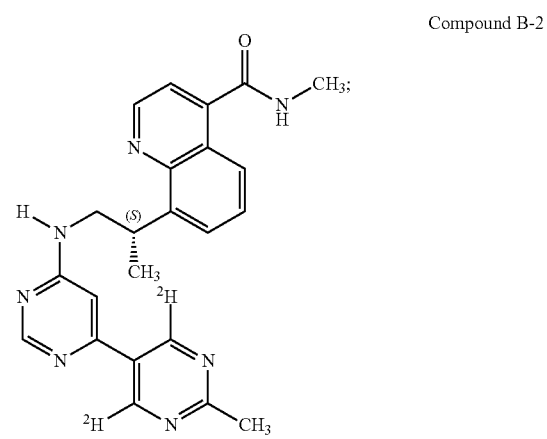

Compound B-2 a co-crystal former selected from adipic acid, citric acid, fumaric acid, maleic acid, succinic acid, and benzoic acid.

32. The method of claim 31, wherein the co-crystal former is adipic acid.

33. The method of claim 32, wherein the co-crystal comprising compound B-2 and adipic acid at a molar ratio of about 1 to 2 adipic acid to Compound B-2.

34. The method of claim 33, wherein the co-crystal is administered in a range of about 50 mg to about 200 mg per day, inclusive.

35. The method of claim 34, wherein the co-crystal is administered in a range of about 50 mg to about 2000 mg per day, inclusive.

36. The method of claim 34, wherein the co-crystal is administered in a range of about 100 mg to about 1500 mg per day, inclusive.

37. The method of claim 1, wherein the DNA-PK inhibitor is administered once, twice, or three times per day.

* * * * *